(12) United States Patent
Shelton, IV et al.

(10) Patent No.: US 12,310,585 B2
(45) Date of Patent: May 27, 2025

(54) ADAPTIVE FIRING CONTROL ALGORITHM BASED ON MECHANICAL ACTUATION OF USER CONTROLS

(71) Applicant: Cilag GmbH International, Zug (CH)

(72) Inventors: Frederick E. Shelton, IV, Hillsboro, OH (US); Shane R. Adams, Lebanon, OH (US); Taylor W. Aronhalt, Loveland, OH (US); Nicholas J. Ross, Franklin, OH (US); Matthew D. Cowperthwait, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 61 days.

(21) Appl. No.: 17/957,933

(22) Filed: Sep. 30, 2022

(65) Prior Publication Data
US 2024/0108335 A1    Apr. 4, 2024

Related U.S. Application Data

(60) Provisional application No. 63/411,445, filed on Sep. 29, 2022.

(51) Int. Cl.
*A61B 17/068*    (2006.01)
*A61B 17/072*    (2006.01)
(Continued)

(52) U.S. Cl.
CPC ...... *A61B 17/07207* (2013.01); *A61B 17/068* (2013.01); *A61B 17/0684* (2013.01);
(Continued)

(58) Field of Classification Search
CPC ............ A61B 17/068; A61B 17/07207; A61B 17/072
See application file for complete search history.

(56) References Cited

U.S. PATENT DOCUMENTS 5,403,312 A * 4/1995 Yates ................. A61B 18/1206
606/49
5,817,084 A   10/1998 Jensen
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Gloria R Weeks
(74) *Attorney, Agent, or Firm* — TROUTMAN PEPPER LOCKE LLP

(57) ABSTRACT

A surgical instrument is disclosed including an end effector configurable between an open state and a clamped state, a firing member movable from an unfired position toward a fired position during a firing stroke, a manually-driveable closure system, a motor-powered firing system, and a control system. The motor-powered firing system is configured to drive the firing member through the firing stroke. The control system is configured to detect, at a first time point, the end effector reaching the clamped state with the manually-driveable closure system, detect, at a second time point, the actuation of the motor-powered firing system, set a firing motion parameter of the motor-powered firing system based on an elapsed time from the first time point to the second time point, and drive the firing member through the firing stroke with the motor-powered firing system using the firing motion parameter.

12 Claims, 61 Drawing Sheets

(51) Int. Cl.
  *A61B 17/32*  (2006.01)
  *A61B 18/14*  (2006.01)
  *A61B 34/30*  (2016.01)
  *G16H 40/63*  (2018.01)
  *H02K 7/116*  (2006.01)
  *H02K 7/14*   (2006.01)
  *A61B 17/00*  (2006.01)
  *A61B 17/29*  (2006.01)
  *A61B 18/00*  (2006.01)
  *A61B 34/20*  (2016.01)
  *A61B 90/00*  (2016.01)

(52) U.S. Cl.
  CPC .... *A61B 17/072* (2013.01); *A61B 17/320092* (2013.01); *A61B 18/1445* (2013.01); *A61B 34/30* (2016.02); *G16H 40/63* (2018.01); *H02K 7/116* (2013.01); *H02K 7/145* (2013.01); *A61B 2017/00017* (2013.01); *A61B 2017/00022* (2013.01); *A61B 2017/00039* (2013.01); *A61B 2017/00075* (2013.01); *A61B 2017/00132* (2013.01); *A61B 2017/00185* (2013.01); *A61B 2017/0019* (2013.01); *A61B 2017/00221* (2013.01); *A61B 2017/00398* (2013.01); *A61B 2017/07257* (2013.01); *A61B 2017/07271* (2013.01); *A61B 2017/07278* (2013.01); *A61B 2017/07285* (2013.01); *A61B 2017/2932* (2013.01); *A61B 2017/320074* (2017.08); *A61B 2018/00642* (2013.01); *A61B 2018/0072* (2013.01); *A61B 2034/2059* (2016.02); *A61B 2090/064* (2016.02)

(56) References Cited

U.S. PATENT DOCUMENTS

| | | | |
|---|---|---|---|
| 5,878,193 A | 3/1999 | Wang et al. | |
| 6,132,368 A | 10/2000 | Cooper | |
| 7,000,818 B2 | 2/2006 | Shelton, IV et al. | |
| 7,422,139 B2 | 9/2008 | Shelton, IV et al. | |
| 7,464,849 B2 | 12/2008 | Shelton, IV et al. | |
| 7,524,320 B2 | 4/2009 | Tierney et al. | |
| 7,670,334 B2 | 3/2010 | Hueil et al. | |
| 7,753,245 B2 | 7/2010 | Boudreaux et al. | |
| 7,845,537 B2 | 12/2010 | Shelton, IV et al. | |
| 7,980,443 B2 | 7/2011 | Scheib et al. | |
| 8,210,411 B2 * | 7/2012 | Yates | A61B 17/3205 227/19 |
| 8,220,688 B2 * | 7/2012 | Laurent | A61B 17/072 227/181.1 |
| 8,308,040 B2 | 11/2012 | Huang et al. | |
| 8,393,514 B2 | 3/2013 | Shelton, IV et al. | |
| 8,505,802 B2 | 8/2013 | Viola et al. | |
| 8,561,870 B2 | 10/2013 | Baxter, III et al. | |
| 8,608,045 B2 | 12/2013 | Smith et al. | |
| 8,685,004 B2 * | 4/2014 | Zemlock | A61B 17/068 606/1 |
| 8,733,613 B2 | 5/2014 | Huitema et al. | |
| 9,016,540 B2 * | 4/2015 | Whitman | A61B 17/072 227/176.1 |
| 9,050,083 B2 * | 6/2015 | Yates | A61B 17/07207 |
| 9,072,535 B2 * | 7/2015 | Shelton, IV | A61B 17/07207 |
| 9,101,358 B2 * | 8/2015 | Kerr | A61B 17/07207 |
| 9,345,481 B2 * | 5/2016 | Hall | A61B 17/07207 |
| 9,804,618 B2 * | 10/2017 | Leimbach | B25F 3/00 |
| 9,808,246 B2 * | 11/2017 | Shelton, IV | A61B 17/07207 |
| 9,913,642 B2 * | 3/2018 | Leimbach | A61B 17/072 |
| 9,987,095 B2 | 6/2018 | Chowaniec et al. | |
| 9,999,472 B2 | 6/2018 | Weir et al. | |
| 10,159,483 B2 | 12/2018 | Beckman et al. | |
| 10,368,865 B2 | 8/2019 | Harris et al. | |
| 10,398,434 B2 * | 9/2019 | Shelton, IV | A61B 34/37 |
| 10,448,948 B2 | 10/2019 | Shelton, IV et al. | |
| 10,639,037 B2 | 5/2020 | Shelton, IV et al. | |
| 10,646,220 B2 | 5/2020 | Shelton, IV et al. | |
| 10,695,057 B2 | 6/2020 | Shelton, IV et al. | |
| 10,716,565 B2 | 7/2020 | Shelton, IV et al. | |
| 10,758,226 B2 | 9/2020 | Weir et al. | |
| 10,828,028 B2 | 11/2020 | Harris et al. | |
| 10,835,245 B2 | 11/2020 | Swayze et al. | |
| 10,842,523 B2 | 11/2020 | Shelton, IV et al. | |
| 10,881,399 B2 | 1/2021 | Shelton, IV et al. | |
| 10,888,321 B2 | 1/2021 | Shelton, IV et al. | |
| 10,973,519 B2 | 4/2021 | Weir et al. | |
| 11,324,501 B2 | 5/2022 | Shelton, IV et al. | |
| 11,369,366 B2 | 6/2022 | Scheib et al. | |
| 11,382,704 B2 | 7/2022 | Overmyer et al. | |
| 11,419,630 B2 | 8/2022 | Yates et al. | |
| 11,628,006 B2 | 4/2023 | Henderson et al. | |
| 2007/0175955 A1 | 8/2007 | Shelton et al. | |
| 2009/0289096 A1 * | 11/2009 | Shelton, IV | A61B 17/07207 227/180.1 |
| 2014/0263541 A1 | 9/2014 | Leimbach et al. | |
| 2014/0263552 A1 * | 9/2014 | Hall | A61B 17/0686 227/176.1 |
| 2017/0079642 A1 | 3/2017 | Overmyer et al. | |
| 2019/0000447 A1 * | 1/2019 | Shelton, IV | A61B 17/07292 |
| 2019/0200981 A1 | 7/2019 | Harris et al. | |
| 2019/0201027 A1 | 7/2019 | Shelton, IV et al. | |
| 2021/0244407 A1 | 8/2021 | Shelton, IV et al. | |

OTHER PUBLICATIONS

IEEE Std 802.3-2012 (Revision of IEEE Std 802.3-2008, published Dec. 28, 2012.

* cited by examiner

| Cartridge Color | Tissue Category | Tissue Type | Tissue Thickness |
|---|---|---|---|
| Color A | Minimum / Indicated | Type A | $t_1$ |
| Color A | Maximum / Design | Type B | $t_2$ |
| Color A | Overstress | Type B | $t_3$ |
| Color B | Minimum / Indicated | Type C | $t_4$ |
| Color B | Maximum / Design | Type C | $t_5$ |
| Color B | Overstress | Type C | $t_6$ |
| Color C | Minimum / Indicated | Type C | $t_7$ |
| Color C | Maximum / Design | Type C | $t_8$ |
| Color C | Overstress | Type C | $t_9$ |
| Color D | Minimum / Indicated | Type C | $t_{10}$ |
| Color D | Maximum / Design | Type C | $t_{11}$ |
| Color D | Overstress | Type C | $t_{12}$ |
| Color E | Minimum / Indicated | Type C | $t_{13}$ |
| Color E | Maximum / Design | Type C | $t_{14}$ |
| Color E | Overstress | Type C | $t_{15}$ |

FIG. 49

ADAPTIVE FIRING CONTROL ALGORITHM BASED ON MECHANICAL ACTUATION OF USER CONTROLS

CROSS-REFERENCE TO RELATED APPLICATIONS

This application claims the benefit under 35 U.S.C. § 119(e) to U.S. Provisional Patent Application Ser. No. 63/411,445, titled METHOD FOR CONTROLLING SURGICAL SYSTEM DURING TISSUE TREATMENT MOTION, filed Sep. 29, 2022, the disclosure of which is herein incorporated by reference in its entirety.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 49 is a table illustrating the transection performance of various staple cartridges, according to at least one aspect of the present disclosure;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
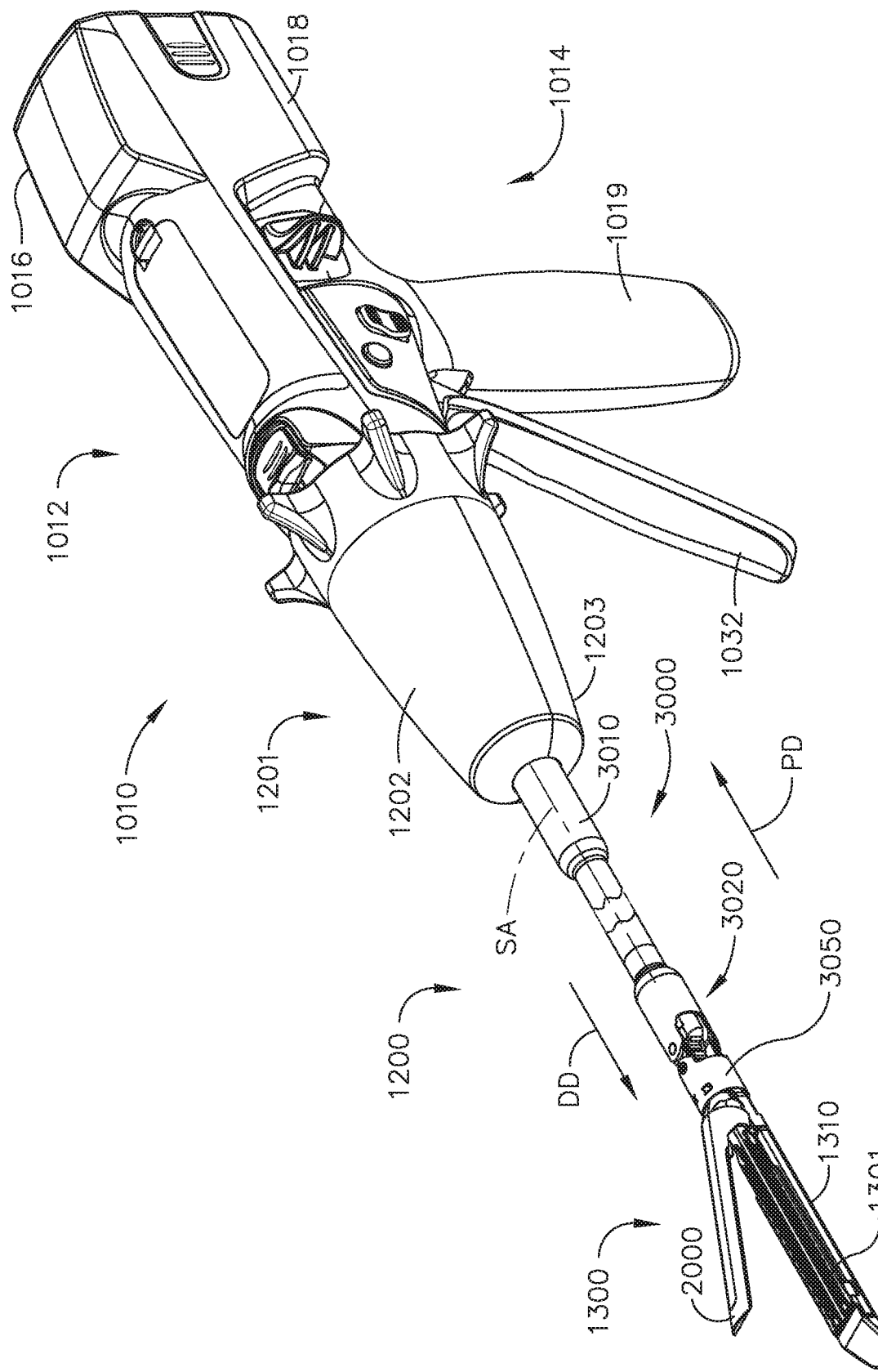
FIG. 1 is a perspective view of a powered surgical stapling system.

Applicant of the present application owns the following U.S. Patent Applications that were filed on even date herewith and which are each herein incorporated by reference in their respective entireties:

U.S. patent application Ser. No. 17/957,917, titled METHOD FOR CONTROLLING SURGICAL SYSTEM DURING TISSUE TREATMENT MOTION; published as US2024/0108334;

U.S. patent application Ser. No. 17/957,923, titled ADAPTING TISSUE TREATMENT MOTION PARAMETERS BASED ON SITUATIONAL PARAMETERS; published as US2024/0108331;

U.S. patent application Ser. No. 17/957,946, titled ADAPTATION OF INDEPENDENT FIRING AND CLOSURE POWERED STAPLING SYSTEMS; published as US2024/0108336;

U.S. patent application Ser. No. 17/957,954, titled MONITORING ONE DRIVE SYSTEM TO ADAPT THE MOTOR DRIVEN ASPECT OF A SECOND DRIVE SYSTEM; published as US2024/0108337;

U.S. patent application Ser. No. 17/957,975, titled ADJUSTMENT OF THE MOTOR CONTROL PROGRAM BASED ON DETECTION OF INDIVIDUAL DEVICE DRIVE TRAIN PROPERTIES; published as US2024/0108338;

U.S. patent application Ser. No. 17/957,984, titled ADJUSTMENT OF A MOTOR CONTROL COMMAND SIGNAL TO ADAPT TO SYSTEM CHANGES; published as US2024/0108339;

U.S. patent application Ser. No. 17/957,990, titled MOTOR ADJUSTMENTS IN ABSENCE OF MOTOR DRIVE SIGNAL; patented as U.S. Pat. No. 11,974,825;

U.S. patent application Ser. No. 17/957,995, titled SURGICAL SYSTEMS WITH SYNCHRONIZED DISTRIBUTED PROCESSING CAPABILITIES; published as US2024/0112798;

U.S. patent application Ser. No. 17/958,001, titled SURGICAL SYSTEM WITH MOTOR RELATIVE CAPACITY INTERROGATIONS; published as US2024/0108333;

U.S. patent application Ser. No. 17/958,008, titled MOTOR CONTROL OF SURGICAL INSTRUMENT SYSTEMS; published as US2024/0108329;

U.S. patent application Ser. No. 17/958,013, titled SURGICAL SYSTEM WITH AMPLITUDE AND PULSE WIDTH MODULATION ADJUSTMENTS; published as US2024/0108421;

U.S. patent application Ser. No. 17/958,024, titled SURGICAL ALGORITHMS WITH INCREMENTAL SENSORY ACTIONS; published as US2024/0108340;

U.S. patent application Ser. No. 17/958,028, titled UTILIZING LOCAL FIRING PARAMETERS TO INITIATE MOTOR CONTROL ADJUSTMENTS IN SURGICAL SYSTEMS; published as US2024/0108341; and U.S. patent application Ser. No. 17/958,037, titled SURGICAL SYSTEMS WITH DYNAMIC FORCE TO FIRE ADJUSTMENTS; patented as U.S. Pat. No. 11,931,037.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 2:
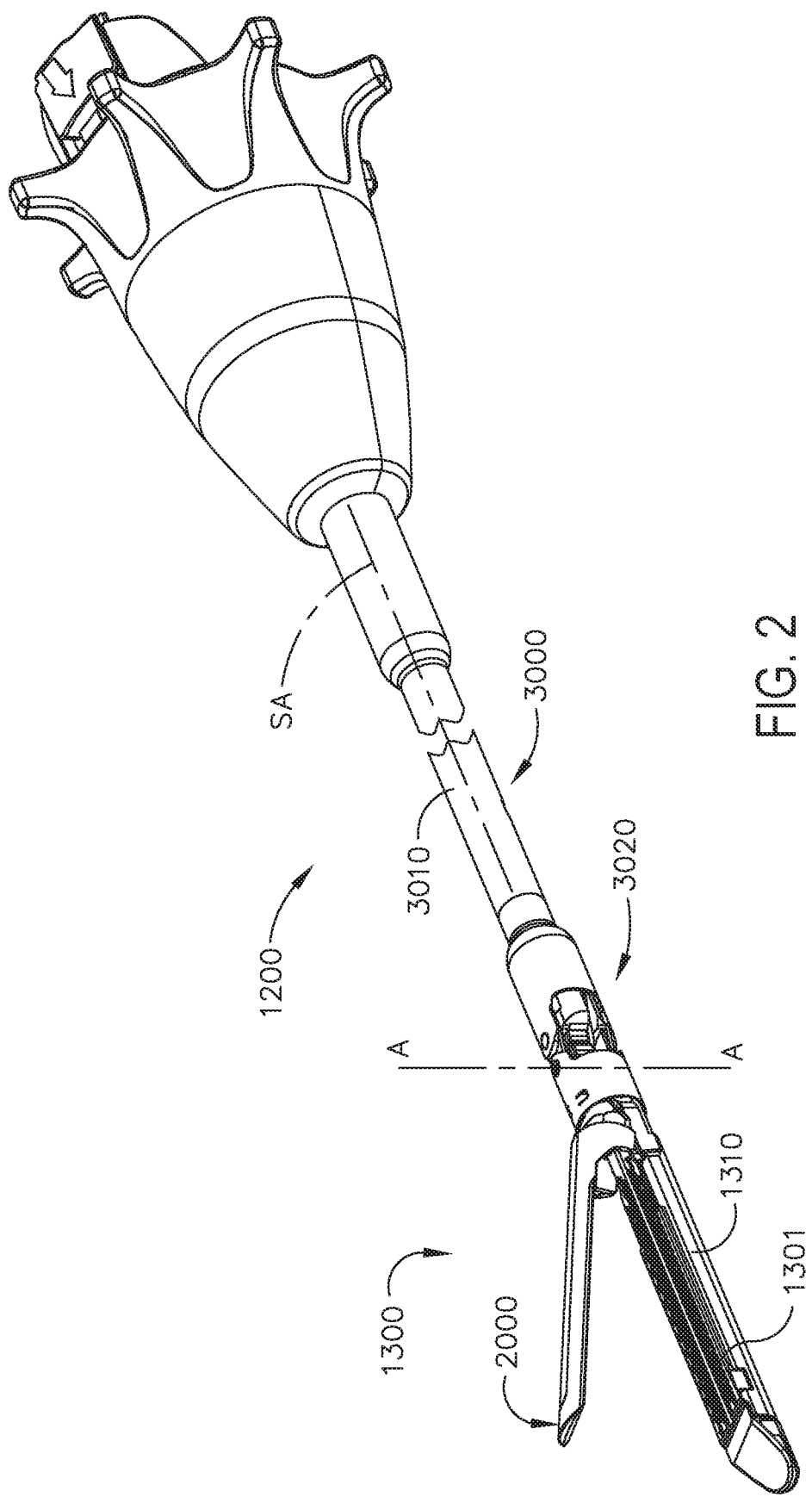
FIG. 2 is a perspective view of an interchangeable surgical shaft assembly of the powered surgical stapling system of FIG. 1.
Figure 3:
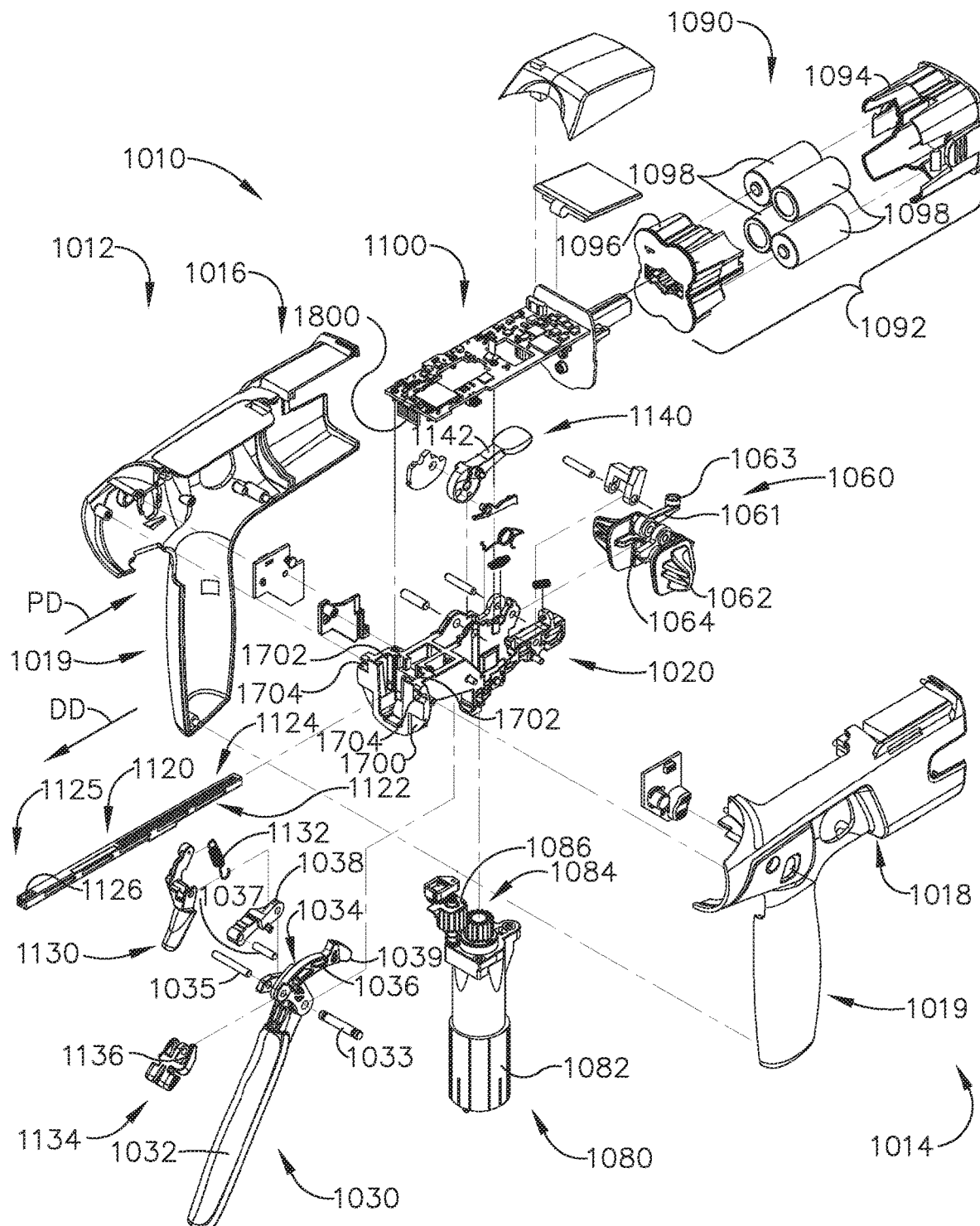
FIG. 3 is an exploded assembly view of portions of a handle assembly of the powered surgical stapling system of FIG. 1.

FIG. 1 illustrates the surgical instrument 1010 that includes an interchangeable shaft assembly 1200 operably coupled to a housing 1012. FIG. 2 illustrates the interchangeable shaft assembly 1200 detached from the housing 1012 or handle 1014. As can be seen in FIG. 3, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019. FIGS. 1 and 3 depict a motor-driven surgical cutting and fastening instrument 1010 that may or may not be reused. In the illustrated embodiment, the instrument 1010 includes a proximal housing 1012 that comprises a handle 1014 that is configured to be grasped, manipulated and actuated by the clinician. The housing 1012 is configured for operable attachment to an interchangeable shaft assembly 1200 that has a surgical end effector 1300 operably coupled thereto that is configured to perform one or more surgical tasks or procedures. As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. In addition, various components may be "housed" or contained in the housing or various components may be "associated with" a housing. In such instances, the components may not be contained within the housing or supported directly by the housing. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, that is incorporated by reference herein in its entirety.

The proximal housing 1012 depicted in FIG. 1 is shown in connection with an interchangeable shaft assembly 1200 (FIGS. 2, 4 and 5) that includes an end effector 1300 that comprises a surgical cutting and fastening device that is configured to operably support a surgical staple cartridge 1301 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener that can be gripped and manipulated by the clinician. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 3, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. More specifically, as illustrated in FIG. 3, the closure trigger 1032 is pivotally coupled to the handle 1014 by a pin 1033. Such arrangement enables the closure trigger 1032 to be manipulated by a clinician such that when the clinician grips the pistol grip portion 1019 of the handle 1014, the closure trigger 1032 may be easily pivoted from a starting or "unactuated" position to an "actuated" position and more particularly to a fully compressed or fully actuated position. The closure trigger 1032 may be biased into the unactuated position by spring or other biasing arrangement (not shown). In various forms, the closure drive system 1030 further includes a closure linkage assembly 1034 that is pivotally coupled to the closure trigger 1032. As can be seen in FIG. 3, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 3, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position towards the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 serves to lock the closure trigger 1032 in the fully actuated position. When the clinician desires to unlock the closure trigger 1032 to permit it to be biased to the unactuated position, the clinician simply pivots the closure release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the closure release button assembly 1062. A magnetic element 1063, such as a permanent magnet, for example, may be mounted to the arm 1061. When the closure release button assembly 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a "Hall Effect" sensor (not shown) can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the closure release button assembly 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system 1080 may also be referred to herein as a "second drive system". The firing drive system 1080 may employ an electric motor 1082 that is located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 3, for example, the power pack 1092 may comprise a proximal housing portion 1094 that is configured for attachment to a distal housing portion 1096. The proximal housing portion 1094 and the distal housing portion 1096 are configured to operably support a plurality of batteries 1098 therein. Batteries 1098 may each comprise, for example, a Lithium Ion ("LI") or other suitable battery. The distal housing portion 1096 is configured for removable operable attachment to the circuit board 1100 which is also operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a set, or rack, of drive teeth 1122 on a longitudinally movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counter-clockwise direction. When the electric motor 1082 is rotated in one direction, the drive member 1120 will be axially driven in the distal direction "DD". When the motor 1082 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014. The firing trigger 1130 may be pivoted between an unactuated position and an actuated position. The firing trigger 1130 may be biased into the unactuated position by a spring 1132 or other biasing arrangement such that when the clinician releases the firing trigger 1130, it may be pivoted or otherwise returned to the unactuated position by the spring 1132 or biasing arrangement. In at least one form, the firing trigger 1130 can be positioned "outboard" of the closure trigger 1032 as was discussed above. In at least one form, a firing trigger safety button 1134 may be pivotally mounted to the closure trigger 1032 by the pin 1035. The safety button 1134 may be positioned between the firing trigger 1130 and the closure trigger 1032 and have a pivot arm 1136 protruding therefrom. When the closure trigger 1032 is in the unactuated position, the safety button 1134 is contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that is configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with teeth 1124 also provided in the drive member 1120. Thus, the clinician can manually retract the drive member 1120 by using the bailout handle assembly 1142 to ratchet the drive member 1120 in the proximal direction "PD". U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein. U.S. Pat. No. 8,608,045, is hereby incorporated by reference herein in its entirety.

Figure 4:
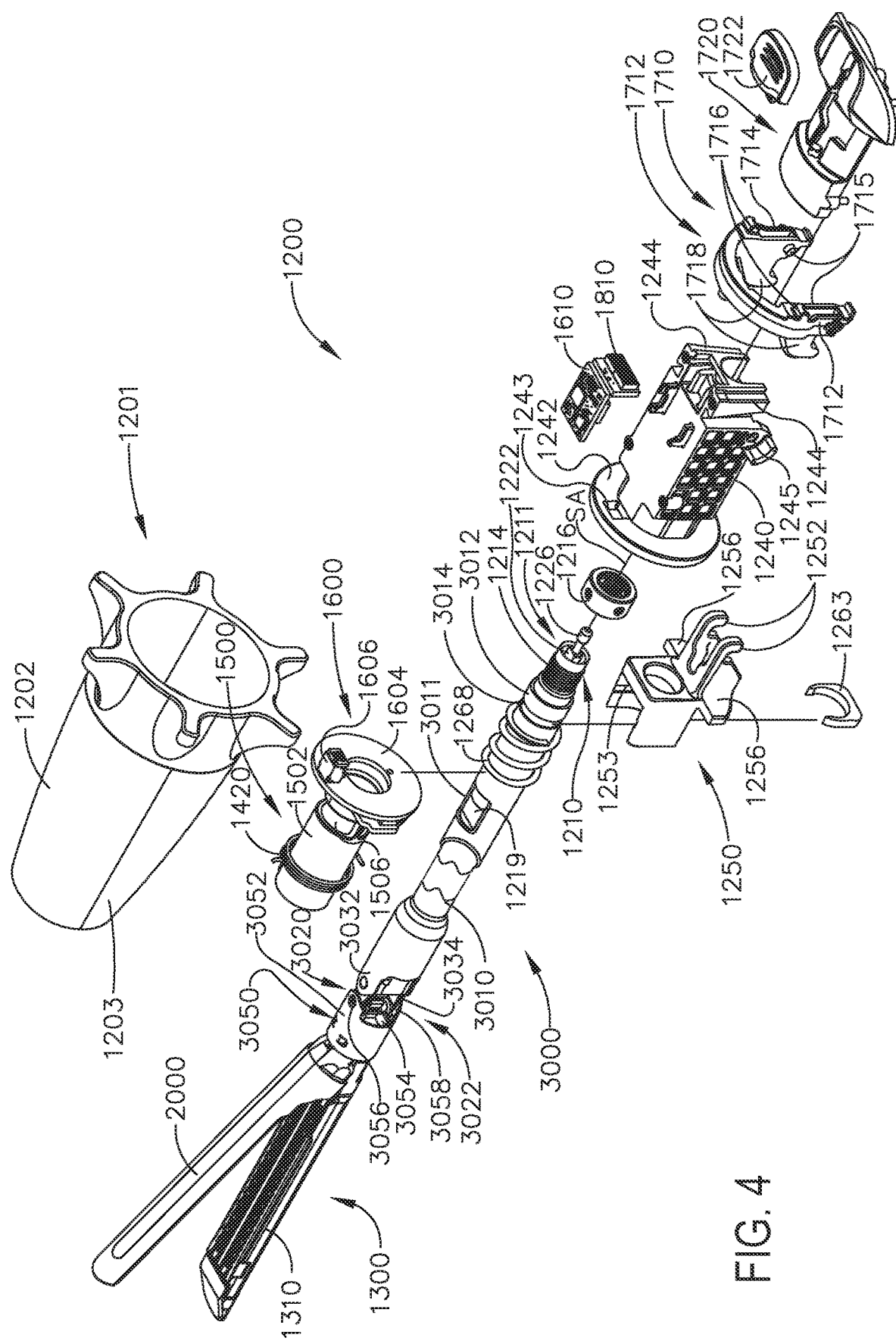
FIG. 4 is an exploded assembly view of the interchangeable surgical shaft assembly of FIG. 2.
Figure 5:
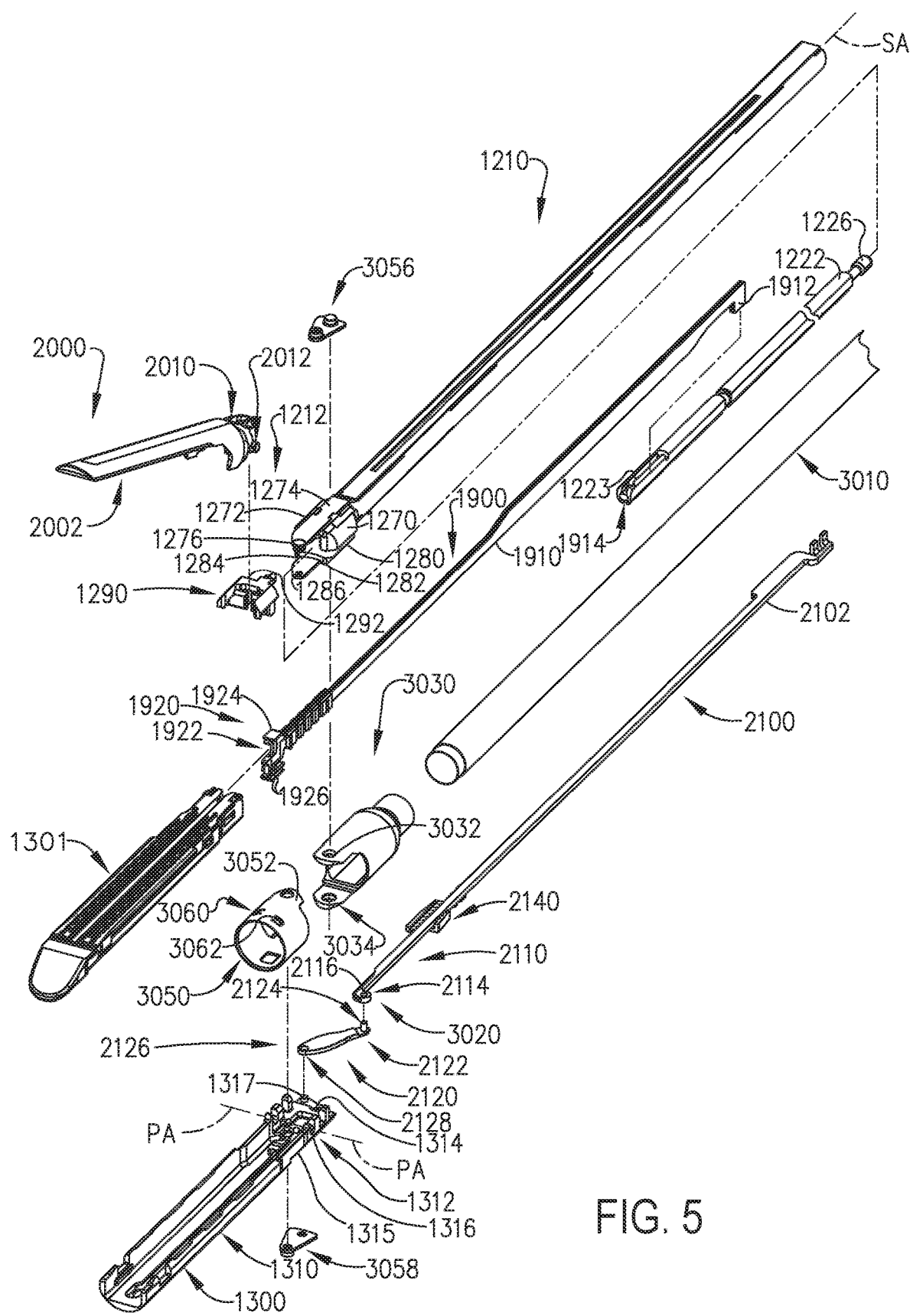
FIG. 5 is another partial exploded assembly view of a portion of the interchangeable surgical shaft assembly of FIG. 4.

Turning now to FIGS. 2 and 5, the interchangeable shaft assembly 1200 includes a surgical end effector 1300 that comprises an elongate channel 1310 that is configured to operably support a staple cartridge 1301 therein. The end effector 1300 may further include an anvil 2000 that is pivotally supported relative to the elongate channel 1310. The interchangeable shaft assembly 1200 may further include an articulation joint 3020 and an articulation lock 2140 which can be configured to releasably hold the end effector 1300 in a desired position relative to a shaft axis SA. Examples of various features of at least one form of the end effector 1300, the articulation joint 3020 and articulation locks may be found in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As can be seen in FIG. 4, the interchangeable shaft assembly 1200 can further include a proximal housing or nozzle 1201 comprised of nozzle portions 1202 and 1203.

The interchangeable shaft assembly 1200 can further include a closure system or closure member assembly 3000 which can be utilized to close and/or open the anvil 2000 of the end effector 1300. The shaft assembly 1200 can include a spine 1210 that is configured to, one, slidably support a firing member therein and, two, slidably support the closure member assembly 3000 which extends around the spine 1210. As can be seen in FIG. 5, a distal end 1212 of spine 1210 terminates in an upper lug mount feature 1270 and in a lower lug mount feature 1280. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a channel cap or anvil retainer 1290 that is attached to a proximal end portion 1312 of the elongate channel 1310. The lower mounting link 1284 includes lower pivot pin 1286 that adapted to be received within a pivot hole 1314 formed in the proximal end portion 1312 of the elongate channel 1310. See FIG. 5. The lower pivot pin 1286 is vertically aligned with the pivot socket 1276 to define an articulation axis AA about which the surgical end effector 1300 may articulate relative to the shaft axis SA. See FIG. 2.

In the illustrated example, the surgical end effector 1300 is selectively articulatable about the articulation axis AA by an articulation system 2100. In one form, the articulation system 2100 includes proximal articulation driver 2102 that is pivotally coupled to an articulation link 2120. As can be most particularly seen in FIG. 5, an offset attachment lug 2114 is formed on a distal end 2110 of the proximal articulation driver 2102. A pivot hole 2116 is formed in the offset attachment lug 2114 and is configured to pivotally receive therein a proximal link pin 2124 formed on the proximal end 2122 of the articulation link 2120. A distal end 2126 of the articulation link 2120 includes a pivot hole 2128 that is configured to pivotally receive therein a channel pin 1317 formed on the proximal end portion 1312 of the elongate channel 1310. Thus, axial movement of proximal articulation driver 2102 will thereby apply articulation motions to the elongate channel 1310 to thereby cause the surgical end effector 1300 to articulate about the articulation axis AA relative to the spine 1210. Further details concerning the construction and operation of the articulation system 2100 may be found in various references incorporated by reference herein including U.S. patent application Ser. No. 15/635,631, filed Jun. 28, 2017, entitled SURGICAL INSTRUMENT WITH AXIALLY MOVABLE CLOSURE MEMBER, now U.S. Patent Application Publication No. 2019/0000464, the entire disclosure of which is hereby incorporated by reference herein. In various circumstances, the proximal articulation driver 2102 can be held in position by an articulation lock 2140 when the proximal articulation driver 2102 is not being moved in the proximal or distal directions. Additional details regarding an example of an articulation lock 2140 may be found in U.S. patent application Ser. No. 15/635,631, now U.S. Patent Application Publication No. 2019/0000464, as well as in other references incorporated by reference herein.

In various circumstances, the spine 1210 can comprise a proximal end 1211 which is rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 4. Such an arrangement facilitates rotatable attachment of the spine 1210 to the chassis 1240 such that the spine 1210 may be selectively rotated about a shaft axis SA relative to the chassis 1240.

Referring primarily to FIG. 4, the interchangeable shaft assembly 1200 includes a closure shuttle 1250 that is slidably supported within the chassis 1240 such that it may be axially moved relative thereto. The closure shuttle 1250 includes a pair of proximally-protruding hooks 1252 that are configured for attachment to the attachment pin 1037 (FIG. 3) that is attached to the second closure link 1038 as will be discussed in further detail below. In at least one example, the closure member assembly 3000 comprises a proximal closure member segment 3010 that has a proximal end 3012 that is coupled to the closure shuttle 1250 for relative rotation thereto. For example, a U shaped connector 1263 is inserted into an annular slot 3014 in the proximal end 3012 of the proximal closure member segment 3010 and is retained within vertical slots 1253 in the closure shuttle 1250. Such an arrangement serves to attach the proximal closure member segment 3010 to the closure shuttle 1250 for axial travel therewith while enabling the proximal closure member segment 3010 to rotate relative to the closure shuttle 1250 about the shaft axis SA. A closure spring 1268 is journaled on the proximal closure member segment 3010 and serves to bias the proximal closure member segment 3010 in the proximal direction "PD" which can serve to pivot the closure trigger 1032 into the unactuated position when the shaft assembly is operably coupled to the handle 1014.

In at least one form, the interchangeable shaft assembly 1200 may further include an articulation joint 3020. Other interchangeable shaft assemblies, however, may not be capable of articulation. As can be seen in FIG. 5, for example, a distal closure member or distal closure tube segment 3030 is coupled to the distal end of the proximal closure member segment 3010. The articulation joint 3020 includes a double pivot closure sleeve assembly 3022. According to various forms, the double pivot closure sleeve assembly 3022 includes an end effector closure tube 3050 having upper and lower distally projecting tangs 3052, 3054. An upper double pivot link 3056 includes upwardly projecting distal and proximal pivot pins that engage respectively an upper distal pin hole in the upper proximally projecting tang 3052 and an upper proximal pin hole in an upper distally projecting tang 3032 on the distal closure tube segment 3030. A lower double pivot link 3058 includes upwardly projecting distal and proximal pivot pins that engage respectively a lower distal pin hole in the lower proximally projecting tang 3054 and a lower proximal pin hole in the lower distally projecting tang 3034. See FIGS. 4 and 5. As will be discussed in further detail below, the closure member assembly 3000 is translated distally (direction "DD") to close the anvil 2000, for example, in response to the actuation of the closure trigger 1032. The anvil 2000 is opened by proximally translating the closure member assembly 3000 which causes the end effector closure sleeve to interact with the anvil 2000 and pivot it to an open position.

As was also indicated above, the interchangeable shaft assembly 1200 further includes a firing member 1900 that is supported for axial travel within the spine 1210. The firing member 1900 includes an intermediate firing shaft portion 1222 that is configured for attachment to a distal cutting portion or knife bar 1910. The intermediate firing shaft portion 1222 may include a longitudinal slot 1223 in the distal end thereof which can be configured to receive a tab 1912 on the proximal end of the distal knife bar 1910. The longitudinal slot 1223 and the proximal end tab 1912 can be sized and configured to permit relative movement therebetween and can comprise a slip joint 1914. The slip joint 1914 can permit the intermediate firing shaft portion 1222 of the firing member 1900 to be moved to articulate the end effector 1300 without moving, or at least substantially moving, the knife bar 1910. Once the end effector 1300 has been suitably oriented, the intermediate firing shaft portion 1222 can be advanced distally until a proximal sidewall of the longitudinal slot 1223 comes into contact with the tab 1912 in order to advance the knife bar 1910 and fire the staple cartridge 1301 positioned within the channel 1310. The knife bar 1910 includes a knife portion 1920 that includes a blade or tissue cutting edge 1922 and includes an upper anvil engagement tab 1924 and lower channel engagement tabs 1926. Various firing member configurations and operations are disclosed in various other references incorporated herein by reference.

Embodiments are also envisioned where, in lieu of a slip joint 1914, a shifter assembly can be used. Details of such a shifter assembly and corresponding components, assemblies, and systems can be found in U.S. patent application Ser. No. 15/635,521, entitled SURGICAL INSTRUMENT LOCKOUT ARRANGEMENT, which is incorporated by reference herein in its entirety.

As can be seen in FIG. 4, the shaft assembly 1200 further includes a switch drum 1500 that is rotatably received on proximal closure member segment 3010. The switch drum 1500 comprises a hollow shaft segment 1502 that has a shaft boss formed thereon for receiving an outwardly protruding actuation pin therein. In various circumstances, the actuation pin extends through a longitudinal slot provided in the lock sleeve to facilitate axial movement of the lock sleeve when it is engaged with the articulation driver. A rotary torsion spring 1420 is configured to engage the boss on the switch drum 1500 and a portion of the nozzle housing 1203 to apply a biasing force to the switch drum 1500. The switch drum 1500 can further comprise at least partially circumferential openings 1506 defined therein which can be configured to receive circumferential mounts extending from the nozzle portions 1202, 1203 and permit relative rotation, but not translation, between the switch drum 1500 and the nozzle 1201. The mounts also extend through openings 3011 in the proximal closure member segment 3010 to be seated in recesses 1219 in the spine 1210. Rotation of the switch drum 1500 about the shaft axis SA will ultimately result in the rotation of the actuation pin and the lock sleeve between its engaged and disengaged positions. In one arrangement, the rotation of the switch drum 1500 may be linked to the axial advancement of the closure tube or closure member. Thus, in essence, actuation of the closure system may operably engage and disengage the articulation drive system with the firing drive system in the various manners described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, and U.S. Pat. No. 9,913,642, entitled SURGICAL INSTRUMENT COMPRISING A SENSOR SYSTEM, the entire disclosures of each being hereby incorporated by reference herein. For example, when the closure tube is in its proximal-most position corresponding to a "jaws open" position, the closure member segment 3010 will have positioned the switch drum 1500 so as to link the articulation system with the firing drive system. When, the closure tube has been moved to its distal position corresponding to a "jaws closed" position, the closure tube has rotated the switch drum 1500 to a position wherein the articulation system is delinked from the firing drive system.

As also illustrated in FIG. 4, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that is mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement permits relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis flange 1242. See FIG. 4. Further details regarding slip ring assembly 1600 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, and U.S. Pat. No. 9,345,481, entitled STAPLE CARTRIDGE TISSUE THICKNESS SENSOR SYSTEM, for example. U.S. patent application Ser. No. 13/803,086, now U.S. Patent Application Publication No. 2014/0263541, U.S. patent application Ser. No. 13/800,067, now U.S. Patent Application Publication No. 2014/0263552, and U.S. Pat. No. 9,345,481 are each hereby incorporated by reference herein in their respective entireties.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to the distal connector flange. In various instances, the shaft assembly 1200 can comprise at least one sensor configured to detect the position of the switch drum 1500.

Referring again to FIG. 4, the chassis 1240 includes at least one, and preferably two, tapered attachment portions 1244 formed thereon that are adapted to be received within corresponding dovetail slots 1702 formed within a distal attachment flange portion 1700 of the frame 1020. See FIG. 3. Each dovetail slot 1702 may be tapered or, stated another way, be somewhat V-shaped to seatingly receive the attachment portions 1244 therein. As can be further seen in FIG. 4, a shaft attachment lug 1226 is formed on the proximal end of the intermediate firing shaft portion 1222. As will be discussed in further detail below, when the interchangeable shaft assembly 1200 is coupled to the handle 1014, the shaft attachment lug 1226 is received in a firing shaft attachment cradle 1126 formed in a distal end 1125 of the longitudinal drive member 1120. See FIG. 3.

Various shaft assembly embodiments employ a latch system 1710 for removably coupling the shaft assembly 1200 to the housing 1012 and more specifically to the frame 1020. As can be seen in FIG. 4, for example, in at least one form, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each have a pivot lug 1715 formed thereon that are adapted to be received in corresponding holes 1245 formed in the chassis 1240. Such arrangement facilitates pivotal attachment of the lock yoke 1712 to the chassis 1240. The lock yoke 1712 may include two proximally protruding lock lugs 1716 that are configured for releasable engagement with corresponding lock detents or grooves 1704 in the distal attachment flange portion 1700 of the frame 1020. See FIG. 3. In various forms, the lock yoke 1712 is biased in the proximal direction by spring or biasing member (not shown). Actuation of the lock yoke 1712 may be accomplished by a latch button 1722 that is slidably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button in the distal direction which also causes the lock yoke 1712 to pivot out of retaining engagement with the distal attachment flange portion 1700 of the frame 1020. When the lock yoke 1712 is in "retaining engagement" with the distal attachment flange portion 1700 of the frame 1020, the lock lugs 1716 are retainingly seated within the corresponding lock detents or grooves 1704 in the distal attachment flange portion 1700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 1032 to grasp and manipulate the target tissue into a desired position. Once the target tissue is positioned within the end effector 1300 in a desired orientation, the clinician may then fully actuate the closure trigger 1032 to close the anvil 2000 and clamp the target tissue in position for cutting and stapling. In that instance, the first drive system 1030 has been fully actuated. After the target tissue has been clamped in the end effector 1300, it may be desirable to prevent the inadvertent detachment of the shaft assembly 1200 from the housing 1012. One form of the latch system 1710 is configured to prevent such inadvertent detachment.

As can be most particularly seen in FIG. 4, the lock yoke 1712 includes at least one and preferably two lock hooks 1718 that are adapted to contact corresponding lock lug portions 1256 that are formed on the closure shuttle 1250. When the closure shuttle 1250 is in an unactuated position (i.e., the first drive system 1030 is unactuated and the anvil 2000 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 2000 is in the closed position), the lock yoke 1712 is prevented from being pivoted to an unlocked position. Stated another way, if the clinician were to attempt to pivot the lock yoke 1712 to an unlocked position or, for example, the lock yoke 1712 was inadvertently bumped or contacted in a manner that might otherwise cause it to pivot distally, the lock hooks 1718 on the lock yoke 1712 will contact the lock lug portions 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange portion 1700 of the frame 1020 such that the tapered attachment portions 1244 formed on the chassis 1240 are aligned with the dovetail slots 1702 in the frame 1020. The clinician may then move the shaft assembly 1200 along an installation axis that is perpendicular to the shaft axis SA to seat the attachment portions 1244 in "operable engagement" with the corresponding dovetail slots 1702. In doing so, the shaft attachment lug 1226 on the intermediate firing shaft portion 1222 will also be seated in the cradle 1126 in the longitudinally movable drive member 1120 and the portions of the pin 1037 on the second closure link 1038 will be seated in the corresponding hooks 1252 in the closure shuttle 1250. As used herein, the term "operable engagement" in the context of two components means that the two components are sufficiently engaged with each other so that upon application of an actuation motion thereto, the components may carry out their intended action, function and/or procedure.

At least five systems of the interchangeable shaft assembly 1200 can be operably coupled with at least five corresponding systems of the handle 1014. A first system can comprise a frame system which couples and/or aligns the frame 1020 or spine 1210 of the shaft assembly 1200 with the frame 1020 of the handle 1014. Another system can comprise a closure drive system 1030 which can operably connect the closure trigger 1032 of the handle 1014 and a closure tube of the shaft assembly 1200. As outlined above, the closure shuttle 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft portion 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 is configured for mating engagement with a corresponding electrical connector 1800 on the circuit board 1100. Further details regarding the circuitry and control systems may be found in U.S. patent application Ser. No. 13/803,086, now U.S. Patent Application Publication No. 2014/0263541 entitled ARTICULATABLE SURGICAL INSTRUMENT COMPRISING AN ARTICULATION LOCK, and U.S. patent application Ser. No. 14/226,142, now U.S. Pat. No. 9,913,642 entitled SURGICAL INSTRUMENT COMPRISING A SENSOR SYSTEM, the entire disclosures of each which were previously incorporated by reference herein. The fifth system may consist of the latching system for releasably locking the shaft assembly 1200 to the handle 1014.

The anvil 2000 in the illustrated example includes an anvil body 2002 that terminates in an anvil mounting portion 2010. The anvil mounting portion 2010 is movably or pivotably supported on the elongate channel 1310 for selective pivotal travel relative thereto about a fixed anvil pivot axis PA that is transverse to the shaft axis SA. In the illustrated arrangement, a pivot member or anvil trunnion 2012 extends laterally out of each lateral side of the anvil mounting portion 2010 to be received in a corresponding trunnion cradle 1316 formed in the upstanding walls 1315 of the proximal end portion 1312 of the elongate channel 1310. The anvil trunnions 2012 are pivotally retained in their corresponding trunnion cradle 1316 by the channel cap or anvil retainer 1290. The channel cap or anvil retainer 1290 includes a pair of attachment lugs that are configured to be retainingly received within corresponding lug grooves or notches formed in the upstanding walls 1315 of the proximal end portion 1312 of the elongate channel 1310. See FIG. 5.

Still referring to FIG. 5, in at least one arrangement, the distal closure member or end effector closure tube 3050 employs two axially offset, proximal and distal positive jaw opening features 3060 and 3062. The positive jaw opening features 3060, 3062 are configured to interact with corresponding relieved areas and stepped portions formed on the anvil mounting portion 2010 as described in further detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, the entire disclosure which has been herein incorporated by reference. Other jaw opening arrangements may be employed.

Figure 6:
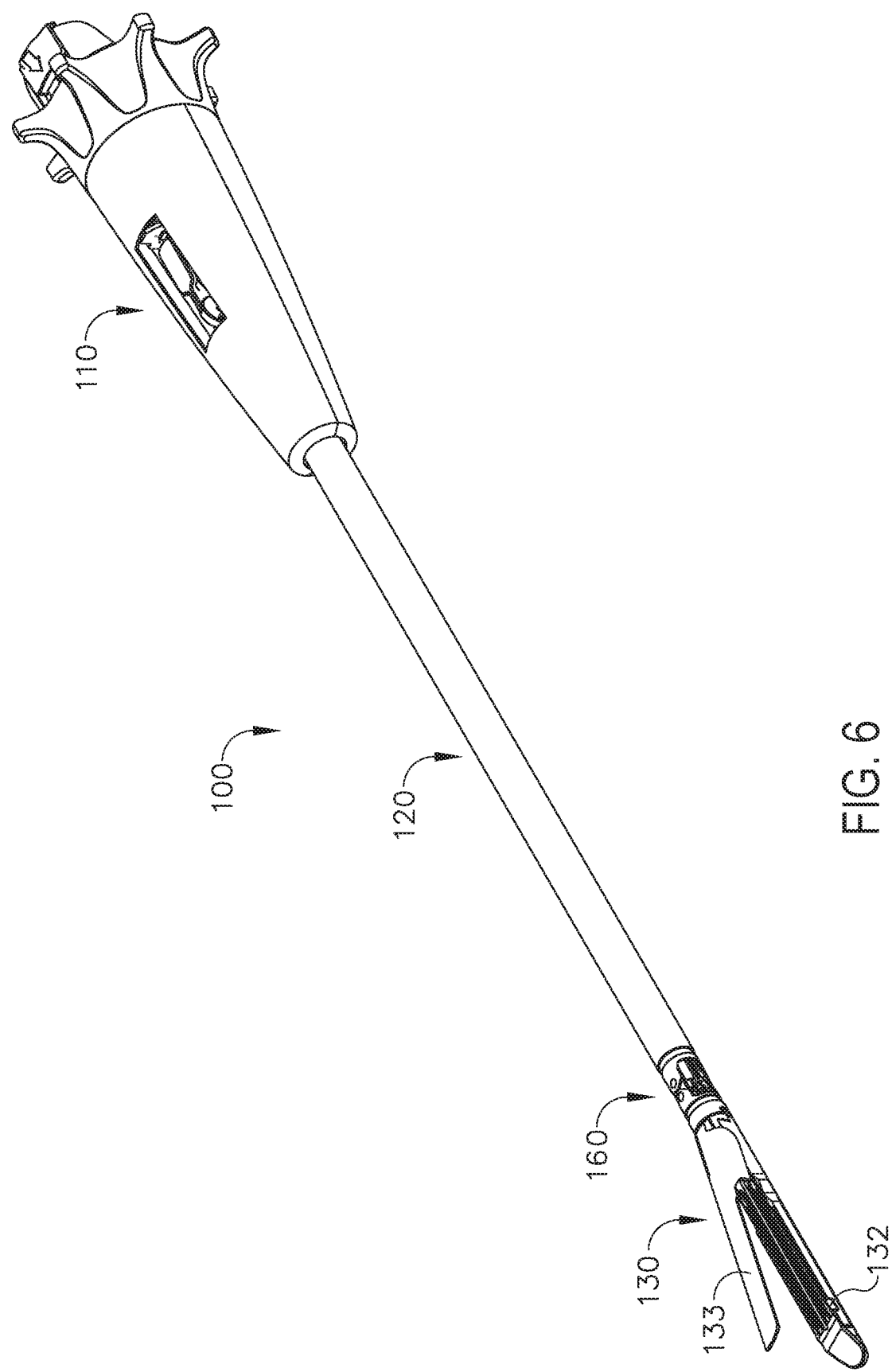
FIG. 6 is a perspective view of a shaft assembly in accordance with at least one embodiment.
Figure 7:
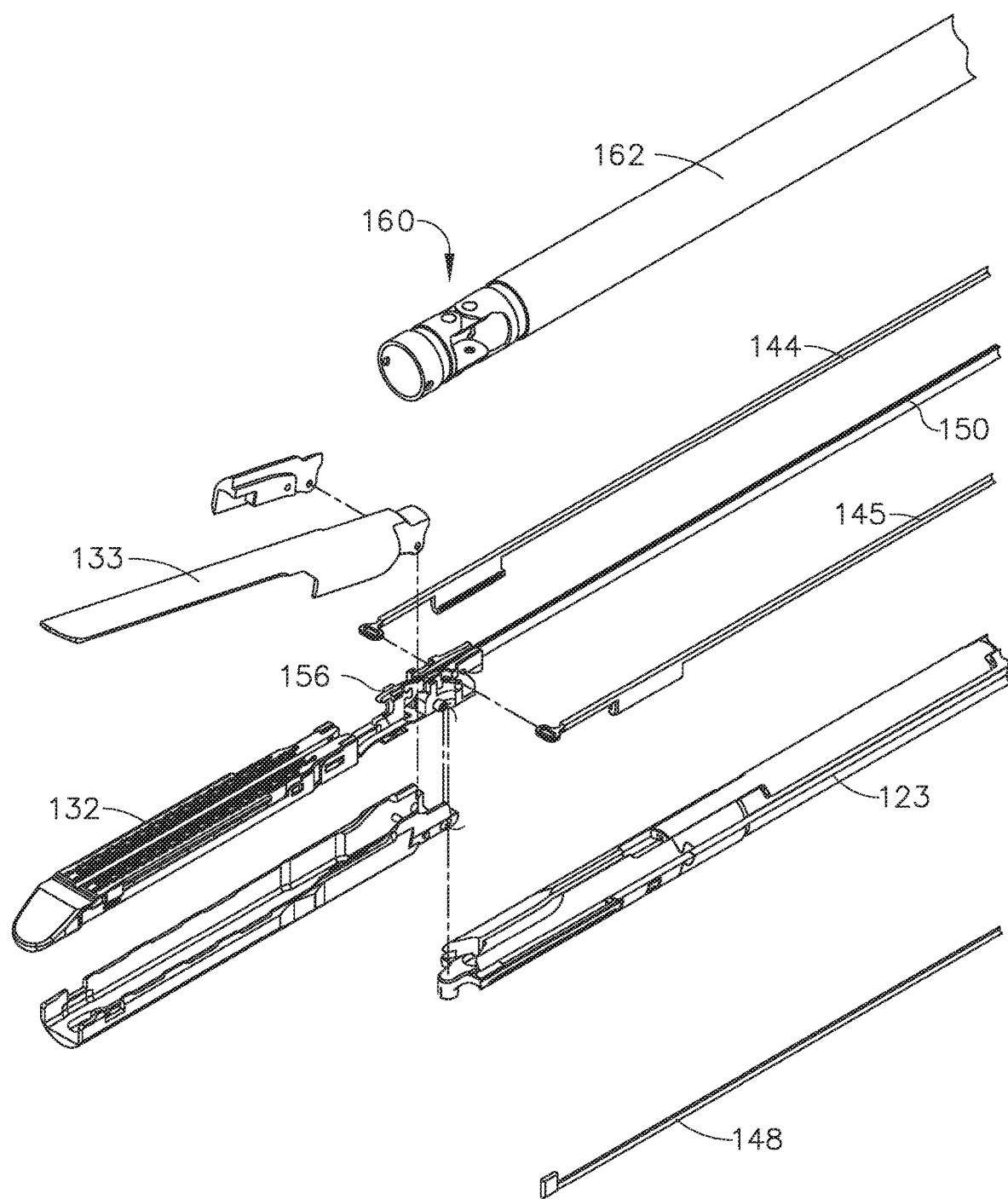
FIG. 7 is an exploded view of a distal end of the shaft assembly of FIG. 6.

A shaft assembly 100 is illustrated in FIGS. 6 and 7. The shaft assembly 100 comprises an attachment portion 110, a shaft 120 extending distally from the attachment portion 110, and an end effector 130 attached to the shaft 120. The shaft assembly 100 is configured to clamp, staple, and cut tissue. The attachment portion 110 is configured to be attached to a handle of a surgical instrument and/or the arm of a surgical robot, for example.

Referring to FIG. 7, the shaft assembly 100 comprises cooperating articulation rods 144, 145 configured to articulate the end effector 130 relative to the shaft 120 about an articulation joint 160. The shaft assembly 100 further comprises an articulation lock bar 148, an outer shaft tube 162, and a spine portion 123.

Referring to FIG. 7, the shaft assembly 100 comprises a firing shaft 150 including a firing member 156 attached to a distal end of the firing shaft 150. The firing member 156 comprises upper camming flanges configured to engage an anvil jaw 133 and lower camming members configured to engage a cartridge jaw 132. The firing shaft 150 is configured to be advanced distally through a closure stroke to clamp the anvil jaw 133 relative to the cartridge jaw 132 with the camming members. Further advancement of the firing shaft 150 through a firing stroke is configured to advance the firing member 156 through the cartridge jaw 132 to deploy staples from the cartridge jaw 132 and cut tissue during the firing stroke. More details of the shaft assembly 100 can be found in U.S. patent application Ser. No. 15/385,887 entitled METHOD FOR ATTACHING A SHAFT ASSEMBLY TO A SURGICAL INSTRUMENT AND, ALTERNATIVELY, TO A SURGICAL ROBOT, which is incorporated by reference in its entirety.

Figure 8:
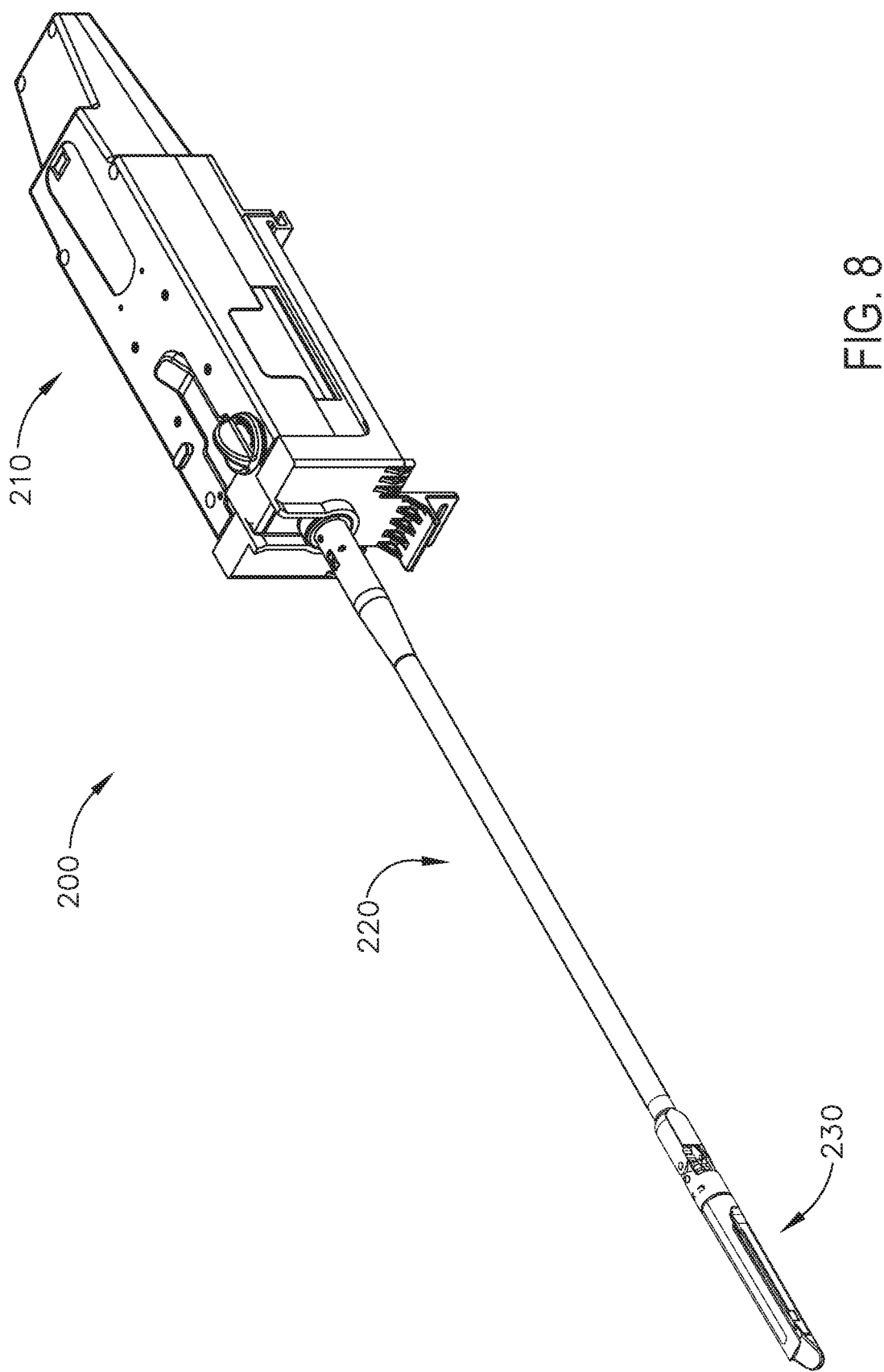
FIG. 8 is a perspective view of a surgical instrument assembly comprising a proximal control interface, a shaft assembly, and an end effector assembly.
Figure 9:
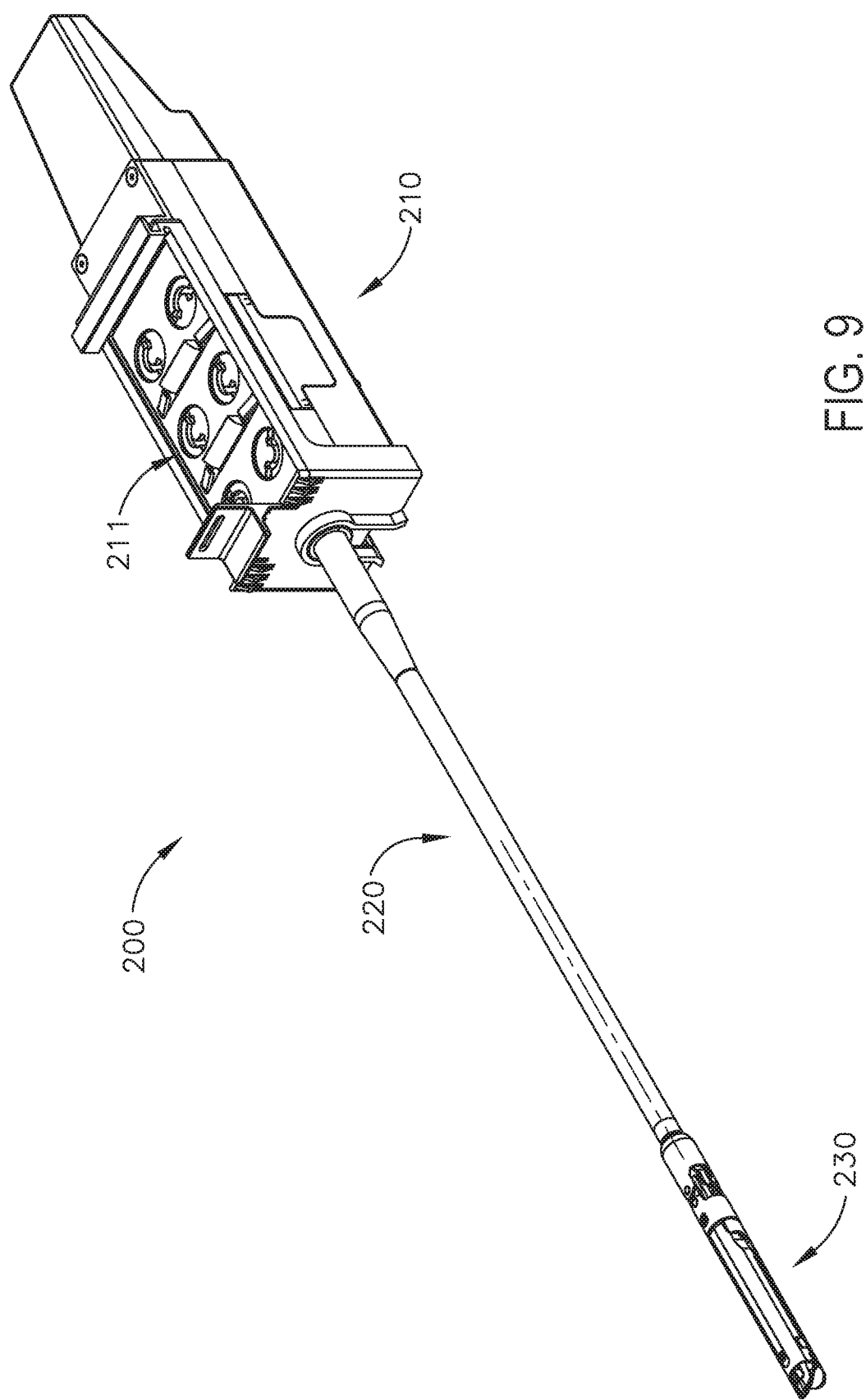
FIG. 9 is a bottom perspective view of the surgical instrument assembly of FIG. 8.

FIGS. 8 and 9 depict a surgical instrument assembly 200 configured to be used with a surgical robot. The surgical instrument assembly 200 is configured to staple and cut tissue, although the surgical instrument assembly 200 could be adapted to treat tissue in any suitable way, such as by applying heat energy, electrical energy, and/or vibrations to the tissue, for example. The surgical instrument assembly 200 comprises a proximal control interface 210 configured to be coupled to a robotic arm of a surgical robot and a shaft assembly 220 configured to be attached to the proximal control interface 210. The shaft assembly 220 comprises an end effector 230 configured to clamp, cut, and staple tissue. The proximal control interface 210 comprises a plurality of drive discs 211, each for actuating one or more functions of the surgical instrument assembly 200. Each drive disc 211 can be independently driven and/or cooperatively driven with one or more other drive discs 211 by one or more motors of the surgical robot and/or robotic arm of the surgical robot. More details about the surgical instrument assembly 200 can be found in U.S. patent application Ser. No. 15/847,297, entitled SURGICAL INSTRUMENTS WITH DUAL ARTICULATION DRIVERS, which is incorporated by reference in its entirety.

Figure 10:
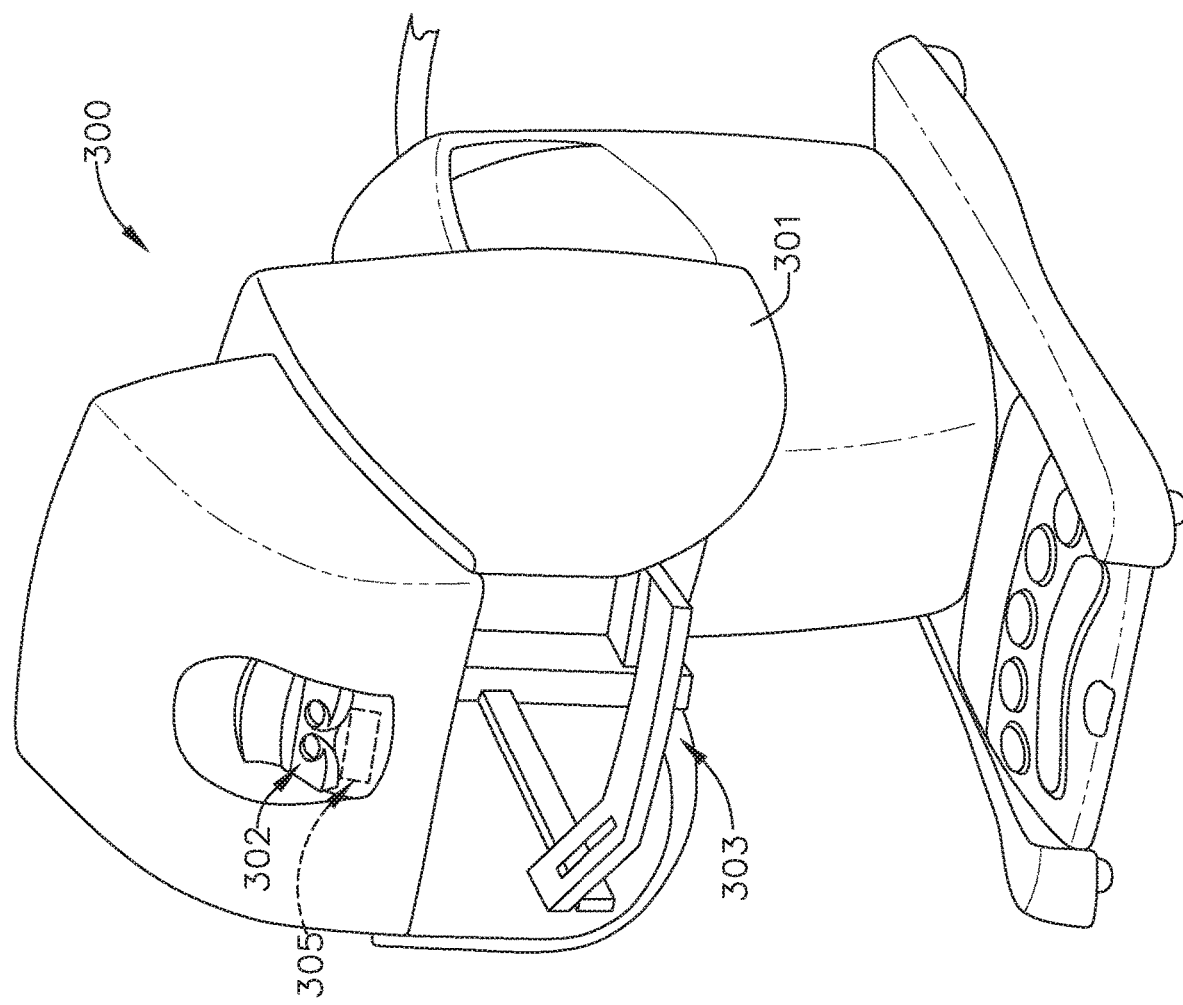
FIG. 10 is a perspective view of an example of one form of robotic controller according to one aspect of this disclosure.
Figure 11:
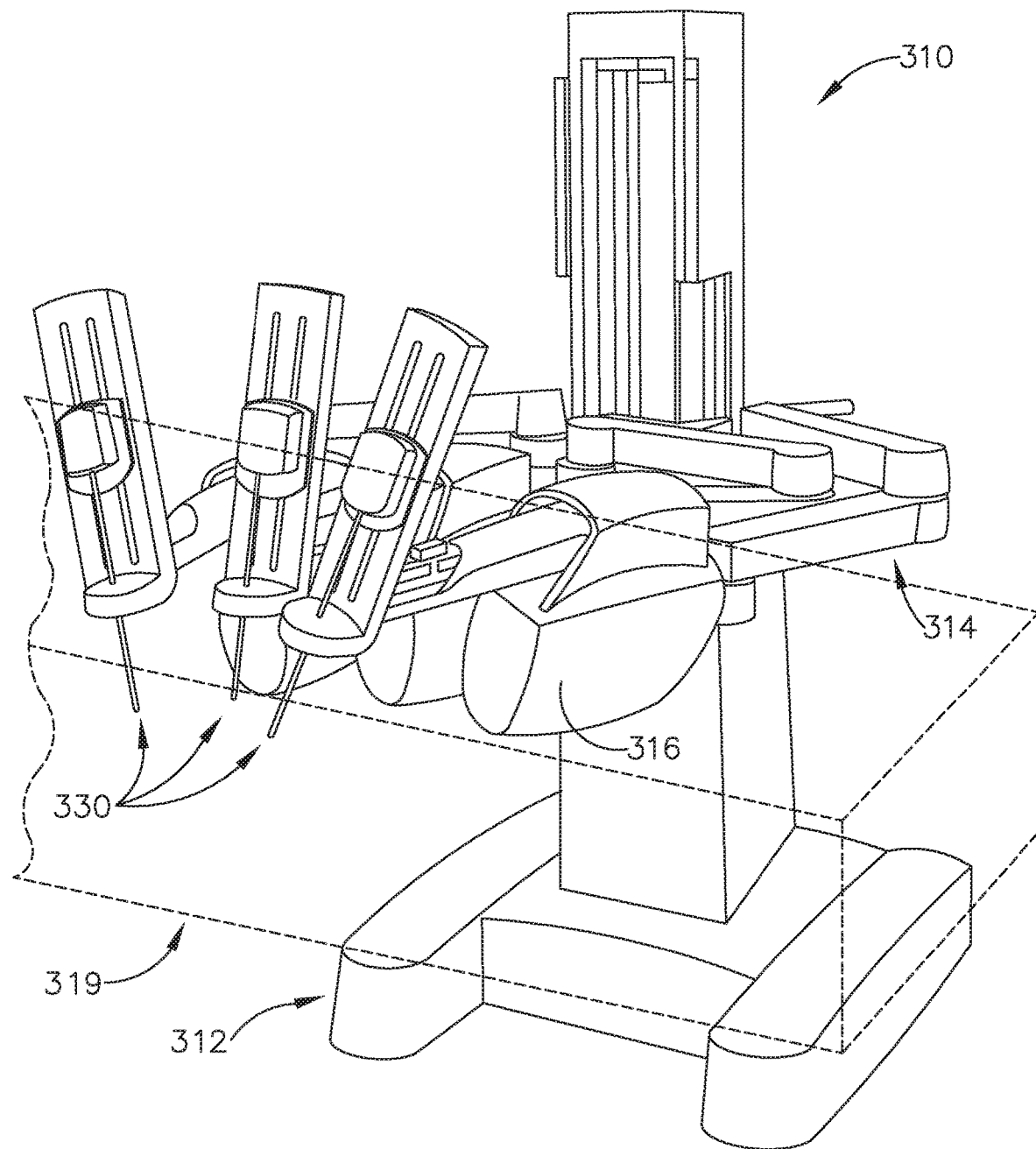
FIG. 11 is a perspective view of an example of one form of robotic surgical arm cart/manipulator of a robotic surgical system operably supporting a plurality of surgical tools according to one aspect of this disclosure.
Figure 12:
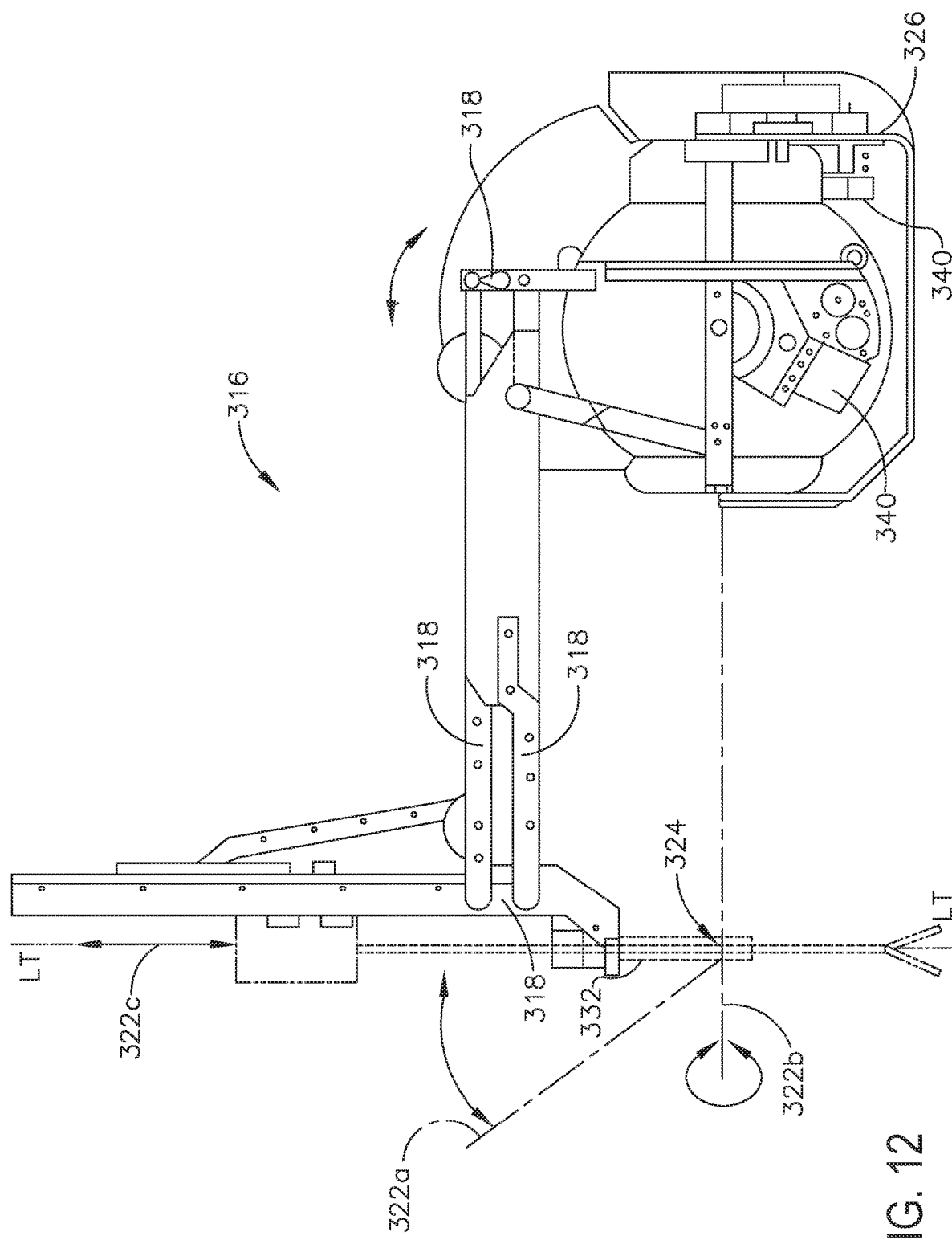
FIG. 12 is a side view of the robotic surgical arm cart/manipulator depicted in FIG. 11 according to one aspect of this disclosure.

Various embodiments disclosed herein may be employed in connection with a robotic system 300 of the type depicted in FIGS. 10-12, for example. FIG. 10 depicts one version of a master controller 301 that may be used in connection with a robotic arm slave cart 310 of the type depicted in FIG. 11. Master controller 301 and robotic arm slave cart 310, as well as their respective components and control systems are collectively referred to herein as a robotic system 300. Examples of such systems and devices are disclosed in U.S. Pat. No. 7,524,320, entitled MECHANICAL ACTUATOR INTERFACE SYSTEM FOR ROBOTIC SURGICAL TOOLS, as well as U.S. Pat. No. 9,072,535, entitled SURGICAL STAPLING INSTRUMENTS WITH ROTATABLE STAPLE DEPLOYMENT ARRANGEMENTS, which are each hereby incorporated by reference herein in their respective entireties. Thus, various details of such devices will not be described in detail herein beyond that which may be necessary to understand various embodiments and forms of the present disclosure. As is known, the master controller 301 generally includes master controllers (generally represented as 303 in FIG. 10) which are grasped by the surgeon and manipulated in space while the surgeon views the procedure via a stereo display 302. The master controllers 301 generally comprise manual input devices which preferably move with multiple degrees of freedom, and which often further have an actuatable handle for actuating tools (for example, for closing grasping jaws, applying an electrical potential to an electrode, or the like).

As can be seen in FIG. 11, in one form, the robotic arm cart 310 may be configured to actuate one or more surgical tools, generally designated as 330. Various robotic surgery systems and methods employing master controller and robotic arm cart arrangements are disclosed in U.S. Pat. No. 6,132,368, entitled MULTI-COMPONENT TELEPRESENCE SYSTEM AND METHOD the entire disclosure of which is hereby incorporated by reference herein. In various forms, the robotic arm cart 310 includes a base 312 from which, in the illustrated embodiment, surgical tools may be supported. In various forms, the surgical tool(s) may be supported by a series of manually articulatable linkages, generally referred to as set-up joints 314, and a robotic manipulator 316. In various embodiments, the linkage and joint arrangement may facilitate rotation of a surgical tool around a point in space, as more fully described in issued U.S. Pat. No. 5,817,084, entitled REMOTE CENTER POSITIONING DEVICE WITH FLEXIBLE DRIVE, the entire disclosure of which is hereby incorporated by reference herein. The parallelogram arrangement constrains rotation to pivoting about an axis 322a, sometimes called the pitch axis. The links supporting the parallelogram linkage are pivotally mounted to set-up joints 314 (FIG. 11) so that the surgical tool further rotates about an axis 322b, sometimes called the yaw axis. The pitch and yaw axes 322a, 322b intersect at the remote center 324, which is aligned along an elongate shaft of a surgical tool. The surgical tool may have further degrees of driven freedom as supported by manipulator 316, including sliding motion of the surgical tool along the longitudinal axis "LT-LT". As the surgical tool slides along the tool axis LT-LT relative to manipulator 316 (arrow 322c), remote center 324 remains fixed relative to base 326 of manipulator 316. Hence, the entire manipulator is generally moved to reposition remote center 324. Linkage 318 of manipulator 316 may be driven by a series of motors 340. These motors actively move linkage 318 in response to commands from a processor of a control system. The motors 340 may also be employed to manipulate the surgical tool. Alternative joint structures and set up arrangements are also contemplated. Examples of other joint and set up arrangements, for example, are disclosed in U.S. Pat. No. 5,878,193, entitled AUTOMATED ENDOSCOPE SYSTEM FOR OPTIMAL POSITIONING, the entire disclosure of which is hereby incorporated by reference herein. Additionally, while the data communication between a robotic component and the processor of the robotic surgical system is primarily described herein with reference to communication between the surgical tool and the master controller 301, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like. In accordance with at least one aspect, various surgical instruments disclosed herein may be used in connection with other robotically-controlled or automated surgical systems and are not necessarily limited to use with the specific robotic system components shown in FIGS. 10-12 and described in the aforementioned references.

Figure 13:
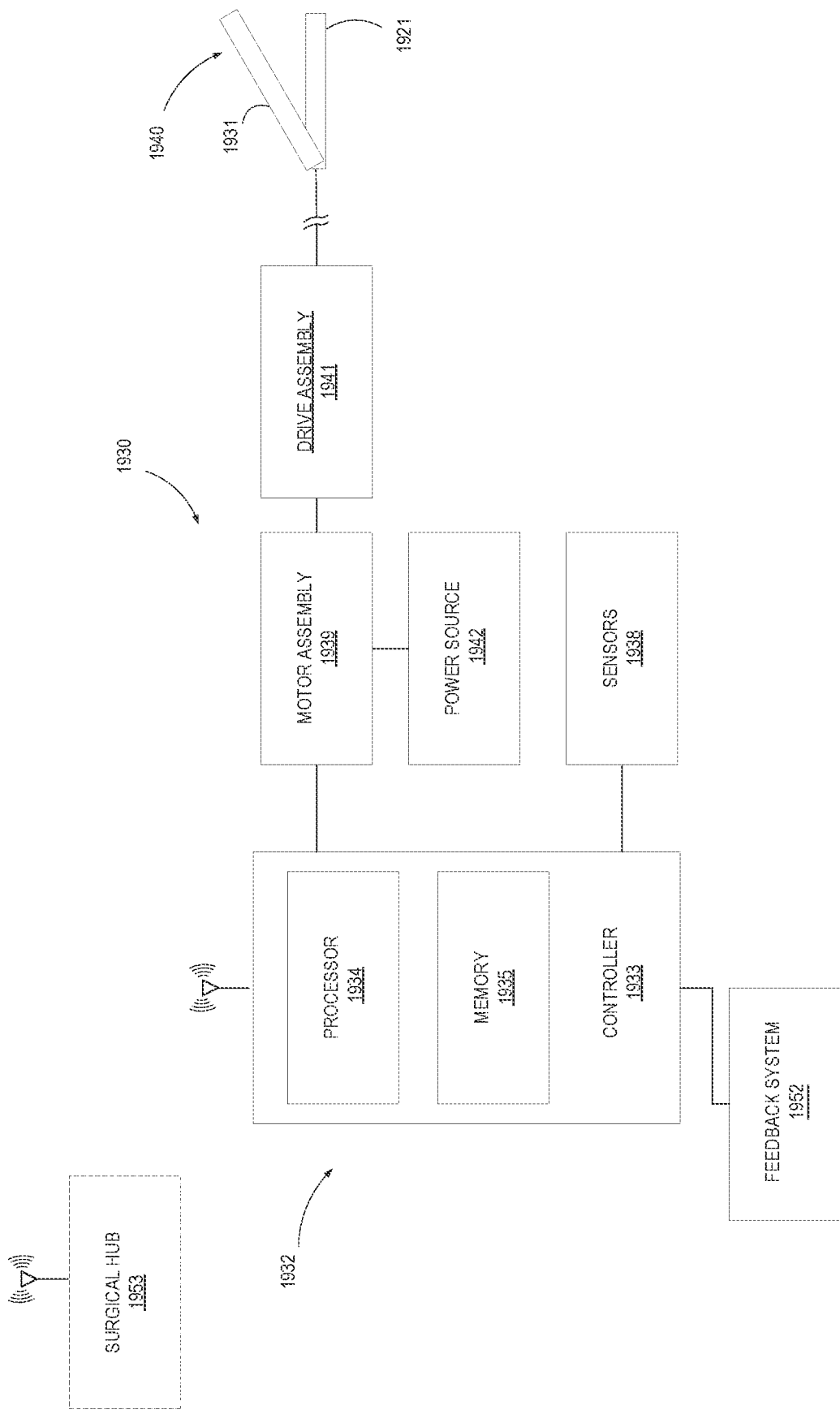
FIG. 13 illustrates a block diagram of a surgical system for use with one or more surgical instruments, tools, and/or robotic systems in accordance with one or more aspects of the present disclosure.

FIG. 13 illustrates a block diagram of a surgical system 1930 for use with one or more surgical instruments, tools, and/or robotic systems in accordance with one or more aspects of the present disclosure. The system 1930 includes a control circuit 1932. The control circuit 1932 includes a microcontroller 1933 comprising a processor 1934 and a storage medium such as, for example, a memory 1935.

A motor assembly 1939 includes one or more motors, driven by motor drivers. The motor assembly 1939 operably couples to a drive assembly 1941 to drive, or effect, one or more motions at an end effector 1940. The drive assembly 1941 may include any number of components suitable for transmitting motion to the end effector 1940 such as, for example, one or more linkages, bars, tubes, and/or cables, for example.

One or more of sensors 1938, for example, provide real-time feedback to the processor 1934 about one or more operational parameters monitored during a surgical procedure being performed by the surgical system 1930. The operational parameters can be associated with a user performing the surgical procedure, a tissue being treated, and/or one or more components of the surgical system 1930, for example. The sensor 1938 may comprise any suitable sensor, such as, for example, a magnetic sensor, such as a Hall effect sensor, a strain gauge, a pressure sensor, an inductive sensor, such as an eddy current sensor, a resistive sensor, a capacitive sensor, an optical sensor, and/or any other suitable sensor.

Further to the above, in various arrangements, the sensors 1938 may comprise any suitable sensor for detecting one or more conditions at the end effector 1940 including, without limitation, a tissue thickness sensor such as a Hall Effect Sensor or a reed switch sensor, an optical sensor, a magneto-inductive sensor, a force sensor, a pressure sensor, a piezo-resistive film sensor, an ultrasonic sensor, an eddy current sensor, an accelerometer, a pulse oximetry sensor, a temperature sensor, a sensor configured to detect an electrical characteristic of a tissue path (such as capacitance or resistance), or any combination thereof. As another example, and without limitation, the sensors 1938 may include one or more sensors located at, or about, an articulation joint extending proximally from the end effector 1940. Such sensors may include, for example, a potentiometer, a capacitive sensor (slide potentiometer), piezo-resistive film sensor, a pressure sensor, a pressure sensor, or any other suitable sensor type. In some arrangements, the sensor 1938 may comprise a plurality of sensors located in multiple locations in the end effector 1940.

In certain aspects, the system 1930 includes a feedback system 1952 which includes one or more devices for providing a sensory feedback to a user. Such devices may comprise, for example, visual feedback devices (e.g., an LCD display screen, a touch screen, LED indicators), audio feedback devices (e.g., a speaker, a buzzer) or tactile feedback devices (e.g., haptic actuators).

The microcontroller 1933 may be programmed to perform various functions such as precise control over the speed and position of the drive assembly 1941. In one aspect, the microcontroller 1933 may be any single-core or multicore processor such as those known under the trade name ARM Cortex by Texas Instruments. In one aspect, the main microcontroller 1933 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 1933 may be configured to compute a response in the software of the microcontroller 1933. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

The motor assembly 1939 includes one or more electric motors and one or more motor drivers. The electric motors can be in the form of a brushed direct current (DC) motor with a gearbox and mechanical links to the drive assembly 1941. In one aspect, a motor driver may be an A3941 available from Allegro Microsystems, Inc.

In various forms, the motor assembly 1939 includes a brushed DC driving motor having a maximum rotational speed of approximately 25,000 RPM. In other arrangements, the motor assembly 1939 may include a brushless motor, a cordless motor, a synchronous motor, a stepper motor, or any other suitable electric motor. The motor driver may comprise an H-bridge driver comprising field-effect transistors (FETs), for example.

The motor assembly 1939 can be powered by a power source 1942. In certain aspects, the power source 1942 includes one or more batteries which may include a number of battery cells connected in series that can be used as the power source to power the motor assembly 1939. In certain circumstances, the battery cells of the power assembly may be replaceable and/or rechargeable. In at least one example, the battery cells can be lithium-ion batteries which can be couplable to and separable from the power assembly.

Further to the above, the end effector 1940 includes a first jaw 1921 and a second jaw 1931. At least one of the first jaw 1921 and the second jaw 1931 is rotatable relative to the other during a closure motion that transitions the end effector 1940 from an open configuration toward a closed configuration. The closure motion may cause the jaws 1921, 1931 to grasp tissue therebetween. In certain arrangements, sensors, such as, for example, a strain gauge or a micro-strain gauge, are configured to measure one or more parameters of the end effector 1940, such as, for example, the amplitude of the strain exerted on the one or both of the jaws 1921, 1931 during a closure motion, which can be indicative of the closure forces applied to the jaws 1921, 1931. The measured strain is converted to a digital signal and provided to the processor 1934, for example. Alternatively, additionally, sensors such as, for example, a load sensor, can measure a closure force and/or a firing force applied to the jaws 1921, 1931.

In various arrangements, a current sensor can be employed to measure the current drawn by a motor of the motor assembly 1939. The force required to advance the drive assembly 1941 can correspond to the current drawn by the motor, for example. The measured force is converted to a digital signal and provided to the processor 1934.

In one form, strain gauge sensors can be used to measure the force applied to the tissue by the end effector 1940, for example. A strain gauge can be coupled to the end effector 1940 to measure the force on the tissue being treated by the end effector 1940. In one aspect, the strain gauge sensors can measure the amplitude or magnitude of the strain exerted on a jaw of an end effector 1940 during a closure motion which can be indicative of the tissue compression. The measured strain is converted to a digital signal and provided to a processor 1934.

The measurements of the tissue compression, the tissue thickness, and/or the force required to close the end effector on the tissue, as respectively measured by the sensors 1938 can be used by the microcontroller 1933 to characterize the selected position of one or more components of the drive assembly 1941 and/or the corresponding value of the speed of one or more components of the drive assembly 1941. In one instance, a memory (e.g. memory 1935) may store a technique, an equation, and/or a look-up table which can be employed by the microcontroller 1933 in the assessment.

The system 1930 may comprise wired or wireless communication circuits to communicate with surgical hubs (e.g. surgical hub 1953), communication hubs, and/or robotic surgical hubs, for example. Additional details about suitable interactions between a system 1930 and the surgical hub 1953 are disclosed in U.S. patent application Ser. No. 16/209,423 entitled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981, the entire disclosure of which is incorporated by reference in its entirety herein.

In various aspects, the control circuit 1932 can be configured to implement various processes described herein. In certain aspects, the control circuit 1932 may comprise a microcontroller comprising one or more processors (e.g., microprocessor, microcontroller) coupled to at least one memory circuit. The memory circuit stores machine-executable instructions that, when executed by the processor, cause the processor to execute machine instructions to implement various processes described herein. The processor may be any one of a number of single-core or multicore processors known in the art. The memory circuit may comprise volatile and non-volatile storage media. The processor may include an instruction processing unit and an arithmetic unit. The instruction processing unit may be configured to receive instructions from the memory circuit of this disclosure.

Alternatively, in certain instances, the control circuit 1932 can be in the form of a combinational logic circuit configured to implement various processes described herein. The combinational logic circuit may comprise a finite state machine comprising a combinational logic configured to receive data, process the data by the combinational logic, and provide an output.

Alternatively, in certain instances, the control circuit 1932 can be in the form of a sequential logic circuit. The sequential logic circuit can be configured to implement various processes described herein. The sequential logic circuit may comprise a finite state machine. The sequential logic circuit may comprise a combinational logic, at least one memory circuit, and a clock, for example. The at least one memory circuit can store a current state of the finite state machine. In certain instances, the sequential logic circuit may be synchronous or asynchronous. In other instances, the control circuit 1932 may comprise a combination of a processor (e.g., processor 1934) and a finite state machine to implement various processes herein. In other aspects, the finite state machine may comprise a combination of a combinational logic circuit (and the sequential logic circuit, for example.

Figure 14:
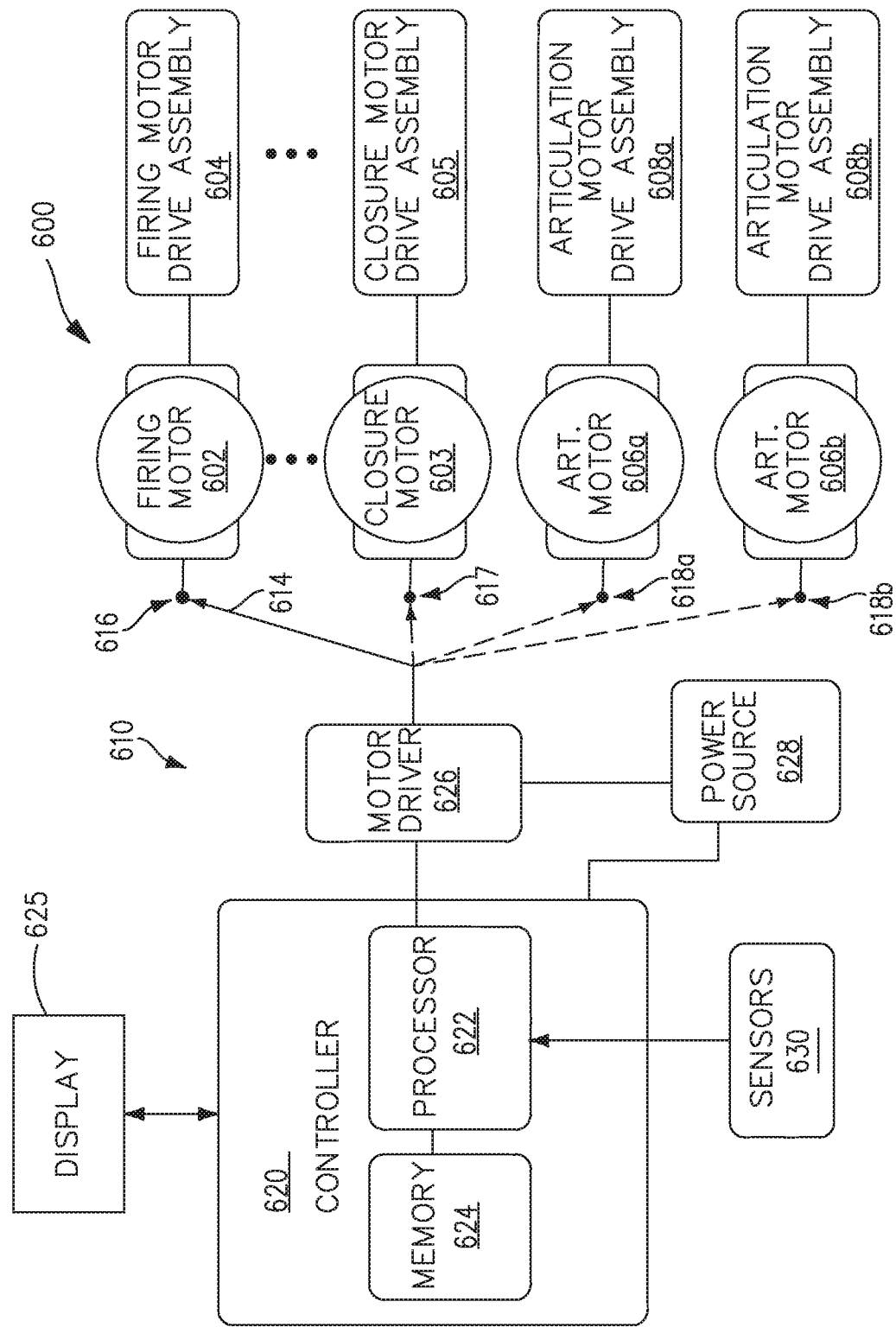
FIG. 14 illustrates a block diagram of a surgical system for use with one or more surgical instruments, tools, and/or robotic systems in accordance with one or more aspects of the present disclosure.

FIG. 14 illustrates a block diagram of a surgical system 600 for use with one or more surgical instruments, tools, and/or robotic systems in accordance with one or more aspects of the present disclosure. The surgical system 600 is similar in many respects to the surgical system 1930, which are not repeated herein at the same of detail for brevity. For example, like the surgical system 1930, the surgical system 600 includes a control circuit comprising a microcontroller 620 comprising a processor 622 and a memory 624, sensors 630, and a power source 628, which are similar, respectively, to the microcontroller 1933, the processor 1934, the memory 1935, and the power source 1942. Additionally, the surgical system 600 includes a plurality of motors and corresponding driving assemblies that can be activated to perform various functions.

In certain instances, a first motor can be activated to perform a first function, a second motor can be activated to perform a second function, a third motor can be activated to perform a third function, a fourth motor can be activated to perform a fourth function, and so on. In certain instances, the plurality of motors can be individually activated to cause firing, closure, and/or articulation motions in an end effector 1940, for example. The firing, closure, and/or articulation motions can be transmitted to the end effector 1940 through a shaft assembly, for example.

In certain instances, the system 600 may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from a staple cartridge into tissue captured by the end effector 1940 and/or the cutting edge of the I-beam element to be advanced to cut the captured tissue, for example. The I-beam element may be retracted by reversing the direction of the motor 602.

In certain instances, the system 600 may include a closure motor 603. The closure motor 603 may be operably coupled to a closure motor drive assembly 605 which can be configured to transmit closure motions, generated by the motor 603 to the end effector 1940, in particular to displace a closure tube to close an anvil and compress tissue between the anvil and the staple cartridge. The closure motions may cause the end effector 1940 to transition from an open configuration to an approximated configuration to grasp tissue, for example. The end effector 1940 may be transitioned to an open position by reversing the direction of the motor 603.

In certain instances, the system 600 may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to a shaft, for example.

As described above, the system 600 may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the system 600 may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 14, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 14, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

In one aspect, the amount of compression applied to tissue may impact the desired firing speed of the firing member, such as firing member 1900, during a firing stroke. The amount of time a surgeon chooses to pre-compress tissue prior to firing is a valuable input to a successful firing. Accordingly, it would be beneficial to establish a modifier for the firing speed, or various other firing motion parameters, based on parameters associated with applying compression to the tissue.

In some embodiments, a parameter associated with applying compression can be an elapsed amount of time that an end effector, such as end effector 1300, has been in a clamped state. In some embodiments, the clamped state is defined as a state where the end effector 1300 is in the closed configuration and the closure trigger 1032 is in the actuated position. In other embodiments, the clamped state is defined as a state where the elongate channel 1310 and the anvil 2000 of the end effector 1300 are within a threshold distance of one another. In other embodiments, the clamped state is defined as a state where the closure trigger 1032 has pivoted a threshold distance away from the unactuated position.

In various embodiments, a timer, as an example, is utilized to measure the elapsed amount of time between when the end effector has entered the clamped state and when a user actuates a firing system, such as the firing drive system 1080, of the surgical instrument. In some embodiments, actuation of the firing drive system 1080 is detected when the firing trigger 1130 is pivoted to the actuated position, such as with a position sensor or a Hall-Effect sensor, as examples. In some embodiments, actuation of the firing system is detected when the power source 1090 supplies an electric current or voltage to the motor 1082, as detected by a current sensor or voltage sensor, respectively.

According to the elapsed amount of time measured by the timer, a control system, such as handle circuit board 1100, can set a firing motion parameter of the firing system. In various embodiments, setting a firing motion parameter includes selecting a value for the firing motion parameter from a look-up table, or based on an equation stored in a memory, for example. It should be understood that other embodiments are envisioned where the control system is similar to controller 1933, and includes a processor, such as processor 1934, and a memory, such as memory 1935. Other embodiments are envisioned where the control system is similar to the controller 620, or any other suitable control system described elsewhere herein.

In some embodiments, the firing motion parameter comprises a duty cycle of a motor, such as motor 1082, that drives the firing member. In some embodiments, the firing motion parameter comprises a velocity of the motor. In some embodiments, the firing motion parameter comprises a current supplied to the motor from a power source, such as power source 1090, power source 1942, or power source 628, as examples. In some embodiments, the firing motion parameter comprises a voltage supplied to the motor. In some embodiments, the firing motion parameter comprises a velocity of the firing member. In some embodiments, the firing motion comprises an acceleration of the firing member. In some embodiments, the firing motion parameter comprises a firing force to the firing member. In some embodiments, the firing motion parameter comprises any suitable parameter associated with the firing system described elsewhere herein.

In various embodiments, setting the firing motion parameter of the firing system comprises adjusting a default firing motion parameter according to the elapsed amount of time measured by the timer. In various embodiments, the default firing motion parameter is stored in a memory and retrieved by the control system. In various other embodiments, the default firing motion parameter comprises a user defined default firing motion parameter.

Figure 15:
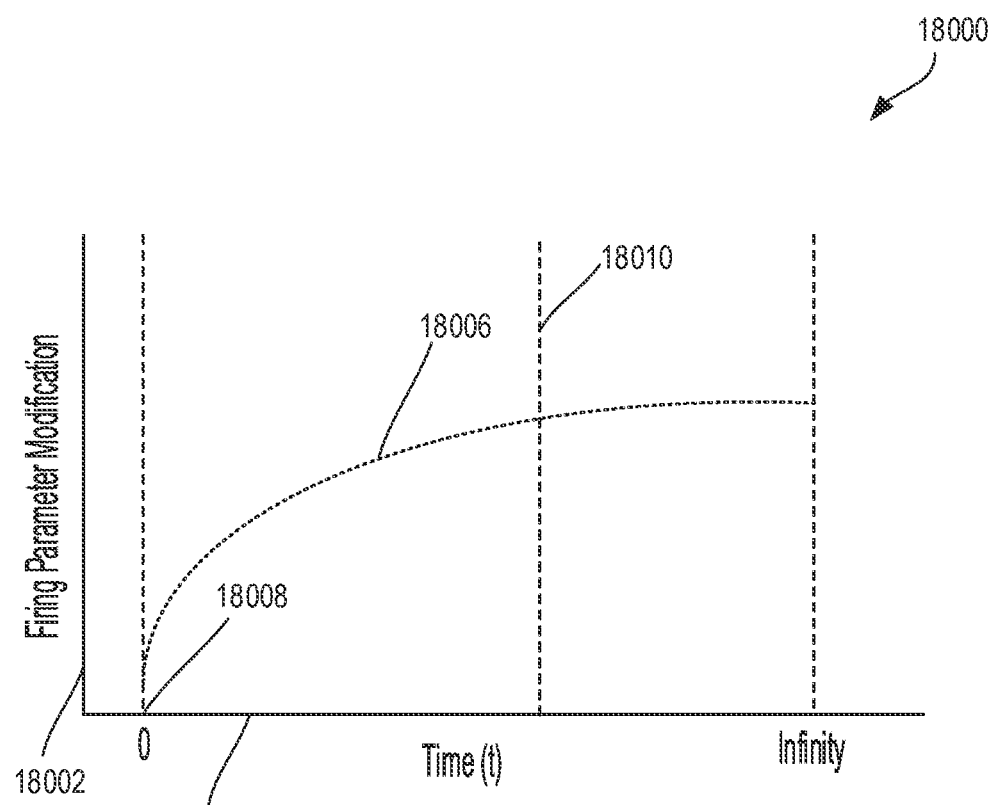
FIG. 15 is a graph that illustrates a firing motion parameter modification of a default firing motion parameter over time, according to at least one aspect of the present disclosure.

Referring now to FIG. 15, a graph 18000 is provided according to at least one aspect of the present disclosure. In various embodiments, aspects of the graph 18000 are stored in a memory, such as memory 1935, and can be retrieved by the control system. For example, one or more portions of the graph 18000 can be stored in the form of one or more equations, look-up tables, and/or any other form suitable for representing the relationship depicted by the graph 18000. As seen in FIG. 15, the graph 18000 illustrates a relationship between a firing motion parameter modification 18002 of the default firing motion parameter and an elapsed time 18004 from which an end effector of a surgical instrument has entered the clamped state. Various techniques can be implemented to measure time lapsed from entry of the clamped state. In one example, once the end effector reaches the clamped state, a timer is initiated. In various instances, as described in greater detail elsewhere in the present disclosure, an end effector of a surgical instrument is operable to grasp tissue between jaws of the end effector. At least one of the jaws can be moved relative to the other jaw toward the clamped state. After attaining the clamped state, a clinician activates a firing system that is responsible for deploying staples into the clamped tissue and, in some instances, advancing a cutting member through the tissue.

Once the control system detects that the firing system has been actuated, the control system identifies a point along a modification curve 18006 of the graph 18000 and adjusts the default firing motion parameter according to the corresponding value from the modification curve 18006. The actuation can, for example, be detected based on one or more sensor readings. For example, the actuation detection can be based on detecting motion a trigger or depression of an actuation button. Additionally, or alternatively, the actuation detection can be based on detecting an initial motion of one or more components of the firing system such as, for example, a firing member, such as firing member 1900.

In some embodiments, the default firing motion parameter can comprise a default duty cycle of a motor, such as motor 1082, as an example. In some embodiments, the default firing motion parameter can comprise a default current supplied to the motor. In some embodiments, the default firing motion parameter can comprise a default voltage applied to the motor. In some embodiments, the default firing motion parameter can comprise a default velocity at which to the motor drives the firing member. Other firing motion parameters are described elsewhere herein. Based on the elapsed length of time measured between the end effector reaching the clamped state and the firing system being actuated, the control system can modify the default firing motion parameter to an adjusted firing motion parameter. In one embodiment, a user can actuate the firing system immediately upon the end effector reaching the clamped state, i.e., at point 18008 on the modification curve 18006. Accordingly, the control system can modify the default firing motion parameter according to the identified value at point 18008 along the modification curve 18006.

In some embodiments, point 18008 corresponds to a value that is less than 1. Utilizing a modifier less than 1 prevents the firing system from driving the firing member at the default parameter, given that the tissue has not been given a sufficient amount of time to relax upon the end effector entering the clamped state. In one embodiment, with a default velocity of $V_1$ and point 18008 corresponding to a value less than 1, the control system causes the motor to drive the firing member at an adjusted velocity of $V_2$ which is less than $V_1$. Accordingly, utilizing the graph 18000 can encourage clinicians to give tissue a sufficient amount of time to relax such that the firing member is not driven using a firing motion parameter that is less than the default firing motion parameter value. Other embodiments are envisioned wherein point 18008 corresponds to a value of 1 or greater than 1.

As can be seen on graph 18000, a threshold 18010 corresponding to a point along modification curve 18006 is provided at which the firing system can be driven using the default firing motion parameter. In some embodiments, the control system can provide feedback to the clinician, such as audible, haptic, visual, or the like, when the threshold 18010 amount of time has been reached or exceed, informing the clinician that a sufficient amount of time has elapsed to allow the default firing motion parameter to be utilized.

In various embodiments, the modification curve 18006 can be represented by an equation defined by:

$$Y=C(A*\log(t+1)+B)$$

wherein A and B are constants, C is the default firing motion parameter, t is time, and Y is the adjusted firing motion parameter. In various embodiments, constants A and B are stored in a memory and retrievable by the control system. In various embodiments, constants A and B are provided by a user at an input interface. In one aspect, constant B corresponds to the modification value at point 18008. In one embodiment, where constant A is 1, constant B is 0.25, and the default firing motion parameter C is a firing speed of $V_1$, the following look-up table can be stored in the memory:

| Time "t" | Adjusted Firing Speed "Y" |
|---|---|
| 0 | 0.25 $V_1$ |
| 1 | 0.55 $V_1$ |
| 2 | 0.73 $V_1$ |
| 3 | 0.85 $V_1$ |
| 4 | 0.95 $V_1$ |
| 4.62 (threshold 18010) | $V_1$ |
| 5 | 1.03 $V_1$ |
| 6 | 1.09 $V_1$ |

Accordingly, in certain instances, where the firing motion parameter is a firing speed (e.g. speed of a firing member effecting a firing stroke of the firing system), the graph 18000 provides an algorithm that modifies the speed of the firing member according to an elapsed amount of time after the end effector has reached the clamped state. It should be noted that the foregoing equation, values, and table are merely examples representing a manner for performing a dynamic modification of the default parameter. Other equations and/or other suitable forms of representing the dynamic modification over time can be implemented.

In various embodiments, the control system can dynamically adjust the firing motion parameter after the firing system has been actuated. In some embodiments, the control system can continuously adjust the firing motion parameter. In some embodiments, the control system can discretely adjust the firing motion parameter, such as adjusting the firing motion parameter every second or every few seconds. In some embodiments, the firing motion parameter can continue to be adjusted according to the modification curve 18006. In one embodiment utilizing the foregoing table, the firing system is actuated after 4 seconds, which causes the firing system to drive the firing member at an adjusted velocity of 0.95 $V_1$. One second into the firing stroke, the control system can adjust the adjusted firing speed to 1.03 $V_1$ (the 5 second point on the foregoing table). Two seconds into the firing stroke, the control system can adjust the firing speed to 1.09 $V_1$ (the 6 second point on the table). Accordingly, the control system can dynamically adjust the firing motion parameter utilized by the firing system based on an elapsed amount of time that the end effector has been in the clamped state, taking into account the time prior to the firing system being actuated and the time after the firing system has been actuated.

Figure 16:
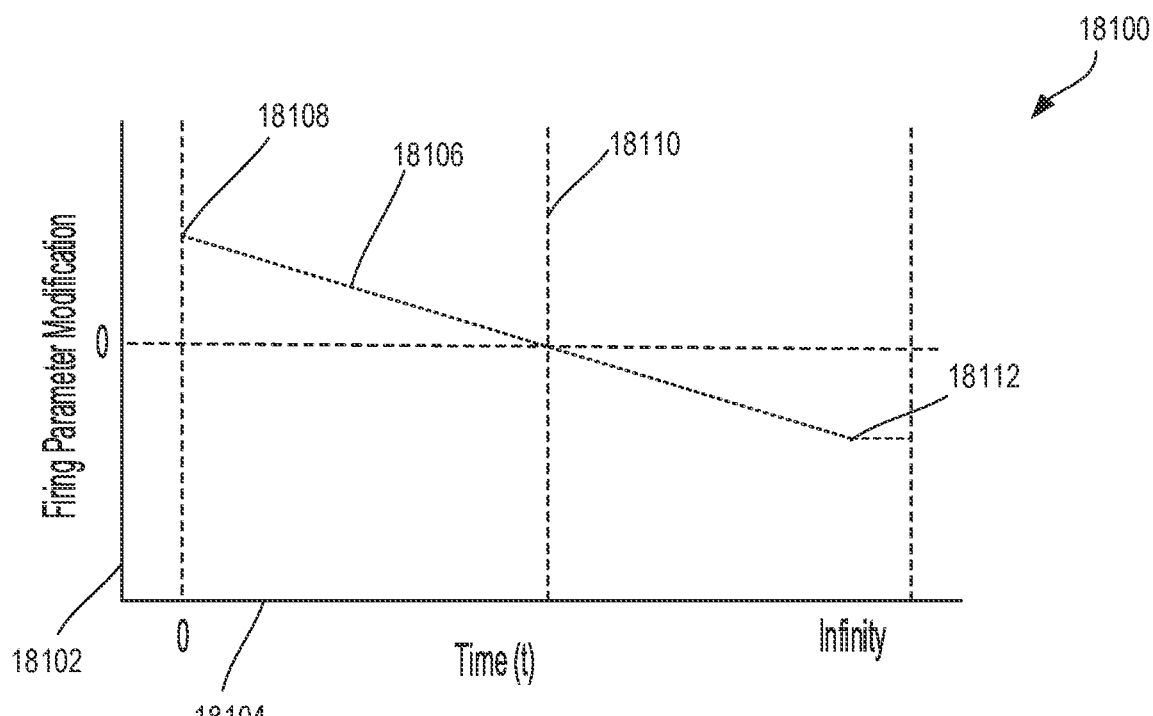
FIG. 16 is a graph that illustrates a firing motion parameter modification of a default firing motion parameter over time, according to at least one aspect of the present disclosure.

Referring now to FIG. 16, a graph 18100 is provided according to at least one aspect of the present disclosure. In various instances, aspects of the graph 18100 can be stored in a memory, such as memory 1935, and can be retrievable by the control system. In various other embodiments, one or more portions of the graph 18100 can be stored in the memory in the form of one or more equations, look-up tables, or any other form suitable for representing the relationship depicted by the graph 18100. As seen in FIG. 16, the graph 18100 illustrates a relationship between a firing motion parameter modification 18102 of the default firing motion parameter and an elapsed time 18104 from which the end effector has entered the clamped state. Various techniques can be implemented to measure time lapsed from entry of the clamped state. In one example, once the end effector reaches the clamped state, a timer is initiated. In various instances, as described in greater detail elsewhere in the present disclosure, an end effector of a surgical instrument is operable to grasp tissue between jaws of the end effector. At least one of the jaws can be moved relative to the other jaw toward the clamped state. After attaining the clamped state, a clinician activates a firing system that is responsible for deploying staples into the clamped tissue and, in some instances, advancing a cutting member through the tissue.

Once the control system detects that the firing system has been actuated, the control system identifies a point along a modification curve 18106 of the graph 18100 and adjusts the default firing motion parameter according to the corresponding value from the modification curve 18006. The actuation can, for example, be detected based on one or more sensor readings. For example, the actuation detection can be based on detecting motion a trigger or depression of an actuation button. Additionally, or alternatively, the actuation detection can be based on detecting an initial motion of one or more components of the firing system such as, for example, a firing member, such as firing member 1900.

In various embodiments, point 18108 corresponds to a value that is greater than 1. In various other embodiments, the point 18108 corresponds to a value of 1. In one embodiment, with a default velocity of $V_1$ and point 18108 corresponding to a 1.5 modification, the control system can cause the motor to drive the firing member at an adjusted velocity of $1.5\ V_1$. In another embodiment, with a default velocity of $V_1$ and point 18108 corresponding to a 1 modification, the control system can cause the motor to drive the firing member at the default velocity of $V_1$.

As can be seen on graph 18100, the modification curve 18106 has a negative slope, resulting in a diminishing adjusted firing motion parameter over time. In various embodiments where the value at point 18108 is greater than 1, a threshold 18110 is provided along curve where the firing system is be driven using the default firing motion parameter. In some embodiments, the control system can provide feedback to the clinician, such as audible, haptic, visual, or the like, when the threshold 18110 amount of time has been reached or exceed, informing the clinician that a sufficient amount of time has elapsed that will result in the default firing motion parameter to be utilized. In various embodiments, the graph 18100 can include a threshold 18112 where the firing parameter no longer diminishes.

In various embodiments, the modification curve 18106 can be represented by an equation defined by:

$$Y = -A*t + (B+C)$$

wherein A and B are constants, C is the default firing motion parameter, t is time, and Y is the adjusted firing motion parameter. In various embodiments, constants A and B are stored in a memory and retrievable by the control system. In various embodiments, constants A and B are provided by a user at an input interface. In one embodiment where point 18108 is desired to be the default firing motion parameter, C is equal to 0. In one embodiment where constant A is 2, constant B is 6, and the default firing motion parameter C is a firing speed of $V_1$, the following look-up table can be stored in the memory:

| Time "t" | Adjusted Firing Speed "Y" |
|---|---|
| 0 | $V_1 + 6$ |
| 1 | $V_1 + 4$ |
| 2 | $V_1 + 2$ |
| 3 (threshold 18110) | $V_1$ |
| 4 | $V_1 - 2$ |
| 5 | $V_1 - 4$ |
| 6 | $V_1 - 6$ |
| 7 | $V_1 - 8$ |

Accordingly, the foregoing graph 18100 provides an algorithm that decreases the speed of the firing member according to an elapsed amount of time after the end effector has reached the clamped state. It should be noted that the foregoing equation, values, and table are merely examples representing a manner for performing a dynamic modification of the default parameter. Other equations and/or other suitable forms of representing the dynamic modification over time can be implemented.

In various embodiments, the control system can dynamically adjust the firing motion parameter after the firing system has been actuated. In some embodiments, the control system can continuously adjust the firing motion parameter. In some embodiments, the control system can discretely adjust the firing motion parameter, such as adjusting the firing motion parameter every second or every few seconds. In some embodiments, the firing motion parameter can continue to be adjusted according to the modification curve 18106 on graph. In one embodiment utilizing the foregoing table, the firing system is actuated after 4 seconds, which causes the firing system to drive the firing member at an adjusted velocity of $V_1 - 2$. One second into the firing stroke, the control system can adjust the adjusted firing speed to $V_1 - 4$ (the 5 second point on the table). Two seconds into the firing stroke, the control system can adjust the firing speed to $V_1 - 6$ (the 6 second point on the table). Accordingly, the control system can dynamically adjust the firing motion parameter utilized by the firing system based on an elapsed amount of time that the end effector has been in the clamped state, taking into account the time prior to the firing system being actuated and the time after the firing system has been actuated.

In various embodiments, the control system can utilize a different graph/look-up table after the firing system has been actuated. In one embodiment utilizing the foregoing table, the firing system is actuated after 4 seconds, which causes the firing system to drive the firing member at an adjusted velocity of $V_1 - 2$. Once the firing system has been actuated, the control system can utilize a different graph/look-up table, such as graph 18000. Utilizing the example graph from above, one second into the firing stroke, the control system can adjust the adjusted firing speed to $1.03\ V_1$ (the 5 second point on the example table in connection with graph 18000). Accordingly, the control system can switch between a diminishing and increasing firing motion parameter adjustment.

In various other embodiments, a graph and/or look-up take is provided according to a modification curve that is parabolic. In various other embodiments, a graph and/or look-up take is provided according to a modification curve that is exponential. In various other embodiments, a graph and/or look-up take is provided that is represented by $Y = A*\sqrt{t} + B$ where A and B are constants, t is time, and Y is the adjusted firing motion parameter. Various other equations and/or other suitable forms of representing the dynamic modification over time can be implemented.

Figure 17:
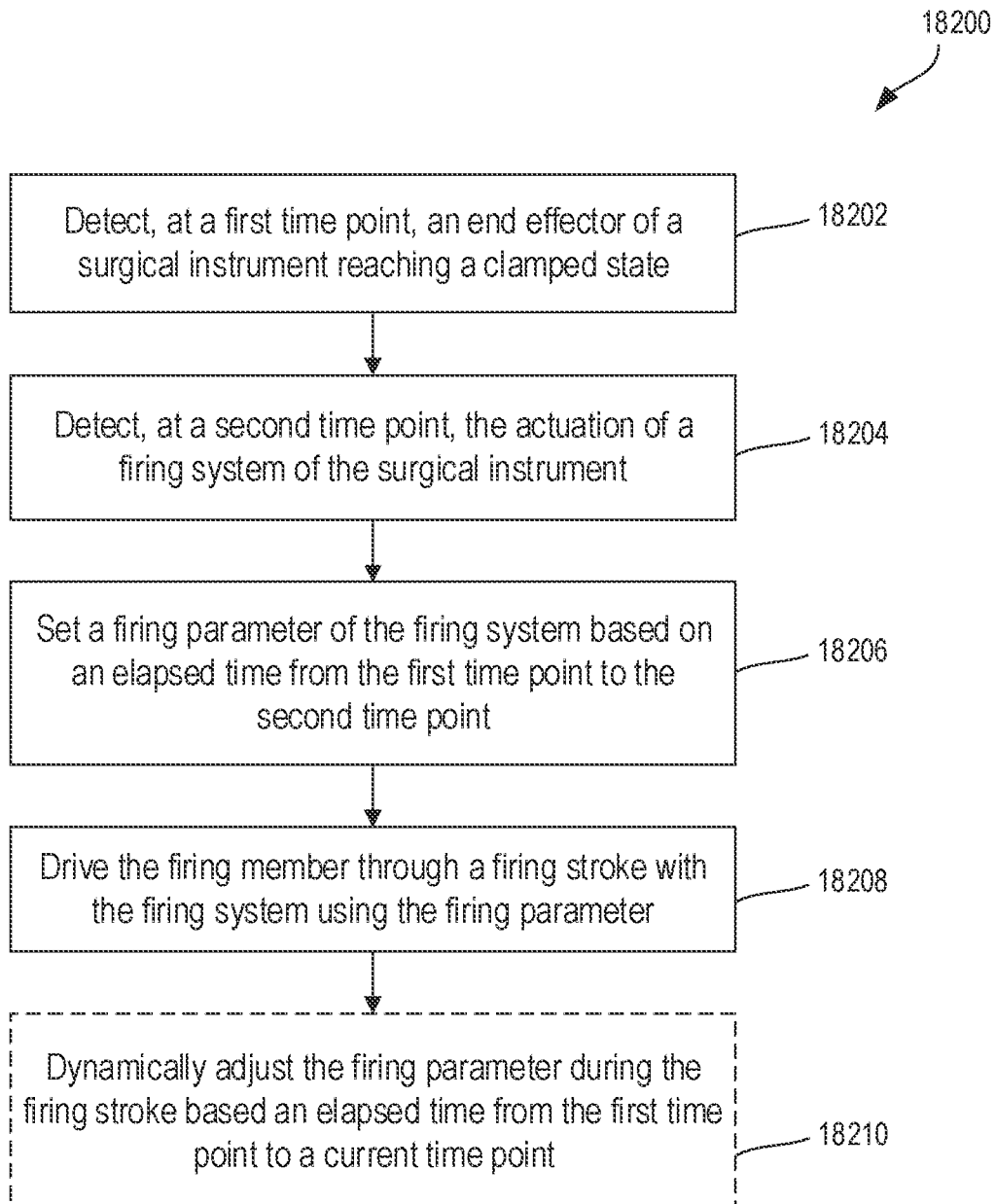
FIG. 17 illustrates a method for controlling a surgical instrument, according to at least one aspect of the present disclosure.

Referring now to FIG. 17, a method 18200 for controlling a surgical instrument is provided, according to at least one aspect of the present disclosure. The method 18200 comprises detecting 18202, at a first time point, an end effector of a surgical instrument reaching a clamped state. In one embodiment, the circuit board 1100 detects when the end effector 1300 reaches the clamped state using a position sensor that can sense when the closure trigger 1032 has reached the actuated position. In one embodiment, the circuit board 1100 detects when the end effector 1300 reaches the clamped state using a Hall-Effect sensor that can sense when the anvil 2000 is within a threshold distance from the elongate channel 1310. In various embodiments, the circuit board 1100 detects when the end effector 1300 reaches the clamped state using any number of sensors that detect the position of components associated with the closure system 3000, such as a position of the closure shuttle 1250, a position of the closure link 1038, or a position of the distal closure tube segment 3030, as examples.

The method 18200 further comprises detecting 18204, at a second time point, the actuation of a firing system of the surgical instrument. In one example embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18200 further comprises setting 18206 a firing motion parameter of the firing system based on an elapsed time from the first time point to the second time point. In various embodiments, the circuit board 1100 can measure, using a timer, an elapsed length of time that has transpired between the end effector 1300 reaching the clamped state and the actuation of the firing drive system 1080. In some embodiments, the circuit board 1100 can retrieve the firing motion parameter from a look-up table stored in a memory, such as memory 1935, according to the elapsed length of time. In some embodiments, the circuit board 1100 can retrieve a modification value from a graph or look-up table, such as graphs 18000, 18100, stored in a memory according to the elapsed length of time that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18200 further comprises driving 18208 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18200 provides the clinician with the freedom to choose how long they wish to maintain the end effector in the clamped state prior to actuating the firing system. Based on an elapsed amount of time in the clamped state, the control system will automatically select an appropriate firing motion parameter for the firing system. In one aspect, "automatically" refers to the control system's ability to select a firing motion parameter without a user input.

In various embodiments, the method 18200 optionally further comprises dynamically adjusting 18210 the firing motion parameter during the firing stroke based an elapsed time from the first time point to a current time point. In some embodiments, the circuit board 1100 can measure, using a timer, an elapsed amount of time, from the end effector reaching the clamped state to a current time point during the firing stroke and dynamically adjust the firing motion parameter. In one embodiment, a user can maintain the end effector in the clamped state for 5 seconds before actuating the firing system and the circuit board 1100 can set the firing motion parameter according to a value corresponding to being in the clamped state at 5 seconds found in a look-up table. During the firing stroke, such as 3 seconds into the firing stroke, as an example, the control system can look to the same look-up table, or a different look-up table, and the corresponding value to being in the clamped state for 8 seconds (5 seconds prior to actuation of the firing system plus 3 seconds into the firing stroke). Accordingly, the control system can dynamically adjust the firing motion parameter according to an elapsed length of time that the tissue has been clamped by the end effector.

In another embodiment, a user can maintain the end effector in the clamped state for 5 seconds before actuating the firing system and the circuit board 1100 can set the firing motion parameter according to a modification value corresponding to being in the clamped state at 5 seconds, such as a modification value determined from FIG. 15 or 16. During the firing stroke, such as 3 seconds into the firing stroke, the control system can look to the same graphs (FIG. 15 or FIG. 16) and the corresponding modification value to being in the clamped state for 8 seconds (5 seconds prior to actuation of the firing system plus 3 seconds into the firing stroke). Accordingly, the control system can continuously adjust the firing motion parameter according to an elapsed length of time that the tissue has been clamped by the end effector utilizing the modification curves.

In some scenarios, a clinician may transition the end effector to the clamped state to clamp onto tissue. After a period of time, the clinician may decide that they wish to reposition the end effector at a different location on the tissue, or the clinician unintentionally, or intentionally, eases their grip on a closure actuator. Therefore, the clinician transitions the end effector from the clamped state toward an unclamped state and reclamps the tissue at the new location. As the tissue had already been clamped prior to the clinician repositioning the tissue, less clamping time may be required to allow the tissue to sufficiently relax before performing a firing stroke. Accordingly, an algorithm is desired that accounts for a clinician unclamping and reclamping onto tissue, such as unclamping and reclamping onto the same tissue that had already been given the opportunity to relax.

Figure 18:
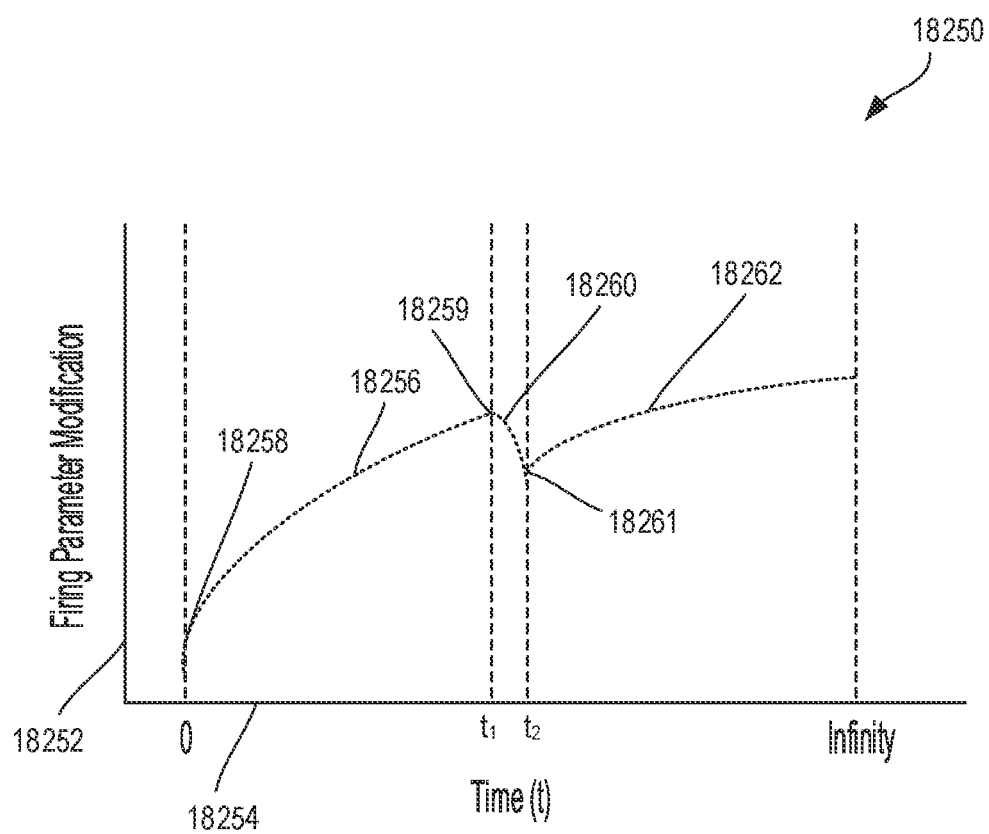
FIG. 18 is a graph that illustrates a firing motion parameter modification of a default firing motion parameter over time, according to at least one aspect of the present disclosure.

Referring now to FIG. 18, a graph 18250 generated by an algorithm is provided according to at least one aspect of the present disclosure. In various instances, the algorithm can be stored in a memory, such as memory 1935, and can be executed by a processor, such as processor 1934. As seen in FIG. 18, the graph 18250 illustrates a relationship between a firing motion parameter modification 18252 of the default firing motion parameter and an elapsed time 18254 from which the end effector has entered the clamped state, taking into account elapsed time that the end effector transitions out of and returns to the clamped state, as will be described in more detail below.

In operation, when a user transitions the end effector to the clamped state, a timer is initiated. In addition, the algorithm implements a first modification curve to track a firing motion parameter modification that will be implemented to a default firing motion parameter to produce an adjusted firing motion parameter. In various embodiments, the first modification curve is represented by an equation, such as a linear equation, a logarithmic equation, a parabolic equation, a $\sqrt{t}$ equal, or any other suitable equation. Referring to FIG. 18, when the control system detects the end effector reaching the clamped state, i.e., point 18258, the control system initiates a timer and a first modification curve 18256 to track a firing motion parameter modification to the default firing motion parameter. In one embodiment, if a user actuates the firing system, the control system will identify a corresponding point along modification curve 18256 according to the determined elapsed time that will be used to modify the default firing motion parameter.

At a point in time after the end effector reaches the clamped state, but before the firing system is actuated, a user may choose to temporarily transition the end effector out of the clamped state to reposition the end effector. Accordingly, the control system detects the end effector transitioning out of the clamped state and implements a second modification curve different from the first modification curve. In various embodiments, the second modification curve is represented by an equation, such as a linear equation, a logarithmic equation, a parabolic equation, a $\sqrt{t}$ equal, or any other suitable equation.

In some embodiments, the control system detects the end effector 1300 transitioning out of the clamped state using a position sensor that can sense when the closure trigger 1032 has moved away from the actuated position. In one embodiment, the control system detects the end effector 1300 transitioning out of the clamped state using a Hall-Effect sensor that can sense when the anvil 2000 has moved a threshold distance from the elongate channel 1310. In various embodiments, the control system detects the end effector 1300 transitioning out of the clamped state using any number of sensors that detect the position of components associated with the closure system 3000, such as a position of the closure shuttle 1250, a position of the closure link 1038, or a position of the distal closure tube segment 3030, as examples.

In one embodiment, referring to FIG. 18, at time $t_1$, the control system detects the end effector transitioning out of the clamped state at point 18259 on the first modification curve 18256. Based on the detection, the control system can initiate a second timer to measure how long the end effector is out of the clamped state, as well as implement a second modification curve 18260. As seen in FIG. 18, the second modification curve 18260 adjusts the value associated with the modification point 18259 from the point along the first modification curve 18256 at the time of the end effector transitioning out of the clamped state. In some embodiments, the second modification curve 18260 can be a negative modification curve, thereby lowering the adjustment to the default firing motion parameter that was provided by the first modification curve 18256. In various other embodiments, the second modification curve 18260 can be a positive modification curve, thereby increasing the adjustment to the default firing motion parameter when the first modification curve was a diminishing modification curve, similar to modification curve 18106. It should be understood that the firing system cannot be actuated while the second modification curve 18260 is being implemented, as the end effector is not within the clamped state.

At a point in time after the end effector transitions out of the clamped state, the end effector can be returned to the clamped state. Accordingly, the control system detects the end effector returning to the clamped state and implements a third modification curve different from the second modification curve. In various embodiments, the third modification curve can be the same as the first modification curve. In various embodiments, the third modification curve can be different from the first modification curve. In various embodiments, the third modification curve is represented by an equation, such as a linear equation, a logarithmic equation, a parabolic equation, a $\sqrt{t}$ equal, or any other suitable equation.

In one embodiment, referring to FIG. 18, at time $t_2$, the control system detects the end effector returning to the clamped state at point 18261 on the second modification curve 18260. Based on the detection, the control system can initiate a third timer to measure how long the end effector is in the clamped state, as well as implement a third modification curve 18262. As seen in FIG. 18, the third modification curve 18262 adjusts the value associated with the modification point 18261 from the point along the second modification curve 18260 at the time of the end effector returning to the clamped state. In one embodiment, if a user actuates the firing system, the control system will identify a point along the third modification curve 18262 according to the determined elapsed time that will be used to modify the default firing motion parameter.

Accordingly, the foregoing algorithm allows a clinician to transition the end effector into and out of the clamped state without entirely resetting the amount of time required to clamp tissue and receive the benefits of the firing motion parameter modification. The algorithm accounts for the time that the end effector is out of the clamped state, while also accounting for the time that the end effector has already clamped onto the tissue. It should be understood that the graph 18250 provided is merely exemplary and can be different depending on the number of times a user transitions the end effector into and out of the clamped state, the amount of time that the end effector is out of the clamped state, and if the end effector is transitioned to the unclamped state at all. In a scenario where the end effector is not transitioned to the unclamped state after point 18258, the algorithm will merely implement the first modification curve, such as first modification curve 18256, when determining the firing motion parameter modification to use when the firing system is actuated.

Figure 19:
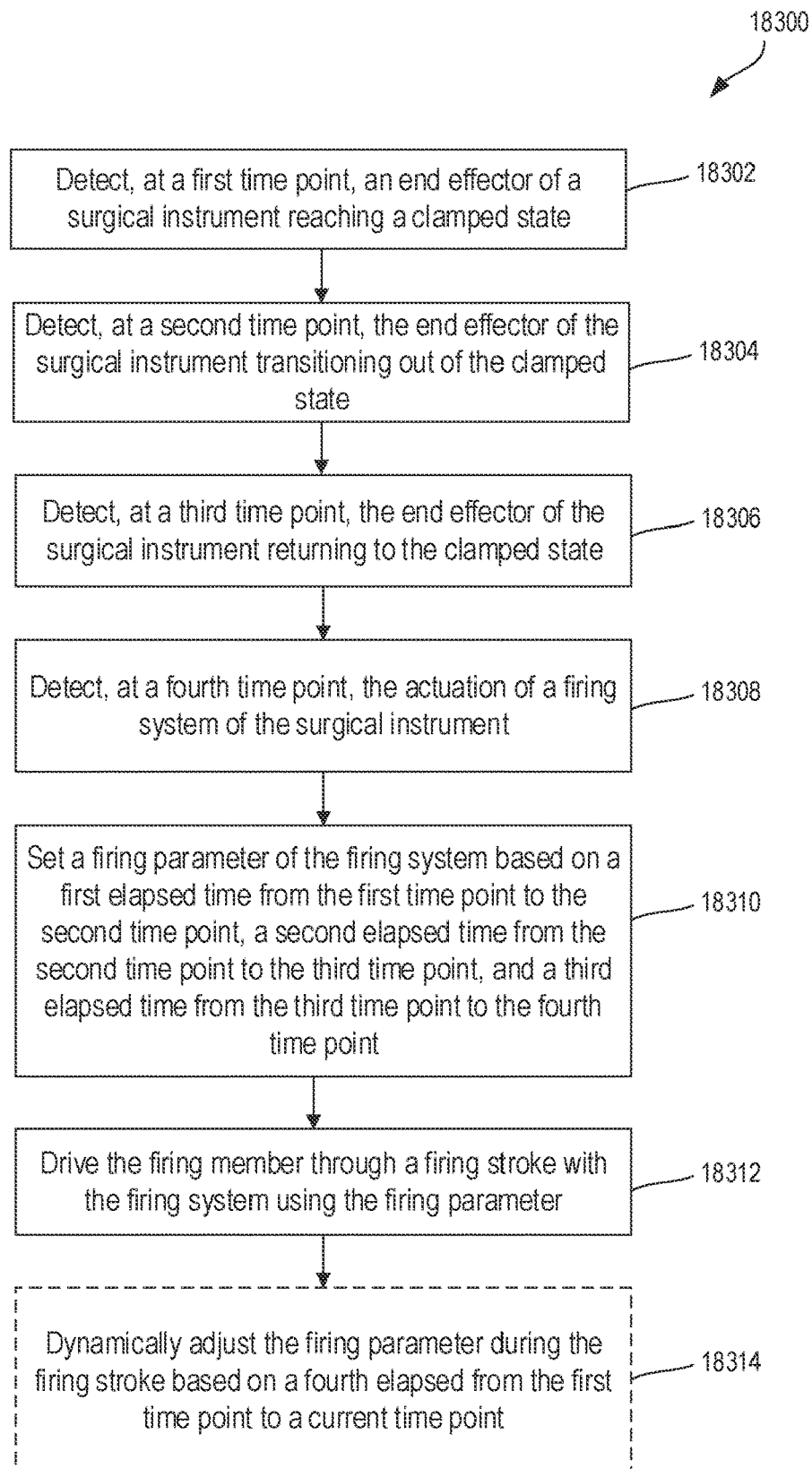
FIG. 19 illustrates a method for controlling a surgical instrument, according to at least one aspect of the present disclosure.

Referring now to FIG. 19, a method 18300 for controlling a surgical instrument is provided, according to at least one aspect of the present disclosure. The method 18300 comprises detecting 18302, at a first time point, an end effector of a surgical instrument reaching a clamped state. In one embodiment, the circuit board 1100 detects when the end effector 1300 reaches the clamped state using a position sensor that can sense when the closure trigger 1032 has reached the actuated position. In one embodiment, the circuit board 1100 detects when the end effector 1300 reaches the clamped state using a Hall-Effect sensor that can sense when the anvil 2000 is within a threshold distance from the elongate channel 1310. In various embodiments, the circuit board 1100 detects when the end effector 1300 reaches the clamped state using any number of sensors that detect the position of components associated with the closure system 3000, such as a position of the closure shuttle 1250, a position of the closure link 1038, or a position of the distal closure tube segment 3030, as examples.

The method 18300 further comprises detecting 18304, at a second time point, the end effector of the surgical instrument transitioning out of the clamped state. In one embodiment, the control system detects the end effector 1300 transitioning out of the clamped state using a Hall-Effect sensor that can sense when the anvil 2000 has moved a threshold distance from the elongate channel 1310. In various embodiments, the control system detects the end effector 1300 transitioning out of the clamped state using any number of sensors that detect the position of components associated with the closure system 3000, such as a position of the closure shuttle 1250, a position of the closure link 1038, or a position of the distal closure tube segment 3030, as examples.

The method 18300 further comprises detecting 18306, at a third time point, the end effector returning to the clamped state. In various embodiments, the control system can detect the end effector returning to the clamped state using the various sensors described above with respect to block 18302.

The method 18300 further comprises detecting 18308, at a fourth time point, the actuation of a firing system of the surgical instrument. In one example embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current being supplied to the motor 1082 from the power source 1090 via a current sensor.

The method 18300 further comprises setting 18310 a firing motion parameter of the firing system based on a first elapsed time from the first time point to the second time point, a second elapsed time from the second time point to the third time point, and a third elapsed time from the third time point to the fourth time point. In various embodiments, the circuit board 1100 can measure, using a timer, an elapsed length of time that has transpired from the first time point to the second time point, the second time point to the third time point, and the third time point to the fourth time point. In some embodiments, the circuit board 1100 can retrieve the firing motion parameter from a look-up table stored in a memory, such as memory 1935, according to the elapsed lengths of time. In some embodiments, the circuit board 1100 can implement an algorithm, such as the algorithm discussed above with respect to graph 18250, to determine a modification value that can be used to adjust a default firing motion parameter.

In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18300 further comprises driving 18312 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18300 provides the clinician with the freedom to choose how long they wish to maintain the end effector in the clamped state prior to actuating the firing system, while also enabling the clinician to unclamp and reclamp the tissue without a modification accumulated from a first modification curve being completely ignored. Based on the elapsed amounts of time, the control system will automatically select an appropriate firing motion parameter for the firing system. In one aspect, "automatically" refers to the control system's ability to select a firing motion parameter without a user input.

In various embodiments, the method 18300 optionally further comprises dynamically adjusting 18314 the firing motion parameter during the firing stroke based an elapsed time from the first time point to a current time point. In some embodiments, the circuit board 1100 can measure, using a timer, an elapsed amount of time, from the end effector reaching the clamped state to a current time point during the firing stroke and dynamically adjust the firing motion parameter. In one embodiment, referring to FIG. 18, in a scenario where a clinician actuates the firing system after time $t_2$, the control system can continue to modify the firing motion parameter during the firing stroke according to the third modification curve 18262. Accordingly, the control system can dynamically adjust the firing motion parameter according to an elapsed length of time that the tissue has been clamped by the end effector utilizing the modification curve.

As referenced above, the amount of compression applied to tissue may impact the desired firing speed of the firing member, such as firing member 1900, during a firing stroke. As an end effector, such as end effector 1300, is transitioned from an open state toward a clamped state, the end effector can reach a partially clamped state. In one aspect, a partially clamped state is defined as a state between the open state and the clamped state where the end effector makes initial contact with the tissue positioned therein. In one aspect, a partially clamped state is defined as a state where the anvil of the end effector is within a threshold distance of the elongate channel of the end effector. In one aspect, a partially clamped state is defined as a state wherein the closure trigger has moved a threshold amount toward the actuated state from the unactuated state. In one aspect, a partially clamped state is defined as a state wherein a firing member responsible for the closure of the end effector has moved a threshold linear distance.

In the partially clamped state, the end effector can begin to apply pressure to the tissue positioned therein, which can cause fluid within the tissue to begin to egress, before the end effector has reached the clamped state. Once the end effector has reached the clamped state, the fluid within the tissue can continue to egress from the tissue positioned between the anvil and the elongate channel of the end effector, further stabilizing the tissue in preparation for stapling and, optionally, cutting. Accordingly, a desired firing speed of the firing member can be dependent upon, among other things, factors that influence tissue stabilization.

Figure 20:
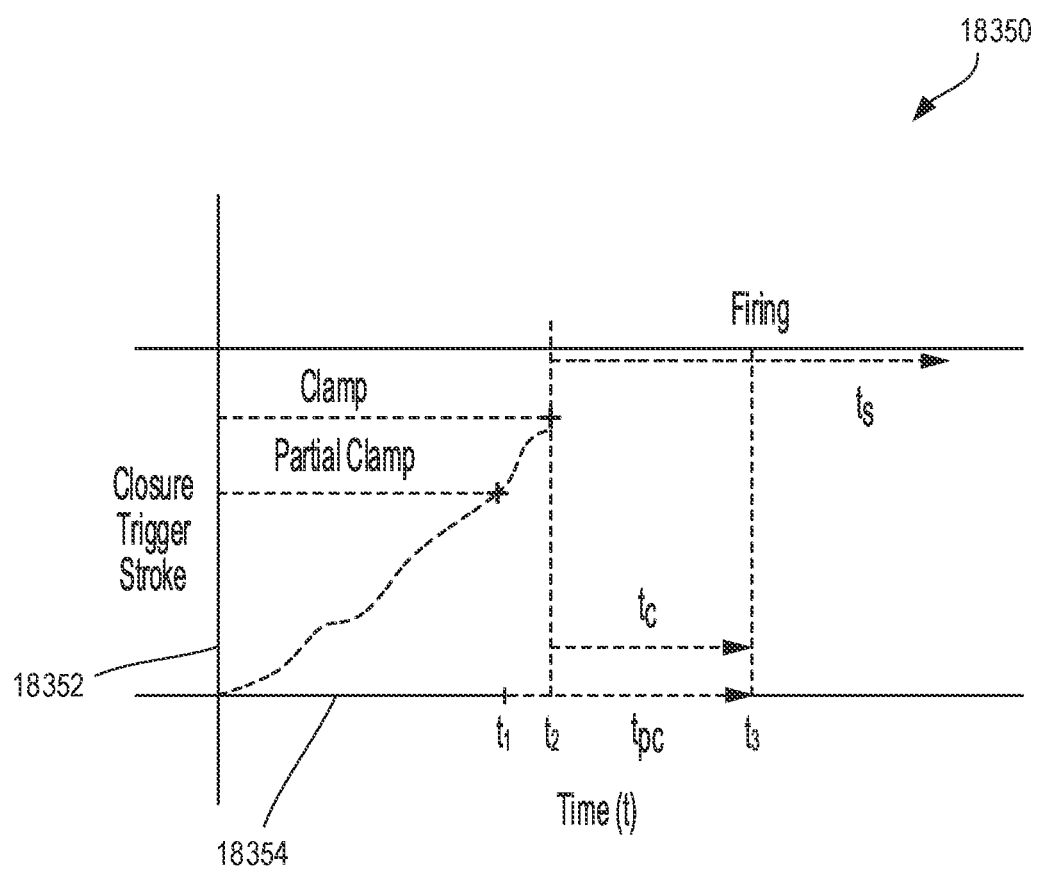
FIG. 20 is a graph that illustrates a closure trigger stroke over time, according to at least one aspect of the present disclosure.

Referring now to FIG. 20, a graph 18350 is provided according to at least one aspect of the present disclosure that illustrates a closure trigger stroke 18352 against time 18354. As shown at $t_0$, the closure trigger, such as closure trigger 1032, is in an unactuated position. In one aspect, the unactuated position of the closure trigger can correspond to the open state of the end effector, such as end effector 1300. In some embodiments, the position of the closure trigger can be monitored by a control system, such as by circuit board 1100, using any number of sensors described elsewhere herein.

From $t_0$ to $t_1$, the closure trigger is pivoted from the unactuated position toward the actuated position, which causes the end effector to transition from the open state toward the clamped state. At $t_1$, the end effector reaches a partially clamped state, which, as described above, can be a state where the end effector makes initial contact with the tissue within the end effector. In some embodiments, the end effector can include a pressure sensor that can detect the initial contact with the tissue as the end effector transitions toward the clamped state. In various embodiments, the inflection point of the load curve is used as a tissue contact or tissue compression initiation point. Upon detection of the end effector reaching the partially clamped state, the control system can initiate a timer to measure an amount of time that the end effector is within the partially clamped state $t_{pc}$ prior to a firing system, such as firing drive system 1080, being actuated. In one aspect, determining the inflection of tissue load versus. a time curve (tissue creep stabilization) could be used to determine the time of tissue stability or completed tissue compression.

In various other embodiments, the closure system can comprise a motor-driven closure system, such as closure motor drive assembly 605, with a closure motor, such as closure motor 603. With the motor driven closure system, the control system can determine the initial tissue contact by monitoring the current provided to the closure motor as a way of determining the magnitude of the clamping load on the jaw of the end effector. In one aspect, a spike in current provided to the closure motor indicates initial tissue contact, which can be indicative of the end effector reaching the partially clamped state.

From $t_1$ to $t_2$, the closure trigger can continue to pivot toward the actuated state, which continues to drive the end effector toward the clamped state. As the end effector transitions toward the clamped state, the anvil of the end effector can apply pressure to the tissue captured within the end effector, forcing fluid within the tissue to egress away and prepare the tissue for being cut and stapled.

At $t_2$, the closure trigger reaches the actuated state, which corresponds to the end effector reaching the clamped stated. In various embodiments, the control system can detect the closure trigger reaching the actuated position and/or the end effector reaching the clamped state utilizing various sensors as described elsewhere herein. Once the end effector reaches the clamped state, the control system can initiate a second timer to measure an amount of time that the end effector is within the clamped state $t_c$ prior to the firing system being actuated.

From $t_2$ to $t_3$, the end effector is maintained in the clamped state to allow for fluid within the tissue to egress away, further stabilizing the tissue prior to cutting and stapling the tissue. In one aspect, the control system can monitor this tissue creep by monitoring the amount of pressure applied by the end effector to the tissue over time. In one aspect, after the end effector reaches the clamped state, pressure detected by the pressure sensor can continuously diminish owing to the fluid moving away from the tissue clamped within the end effector. The control system can determine when the tissue within the end effector has stabilized by monitoring this change in pressure over time. In some embodiments, the tissue can be stabilized when the pressure change over time detected by the pressure sensor is substantially zero. In some embodiments, the tissue can be stabilized when the pressure change over time is less than a threshold rate of change over time. In some embodiments, the control system can determine that the tissue has stabilized after a threshold amount of time has passed after the end effector has reached the clamped state. In some embodiments, the control system can determine that the tissue has stabilized after a threshold amount of time has passed after the end effector has reached the partially clamped state.

At $t_3$, the control system can detect the actuation of the firing system. In some embodiments, the control system detects actuation of the firing system by detecting the firing trigger 1130 being pivoted to the actuated position. In some embodiments, the control system detects actuation of the firing system by detecting the power source 1090 providing a current or voltage to the motor 1082. Other embodiments of how the control system can detect actuation of the firing system are described elsewhere herein. Upon detecting actuation of the firing system, the control system can set a firing motion parameter of the firing system based upon a variety of factors measured by the control system from $t_0$ to $t_3$. In various embodiments, the firing motion parameter can be based on an elapsed time between $t_1$ and $t_2$, an elapsed time from $t_2$ to $t_3$, or combinations thereof.

In various embodiments, after setting the firing motion parameter of the firing system, the control system can drive the firing member through a firing stroke with the firing system using the firing motion parameter. In some embodiments, the firing system can control the motor to drive the firing member through the firing stroke using the firing motion parameter. In one embodiment, the firing motion parameter comprises a current supplied to the motor. In one embodiment, the firing motion parameter comprises a voltage supplied to the motor. In one embodiment, the firing motion parameter comprises a duty cycle of the motor. In one embodiment, the firing motion parameter comprises a velocity of the motor. In one embodiment, the firing motion parameter comprises a velocity of the firing member. Other exemplary firing motion parameters are described elsewhere herein.

In various embodiments, during the firing stroke, the control system can dynamically adjust the firing motion parameter. In one aspect, the control system can continue to monitor stabilization of the tissue and adjust the firing motion parameter as the tissue becomes more stable. In some embodiments, the control system dynamically adjusts the firing motion parameter based on an elapsed time from $t_1$ to a current time point of the firing stroke. In some embodiments, the control system dynamically adjusts the firing motion parameter based on an elapsed time from $t_2$ to a current time point of the firing stroke, i.e., the tissue stabilization time $t_5$. In some embodiments, the control system dynamically adjusts the firing motion parameter based on an elapsed time from $t_3$ to a current time point of the firing stroke. In some embodiments, the control system dynamically adjusts the firing motion parameter based on elapsed times from $t_1$, $t_2$, and $t_3$ to a current time point of the firing stroke. Accordingly, the firing motion parameter is dynamically adjusted during the firing stroke as the tissue becomes more stable.

Figure 21:
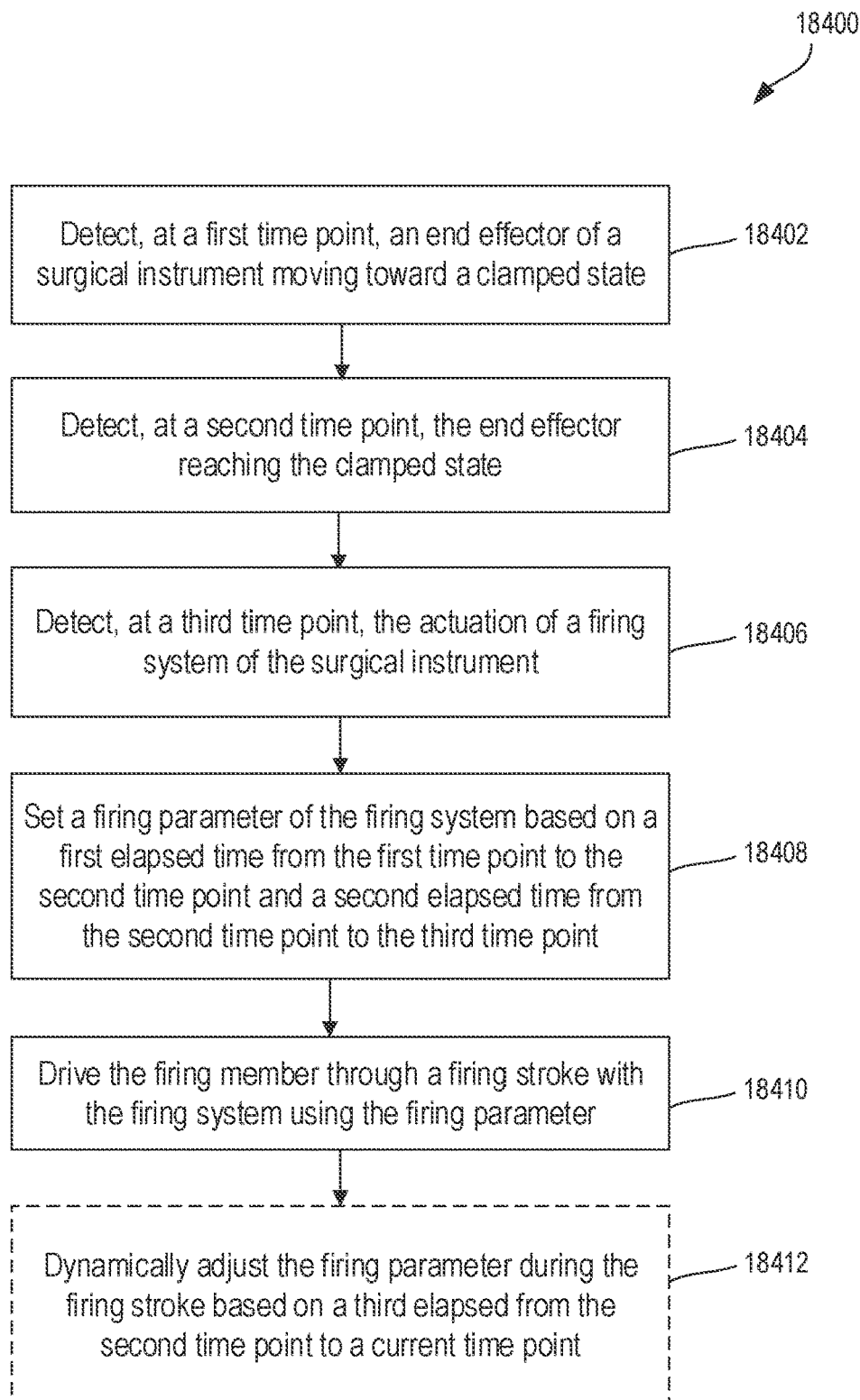
FIG. 21 illustrates a method for controlling a surgical instrument, according to at least one aspect of the present disclosure.

Referring now to FIG. 21, a method 18400 for controlling a surgical instrument is provided, according to at least one aspect of the present disclosure. The method 18400 comprises detecting 18402, at a first time point, an end effector of a surgical instrument moving toward a clamped state. In one embodiment, the circuit board 1100 detects the end effector 1300 moving toward the clamped state using a position sensor that can sense when the closure trigger 1032 is moving toward the actuated position. In one embodiment, the circuit board 1100 detects when the end effector 1300 moves toward the clamped state using a Hall-Effect sensor that can sense the anvil 2000 moving relative to the elongate channel 1310. In various embodiments, the circuit board 1100 detects when the end effector moves toward the clamped state using any number of sensors that detect the position of components associated with the closure system 3000, such as a position of the closure shuttle 1250, a position of the closure link 1038, or a position of the distal closure tube segment 3030, as examples.

The method 18400 further comprises detecting 18404, at a second time point, the end effector reaching the clamped state. In various embodiments, the control system can detect the end effector reaching the clamped state using various sensors described elsewhere herein.

The method 18400 further comprises detecting 18406, at a third time point, the actuation of a firing system of the surgical instrument. In one example embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18400 further comprises setting 18408 a firing motion parameter of the firing system based on a first elapsed time from the first time point to the second time point and a second elapsed time from the second time point to the third time point. In various embodiments, the circuit board 1100 can measure, using a timer, the elapsed lengths of time that has transpired from when the end effector began to move toward the clamped state, reached the clamped state, and when the firing system was actuated. In some embodiments, the circuit board 1100 can retrieve the firing motion parameter from a look-up table stored in a memory, such as memory 1935, according to the elapsed lengths of time. In some embodiments, the circuit board 1100 can retrieve a modification value from a graph or look-up table according to the elapsed lengths of time that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18400 further comprises driving 18410 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18400 provides the clinician with the freedom to choose how fast or slow they wish to transition the end effector to the clamped state and how long to maintain the end effector in the clamped state prior to actuating the firing system. In one aspect, closure speed acts as both effectively a portion of the clamped timing and since tissue is viscoelastic, also the tissue compression magnitude magnifier. Based on the elapsed amounts of time, the control system will automatically select an appropriate firing motion parameter for the firing system. In one aspect, "automatically" refers to the control system's ability to select a firing motion parameter without a user input.

In various embodiments, the method 18400 optionally further comprises dynamically adjusting 18412 the firing motion parameter during the firing stroke based an elapsed time from the second time point to a current time point. In some embodiments, the circuit board 1100 can measure, using a timer, an elapsed amount of time, from the end effector reaching the clamped state to a current time point during the firing stroke and dynamically adjust the firing motion parameter. Accordingly, the control system can dynamically adjust the firing motion parameter according to an elapsed length of time that the tissue has been clamped by the end effector and been allowed to stabilize.

Figure 22:
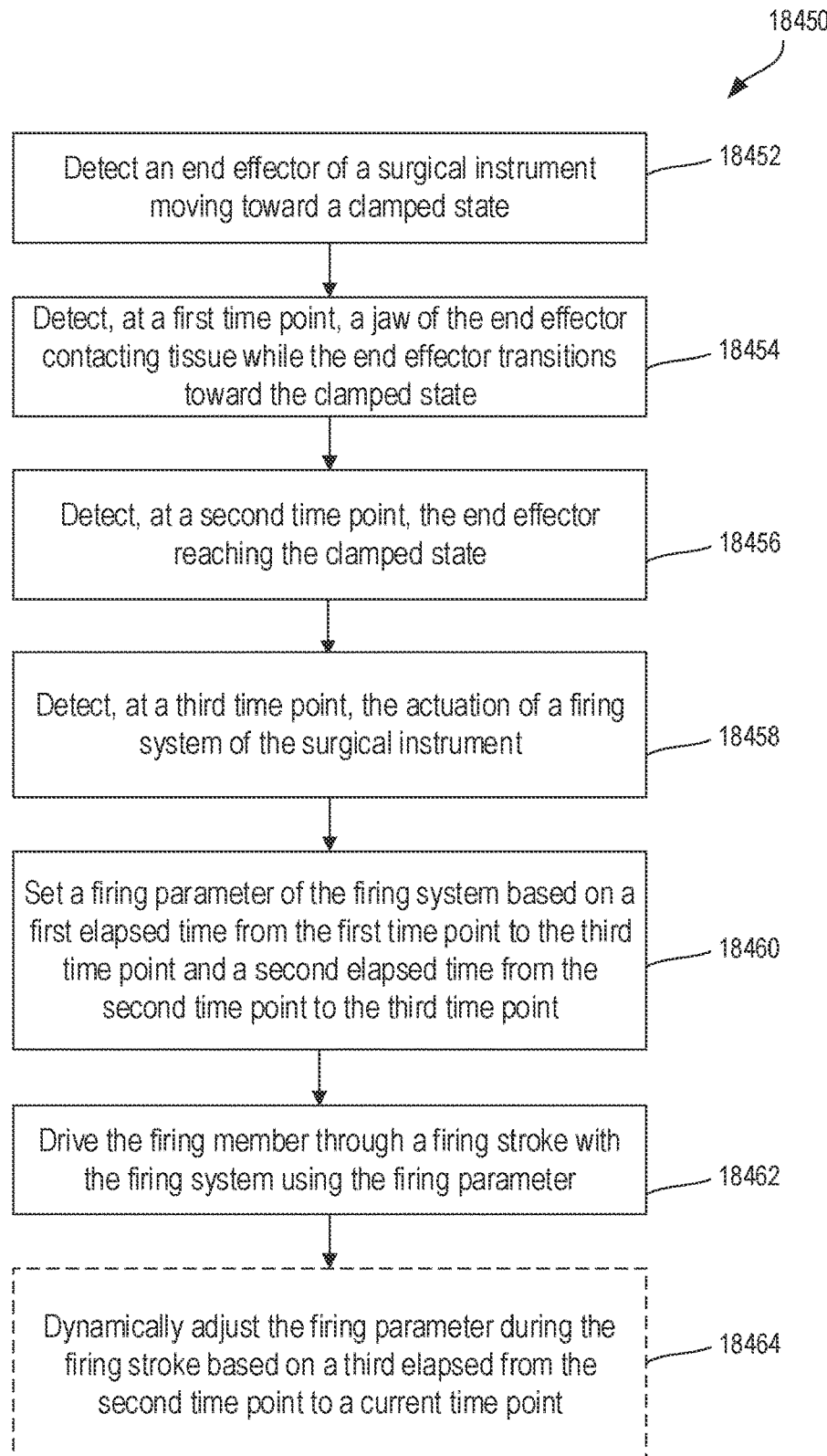
FIG. 22 illustrates a method for controlling a surgical instrument, according to at least one aspect of the present disclosure.

Referring now to FIG. 22, a method 18450 for controlling a surgical instrument is provided, according to at least one aspect of the present disclosure. The method 18450 comprises detecting 18452 an end effector of a surgical instrument moving toward a clamped state. In one embodiment, the circuit board 1100 detects the end effector 1300 moving toward the clamped state using a position sensor that can sense when the closure trigger 1032 is moving toward the actuated position. In one embodiment, the circuit board 1100 detects when the end effector 1300 moves toward the clamped state using a Hall-Effect sensor that can sense the anvil 2000 moving relative to the elongate channel 1310. In various embodiments, the circuit board 1100 detects when the end effector moves toward the clamped state using any number of sensors that detect the position of components associated with the closure system 3000, such as a position of the closure shuttle 1250, a position of the closure link 1038, a position of the distal closure tube segment 3030, as examples.

The method 18450 further comprises detecting 18454, at a first time point, a jaw of the end effector contacting tissue while the end effector transitions toward the clamped state. In various embodiments, the control system can detect initial contact of the anvil 2000 of the end-effector 1300 with the tissue utilizing a pressure sensor. In some embodiments, the control system is able to detect initial contact of the anvil 2000 with the tissue using various other sensors described elsewhere herein.

The method 18450 further comprises detecting 18456, at a second time point, the end effector reaching the clamped state. In various embodiments, the control system can detect the end effector reaching the clamped state using various sensors described elsewhere herein.

The method 18450 further comprises detecting 18458, at a third time point, the actuation of a firing system of the surgical instrument. In one embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18450 further comprises setting 18460 a firing motion parameter of the firing system based on a first elapsed time from the first time point to the second time point and the second time point to the third time point. In various embodiments, the circuit board 1100 can measure, using a timer, the elapsed lengths of time that has transpired from when the end effector makes initial contact with the tissue, reaches the clamped state, and when the firing system is actuated. In some embodiments, the circuit board 1100 can retrieve the firing motion parameter from a look-up table stored in a memory, such as memory 1935, according to the elapsed lengths of time. In some embodiments, the circuit board 1100 can retrieve a modification value from a graph or look-up table according to the elapsed lengths of time that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18450 further comprises driving 18462 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18450 provides the clinician with the freedom to choose how long they wish to apply pressure to the tissue, both between when the end effector first applies pressure in the partially clamped state and when the end effector reaches the clamped state, prior to actuating the firing system. Based on the elapsed amounts of time, the control system will automatically select an appropriate firing motion parameter for the firing system. In one aspect, "automatically" refers to the control system's ability to select a firing motion parameter without a user input.

In one aspect, part of the total clamping time includes portions of the closure stroke where the closure system is actuated enough, such as beyond the partially clamped state, or clamped slow enough and adequately enough to induce creep effects. This would enable the surgeon to utilize known techniques of slow clamping or repetitive clamping (more pressure followed by less pressure repeatedly as they urge the end effector to the clamped state). In this manner, the user is encouraged to use what has worked for them in the past, and the algorithms counts or further improves from that technique. In various embodiments, feedback on the rate or magnitude of this slow or repeated clamp is provided to the user on a display to allow the user to produce a more repeatable effect from patient to patient.

In various embodiments, the method 18450 optionally further comprises dynamically adjusting 18464 the firing motion parameter during the firing stroke based an elapsed time from the second time point to a current time point. In some embodiments, the circuit board 1100 can measure, using a timer, an elapsed amount of time, from the end effector reaching the clamped state to a current time point during the firing stroke and dynamically adjust the firing motion parameter. Accordingly, the control system can dynamically adjust the firing motion parameter according to an elapsed length of time that the tissue has been clamped by the end effector and been allowed to stabilize.

In one aspect, a firing motion parameter of the firing system can be set according to the amount of compression applied to the tissue prior to the actuation of the firing system. In one embodiment, with a precompression time of $t_1$ (a lower precompression threshold), the initial firing speed of the firing member can be a constant value, such as $V_1$. In one embodiment, $t_1$ comprises 5 seconds and $V_1$ comprises 6 mm/sec. With a precompression time between $t_1$ and $t_2$ (an intermediate precompression threshold range), the initial firing speed can be a function represented as:

$$Y=(A+B(t-C))$$

where Y is the initial firing speed, t is precompression time, and A, B, and C are constants. In some embodiments, $t_2$ comprises 15 seconds, A is 6, B is 1.6, and C is 5, such that, at 10 seconds of precompression, as an example, the initial firing speed is 14 mm/sec. With a precompression time greater than of $t_2$ (an upper precompression threshold), the initial firing speed can be a constant value, such as $V_2$. In some embodiments, $V_2$ comprises 22 mm/sec. Accordingly, the firing motion parameter can vary according to the amount of precompression applied to the tissue before actuation of the firing system.

In various embodiments, the articulation angle of the end effector is utilized, along with the other parameters described herein above, such as clamping time, clamping speed, tissue pressure level, etc., to determine an appropriate firing motion parameter for the firing system. Referring to FIG. 1, the interchangeable shaft assembly 1200 can define a shaft axis extending from a proximal end thereof to a distal end thereof. Furthermore, the end effector 1300 can define an end effector axis extending from a proximal end thereof to a distal end thereof. In one aspect, the end effector is considered to be in a "home position" when the end effector axis is aligned with the shaft axis, as can be seen in FIG. 1. In some embodiments, the control system, such as circuit board 1100, can detect the angle of the end effector away from the home position when selecting a firing motion parameter for the firing system. In various embodiments, the control system can detect the angle of articulation using various sensors, encoders, or the like described elsewhere herein. When the end effector is articulated, slowing down the speed and reducing firing loads may help to minimize tip movement of the end effector, as well as reduce stalling.

In various embodiments, the firing motion parameter can be adjusted a certain percentage for every degree of articulation that the end effector is away from the home position. In one embodiment, the firing motion parameter can be decreased 1% for each angle of articulation. In one embodiment, the firing motion parameter can be decreased more than 1% for each angle of articulation. In some embodiments, the firing motion parameter can be adjusted the more the end effector is articulated away from the home position, i.e., a non-linear change.

In one aspect, rather than adjusting the firing motion parameter, the control system can require additional clamping time to the tissue prior to allowing actuation of the firing system. In some embodiments, the surgical instrument can include a lockout that prevents actuation of the firing system prior to a required amount of clamping time elapsing, as determined by the control system from the articulation angle. In one embodiment, when the end effector is in the home position, the control system can require a first amount of clamping time $t_1$ prior to enabling the firing system. In some embodiments, the first amount of clamping time $t_1$ comprises 15 seconds of clamping time. When the end effector is articulated a first angle $\theta_1°$ from the home position, the control system can require an additional amount of clamping time $t_2$ in addition to the first amount of clamping time $t_1$ prior to enabling the firing system. In some embodiments, the first angle $\theta_1$ comprises 45° and the additional clamping time comprises 5 seconds of clamping time.

Figure 23:
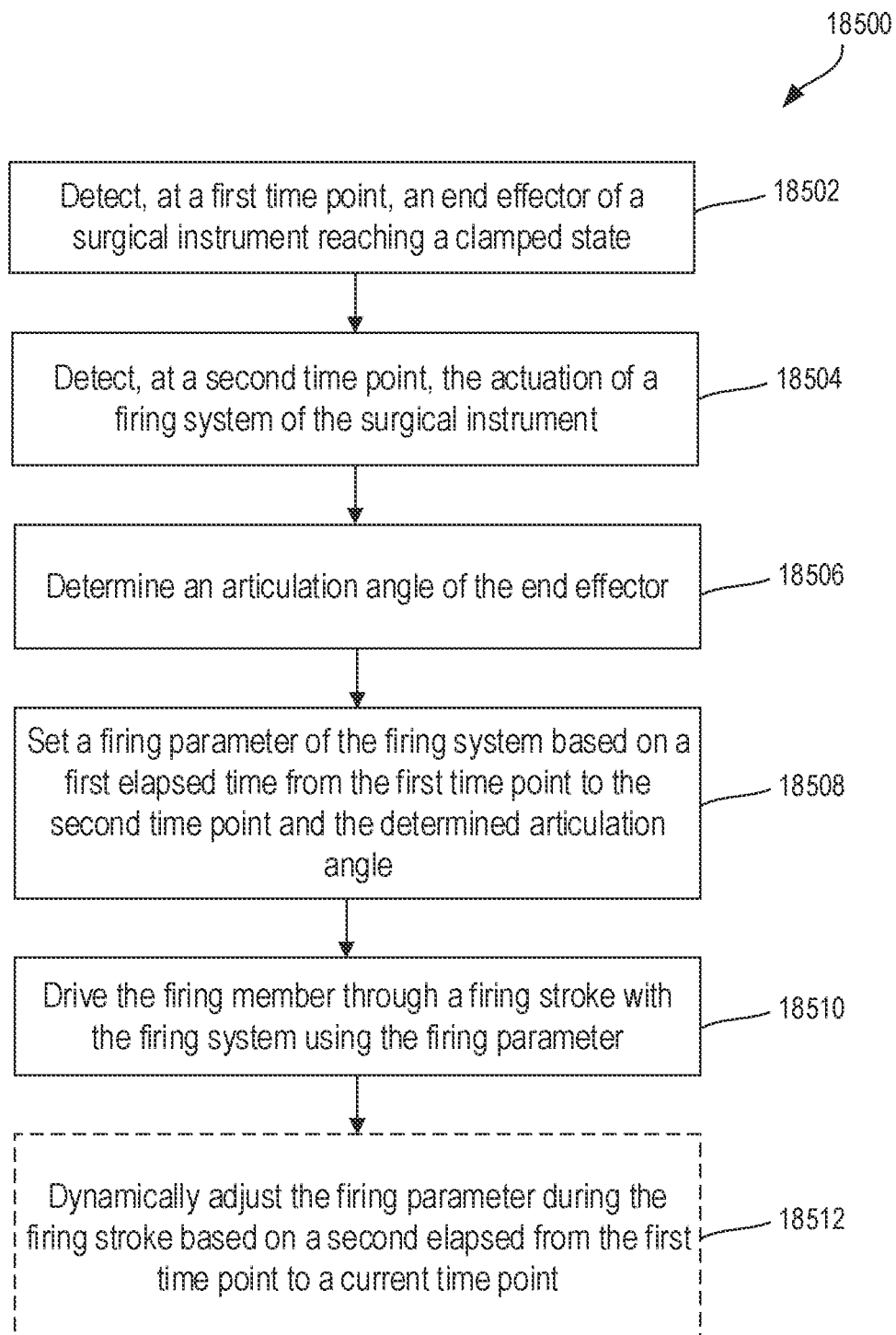
FIG. 23 illustrates a method for controlling a surgical instrument, according to at least one aspect of the present disclosure.

Referring now to FIG. 23, a method 18500 for controlling a surgical instrument is provided, according to at least one aspect of the present disclosure. The method 18500 comprises detecting 18502, at a first time point, an end effector of a surgical instrument reaching a clamped state. In one embodiment, the circuit board 1100 detects the end effector 1300 reaching the clamped state using a position sensor that can sense when the closure trigger 1032 has reached the actuated position. In one embodiment, the circuit board 1100 detects when the end effector 1300 has reached the clamped state using a Hall-Effect sensor that can sense the anvil 2000 is within a threshold distance from the elongate channel 1310. In various embodiments, the circuit board 1100 detects when the end effector has reached the clamped state using any number of sensors that detect the position of components associated with the closure system 3000, such as a position of the closure shuttle 1250, a position of the closure link 1038, or a position of the distal closure tube segment 3030, as examples.

The method 18500 further comprises detecting 18504, at a second time point, the actuation of a firing system of the surgical instrument. In one embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18500 further comprises detecting 18506 the actuation angle of the end effector. In one embodiment, the circuit board 1100 can detect the articulation angle of the end effector by detecting an angle of the end effector relative to the elongate shaft using any number of sensors or encoders described elsewhere herein.

The method 18500 further comprises setting 18508 a firing motion parameter of the firing system based on a first elapsed time from the first time point to the second time point and the articulation. In various embodiments, the circuit board 1100 can measure, using a timer, the elapsed length of time that has transpired from when the end effector reaches the clamped state and when the firing system is actuated. In some embodiments, the circuit board 1100 can retrieve the firing motion parameter from a look-up table stored in a memory, such as memory 1935, according to the elapsed length of time and the articulation angle. In some embodiments, the circuit board 1100 can retrieve a modification value from a graph or look-up table according to the elapsed length of time and the articulation angle that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18500 further comprises driving 18510 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18500 provides the clinician with the freedom to choose how long they wish to apply pressure to the tissue in the clamped state and what angle they wish the end effector to be at prior to actuating the firing system. Based on the elapsed amount of time and the articulation angle, the control system will automatically select an appropriate firing motion parameter for the firing system. In one aspect, "automatically" refers to the control system's ability to select a firing motion parameter without a user input.

In various embodiments, the method 18500 optionally further comprises dynamically adjusting 18512 the firing motion parameter during the firing stroke based an elapsed time from the first time point to a current time point. In some embodiments, the circuit board 1100 can measure, using a timer, an elapsed amount of time, from the end effector reaching the clamped state to a current time point during the firing stroke and dynamically adjust the firing motion parameter. Accordingly, the control system can dynamically adjust the firing motion parameter according to an elapsed length of time that the tissue has been clamped by the end effector and been allowed to stabilize.

Figure 24:
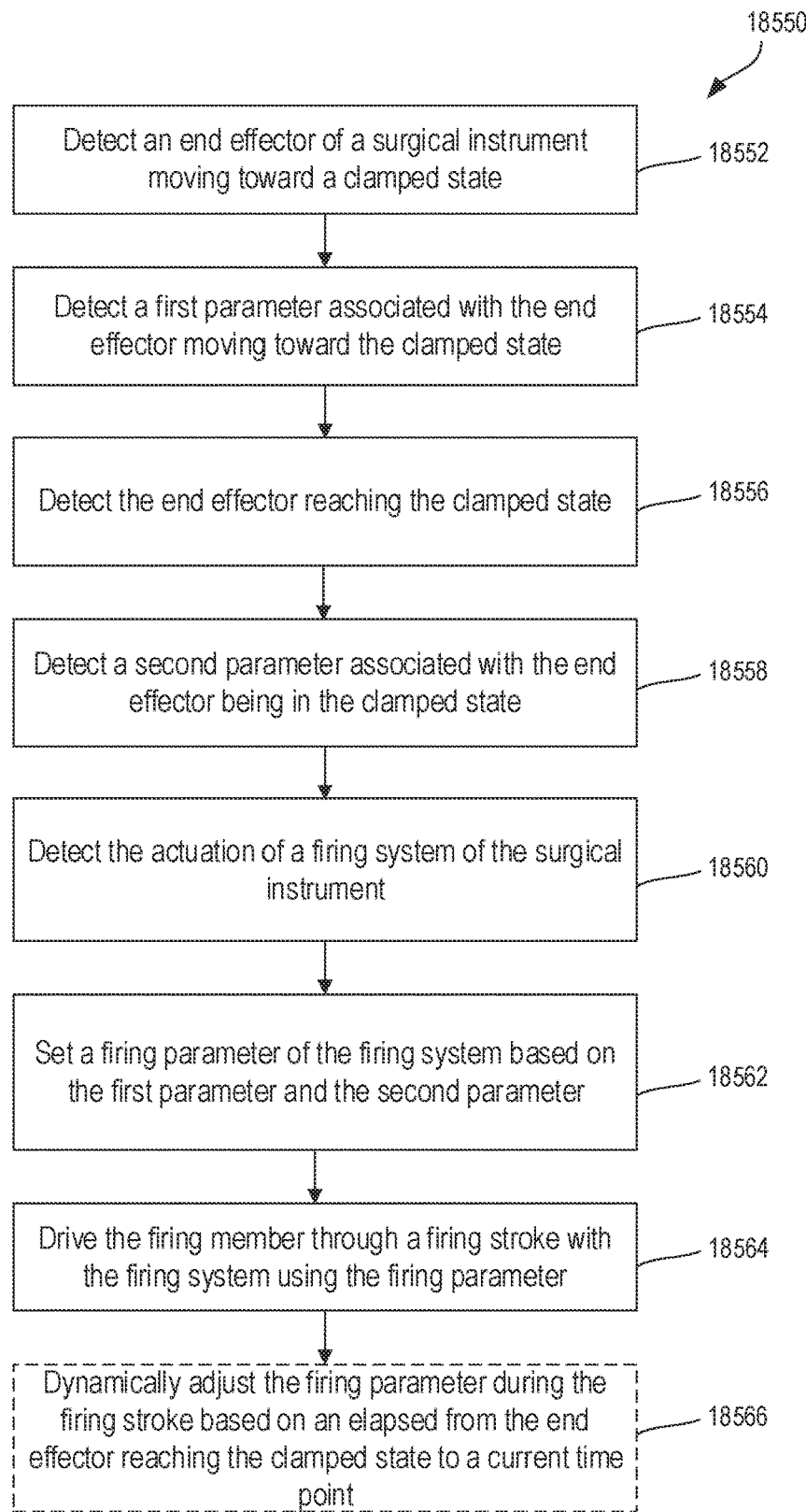
FIG. 24 illustrates a method for controlling a surgical instrument, according to at least one aspect of the present disclosure.

Referring now to FIG. 24, a method 18550 for controlling a surgical instrument is provided, according to at least one aspect of the present disclosure. The method 18550 comprises detecting 18502, at a first time point, an end effector of a surgical instrument moving toward a clamped state. In one embodiment, the circuit board 1100 detects the end effector 1300 moving toward the clamped state using a position sensor that can sense when the closure trigger 1032 is moving toward the actuated position. In one embodiment, the circuit board 1100 detects when the end effector 1300 moves toward the clamped state using a Hall-Effect sensor that can sense the anvil 2000 moving relative to the elongate channel 1310. In various embodiments, the circuit board 1100 detects when the end effector 1300 moves toward the clamped state using any number of sensors that detect the position of components associated with the closure system 3000, such as a position of the closure shuttle 1250, a position of the closure link 1038, or a position of the distal closure tube segment 3030, as examples.

The method 18550 further comprises detecting 18554 a first parameter associated with the end effector moving toward the clamped state. In one embodiment, the first parameter comprises a time taken to reach the clamped state. In one embodiment, the first parameter comprises a time taken to reach the partially clamped state. In one embodiment, the first parameter comprises a time taken to reach the clamped state from the partially clamped state. In one embodiment, the first parameter comprises a rate at which the end effector transitions to the clamped state. In one embodiment, the first parameter comprises a speed at which the end effector transitions to the clamped state. In one embodiment, the first parameter comprises an amount of pressure applied to tissue within the end effector as the end effector transitions to the clamped state. In one embodiment, the first parameter comprises an elapsed time from when the end effector first applies pressure to tissue to when the end effector reaches the clamped state. In various embodiments, the first parameter comprises any combination of the foregoing parameters or other parameters associated with the end effector transitioning to the clamped state, as described elsewhere herein.

The method 18550 further comprises detecting 18556 the end effector reaching the clamped state. In various embodiments, the control system detects the end effector reaching the clamped state using any number of sensors or encoders described elsewhere herein.

The method 18550 further comprises detecting 18558 a second parameter associated with the end effector being in the clamped state. In one embodiment, the second parameter comprises an elapsed time the end effector is in the clamped state until the actuation of the firing system of the surgical instrument. In one embodiment, the second parameter comprises an articulation angle of the end effector. In one embodiment, the second parameter comprises a rate of change of pressure applied to the tissue within the end effector. In various embodiments, the second parameter comprises any combination of the foregoing parameters or other parameters associated with the end effector being in the clamped state, as described elsewhere herein.

The method 18550 further comprises detecting 18560 the actuation of a firing system of the surgical instrument. In one embodiment, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18550 further comprises setting 18552 a firing motion parameter of the firing system based on the first parameter and the second parameter. In some embodiments, the circuit board 1100 can retrieve the firing motion parameter from a look-up table stored in a memory, such as memory 1935, according to the first parameter and the second parameter. In some embodiments, the circuit board 1100 can retrieve a modification value from a graph or look-up table according to the first parameter and the second parameter that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18550 further comprises driving 18564 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

Accordingly, the foregoing method 18550 provides the clinician with the freedom to manipulate the end effector in numerous ways of their choosing prior to actuating the firing system. Based on the detected parameters, the control system will automatically select an appropriate firing motion parameter for the firing system. In one aspect, "automatically" refers to the control system's ability to select a firing motion parameter without a user input.

In various embodiments, the method 18550 optionally further comprises dynamically adjusting 18566 the firing motion parameter during the firing stroke based an elapsed time from the end effector reaching the clamped state to a current time point. In some embodiments, the circuit board 1100 can measure, using a timer, an elapsed amount of time from the end effector reaching the clamped state to a current time point during the firing stroke and dynamically adjust the firing motion parameter. Accordingly, the control system can dynamically adjust the firing motion parameter according to an elapsed length of time that the tissue has been clamped by the end effector and been allowed to stabilize.

During a surgical procedure, a clinician may transition the end effector to the clamped state to capture tissue within the end effector. While clamped, fluid may egress away from the clamped tissue, therefore stabilizing the tissue in preparation for cutting and stapling. Furthermore, a timer can be initiated such that an appropriate firing motion parameter can be utilized when the firing system is actuated, as described elsewhere herein. However, prior to actuating the firing system, the clinician may decide that they wish to reposition the end effector to a new location on the tissue that is more suitable for cutting and stapling. To accomplish this, the clinician may transition the end effector out of the clamped state and reclamp the tissue at the new location on the tissue.

In some instances, when the end effector is transitioned away from the clamped state, the timer can be reset such that, when the end effector is returned to the clamped state, the timer can be reinitiated as if it were the first time the tissue had been clamped. However, in some instances, when the end effector is transitioned less than a threshold amount away from the clamped state, the timer may resume as if the end effector were still in the clamped state. Accordingly, the firing motion parameter can be selected based on not only an elapsed time that the tissue is held in the clamped state but also the time that the end effector is transitioned away from the clamped state less than a threshold amount. Accordingly, the control system can allow a clinician to modify a position of the end effector without losing the clamping time that was accumulated prior to repositioning the tissue.

Figure 25:
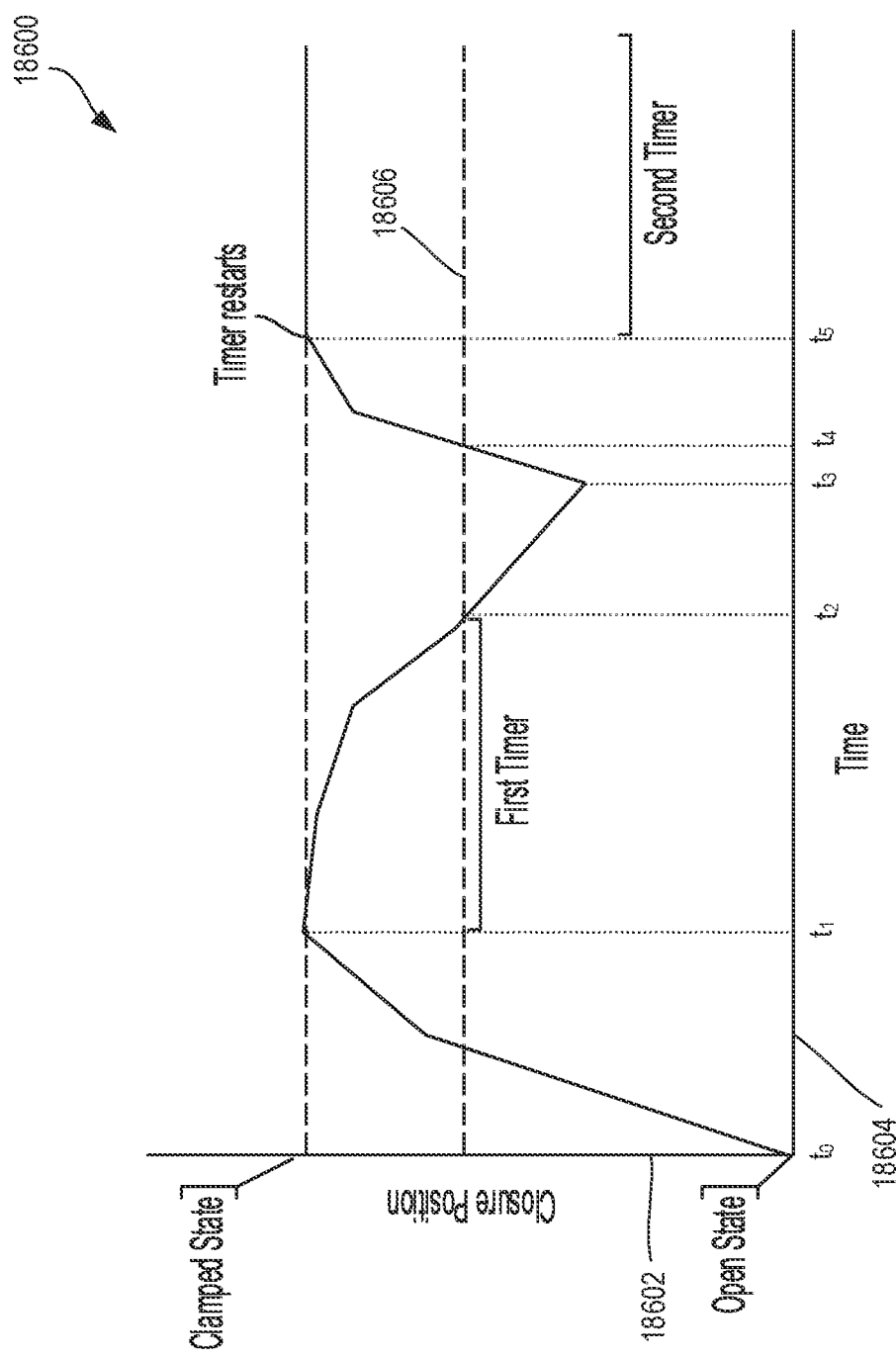
FIG. 25 is a graph that illustrates a closure state of an end effector over time, according to at least one aspect of the present disclosure.

Referring now to FIG. 25, a graph 18600 is provided according to at least one aspect of the present disclosure. The graph illustrates closure position of the end effector 18602 over time 18604. In some embodiments, the closure position can be the position of the closure trigger 1032 between the unactuated position and the actuated position.

At $t_0$, the anvil 2000 is in an open state, which can correspond to the closure trigger being in the unactuated position. From $t_0$ to $t_1$, the anvil 2000 is moved toward the clamped state using the closure trigger 1032. At $t_1$, the control system detects the end effector reaching the clamped state, as described elsewhere herein, and initiates a timer.

At $t_1$, a clinician decides that they wish to reposition the end effector to a new location more appropriate for cutting and stapling. Accordingly, as seen after $t_1$, the anvil 2000 is moved out of the clamped state toward the unclamped state. As the anvil 2000 moves from the unclamped state, the control system can maintain the timer running until the control system detects that the anvil 2000 has moved a threshold amount 18606 away from the elongate channel 1310. In various embodiments, the threshold amount can be stored in a memory and retrieved by the control system. In various embodiments, the threshold amount can be user defined and input at an input interface. In various embodiments, the control system can detect the position of the anvil 2000 relative to the elongate channel 1310 using any number of sensors or the like described elsewhere herein. In various embodiments, the threshold amount 18606 can be a distance that the anvil 2000 travels from the elongate channel 1310 while still maintaining contact with the tissue positioned within the end effector. Accordingly, despite being out of the clamped state, within a partially clamped state, the anvil 2000 is still applying pressure to the tissue, causing fluid to egress away.

At $t_2$, the control system detects that the anvil 2000 has transitioned the threshold amount away from the elongate channel 1310 and, therefore, resets the timer. From $t_2$ to $t_3$, the clinician continues to move the anvil 2000 away from the elongate channel 1310. During the time from $t_2$ to $t_3$, the timer is not running. At $t_3$, the clinician starts to move the anvil 2000 back towards the clamped state. At $t_4$, the anvil 2000 reaches the threshold amount from the elongate channel 1310, but the timer does not restart. However, various embodiments are envisioned where the timer reinitiates when the anvil 2000 is within the threshold amount from the elongate channel 1310. Various other embodiments are envisioned where the timer reinitiates when the anvil 2000 makes contact with the tissue prior to reaching the clamped state.

At $t_5$, the anvil 2000 is returned to the clamped state and the timer is reinitiated. At this time, the clinician can maintain the end effector in the clamped state until they wish to actuate the firing system. When the firing system is actuated, the firing system only takes into account the second elapsed time, not the first elapsed time, as the end effector was transitioned a threshold amount away from the clamped state.

Figure 26:
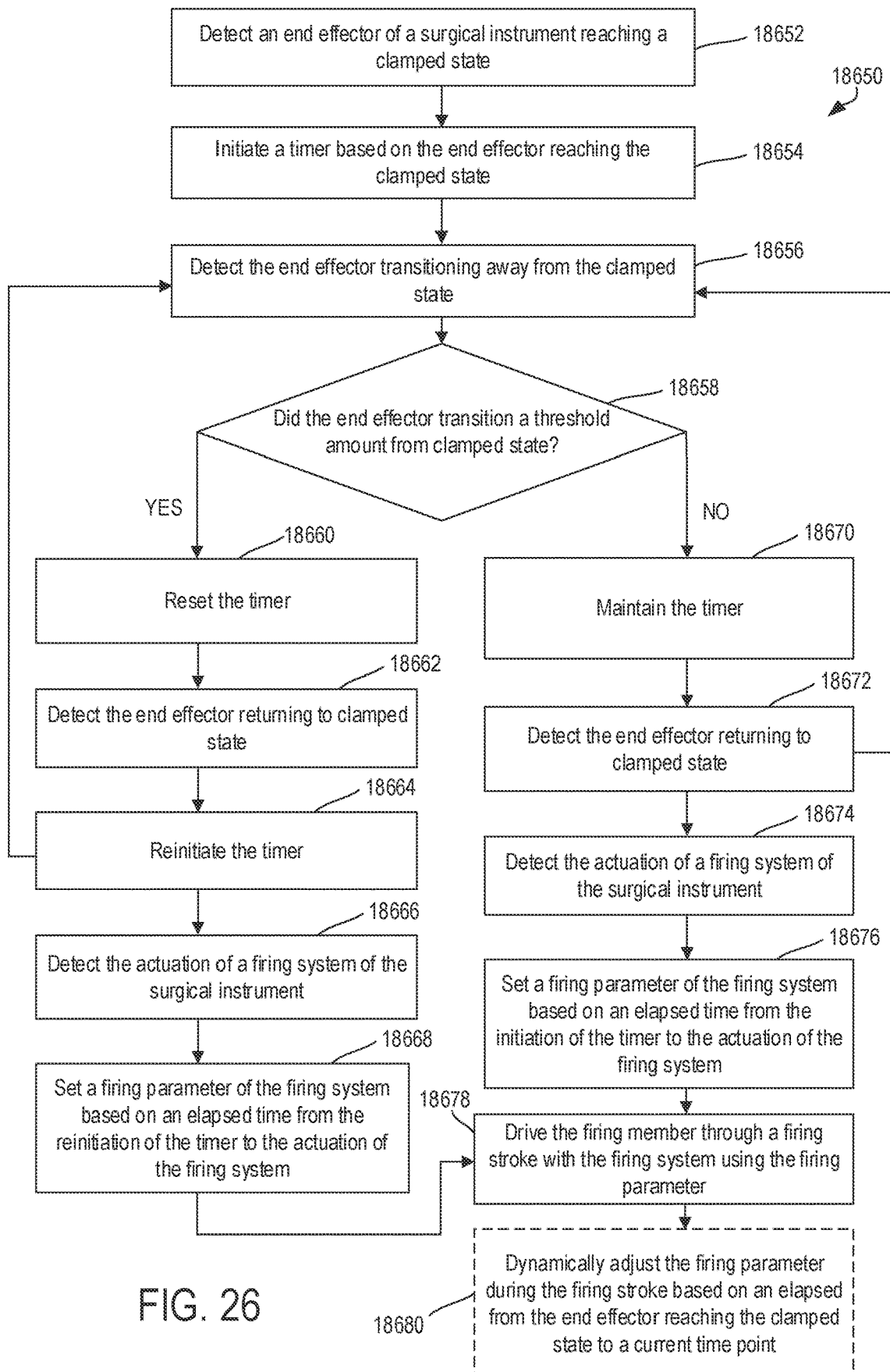
FIG. 26 illustrates a method for controlling a surgical instrument, according to at least one aspect of the present disclosure.

Referring now to FIG. 26, a method 18650 for controlling a surgical instrument is provided, according to at least one aspect of the present disclosure. The method 18650 comprises detecting 18652 an end effector of a surgical instrument reaching a clamped state. In one embodiment, the circuit board 1100 detects the end effector 1300 reaching the clamped state using a position sensor that can sense when the closure trigger 1032 has reached the actuated position. In one embodiment, the circuit board 1100 detects when the end effector 1300 has reached the clamped state using a Hall-Effect sensor that can sense the anvil 2000 is within a threshold distance from the elongate channel 1310. In various embodiments, the circuit board 1100 detects when the end effector 1300 has reached the clamped state using any number of sensors that detect the position of components associated with the closure system 3000, such as a position of the closure shuttle 1250, a position of the closure link 1038, or a position of the distal closure tube segment 3030, as examples.

The method 18650 further comprises initiating 18654 a timer based on the end effector reaching the clamped state. In some embodiments, the circuit board 1100 can measure an elapsed time that the end effector is in the clamped state until the control system detects actuation of the firing system. In one embodiment, after initiation of the timer at 18654, the control system detects actuation of the firing system. Accordingly, the method 18650 can set a firing motion parameter of the firing system based on the elapsed times, similar to what is described for method 18200.

The method 18650 further comprises detecting 18656 the end effector transitioning away from the clamped state. In some embodiments, the control system can detect the end effector transitioning away from the clamped state using any suitable sensors described elsewhere herein.

The method 18650 further comprises determining 18658 if the end effector transitioned a threshold amount from the clamped state. In some embodiments, the control system determines if the end effector transitioned the threshold amount by comparing a distance between the anvil 2000 and the elongate channel 1310 to the threshold value. In some embodiments, the control system determines if the end effector transitioned the threshold amount by comparing a distance that the closure trigger traveled from the actuated position.

Based on the control system determining that the end effector transitioned the threshold amount from the clamped state, the method 18650 proceeds with resetting 18660 the timer. In some embodiments, resetting the timer comprises resetting the timer back to zero. In some embodiments, resetting the timer can comprise setting the timer to a value other than zero.

The method 18650 further comprises detecting 18662 that the end effector returned to the clamped state. In some embodiments, the control system can detect the end effector returning to the clamped state using any number of sensors described elsewhere herein.

The method 18650 further comprises reinitating 18664 the timer, based on the end effector returning to the clamped state. In some embodiments, the control system can reinitiate the reset timer based on the detection of the end effector retuning to the clamped state, similar to what is seen at $t_5$ of FIG. 25.

After reinitiation 18664 of the timer, the user can choose to again transition the end effector away from the clamped state to reposition the end effector. Accordingly, the method can proceed again to detecting 18656 the end effector transitioning away from the clamped state, as described above. Furthermore, after reinitiation of the timer, the method 18650 further comprises detecting 18666 the actuation of a firing system of the surgical instrument. In some embodiments, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18650 further comprises setting 18668 a firing motion parameter of the firing system based on an elapsed time from the reinitiation of the timer to the actuation of the firing system. In various embodiments, the circuit board 1100 can interrogate the timer to determine an elapsed length of time that has transpired from reinitiation of the timer and when the firing system was actuated. In some embodiments, the circuit board 1100 can retrieve the firing motion parameter from a look-up table stored in a memory, such as memory 1935, according to the elapsed length of time. In some embodiments, the circuit board 1100 can retrieve a modification value from a graph or look-up table according to the elapsed length of time that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters.

The method 18650 further comprises driving 18678 the firing member through a firing stroke with the firing system using the firing motion parameter. In some embodiments, the circuit board 1100 can cause the motor 1082 of the firing drive system 1080 to drive the firing member 1900 through a firing stroke using the firing motion parameter, which causes the firing member 1900 to deploy staples removably stored in the staple cartridge 1301.

In various embodiments, the method 18650 optionally further comprises dynamically adjusting 18680 the firing motion parameter during the firing stroke based an elapsed time from the end effector reaching the clamped state to a current time point. In some embodiments, the circuit board 1100 can measure, using a timer, an elapsed amount of time, from the end effector reaching the clamped state to a current time point during the firing stroke and dynamically adjust the firing motion parameter. In some embodiments, the elapsed time is measured only after the end effector returned to the clamped state. In some embodiments, the elapsed time is measured from the end effector initially reaching the clamped state. Accordingly, the control system can dynamically adjust the firing motion parameter according to an elapsed length of time that the tissue has been clamped by the end effector and been allowed to stabilize.

Based on the control system determining that the end effector did not transition the threshold amount from the clamped state, the method 18650 proceeds with maintaining 18670 the timer. In some embodiments, maintaining the timer comprises allowing the timer to continue to run and measure the elapsed time from the end effector reaching the clamped state.

The method 18650 further comprises detecting 18672 that the end effector returned to the clamped state. In some embodiments, the control system can detect the end effector returning to the clamped state using any number of sensors described elsewhere herein.

After detecting 18672 the end effector returning to the clamped state, the user can choose to again transition the end effector away from the clamped state to reposition the end effector. Accordingly, the method can proceed again to detecting 18656 the end effector transitioning away from the clamped state, as described above. Furthermore, after detecting 18672 the end effector returning to the clamped state, the method 18650 further comprises detecting 18674 the actuation of a firing system of the surgical instrument. In some embodiments, the circuit board 1100 detects the actuation of the firing drive system 1080 when the firing trigger 1130 is pivoted to the actuated position. In one embodiment, actuation of the firing drive system 1080 is detected when the circuit board 1100 detects a current bring supplied to the motor 1082 from the power source 1090 via a current sensor.

The method 18650 further comprises setting 18676 a firing motion parameter of the firing system based on an elapsed time from the initiation of the timer to the actuation of the firing system. In various embodiments, the circuit board 1100 can interrogate the timer to determine an elapsed length of time that has transpired from the initiation of the timer and when the firing system was actuated. In some embodiments, the circuit board 1100 can retrieve the firing motion parameter from a look-up table stored in a memory, such as memory 1935, according to the elapsed length of time. In some embodiments, the circuit board 1100 can retrieve a modification value from a graph or look-up table according to the elapsed length of time that can be used to adjust a default firing motion parameter. In one embodiment, the firing motion parameter can comprise a duty cycle of the motor 1082. In one embodiment, the firing motion parameter can comprise a velocity of the motor 1082. In some embodiments, setting the firing motion parameter can comprise setting multiple firing motion parameters. In various embodiments, setting the firing motion parameter can be based on a variety of other parameters described elsewhere herein, such as the articulation angle, the time since initiation tissue contact, the speed of moving toward the clamped state, or combinations thereof, as examples.

Similar to above, the method 18650 comprises driving 18678 the firing member through a firing stroke with the firing system using the firing motion parameter and dynamically adjusting 18680 the firing motion parameter during the firing stroke based an elapsed time from the end effector reaching the clamped state to a current time point. In some embodiments, the elapsed time is measured only after the end effector returned to the clamped state. In some embodiments, the elapsed time is measured from the end effector initially reaching the clamped state.

Accordingly, the foregoing method 18650 provides the clinician with the freedom to manipulate the end effector in numerous ways of their choosing prior to actuating the firing system, while also allowing the end effector to transition away from the clamped state without potentially losing the benefit of accumulated clamping time already incurred. Based on the detected parameters, the control system will automatically select an appropriate firing motion parameter for the firing system. In one aspect, "automatically" refers to the control system's ability to select a firing motion parameter without a user input.

Clamping systems that utilize position control closure are plagued by operating in a manner where a closure stoke produces a specific force to tissue captured within the end effector after the end effector has been placed into a clamped state. As the tissue thins due to tissue creep, this specific force applied to the tissue diminishes over time. For example, referring to FIGS. 27 and 28, a response profile 4000 from a clamping system utilizing position control closure is provided, according to at least one aspect of the present disclosure. At $t_0$, the end effector begins in an open state, during which time the closure force 4002 applied by the end effector to the tissue is zero. From $t_0$ to $t_1$, the end effector is transitioned toward a clamped state by a closure member, which causes a gradual increase in the closure force 4002 applied to the tissue. At $t_1$, the closure member reaches the end of its closure stroke, corresponding to the end effector reaching the clamped state. In the clamped state, the closure force 4002 reaches a maximum closure force $FTC_{maxPC}$.

Figure 27:
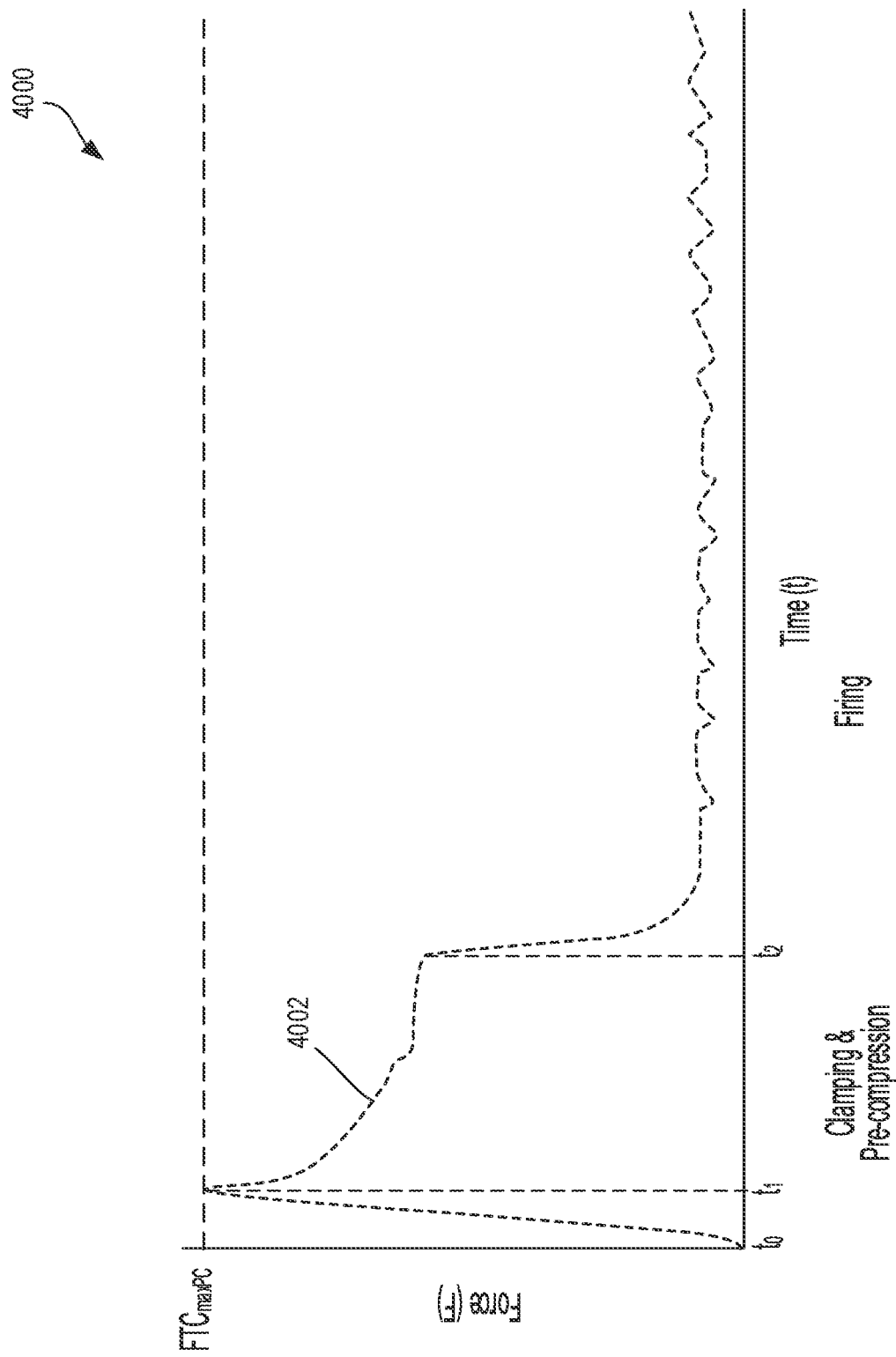
FIG. 27 illustrates a response profile from a clamping system utilizing a position control closure system, according to at least one aspect of the present disclosure.
Figure 28:
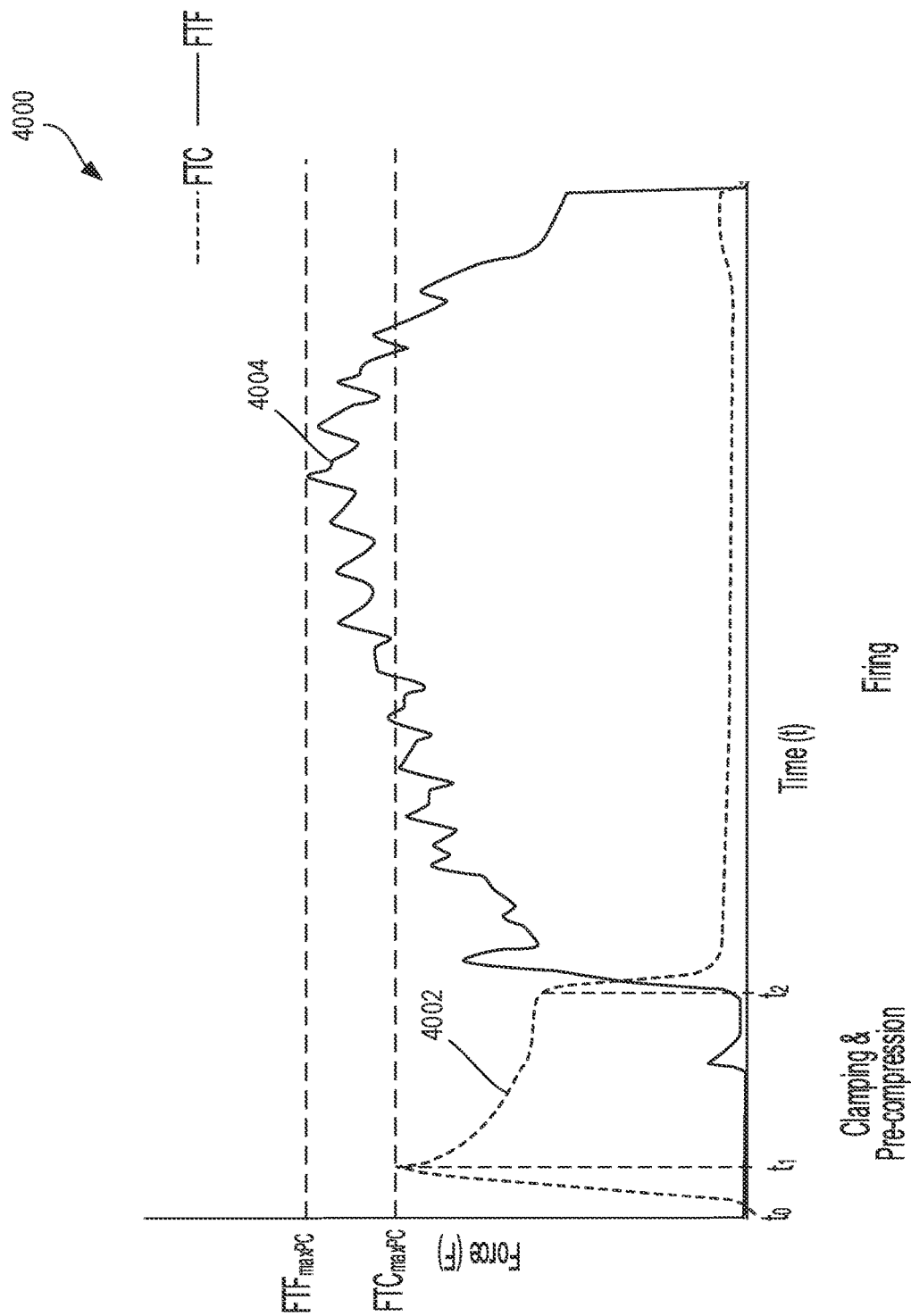
FIG. 28 illustrates a response profile from a clamping system utilizing a position control closure system, according to at least one aspect of the present disclosure.

A problem with these clamping systems is that they do not have the ability to continue to advance their closure members once they have completed their closure stroke, and thus, the force applied to the tissue drops over time, as fluid egresses from the clamped tissue. For example, as seen in FIGS. 27 and 28, once the maximum closure force $FTC_{maxPC}$ is applied to the tissue at $t_1$, the closure force 4002 gradually diminishes over time because of tissue creep/tissue thinning. At $t_2$, the firing system of the surgical instrument is actuated, causing the closure force 4002 to sharply drop.

Referring to FIG. 27, as a result of the diminishing closure force 4002 after reaching $FTC_{maxPC}$, the force to fire 4004 the firing drive, such as firing motor drive assembly 604, of the surgical instrument reaches a force $FTF_{maxPC}$ that is greater than $FTC_{maxPC}$. This large force to fire places a lot of stress on the firing motor, such as firing motor 602, of the firing drive.

Some attempts have been made to store energy in a spring or other mechanical storing means, and then allow the clamping system to continue to advance, but these means also lower force as the tissue thins, just not as abruptly. A preferred manner would be to hold the load constant or even "overload" the tissue slightly with each adjustment to creep and bring the tissue to its thinnest, stable state as quickly, uniformly, and repeatably as possible. This preferred manner can result in better surgical outcomes and lower stresses on the firing system.

In one aspect, load control of the closure system enables the closure load, and therefore, the clamping force, to stay at an elevated level, improving the pre-firing compression of the tissue, and ultimately, resulting in lower forces to fire. Viscoelastic creep of tissue is maximized by the magnitude of the force, the duration of the force and the rate that the force was applied.

Figure 29:
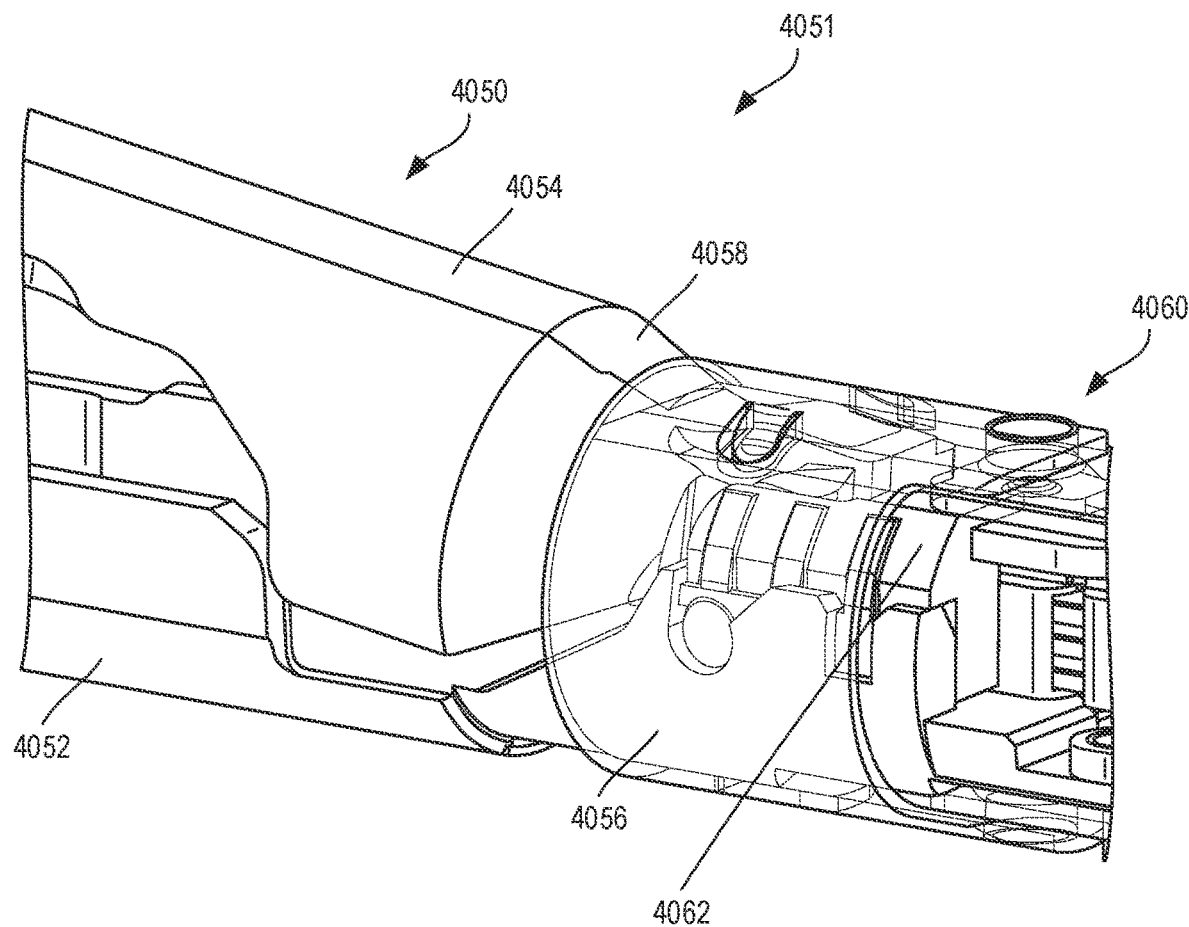
FIG. 29 illustrates an end effector of a surgical instrument in an open state, according to at least one aspect of the present disclosure.
Figure 30:
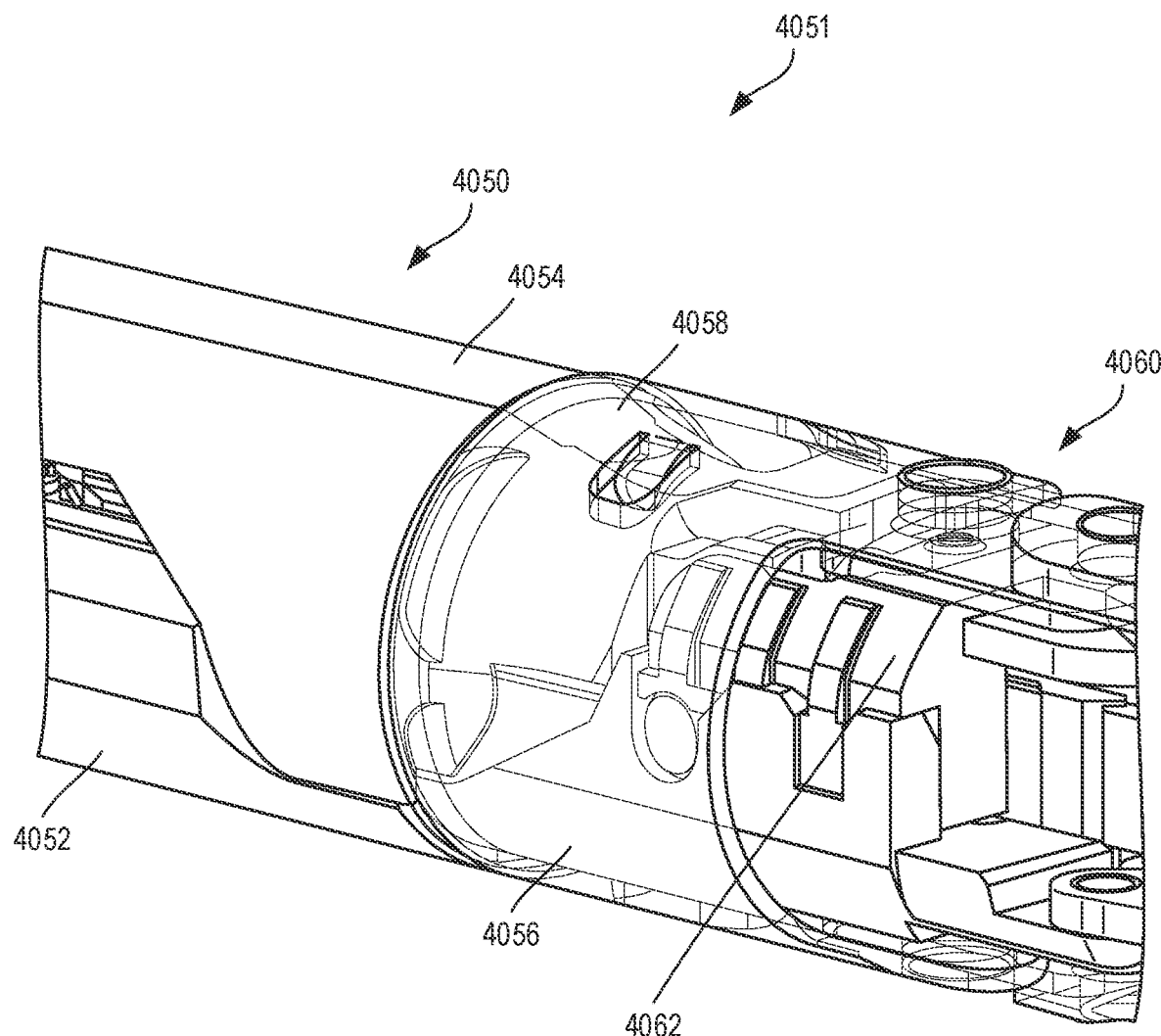
FIG. 30 illustrates the end effector of FIG. 29 in a clamped state, according to at least one aspect of the present disclosure.
Figure 31:
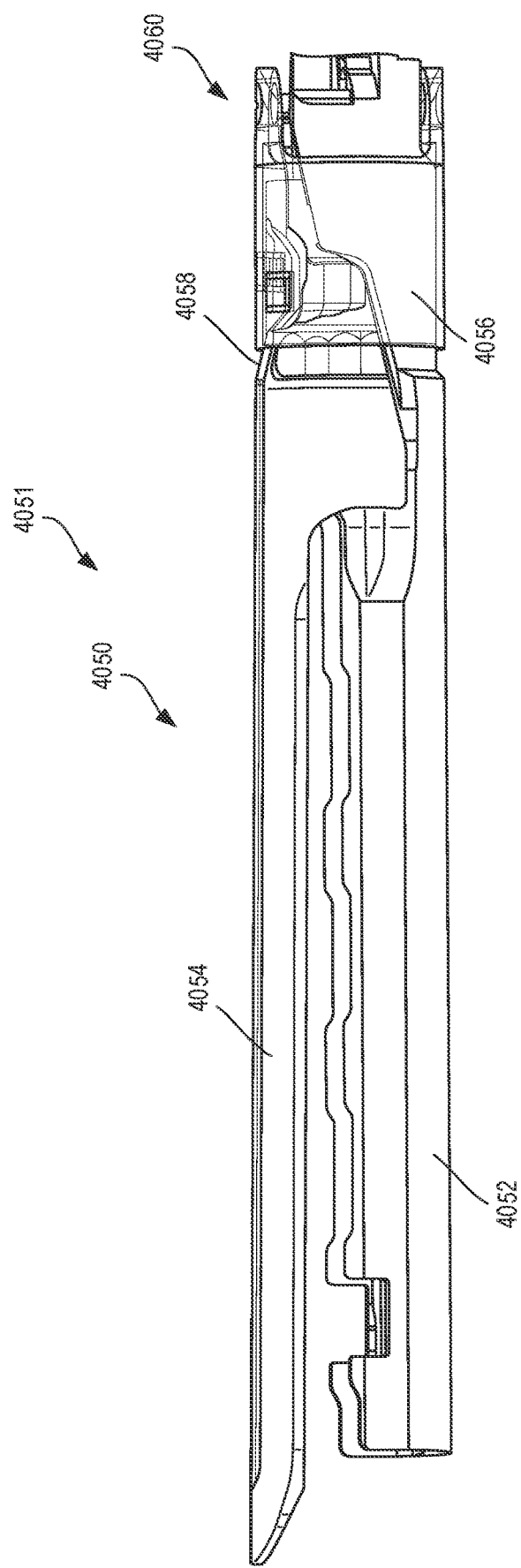
FIG. 31 illustrates a side view of the end effector of FIG. 30, according to at least one aspect of the present disclosure.

Referring now to FIGS. 29-31, an end effector 4050 of a surgical instrument 4051 is provided, according to at least one aspect of the present disclosure. The end effector 4050 includes an elongate channel 4052, which is similar in many respects to elongate channel 1310, and an anvil 4054, which is similar in many respects to anvil 2000, pivotably supported relative to the elongate channel 4052. The surgical instrument 4051 includes a closure ring 4056 that is axially movable relative to the end effector 4050 between a proximal position, illustrated in FIG. 29, and a distal position, illustrated in FIG. 30. In various embodiments, the closure ring 4056 is part of a motor-driven closure system, such as closure motor drive assembly 605, and is drivable between the proximal position and distal position by a motor, such as closure motor 603. In various embodiments, the closure ring 4056 is part of a manually driven closure system, such as closure system 3000, and is drivable between the proximal position and distal position in response to a manual input, such as rotation of a closure trigger 1032 by a clinician.

The surgical instrument 4051 further includes an articulation joint 4060 that rotatably connects the end effector 4050 to an elongate shaft of the surgical instrument, allowing the end effector 4050 to rotate relative to the elongate shaft into a plurality of articulation positions away from a central axis extending centrally through the elongate shaft. The surgical instrument 4051 further includes a spine 4062 configured to provide structural support to the surgical instrument 4051 and to protect various internal components of the surgical instrument 4051.

In operation, the closure ring 4056 is driven from the proximal position toward the distal position by the closure system, such as the motor-driven closure system or manually driven closure system. As the closure ring 4056 is driven toward the distal position, the closure ring 4056 cammingly engages a ramp 4058 formed at a proximal end of the anvil 4054, thereby camming the anvil 4054 toward a clamped state, as shown in FIG. 30, to grasp tissue by the end effector. In some embodiments, the closure ring 4056 is similar in manner to the distal closure tube segment described in U.S. Pat. No. 11,324,501, which is hereby incorporated reference in its entirety herein. In various embodiments, the end effector 4050 includes a spring that biases the anvil 4054 toward the open position when the closure ring 4056 is moved toward the proximal position.

In some embodiments, the clamped state is defined as a state where the end effector 1300 is in the closed configuration and the closure trigger 1032 is in the actuated position. In other embodiments, the clamped state is defined as a state where the elongate channel 1310 and the anvil 2000 of the end effector 1300 are within a threshold distance of one another. In other embodiments, the clamped state is defined as a state where the closure trigger 1032 has pivoted a threshold distance away from the unactuated position.

In other embodiments, the closure system causes the elongate channel to move toward the anvil to achieve a closed position. In yet other embodiments, the closure system causes the anvil and the elongate channel to move toward each other to achieve the closed position. A number of embodiments described by the present disclosure include a closure system comprising a movable anvil and a fixed elongate channel. Nonetheless, it is readily understood that such embodiments can be equally implemented using a movable elongate channel and a fixed anvil or a movable elongate channel and a movable anvil.

Figure 32:
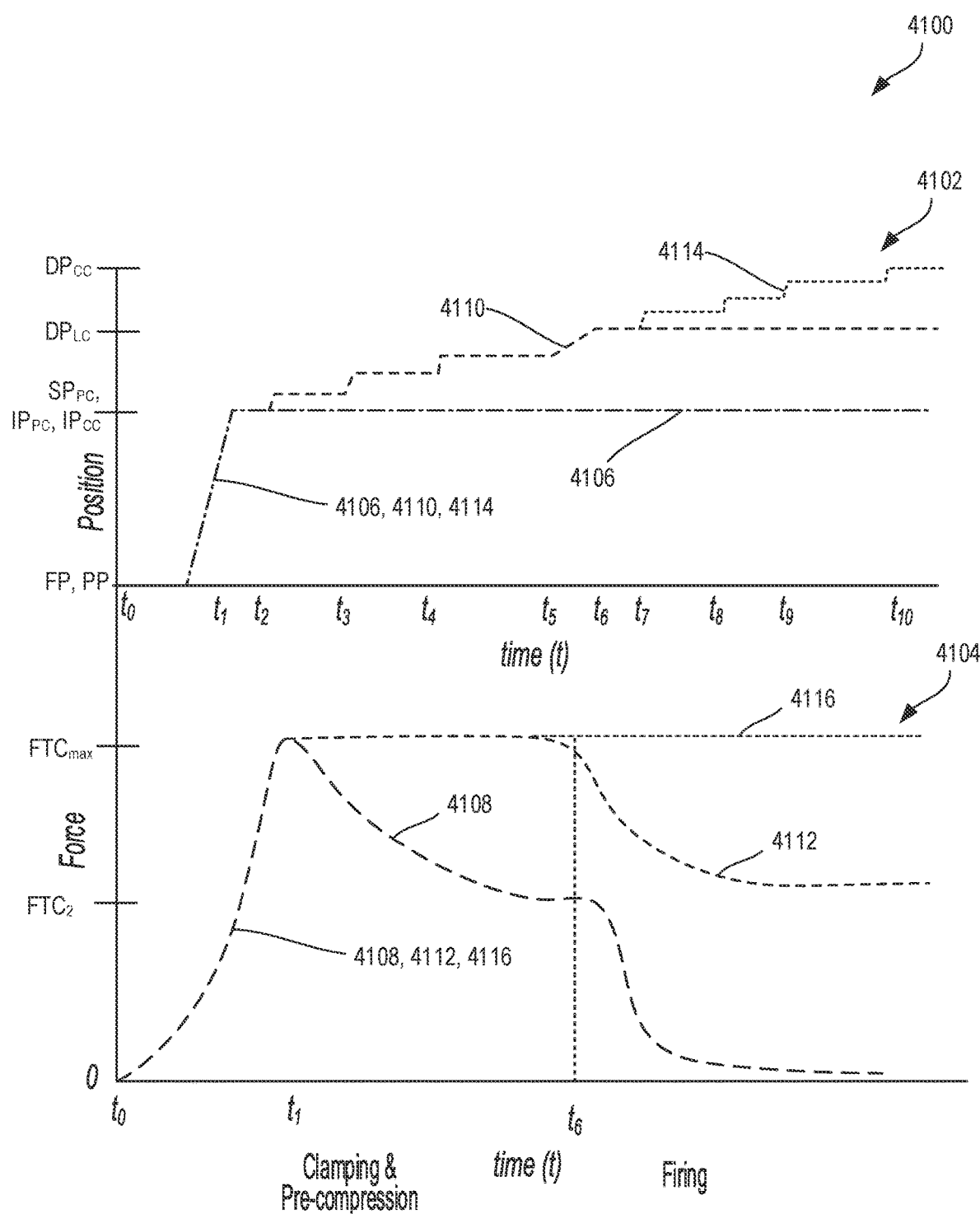
FIG. 32 illustrates graphs illustrating the differences between a position control closure system and load control closure systems, according to at least one aspect of the present disclosure.

Referring now to FIG. 32, graphs 4100 illustrating the differences between a position control closure system and load control closure systems are provided, according to at least one aspect of the present disclosure. The upper graph 4102 illustrates the position of the respective closure members of each system, as will be discussed in more detail below, over time. The lower graph 4104 illustrates the relationship between the closure loads applied by the respective end effectors over time.

With a position control closure system, a closure member moves between a first position, corresponding to an end effector being in the open state, and a second position, corresponding to the end effector being in the clamped state. Referring to the upper graph 4102, at $t_0$, the closure member begins in the first position FP, corresponding to the end effector being in the open state. When the end effector is in the open state, no force is applied to the tissue captured within the end effector, as seen in the lower graph 4104.

As the closure member moves toward the second position $SP_{PC}$, represented by line 4106, the end effector transitions toward the clamped state, causing the closure force applied by the end effector, represented by line 4108, to increase. At $t_1$, the closure member reaches the second position $SP_{PC}$, which corresponds to the end effector being in the clamped state. As seen in lower graph 4104, in the clamped state, the end effector applies a maximum closure force $FTC_{max}$ to the tissue.

As the closure member is no longer able to advance beyond the second position $SP_{PC}$, the force applied to the tissue begins to diminish as a result of tissue thinning and tissue creep. From $t_2$ to $t_3$, the tissue force 4108 drops below $FTC_{max}$. At $t_3$, the firing system is actuated, causing the applied force to further sharply drop.

As referenced above, utilizing a load control closure system would enable the closure load, and therefore, the clamping force, to stay at an elevated level, improving the pre-firing compression of the tissue. In various embodiments, the surgical instrument 4051 is utilized to provide such load control. In some embodiments, a control system, such as controller 620, can control the closure of the end effector 4050 with the closure ring 4056 according to forces sensed with sensors, such as any suitable sensor described elsewhere herein, such as a force sensor or a current sensor, as explained in more detail below. It should be understood that the control system can be any suitable control system described elsewhere herein, such as circuit board 1100 or controller 1933, as examples.

Referring to the upper graph 4102, at $t_0$, the closure ring 4056 begins in the proximal positon PP, corresponding to the end effector 4050 being in the open state, i.e., the anvil 4054 being spaced apart from the elongate channel 4052, as seen in FIG. 29. When the end effector 4050 is in the open state, no force is applied to the tissue captured within the end effector 4050, as seen in the lower graph 4104.

As the closure ring 4056 moves toward the distal position $DP_{LC}$, represented by line 4110, the end effector transitions toward the clamped state, causing the closure force applied by the end effector, represented by line 4112, to increase. It should be understood, as seen in the graphs 4100, that line 4106 and line 4110 overlap and line 4108 and line 4112 overlap, and are, therefore, represented as single lines for the sake of simplicity. At $t_1$, the closure ring 4056 reaches an intermediate position $IP_{LC}$ that is intermediate the proximal position PP and the distal position $DP_{LC}$, which corresponds to the end effector 4050 being in a partially clamped state. As seen in the lower graph 4104, in the partially clamped state, the end effector 4050 applies a maximum closure force $FTC_{max}$ to the tissue. It should be understood that further advancement of the closure ring 4056 would result in an $FTC_{max}$ greater than what is represented in lower graph 4104.

In one aspect, a partially clamped state is defined as a state between the open state and the clamped state where the end effector makes initial contact with the tissue positioned therein. In one aspect, a partially clamped state is defined as a state where the anvil of the end effector is within a threshold distance of the elongate channel of the end effector. In one aspect, a partially clamped state is defined as a state wherein the closure trigger has moved a threshold amount toward the actuated state from the unactuated state. In one aspect, a partially clamped state is defined as a state wherein a firing member responsible for the closure of the end effector has moved a threshold linear distance.

In the intermediate position $IP_{LC}$, the control system halts advancement of the closure ring 4056. In various embodiments, the intermediate position $IP_{LC}$ corresponds to a position that is a threshold distance away from the proximal position PP. In various embodiments, the intermediate position $IP_{LC}$ corresponds to a positon where a threshold amount of force is applied to the tissue. In some embodiments, the threshold amount of force is stored in a memory, such as memory 1935, and is retrievable by the control system. In some embodiments, the threshold amount of force is user-provided at an input interface. In some embodiments, the intermediate position $IP_{LC}$ corresponds to a predefined distance up the ramp 4058 of the anvil 4054.

In the partially clamped state, the control system monitors the force applied by the anvil 4054 by interrogating, or receiving signals from, the sensors. In various embodiments, the sensors comprise force sensors positioned at the end effector to directly measure the force applied to the tissue. In various embodiments, the sensors comprise current sensors that measure an amount of current supplied to the closure motor to determine the closure force.

After the occurrence of an event, the control system controls the closure system to resume advancement of the closure ring 4056 toward the distal position $DP_{LC}$. In various embodiments, the event comprises a threshold amount of time elapsing from when the closure ring 4056 was halted. In various embodiments, the event comprises the control system detecting a decrease in the force applied by the anvil 4054. In various embodiments, the event comprises the control system detecting the force applied by the anvil 4054 dropping a threshold amount from the maximum closure force $FTC_{max}$.

As seen in the upper graph 4102 and the lower graph 4104, the control system continuously monitors the force applied by the end effector 4050 and discretely advances 4110 the closure ring 4056. Specifically, as seen at times $t_2$, $t_3$, $t_4$, and $t_5$ of the upper graph 4102, the control system discretely advances the closure ring such that the closure force 4112 applied by the end effector remains constant, or at least substantially constant. In one embodiment, the control system causes the closure system to drive 4110 the closure ring 4056 at $t_2$ such that the force 4112 remains at the $FTC_{max}$. Once the $FTC_{max}$ is achieved, the control system causes the closure ring 4056 to again halt advancement and the control system again monitors for an event, as described above, to continue advancement of the closure ring 4056, such as again at $t_3$ upon occurrence of an event. In various other embodiments, rather than discretely advancing the closure ring, the control system continuously moves the closure ring 4056 at a rate that results in the force 4112 applied by the end effector remaining constant, or at least substantially constant.

The control system continues the above-described halting and advancement of the closure ring 4056 until the closure ring 4056 reaches the distal position $DP_{LC}$, shown on the upper graph 4102 at $t_6$. Once in the distal position $DP_{LC}$ at $t_6$, the user can actuate the firing system, such as firing motor drive assembly 604, to drive a firing member, such as firing member 1900, with a motor, such as firing motor 602, to cut and deploy staples from a staple cartridge, such as staple cartridge 1301, positioned in the end effector 4050. In various embodiments, the control system can provide haptic, visual, audible, or any other suitable feedback, informing the clinician that the closure ring 4056 has reached the distal position $DP_{LC}$. In various embodiments, once the closure ring 4056 reaches the distal position $DP_{LC}$, the user can wait an amount of time prior to actuating the firing system, giving the end effector 4050 the opportunity to apply additional force to the tissue. In various other embodiments, the control system can require a threshold amount of time to transpire prior to enabling the firing system. In some embodiments, the control system can provide haptic, audible, or visual feedback once the threshold amount of time has transpired, informing the clinician that the firing system can be actuated.

Figure 33:
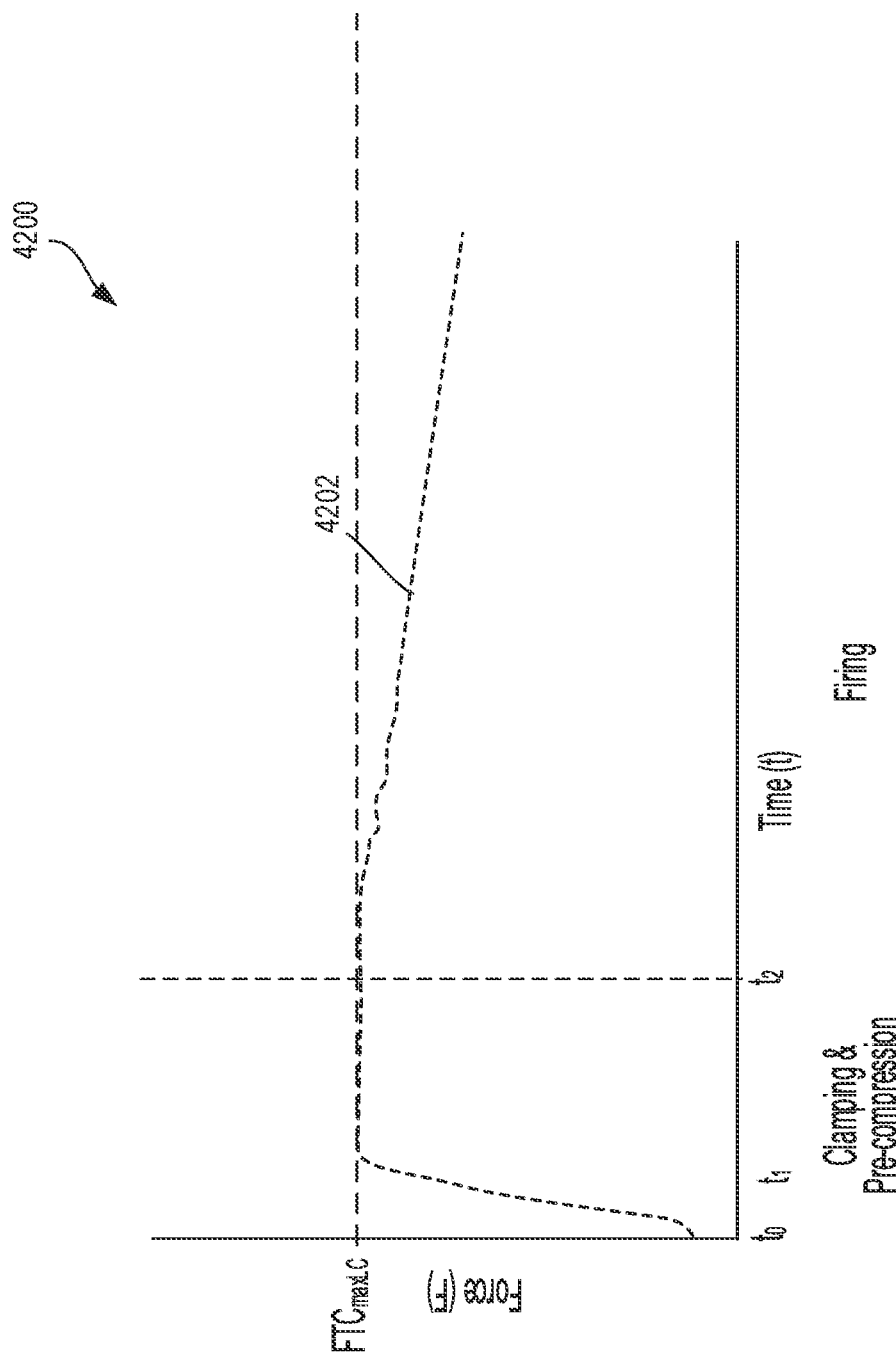
FIG. 33 illustrates a response profile from a clamping system utilizing a load control closure system, according to at least one aspect of the present disclosure.
Figure 34:
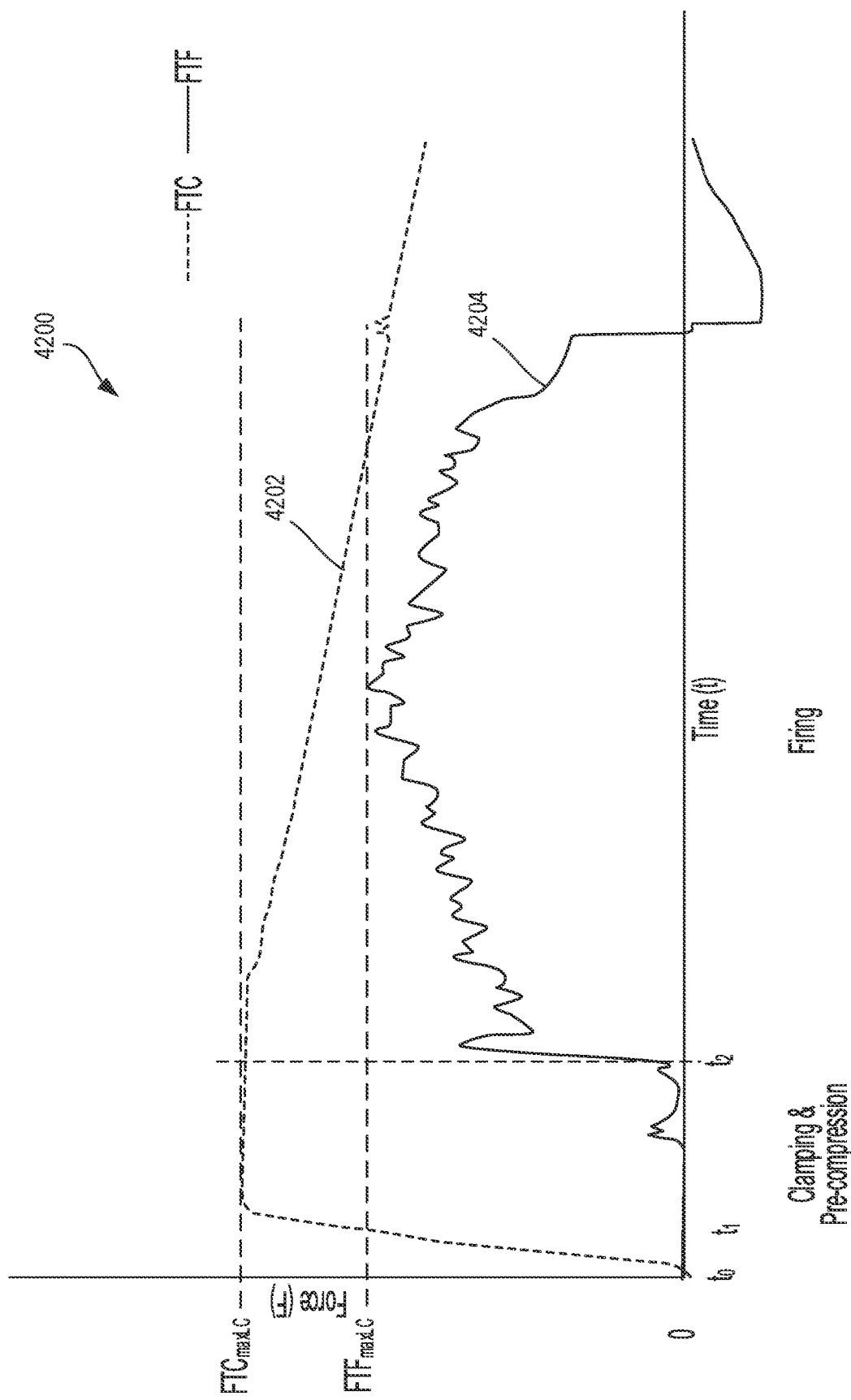
FIG. 34 illustrates a response profile from a clamping system utilizing a load control closure system, according to at least one aspect of the present disclosure.

Referring now to FIGS. 33 and 34, a response profile 4200 from a clamping system, such clamping system utilizing closure ring 4056, utilizing load control closure is provided. At $t_0$, the end effector, such as end effector 4050, begins in an open state, during which time the closure force 4202 applied by the end effector to the tissue is zero. From $t_0$ to $t_1$, the end effector is transitioned toward the clamped state by a closure member, such as the closure ring 4056, which causes a gradual increase in the closure force 4202. At $t_1$, the closure member reaches an intermediate closure stroke position, such as intermediate position $IP_{LC}$, corresponding to the end effector reaching a partially clamped state. In the partially clamped state, the closure force 4202 reaches a maximum closure force $FTC_{max}$.

As seen in FIGS. 33 and 34 and as described above, once the maximum amount of force $FTC_{maxLC}$ is applied to the tissue at $t_1$, the closure member can be discretely, or continuously, advanced such that the maximum amount of force $FTC_{maxLC}$ is maintained, or at least substantially maintained. At $t_2$, the closure member reaches its distal position, such as distal position $DP_{LC}$, and the firing system is actuated. As seen in FIG. 34, the force to fire 4204 the firing drive of the surgical instrument reaches a force $FTF_{maxLC}$ that is less than that of the $FTC_{max}$, as well as being less than the force to fire $FTF_{maxPC}$ for a position control closure system, as described above and shown in FIG. 27. Accordingly, the load control closure system reduces the force to fire necessary by the firing system, which can prolong the life of the firing system. The load control closure system brings the tissue to its thinnest, stable state as quickly, uniformly, and repeatably as possible and results in better surgical outcomes.

As described above, the load control closure system utilizing end effector 4050 utilizes a closure ring 4056 that is discretely, or continuously, advanced such that the load provided by the end effector can be maintain at a maximum value for a longer period of time prior to the actuation of the firing system. In various other embodiments, the present disclosure provides a load control closure system that discretely, or continuously, advances a closure member during at least a portion of the firing stroke to maintain a constant, or at least substantially constant, closure load during at least a portion of the firing stroke.

Referring again to the upper graph 4102 of FIG. 32, at $t_0$, the closure ring 4056 begins in the proximal positon PP, corresponding to the end effector 4050 being in the open state, i.e., the anvil 4054 being spaced apart from the elongate channel 4052, as seen in FIG. 29. When the end effector 4050 is in the open state, no force is applied to the tissue captured within the end effector 4050, as seen in the lower graph 4104.

As the closure ring 4056 moves toward the distal position $DP_{CC}$, represented by line 4114, the end effector transitions toward the clamped state, causing the closure force applied by the end effector, represented by line 4116, to increase. It should understood, as seen in the graphs 4100, that line 4114 overlaps lines 4110, 4106 and line 4116 overlaps lines 4112, 4108, and are, therefore, represented as a single line for the sake of simplicity. At $t_1$, the closure ring 4056 reaches an intermediate position $IP_{CC}$ that is intermediate the proximal position PP and the distal position $DP_{CC}$, which corresponds to the end effector 4050 being in a partially clamped state. As seen in the lower graph 4104, in the partially clamped state, the end effector 4050 applies a maximum closure force $FTC_{max}$ to the tissue. It should be understood that further advancement of the closure ring 4056 would result in an $FTC_{max}$ greater than what is represented in lower graph 4104.

In the intermediate position $IP_{CC}$, the control system halts advancement of the closure ring 4056. In various embodiments, the intermediate position $IP_{CC}$ corresponds to a position that is a threshold distance away from the proximal position PP. In various embodiments, the intermediate position $IP_{CC}$ corresponds to a positon where a threshold amount of force is applied to the tissue. In some embodiments, the threshold amount of force is stored in a memory, such as memory 1935, and is retrievable by the control system. In some embodiments, the threshold amount of force is stored in a look-up table in the memory or is a retrievable value from the memory. In some embodiments, the threshold amount of force is user-provided at an input interface. In some embodiments, the intermediate position $IP_{CC}$ corresponds to a predefined distance up the ramp 4058 of the anvil 4054.

In the partially clamped state, the control system monitors the force applied by the anvil 4054 by interrogating, or receiving signals from, the sensors. In various embodiments, the sensors comprise force sensors positioned at one or more portions of the closure system and/or the end effector to measure the force applied by the end effector to the tissue. In various embodiments, the sensors comprise current sensors that measure an amount of current supplied to the closure motor to determine the closure force.

After the occurrence of an event or a condition, as referenced above, the control system controls the closure system to resume advancement of the closure ring 4056 toward the distal position $DP_{CC}$. In various embodiments, the event comprises a threshold amount of time elapsing from when the closure ring 4056 was halted. In various embodiments, the event comprises the control system detecting a decrease in the force applied by the anvil 4054. In various embodiments, the event comprises the control system detecting the force applied by the anvil 4054 dropping a threshold amount from the maximum closure force $FTC_{max}$.

As seen in the upper graph 4102 and the lower graph 4104, the control system continuously monitors the force applied by the end effector 4050 and discretely advances 4114 the closure ring 4056. Specifically, as seen at times $t_2$ through $t_1o$ of the upper graph 4102, the control system discretely advances the closure ring such that the closure force 4116 applied by the end effector remains constant, or at least substantially constant. It should be understood that line 4114 and line 4110 overlap and line 4116 and line 4112 overlap between $t_2$ and $t_7$ and are, therefore, represented as single lines for simplicity.

In one embodiment, the control system causes the closure system to drive 4114 the closure ring 4056 at $t_2$ such that the force 4116 remains at the $FTC_{max}$. Once the $FTC_{max}$ is achieved, the control system causes the closure ring 4056 to again halt advancement and the control system again monitors for an event, as described above, to continue advancement of the closure ring 4056, such as again at $t_3$ upon occurrence of an event. In various other embodiments, rather than discretely advancing the closure ring, the control system continuously moves the closure ring at a rate that results in the force 4112 applied by the end effector tp remain constant, or at least substantially constant.

The control system continues the above-described halting and advancement of the closure ring 4056 until the firing system is actuated at $t_6$, which is a time prior to the closure ring reaching its distal position $DP_{CC}$. Once the firing system has been actuated, the control system continues to advance the closure ring 4056 toward the distal position $DP_{CC}$, as described above, such that the closure system and the firing member of the firing system are operating simultaneously. The continued advancement of the closure ring 4056 maintains the force 4116 applied by the end effector at the $FTC_{max}$ during at least a portion of the firing stroke.

Figure 35:
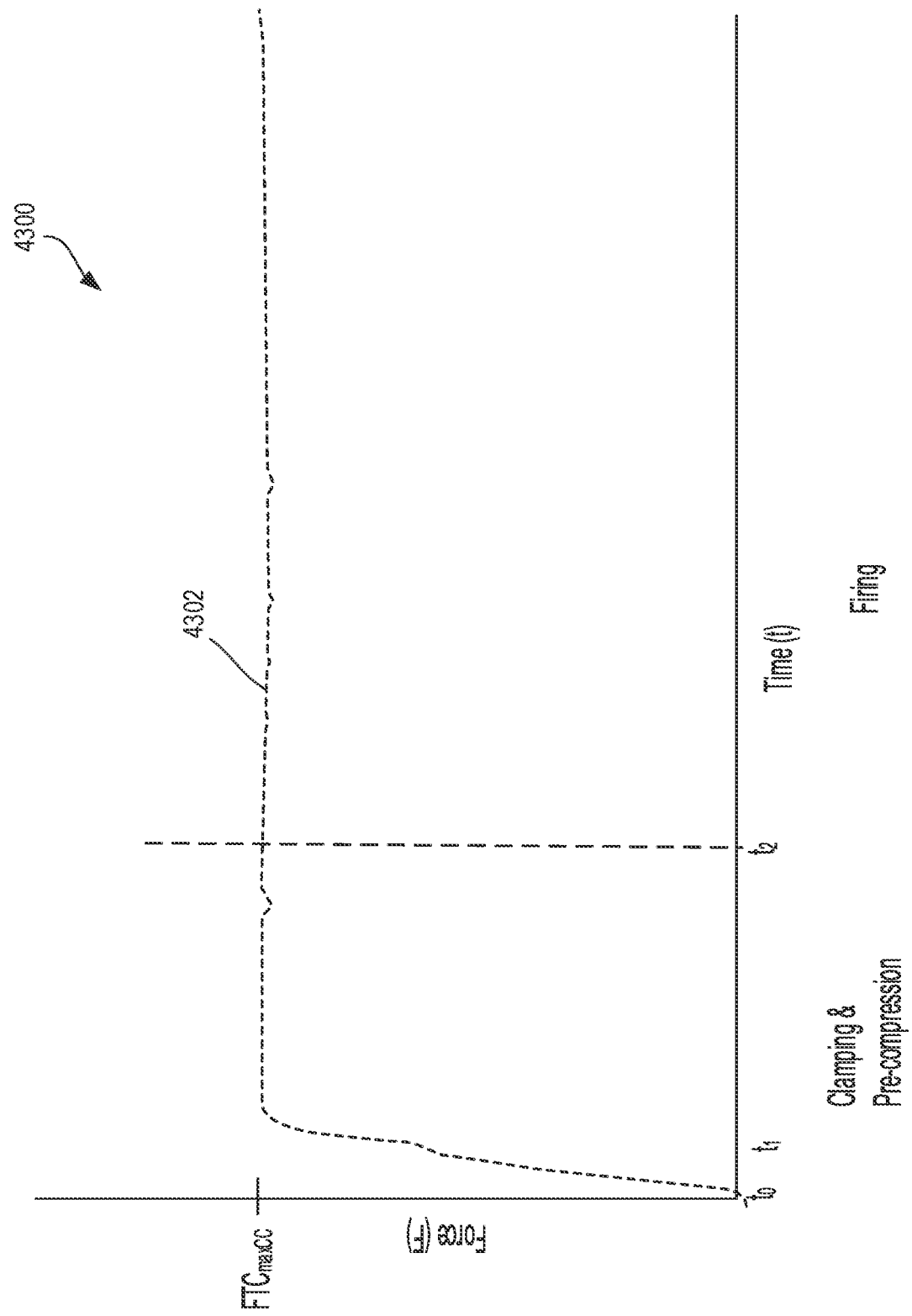
FIG. 35 illustrates a response profile from a clamping system utilizing a load control closure system, according to at least one aspect of the present disclosure.
Figure 36:
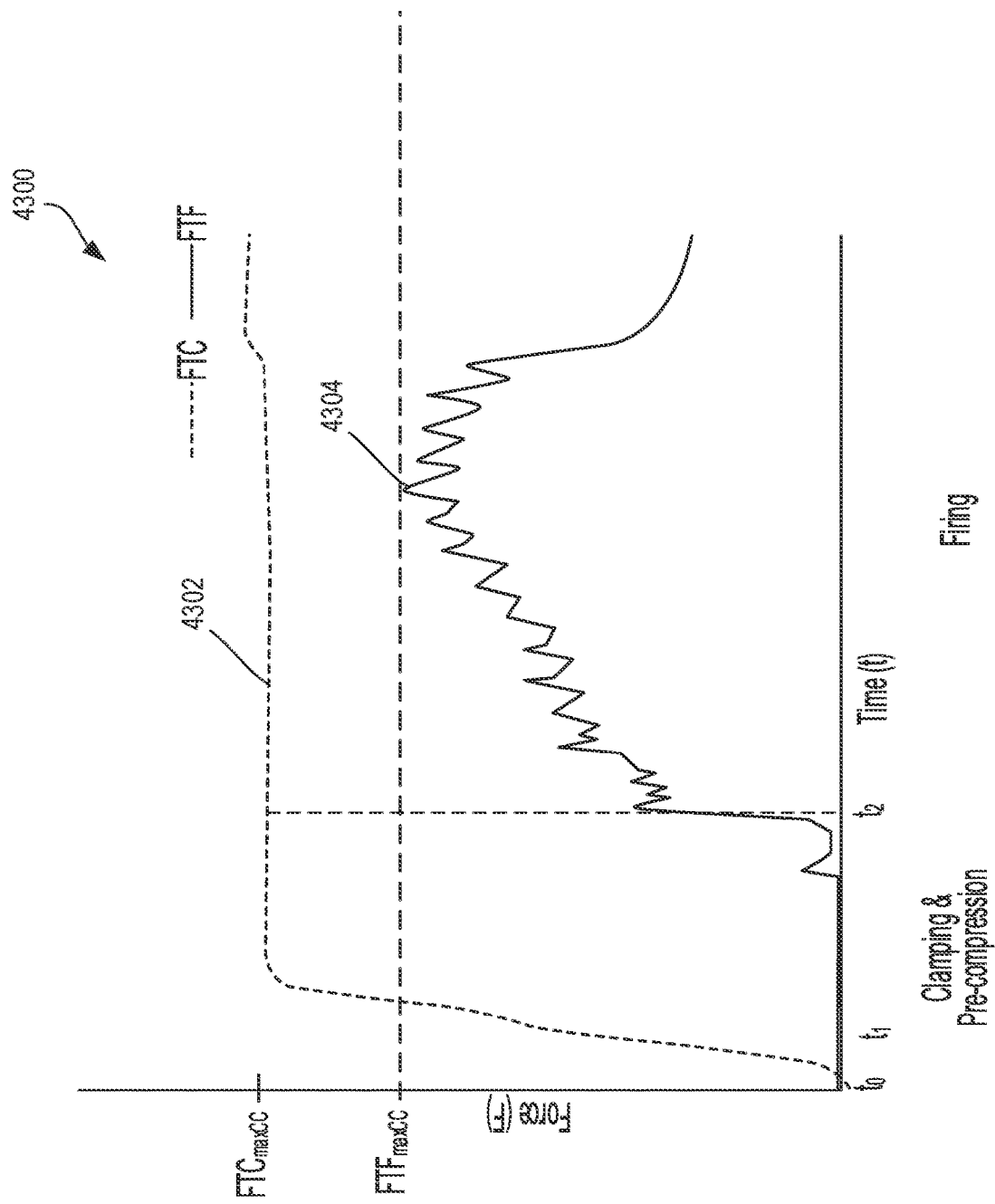
FIG. 36 illustrates a response profile from a clamping system utilizing a load control closure system, according to at least one aspect of the present disclosure.

Referring now to FIGS. 35 and 36, a response profile 4300 from a clamping system, such clamping system utilizing closure ring 4056, utilizing load control closure during a portion of the firing stroke is provided, according to at least one aspect of the present disclosure. At $t_0$, the end effector, such as end effector 4050, begins in an open state, during which time the closure force 4302 applied by the end effector to the tissue is zero. From $t_0$ to $t_1$, the end effector is transitioned toward the clamped state by a closure member, such as closure ring 4056, which causes a gradual increase in the closure force 4302. At $t_1$, the closure member reaches an intermediate closure stroke position, such as intermediate position $IP_{CC}$, corresponding to the end effector reaching a partially clamped state. In the partially clamped state, the closure force 4302 reaches a maximum closure force $FTC_{max}$.

As seen in FIGS. 35 and 36 and as described above, once the maximum amount of force $FTC_{maxCC}$ is applied to the tissue at $t_1$, the closure member can be discretely, or continuously, advanced such that the maximum amount of force $FTC_{maxCC}$ is maintained. At $t_2$, the firing system is actuated. As shown in FIGS. 35 and 36, the closure member continues to advance towards its distal position, such as $DP_{CC}$, to maintain the maximum closure force $FTC_{maxCC}$ to the tissue during at least a portion of the firing stroke. As seen in FIG. 36, the force to fire 4304 the firing drive of the surgical instrument reaches a force $FTF_{maxCC}$ that is less than that of the $FTC_{maxCC}$, as well as is less than the force to fire $FTF_{maxPC}$ for a position control closure system, as described above and shown in FIG. 27. In various embodiments, the continued advancement of the closure member during at least a portion of the firing stroke can also result in a force to fire profile that is different than the force to file profile for load control closure systems where the closure member reaches its distal position prior to the actuation of the firing system. Accordingly, the load control closure system reduces the force to fire necessary by the firing system, which can prolong the life of the firing system. The load control closure system brings the tissue to its thinnest, stable state as quickly, uniformly, and repeatably as possible, and results in better surgical outcomes.

Figure 37:
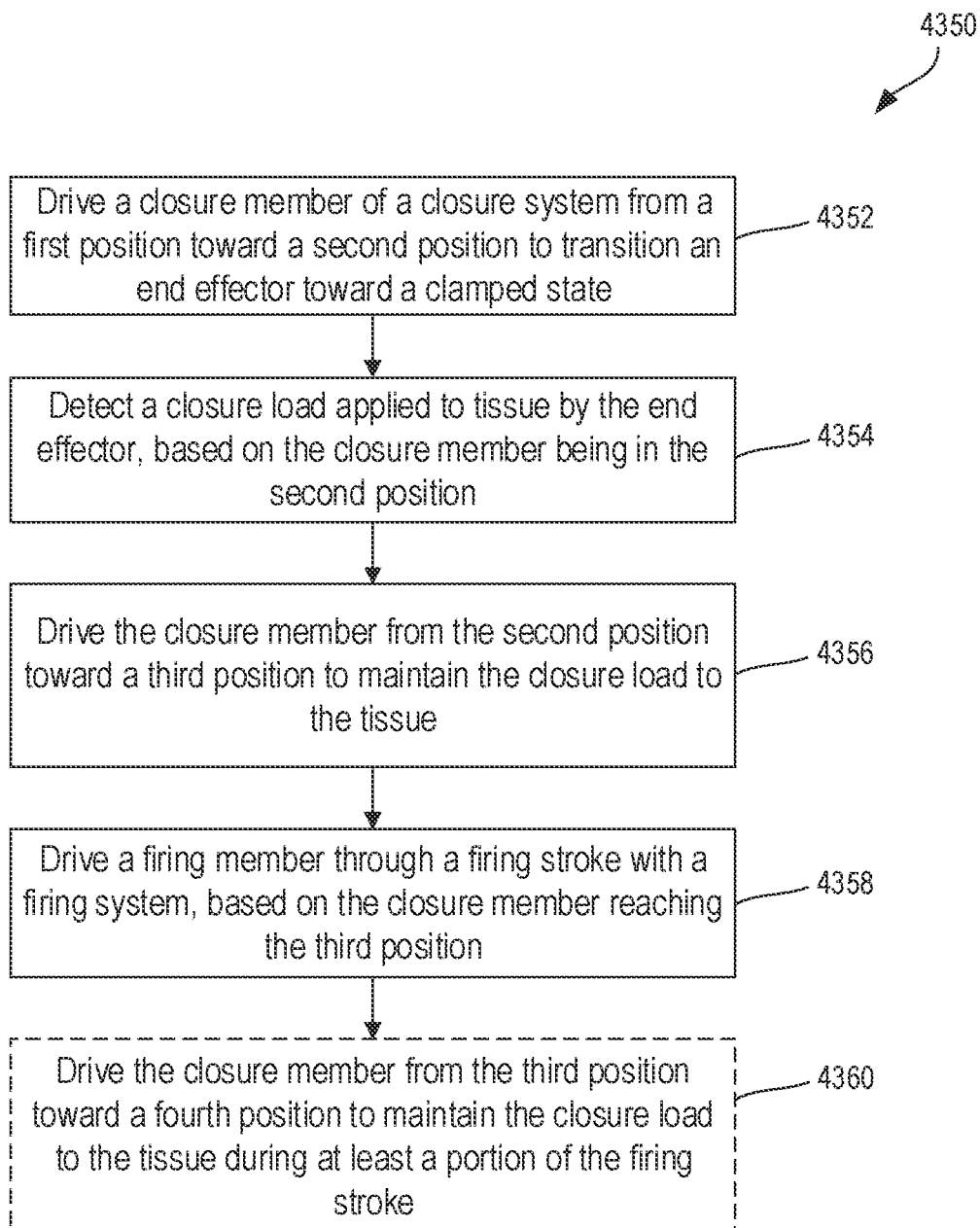
FIG. 37 illustrates a method for controlling a surgical instrument, according to at least one aspect of the present disclosure.

Referring now to FIG. 37, a method 4350 for controlling a surgical instrument is provided, according to at least one aspect of the present disclosure. The method 4350 comprises driving 4352 a closure member of a closure system from a first position toward a second position to transition an end effector toward a clamped state. In some embodiments, a control system, such as controller 620, can control a motor, such as closure motor 603, of a motor-powered closure system, such as closure motor drive assembly 605, to drive a closure member, such as closure ring 4056, from a first position, such as the proximal position PP, toward a second position, such as intermediate position $IP_{LC}$ or intermediate position $IP_{CC}$. Driving the closure member can cause an end effector, such as end effector 4050, to transition toward a clamped state to capture and apply force to tissue within the end effector.

The method 4350 further comprises detecting 4354 a closure load applied to tissue by the end effector, based on the closure member being in the second position. In various embodiments, the control system detects a force applied by the end effector utilizing force sensors or current sensors with the closure member in the second position. In some embodiments, the closure force can be a maximum closure force to be applied to the tissue, as described elsewhere herein.

The method 4350 further comprises driving 4356 the closure member from the second position toward a third position to maintain the closure load to the tissue. In various embodiments, as described elsewhere herein, the control system can control the closure system to discretely, or continuously, move the closure member, such as closure ring 4056, so as to maintain a constant, or least substantially constant, closure load to the tissue.

The method 4350 further comprises driving 4358 a firing member through a firing stroke with a firing system, based on the closure member reaching the third position. In various embodiments, as described elsewhere herein, the control system can control a motor, such as firing motor 602, of a firing system, such as firing motor drive assembly 604, to drive a firing member, such as firing member 1900, through a firing stroke. In some embodiments, driving the firing member causes staples to be deployed from a staple cartridge, such as staple cartridge 1301. In various embodiments, the third position of the closure member comprises a distal position of the closure member, such as $DP_{LC}$. In various embodiments, the third position of the closure member comprises a position that is proximal to its distal position, such as distal position $DP_{CC}$.

The method 4350 optionally further comprises driving 4360 the closure member from the third position toward a fourth position to maintain the closure load to the tissue during at least a portion of the firing stroke. In various embodiments, as described above, when the firing system is actuated, the closure member can be in a position that is proximal to its distal position, such as distal position $DP_{CC}$. Accordingly, the control system can continue to control the closure system to discretely, or continuously, advance the closure member during at least a portion of the firing stroke to maintain the closure load constant, or at least substantially constant. In various embodiments, the fourth position corresponds to the distal position $DP_{CC}$. In various embodiments, the fourth position corresponds to a position that is proximal to the distal position $DP_{CC}$. In various embodiments, the closure member is moving during the entirety of the firing stroke. In some embodiments, the closure member and the firing member complete their respective strokes at the same, or at least substantially the same, time. In various embodiments, the closure member finishes its closure stroke prior to the firing member completing its firing stroke. In various embodiments, the firing member finishes its firing stroke prior to the closure member completing its closure stroke.

During a closure stroke of a surgical instrument, it is desirable for all tissue layers to be captured within the jaws of the end effector such that all of the tissue layers are captured within the staple line for any given transection. During the closure of the end effector, excessive clamping speed can cause the tissue layers to be pushed out of the end effector, ultimately resulting in a non-optimal staple line seal. This tissue flow during clamping can also cause the desired transection location on the tissue to shift within the end effector, such as pushing tissue out of the distal tip of the end effector, ultimately resulting in additional firings of the surgical instrument being required. Managing this clamping speed can help maintain the desired transection location of the tissue within the end effector.

In various embodiments, a surgical instrument including an end effector and a clamping system, such as closure motor drive assembly 605, can be utilized to clamp tissue during a clamping stroke. Sensors, such as any suitable sensors described elsewhere herein, can be utilized to monitor the amount of clamping force applied by the end effector during the clamping stroke. During the clamping process, a control system, such as controller 620, coupled to the sensors can monitor the load curve, predict an expected tissue load, and compare the predicted tissue load to a closure load threshold.

In some embodiments, if the predicted load is expected to reach or exceed the closure load threshold, the control system causes the closure system to slow the closure speed, allowing for relaxation of the tissue during clamping and maintaining the desirable tissue in the jaws of the end effector. In various embodiments, the closure load threshold is stored in a memory, such as memory 624, and is retrievable by the control system. In various embodiments, the closure load threshold is user defined by a user at an input interface.

In some embodiments, if the predicted load is expected to reach or exceed the closure load threshold, the control system causes the closure system to intermittently pause the clamping stroke, allowing for relaxation of the tissue during clamping and maintaining the desirable tissue in the jaws of the end effector. In various embodiments, if the predicted load is expected to reach or exceed the closure load threshold, the control system causes the closure system to intermittently pause and slow the clamping stroke, allowing for relaxation of the tissue during clamping and maintaining the desirable tissue in the jaws of the end effector.

In some embodiments, when the control system causes the end effector to pause its clamping stroke, the control system causes the jaws to maintain the clamp force for a period of time. In various embodiments, the period of time is a predefined period of time. In various embodiments, the period of time is a variable period of time. In some embodiments, the variable period of time is based on a rate of change of the clamping load. In some embodiments, the variable period of time is based on a predicted amount that the closure load was expected to exceed the closure load threshold, such as at the time of the closure stroke completing. In various embodiments, the variable period of time is based on a gap between the anvil and the elongate channel of the end effector. In various embodiments, the variable period of time is based on a type of staple cartridge removably positioned in the end effector. In various embodiments, the variable period of time is based on a magnitude of the closure load. In various embodiments, the variable period of time is based on an amount of time that has elapsed since the end effector first made contact with the tissue during the clamping stroke. In various embodiments, the variable period of time is based on an elapsed time since the user actuated a secondary closure system of the surgical instrument.

In various embodiments, the period of time is an adaptive period of time. In various embodiments, the adaptive period of time is based on a location of the anvil relative to the elongate channel. In various embodiments, the adaptive period of time is based on the success and failures of previous clamping strokes. In some embodiments, the success and failures of previous clamping strokes is stored in a memory, such as memory 624, and is retrievable by the control system in order to set the variable period of time. In various embodiments, the adaptive period of time is based on techniques used by the clinician for the manual operation or positioning of the end effector. In various embodiments, the adaptive period of time is based on outputs from a surgical hub, such as the surgical hub described in U.S. Patent Application Publication No. 2020/0078070, which is hereby incorporated by reference in its entirety herein. In various embodiments, the adaptive period of time is based on outputs from a multispectral imaging system, such as the imaging system described in U.S. Pat. No. 11,369,366, which is hereby incorporated by reference in its entirety herein.

Once the predefined period of time has elapsed, the control system can cause the end effector to reattempt its clamping stroke at a speed to manage the tissue flow. In various other embodiments, the speed is a set speed. In various embodiments, the speed is a stepped speed. In various embodiments, the speed is a reduced speed compared to the speed prior to the end effector pausing its clamping stroke. In various embodiments, the speed is the same speed compared to the speed prior to the end effector pausing its clamping stroke.

Figure 38:
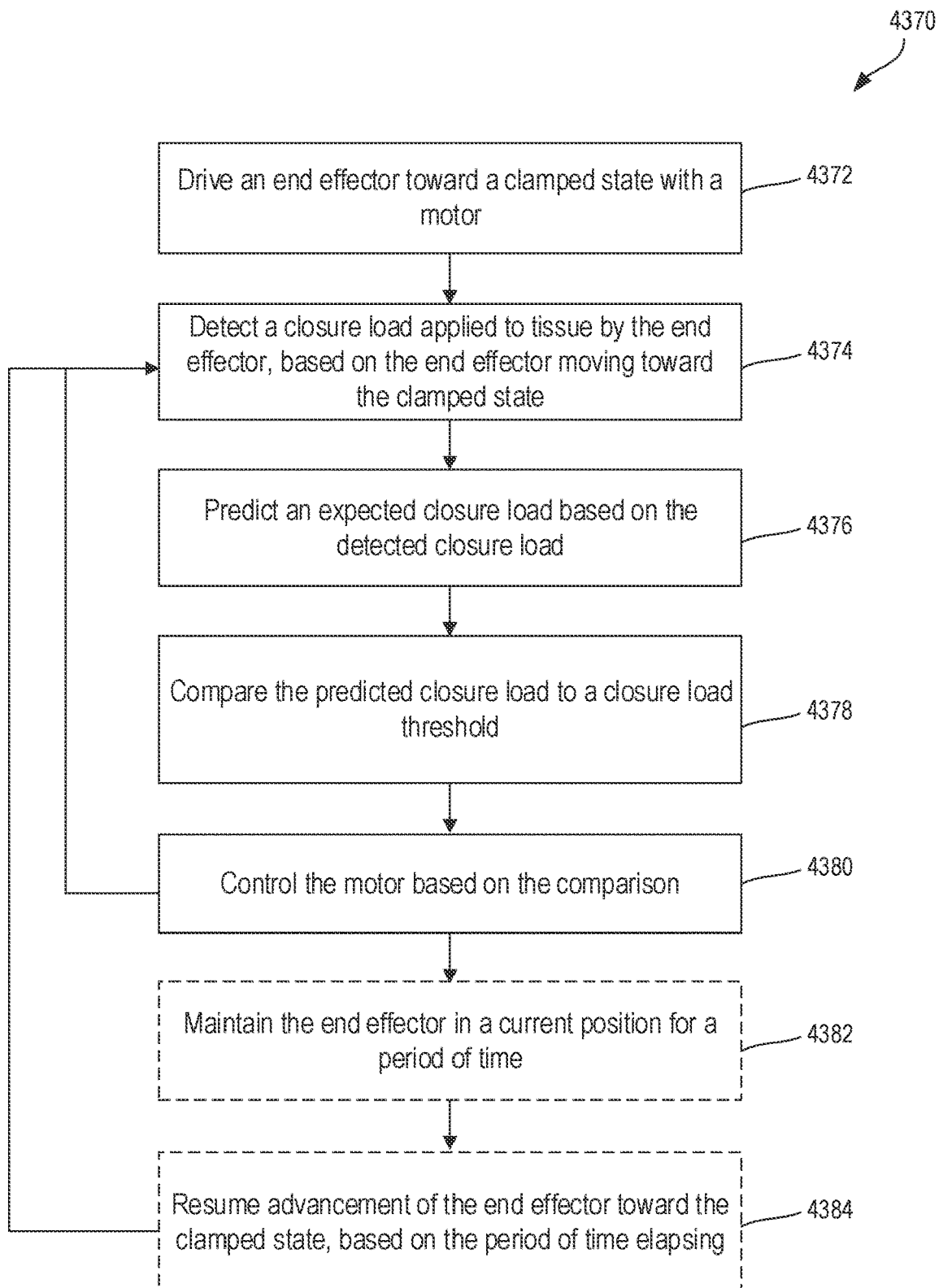
FIG. 38 illustrates a method for controlling a surgical instrument, according to at least one aspect of the present disclosure.

Referring now to FIG. 38, a method 4370 for controlling a surgical instrument is provided, according to at least one aspect of the present disclosure. The method 4370 comprises driving 4372 an end effector toward a clamped state with a motor. In various embodiments, a control system, such as controller 620, transmits a control signal to a motor, such as closure motor 603, to cause a closure system, such as closure motor drive assembly 605, to drive an end effector, such as end effector 1300, toward a clamped state.

The method 4370 further comprises detecting 4374 a closure load applied to tissue by the end effector, based on the end effector moving toward the clamped state. In various embodiments, the control system detects the closure load the end effector applies to tissue using sensors, such as any suitable sensors described elsewhere herein. In some embodiments, the sensors comprise force sensors that detect an amount of force the end effector applies to the tissue. In some embodiments, the sensors comprise current sensors that sense an amount of current applied to the motor.

The method 4370 further comprises predicting 4376 an expected closure load based on the detected closure load. In various embodiments, the control system can predict an expected closure load based on a rate of change of the closure load. In various embodiments, the control system can predict an expected closure load based on a trajectory of the closure load. In various embodiments, the control system can predict an expected closure load based on various sensor readings obtained from the sensors.

The method 4370 further comprises comparing 4378 the predicted closure load to a closure load threshold. In some embodiments, the control system can compare the predicted closure load to the closure load threshold to determine if the predicted closure load will reach or exceed the closure load threshold. In various embodiments, the control system can determine if the predicted closure load will reach or exceed the closure load threshold prior to the end effector reaching the clamped state. In various embodiments, the closure load threshold is stored in a memory, such as memory 624, and is retrievable by the control system. In various embodiments, the closure load threshold is user defined by a user at an input interface.

The method 4370 further comprises controlling 4380 the motor based on the comparison. In various embodiments, based on the results of the comparison, the control system can transmit a control signal to the motor. In some embodiments, if the predicted closure load is expected to reach or exceed the closure load threshold prior to completion of the closure stroke, the control system transmits a control signal to the motor. In some embodiments, if the predicted closure load is expected to reach or exceed the closure load threshold prior to the anvil reaching a threshold distance from the elongate channel, the control system transmits a control signal to the motor. In some embodiments, the control signal decreases the speed of the motor, thereby slowing the rate at which the end effector transitions to the clamped state. In some embodiments, the control signal pauses the motor, thereby halting the end effector from transitioning to the clamped state. In various embodiments, if the predicted closure load is expected to reach or exceed the closure load threshold, the control system can allow the end effector to continue applying a load to the tissue. In such embodiments, the control system can predict a time in which the closure load threshold will be exceeded and, accordingly, control the motor at the predicted time. Accordingly, the control system predicts and plans for when a closure load threshold will be reached or exceeded, rather than being reactive when the control system detects the closure load threshold being exceeded. Such planning and predicting allows the control system to devise a suitable response before the closure load threshold is reached or exceeded.

In various embodiments, based on the control system decreasing the speed of the motor, the control system continues to predict an expected closure load and compare the predicted closure load to the closure load threshold as the end effector transitions to the clamped state. If the control system again detects that the predicted closure load is expected to reach or exceed the closure load threshold prior to the end effector reaching the clamped state, the control system further decreases the speed of the motor such that the predicted closure load stays below the closure load threshold. In various other embodiments, the control system pauses the motor and resumes movement of the end effector toward the clamped state after a period of time. Accordingly, the method 4370 is an iterative method to maintain the tissue within the end effector.

The method 4370 further comprises maintaining 4382 the end effector in a current position for a period of time. In various embodiments, when the control system transmits a control signal to the motor to halt the end effector from transitioning toward the clamped state, the control system maintains the jaws of the end effector in its current position for a period of time. In various embodiments, the period of time comprises a predefined period of time. In various embodiments, the period of time comprises a variable period of time, as described elsewhere herein. In various embodiments, the period of time comprises an adaptive period of time, as described elsewhere herein.

The method 4370 further comprises resuming 4384 advancement of the end effector toward the clamped state, based on the period of time elapsing. In various embodiments, after the period of time has elapsed, the control system causes the motor to resume advancement of the end effector toward the clamped state utilizing the closure drive system.

In various embodiments, similar to above, after the control system resumes advancement of the end effector toward the clamped state, the control system continues to predict an expected closure load and compare the predicted closure load to the closure load threshold as the end effector transitions to the clamped state. If the control system again detects that the predicted closure load is expected to reach or exceed the closure load threshold prior to the end effector reaching the clamped state, the control system again halts the end effector from transitioning toward the clamped state and waits a period of time. In various other embodiments, the control system slows the motor if the control system has already paused and resumes movement of the end effector toward the clamped state. Accordingly, the method 4370 is an iterative method to maintain the tissue within the end effector.

Figure 39:
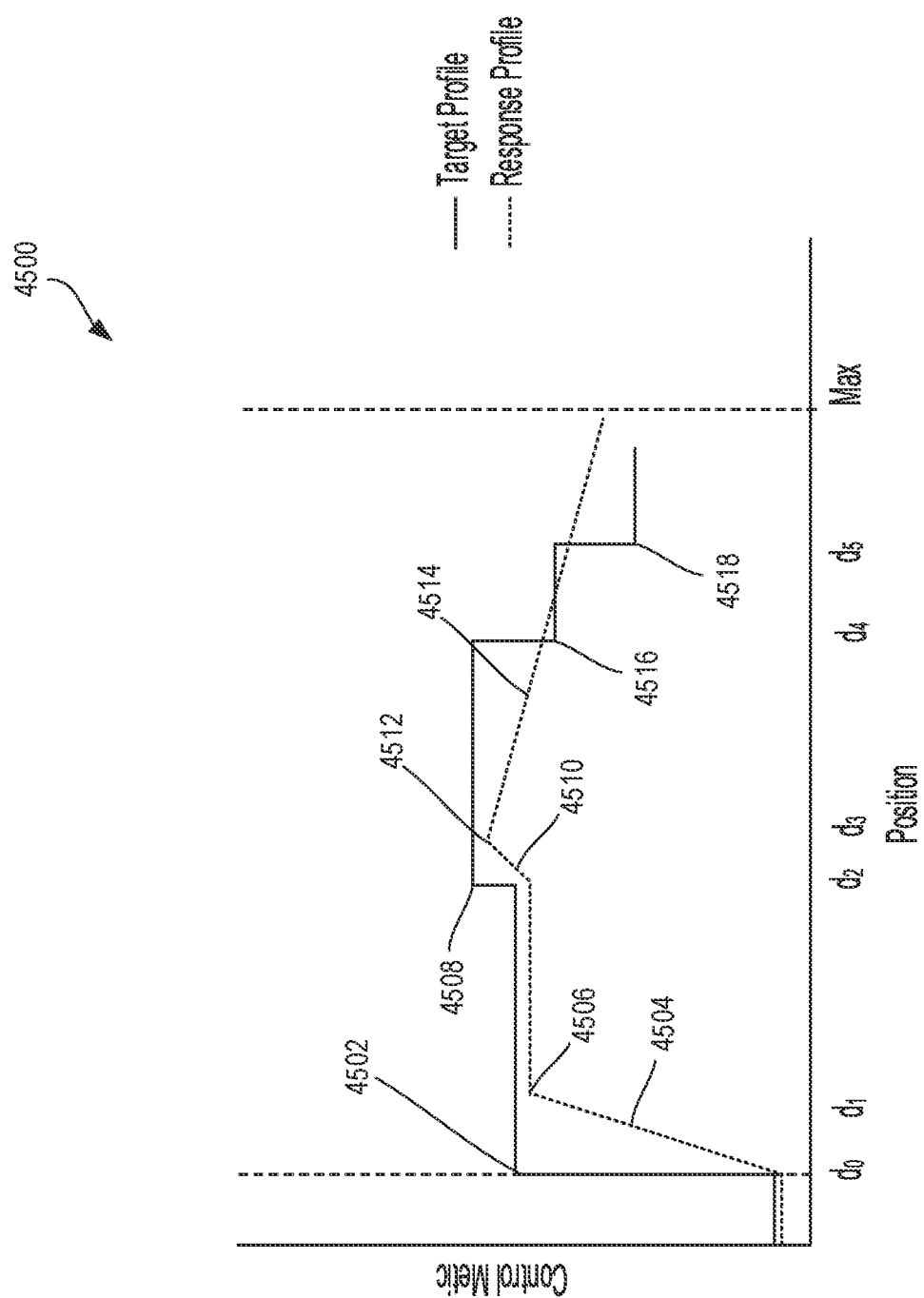
FIG. 39 illustrates a target and response signal profiles of a motor, according to at least one aspect of the present disclosure.

Referring now to FIG. 39, a graph 4500 illustrating a target and response profile for a motor is provided, according to at least one aspect of the present disclosure. The graph 4500 illustrates a control metric against a position of a closure member, as will be described in more detail below. In some embodiments, the control metric comprises a speed of the motor. In some embodiments, the control metric comprises a PWM of the motor.

In operation, a control system, such as controller 620, sets a target control metric for a motor, such as any number of motors described elsewhere herein, to drive a function of the surgical instrument. In various embodiments, the motor comprises a firing motor, such as firing motor 602, that drives a firing member, such as firing member 1900, through a firing stroke. In various embodiments, the motor comprises a closure motor, such as closure motor 603, that drives a closure member, such as closure ring 4056, through a closure stroke.

As shown in FIG. 39, at position $d_0$ of a firing member, such as an unfired position thereof, the control system sets a first target control metric 4502 of the motor. In response to the first target control metric 4502, the motor ramps up 4504 toward the first target control metric 4502, ultimately reaching a first response control metric 4506, less than the first target control metric 4502, at position $d_1$ of the firing stroke of the firing member. The control system maintains the first target control metric 4502 of the motor until the firing member reaches $d_2$ of the firing stroke, at which point the control system sets a second target control metric 4508 of the motor. In response to the second target control metric 4508, the motor ramps up 4510 toward the second target control metric 4508, ultimately reaching a second response control metric 4512 less that the second target control metric 4508, at position $d_3$ of the firing stroke of the firing member.

Owing to various external factors, such as frictional losses of the system and/or thick tissue positioned within the end effector of the surgical instrument, the response control metric of the firing member ramps down 4514 despite the control system maintaining the second target control metric 4508. In response to the downward slopping response profile, in order to optimize the system and not drive the motor at a target control metric that it is unable to achieve, the control system sets diminishing target control metrics 4516, 4518 at positions $d_4$ and $d_5$ of the firing stroke, respectively. The reductions in target control metrics prevent the motor from overworking. Accordingly, the control system dynamically adjusts the target control metrics to more suitable target control metrics, based on the response profile of the motor.

During the foregoing setting of target profiles to drive the motor, any number of sensors can be utilized by the control system in order to determine the actual response profile of the motor. In some embodiments, analog signals indicative of the response profile can be fed back to a processor, such as processor 622, of the control system in order to make the necessary adjustments to the target control metrics. Upon receipt of the analog signal, the processor converts the analog signal to a digital signal using an integral A/D converter such that the processor can process the signal indicative of the response profile. In one aspect, servo motors controlled by the processor must utilize digital signals and will not work with analog signals. These A/D conversions within the processor, however, take computing cycles and resources that the processor could deploy elsewhere, thus limiting a speed at which the processor operates. Accordingly, it is desirable to feed a digital signal to the processor in order to allow the processor to focus its resources on other tasks.

In various embodiments, an A/D converter is placed upstream of the processor, such as prior to the input of the processor. The upstream A/D converter receives any number of analog signals from sensors through the surgical instrument and converts these signals to digital signals. These digital signals are fed into the processor, allowing the processor to make necessary adjustments without needing to allocate bandwidth to perform the A/D conversion itself.

Figure 40:
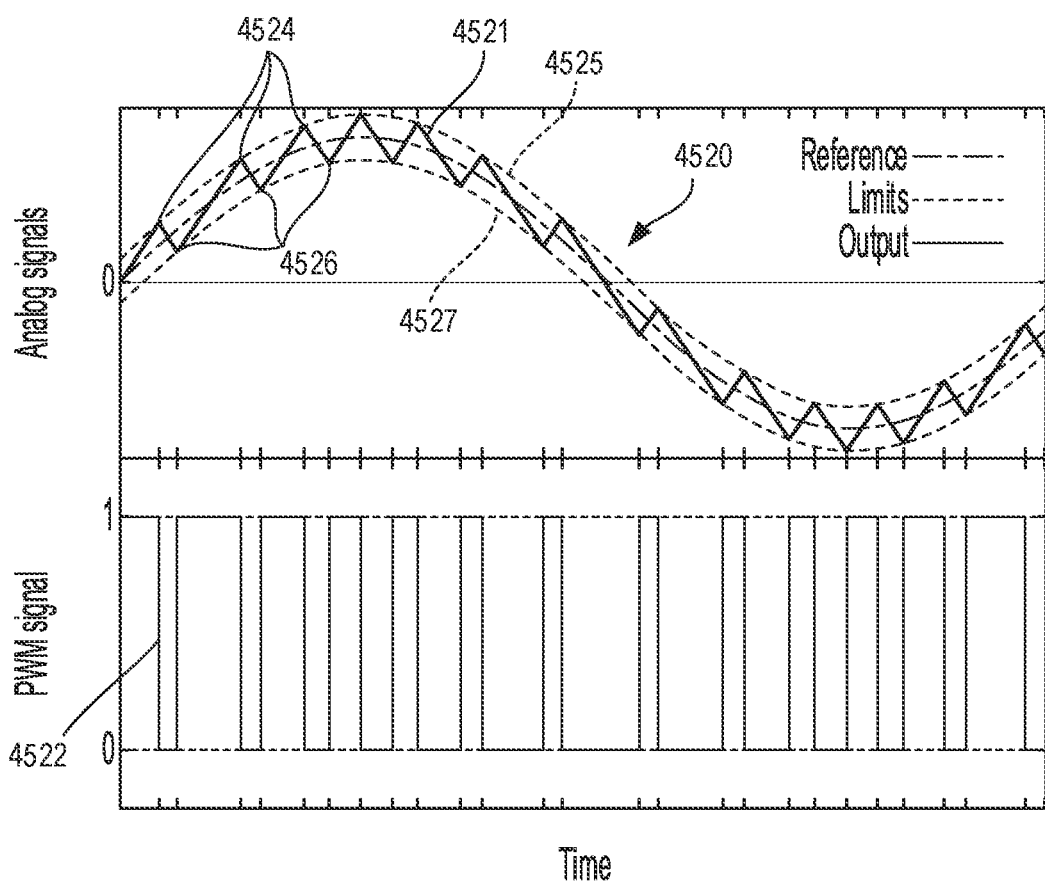
FIG. 40 illustrates the conversion of an analog signal to a PWM digital signal, according to at least one aspect of the present disclosure.

In some embodiments, the input signal to the A/D converter comprises a ramped analog signal 4520, such as is shown in FIG. 40. In various embodiments, the A/D converter converts the analog signal 4520 to a PWM digital signal 4522 according to the peaks 4524 and valleys 4526 of the output signal 4521 of the analog signal 4520 reaching limits 4525, 4527 that bind the output signal 4521. As shown in FIG. 40, the input signal to the A/D converter transitions low when a peak 4524 reaches the upper limit 4525 and transitions high when a valley 4526 reaches the lower limit 4527. Furthermore, the length of the PWM signal is controlled according to the elapsed time between peaks 4524 and valleys 4526.

In various embodiments, the analog signal fed to the A/D converter comprises an analog speed signal. In some embodiments, the analog speed signal is indicative of the speed of the motor. The A/D converter converts this signal to a digital signal and feeds the converted signal to the processor. In various embodiments, the analog speed signal can be generated using 1-wire tach speed sensing. In some embodiments, the 1-wire tach speed sensing measures the speed of the shaft of the motor. In various embodiments, the analog speed signal is generated by using a varistor that can monitor the voltage spikes applied to the motor. In various embodiments, the analog speed signal is generated using PWM angle-based sensors that determine the rate of change of the speed of the motor. In various embodiments, the analog speed signal is generated using a raw signal from a sensor with a comparator circuit that can be used to determine the speed of the motor.

In various embodiments, a resistive slide sensor is placed in one or both of the anvil, such as anvil 2000, and the elongate channel, such as elongate channel 1310, or an end effector, such as end effector 1300, to determine the relative and/or absolute position of a firing member, such as firing member 1900, during a firing stroke. Based on the sensed position and a timer, an analog signal indicative of the speed of the firing member can be generated and fed to the A/D converter. In various embodiments, the resistive slide sensor (s) determine a rate of change in the resistance to generate a signal indicative of the speed of the firing member. In some embodiments, a slope detector is utilized to determine the rate of change. In some embodiments, a differentiator amplifier is utilized to determine the rate of change.

In various embodiments, an analog signal indicative of the speed of the motor is generated based on variations in sound that emit from the motor. In some embodiments, the sound variations are detected by a microphone. In some embodiments, the sound variations are detected by a sound card. In some embodiments, the sound variations are generated and/or amplified by placing a component, such as a card, in the motor assembly. In various embodiments, the analog signal indicative of the speed of the motor is generated using strobing speed sensors.

As described elsewhere herein, a closure system can utilize a motor to drive an end effector of a surgical instrument to a clamped state to capture tissue within the end effector. As the effector transitions to the clamped state, the anvil of the end effector makes contact with the tissue. The resulting impact can slow the motor output and, in some cases, can even cause the motor to stall. In another aspect, a firing system can utilize a motor to drive a firing member of a surgical instrument through a firing stroke to cut tissue captured within the end effector and deploy staples from a staple cartridge positioned in the end effector. Similarly, the impact of the firing member on the tissue and the staple drives can result in the motor output being slowed and potentially stalling. In such scenarios, higher torques from the motor are required that would cause a standard motor to stall. Accordingly, it would be desirable to add inertia to the motor(s) in order to compensate for losses associated with high torque requirements. Furthermore, it would be desirable to add inertia to the motor(s) to compensate for losses associated with 25% motor speed losses.

Figure 41:
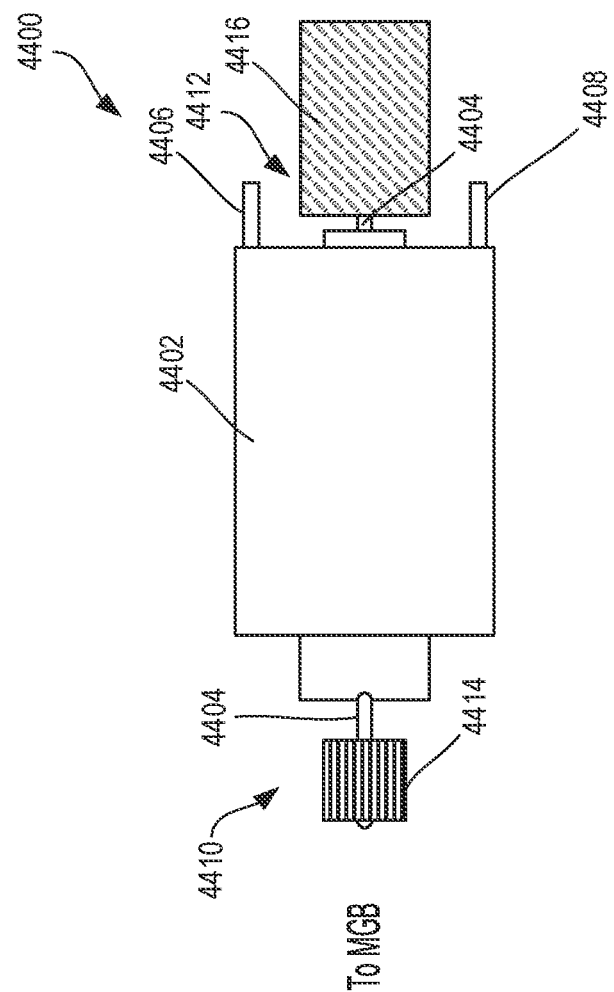
FIG. 41 illustrates a motor with improved inertia, according to at least one aspect of the present disclosure.

Referring now to FIG. 41, a motor 4400 is provided, according to at least one aspect of the present disclosure. The motor 4400 includes a housing 4402, an output shaft 4404, a first contact 4406, and a second contact 4408. In various embodiments, a first wire from a power source couples to the first contact 4406 and a second wire from the power source couples to the second contact 4408. In one aspect, to rotate the output shaft 4404 in a first, clockwise direction, a positive polarity is provided to the first contact 4406 and a negative polarity is provided to the second contact 4408 from the power source. To rotate the output shaft 4404 in a second, counterclockwise direction, a negative polarity is provided to the first contact 4406 and a positive polarity is provided to the second contact 4408, from the power source.

As seen in FIG. 41, the output shaft 4404 includes a first end 4410 that extends from a first side of the housing 4402 and a second end 4412 that extends from a second side of the housing 4402. In various embodiments, a gear 4414 is coupled to the first end 4410 of the output shaft 4404. In some embodiments, the gear 4414 is in mechanical communication with a motor gear box ("MGB") downstream of the motor 4400 such that the motor 4400 can drive a function of the surgical instrument. In some embodiments, the function is transitioning an end effector between an open and clamped state. In some embodiments, the function is driving a firing member through a firing stroke. In various embodiments, the gear 4414 is comprised of a metal, such as tungsten, platinum, hafnium, tantalum, rhenium, osmium, iridium, gold, mercury, thallium, lead, or any other suitable transition or post-transition metal, to add inertia to the motor 4400 in order to make up for inertial losses when operating the motor 4400. In various embodiments, a ring or flywheel 4416 is coupled to the second end 4412 of the output shaft 4404 to further add inertia to the motor 4400 in order to make up for inertial losses when operating the motor 4400. In various embodiments, the ring 4416 is comprised of a metal, such as tungsten, platinum, hafnium, tantalum, rhenium, osmium, iridium, gold, mercury, thallium, lead, or any other suitable transition or post-transition metal.

Figure 42:
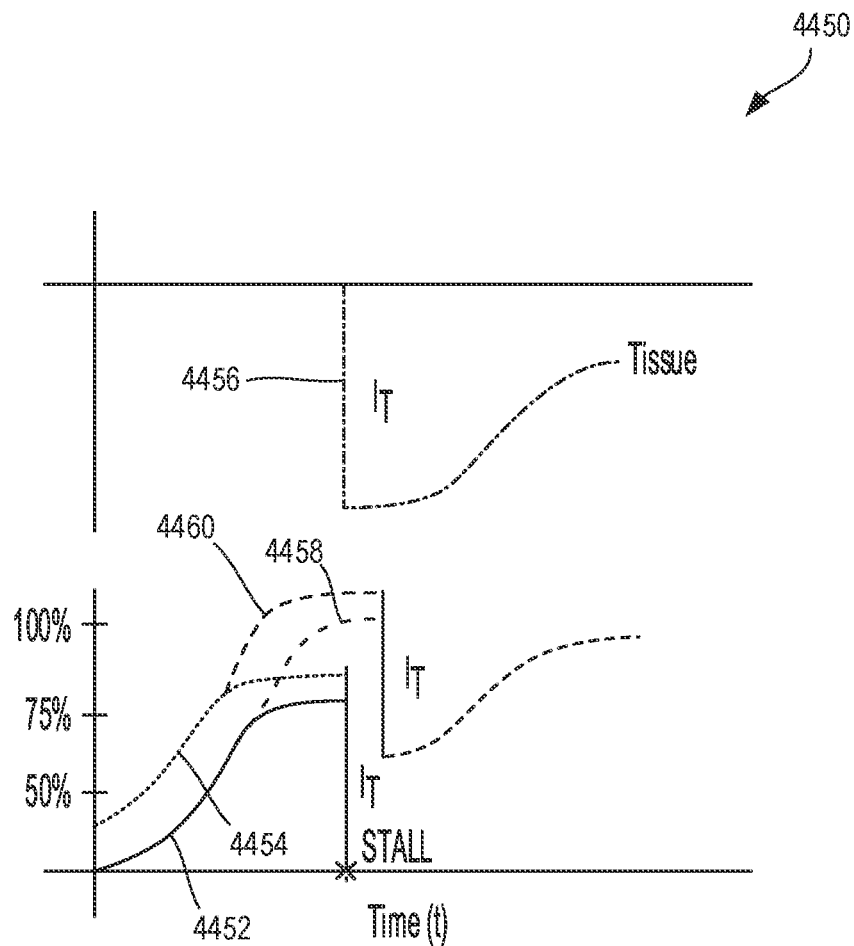
FIG. 42 illustrates a graph that illustrates current motors against the motor of FIG. 41, according to at least one aspect of the present disclosure.

Referring now to FIG. 42, a graph 4450 is provided that illustrates current motors against the improved motor 4400, according to at least one aspect of the present disclosure. In operation, current motors operate with a motor speed 4452 of 75% and an inertial speed 4454 of 75%. When current motors encounter thick tissue, inertial resistance $I_T$ 4456 from the thick tissue causes the motor speed 4452 and inertial speed 4454 of the current motors to stall. With the improved motor 4400, the motor 4400 is able to operate with a greater speed 4458 (100%) and greater inertial speed 4460 (100%) such that the inertial resistance from the tissue $I_T$ 4456 does not result in the motor stalling.

Figure 43:
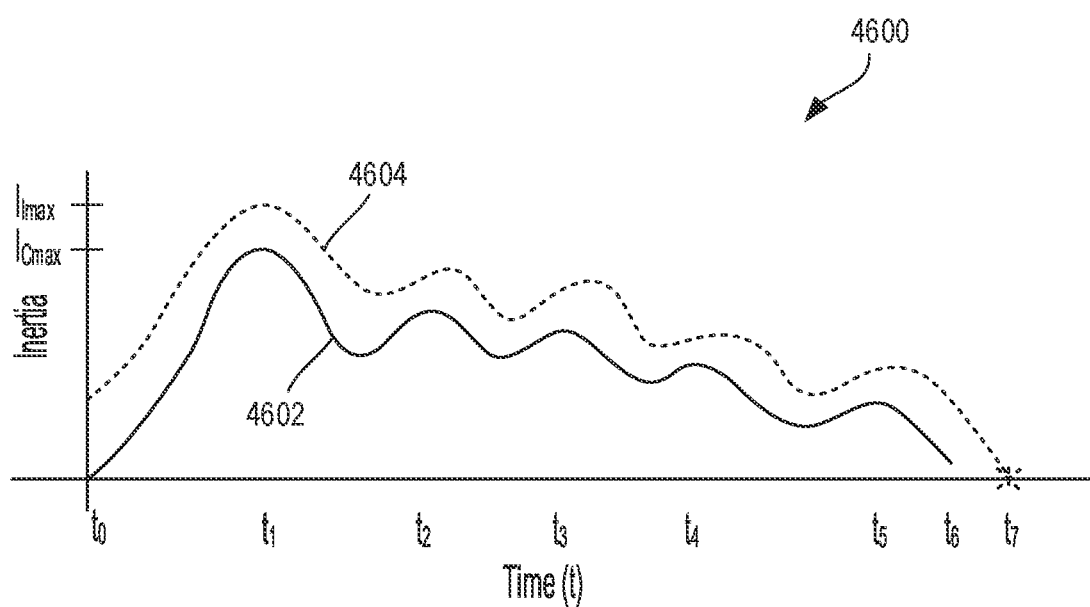
FIG. 43 illustrates a graph that illustrates current motors against the motor of FIG. 41, according to at least one aspect of the present disclosure.

Referring now to FIG. 43, a graph 4600 is provided that illustrates current motors against the improved motor 4400, according to at least one aspect of the present disclosure. In operation, current motors operate to perform a function of the end effector, such as driving a firing member through a firing stroke to cut tissue and deploy staples. As shown in the graph 4600, the inertia 4602 of the current motor ramps up to $I_{Cmax}$ from $t_0$ to $t_1$. At $t_1$, the firing member encounters resistance, such as thick tissue, that causes the current motor to lose inertia. The current motor attempts to ramp up to $I_{Cmax}$ after $t_1$, but again encounters resistance at $t_2$ prior to reaching $I_{Cmax}$. This attempted ramp up and resistance continues as the motor drives the firing member through the firing stroke from $t_2$, such as at $t_3$, $t_4$, and $t_5$. As the motor is unable to sufficiently recover inertia during the firing stroke prior to experiencing the additional resistance at $t_3$, $t_4$, and $t_5$, the motor ultimately stalls at $t_6$.

With the improved motor 4400, the motor 4400 is able to encounter additional resistance prior to stalling. As shown in the graph 4600, the inertia 4604 of the motor 4400 ramps up to $I_{Imax}$, which is greater than $I_{Cmax}$, from $t_0$ to $t_1$. Similar to the current motors, the firing member encounters resistance as the motor 4400 drives the firing member through its firing stroke, such as at $t_1$-$t_5$. However, owing to the additional inertia added to the system, the motor 4400 does not stall until $t_7$, which is a time later than $t_5$. Accordingly, the improved motor 4400 is able to withstand greater resistance than current motors.

In various embodiments, a control system, such as controller 620, can control the motor 4400 such that vibrations are induced within the closure system and/or firing system, such that fluid within the tissue is driven away from the tissue. A method of such vibration control is described in U.S. Patent Application Publication No. 2021/0059773, which is hereby incorporated by reference in its entirety herein. In various embodiments, the control system can oscillate or pulse the closure and/or firing system in order to induce fluid movement from the tissue and, thus, provide relief to the motor during operation thereof.

In some instances, it would be beneficial to control a firing system, such as firing motor drive assembly 604, based on various types of feedback received by sensors, such as any suitable sensors described elsewhere herein. In some embodiments, the feedback includes a selected staple cartridge reload, an articulation angle of the end effector, the amount of precompression applied to the tissue prior to firing the firing system, or various combinations thereof. In one aspect, clamping and precompression feedback, along with reload selection and articulation angle, are predictive of firing loads. Accordingly, the control system can compensate for predictive firing loads based on these parameters.

In various embodiments, a control system, such as controller 620, can predict a firing load based on one or multiple of the foregoing parameters. Before enabling the firing system, the control system can predict if the firing loads are outside an expected range. In various embodiments, the expected range is stored in a memory, such as memory 624, and retrievable by the control system. In various embodiments, the expected range is user defined. In one aspect, if the predicted firing load is outside of the expected range, the control system can cause the closure system, such as closure motor drive assembly 605, to continue to advance a closure member, such as closure ring 4056, to increase the closure force, which will decrease the predicted firing load. The closure force can be increased until the predicted firing load is within range.

In various embodiments, the control system provides feedback to the clinician, such as feedback on a display, informing the clinician if the predicted firing load cannot be brought within range. In such embodiments, the control system can suggest a corrective action, such as suggesting a more appropriate staple cartridge reload, a different articulation angle, or any other suitable corrective action that will lower the predicted firing load.

In some aspects, the predicted firing load is used to assign the initial firing speed of a firing member, such as firing member 1900. During the firing stroke of the firing member, the control system causes the closure member, such as closure ring 4056, to discretely, or continuously, advance, as discussed elsewhere herein, in order to lower the firing loads experienced by the firing system.

In many instances, it would be desirable to adapt both the closure system and the firing system during a surgical cutting and stapling procedure. In one aspect, adapting both systems based on inputs obtained before and/or during the surgical stapling and cutting procedure optimizes the systems and ensures that proper parameters are utilized, resulting in better surgical outcomes. In addition, it would be desirable to adapt the firing system based on monitored inputs received while the closure system transitions an end effector of a surgical instrument to the clamped state, both before and/or during actuation of the firing system.

Figure 44:
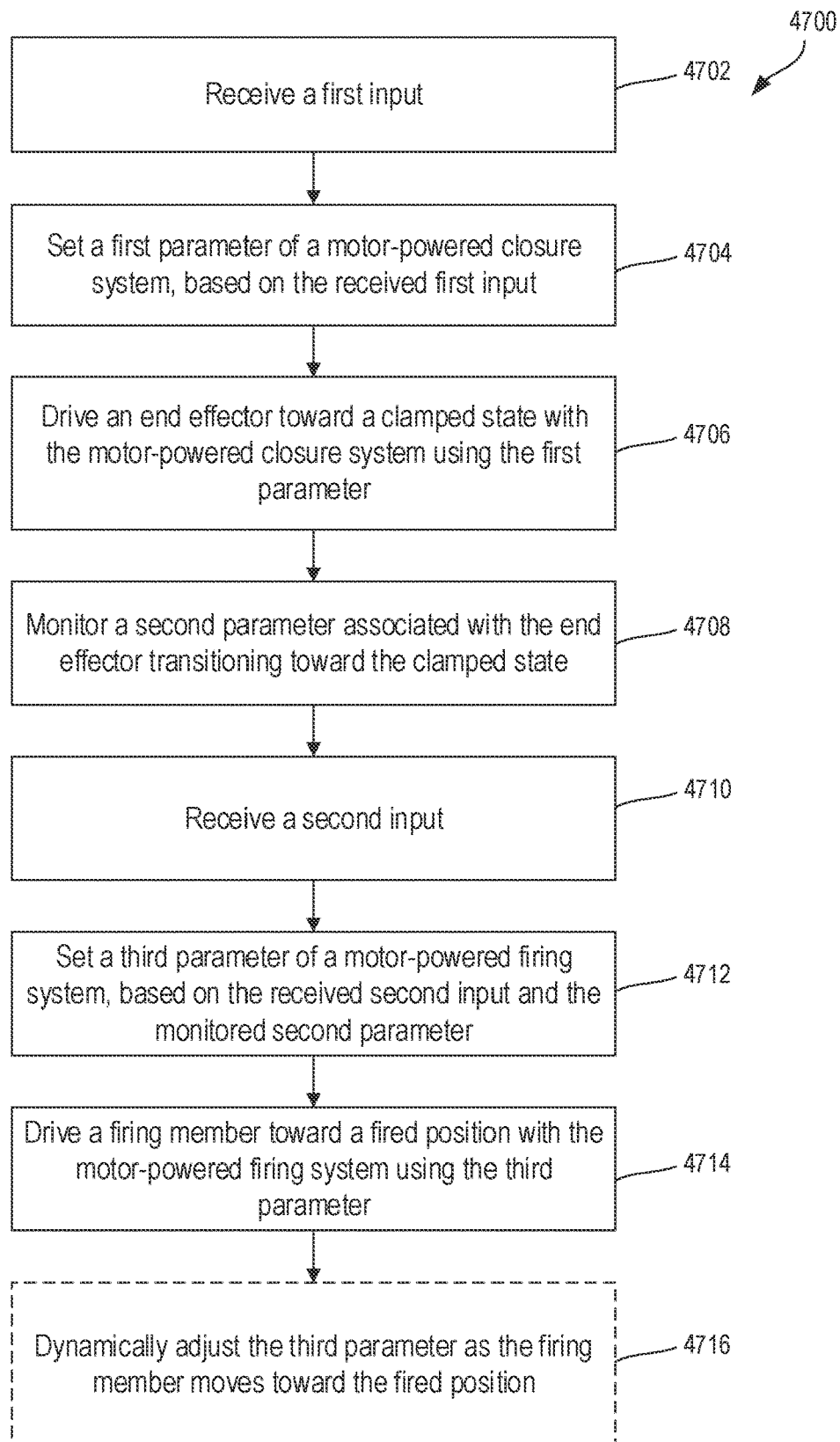
FIG. 44 illustrates a method for controlling a surgical instrument, according to at least one aspect of the present disclosure.

Referring now to FIG. 44, a method 4700 for controlling a surgical instrument is provided, according to at least one aspect of the present disclosure. The method 4700 comprises receiving 4702 a first input. In various embodiments, the first input comprises a user-provided input at an input interface. In various embodiments, the first input comprises an input received from a sensor within the surgical instrument, such as any suitable sensor described elsewhere herein. In some embodiments, the received input comprises a type of staple cartridge positioned within the end effector. In various embodiments, the surgical instrument includes a radio-frequency identified ("RFID") scanner in operable communication with a control system, such as controller 620, of the surgical instrument and the staple cartridge comprises an RFID tag. The RFID scanner can interrogate the RFID tag such that the control system can determine the type of staple cartridge positioned in the end effector.

In various embodiments, the receive input comprises a parameter associated with an end effector, such as end effector 1300, transitioning to a clamped state. In some embodiments, the parameter comprises an amount of time taken for a closure system, such as closure motor drive assembly 605, to transition the end effector to the clamped state. In some embodiments, the parameter comprises an amount of time taken for a closure system to transition the end effector to a partially clamped state. In some embodiments, the parameter comprises a load that the end effector is applying to tissue within the jaws of the end effector. In some embodiments, the received input comprises a parameter associated with the tissue captured within the end effector. In some embodiments, the parameter comprises an impedance of the tissue. In some embodiments, the parameter comprises a rate of change of force applied to the tissue. In some embodiments, the parameter comprises a type of tissue captured by the end effector.

The method 4700 further comprises setting 4704 a first parameter of a motor-powered closure system, based on the received first input. In various embodiments, the control system can utilize the received input(s) to set a parameter for a motor-powered closure system, such as closure motor drive assembly 605. In some embodiments, the control system compares the received input(s) to predefined values stored in a memory, such as memory 624, in order to determine the first parameter. In some embodiments, the first parameter comprises a speed of a closure motor, such as closure motor 603. In some embodiments, the first parameter comprises a duty cycle to the closure motor. In some embodiments, the first parameter comprises an amount of current or voltage supplied to the closure motor from a power source, such as power source 628. Other parameters for a motor-powered closure system are described elsewhere herein. Accordingly, the control system is able to adapt the closure system according to received inputs.

The method 4700 further comprises driving 4706 an end effector toward a clamped state with the motor-powered closure system using the first parameter. In various embodiments, the control system can transmit a control signal to the closure motor, causing the motor-powered closure system, such as closure-motor drive assembly 605, to drive the end effector toward the clamped state using the first parameter.

The method 4700 further comprises monitoring 4708 a second parameter associated with the end effector transitioning toward the clamped state. In various embodiments, the control system can interrogate any number of sensors within the surgical instrument, such as force sensors or pressure sensors, as examples, to monitor parameters associated with the end effector transitioning toward the clamped state. In various embodiments, the second parameter comprises an amount of time taken to transition the end effector to the clamped state. In various embodiments, the second parameter comprises a rate at which the end effector transitions toward the clamped state. In various embodiments, the second parameter comprises an amount of force applied to the tissue captured within the end effector. In various embodiments, the second parameter comprises an amount of time taken to transition the end effector to the partially clamped state. Other parameters associated with transitioning an end effector toward a clamped state are described elsewhere herein. In various embodiments, the method 4700 further comprises dynamically adjusting the first parameter, based on the monitored second parameter. Accordingly, the control system is capable of adapting the closure system based on monitored inputs as the end effector transitions to the clamped state.

The method 4700 further comprises receiving 4710 a second input. In various embodiments, the second input comprises a user-provided input at an input interface. In various embodiments, the second input comprises an input received from a sensor within the surgical instrument, such as any suitable sensor described elsewhere herein. In some embodiments, the received input comprises a type of staple cartridge positioned within the end effector. In various embodiments, the surgical instrument includes an RFID scanner in operable communication with a control system, such as controller 620, of the surgical instrument, and the staple cartridge comprises an RFID tag. The RFID scanner can interrogate the RFID tag such that the control system can determine the type of staple cartridge positioned in the end effector.

The method 4700 further comprises setting 4712 a third parameter of a motor-powered firing system, based on the received second input and the monitored second parameter. In various embodiments, the control system can utilize the received input(s), as well as the monitored parameter of the end effector moving to the clamped state, to set a parameter for a motor-powered firing system, such as firing motor drive assembly 604. In some embodiments, the control system compares the received input(s) and monitored parameter to predefined values stored in a memory, such as memory 624, in order to determine the third parameter. In some embodiments, the third parameter comprises a speed of a firing motor, such as firing motor 602. In some embodiments, the third parameter comprises a duty cycle to the firing motor. In some embodiments, the third parameter comprises an amount of current or voltage supplied to the firing motor from a power source, such as power source 628. Other parameters for a motor-powered firing system are described elsewhere herein. Accordingly, the control system is able to adapt the firing system according to received inputs and inputs obtained while the end effector is transitioned to the clamped state.

The method 4700 further comprises driving 4714 a firing member toward a fired position with the motor-powered firing system using the third parameter. In various embodiments, the control system can transmit a control signal to the firing motor, causing the motor-powered firing system, such as firing motor drive assembly 604, to drive a firing member, such as firing member 1900, toward a fired position, which causes staples removably stored in a staple cartridge, such as staple cartridge 1301, to be deployed therefrom.

In some embodiments, the control system is configured to drive the firing member toward the fired position at a time after the motor-powered closure system has placed the end effector into the clamped state. In various other embodiments, the control system is configured to drive the firing member toward the fired position as the control system drives the end effector toward the clamped state. In such embodiments, the firing system and the closure system are simultaneously operated, or operated in an overlapping fashion, by the control system. Such simultaneous operation allows the control system to monitor parameters associated with the closure of the end effector and adapt the firing system based on these monitored parameters. In various embodiments, the control system can monitor parameters associated with driving the firing member, such as a force to fire, and adapt the closure system based on these monitored parameters. Accordingly, the control system can dynamically adapt one system according to inputs received from the other system while both systems are being operated.

The method 4700 optionally further comprises dynamically adjusting 4716 the third parameter as the firing member moves toward the fired position. In various embodiments, the control system monitors parameters associated with the clamping system or the firing system and dynamically adjusts, or adapts, the third parameter accordingly. In some embodiments, the control system adapts the third parameter based on how long the end effector has been in a clamped state. In some embodiments, the control system adapts the third parameter based on how long the end effector has been in a partially clamped state. In some embodiments, the control system adapts the third parameter based on a rate of change in force applied to the tissue within the jaws of the end effector. In some embodiments, the control system adapts the third parameter based on a force to fire the firing member. In some embodiments, the control system adapts the third parameter based on parameters associated with the end effector transitioning toward the clamped state, as described above. Accordingly, the control system can dynamically adjust the firing system during the firing stroke of the firing member.

In some instances, when a closure system is driven in a position control manner, as discussed elsewhere herein, the load applied by the end effector to the tissue drops based on both tissue creep and other shaft actuation systems operated in a similar direction to the closure system. This relationship could be used to not only affect the load control of the closure system to balance loading, but also as a measure of the firing system load state. Accordingly, this relationship could be used to determine an optimal firing parameter, such as an optimal advancement speed, of a firing member, such as firing member 1900. Furthermore, this relationship can be used to determine the timing and length of pauses of wait cycles for the firing member during the firing stroke, such as firing member 1900.

In addition, the type of tissue and/or disease state thereof can be detected during closure of the end effector based on tissue creep and clamp pressures. The detected type of tissue and/or disease state thereof can further be used to control the advancement speed of the firing member to minimize tearing and load on to the tissue. Accordingly, the present disclosure provides, among other things, a means of controlling the advancement speed of a firing system based on closure loads of a control system and types of tissue, as described in more detail below.

In various embodiments, a surgical instrument including an end effector and a clamping system, such as closure motor drive assembly 605, is utilized to clamp tissue during a clamping stroke. Sensors, such as any number of sensors described elsewhere herein, can be utilized to monitor the load applied by the end effector during the clamping stroke. In various embodiments, the sensors measure the load applied by the end effector by measuring a current through a closure motor, such as closure motor 603, of the clamping system. In various other embodiments, the sensors measure the load applied by the end effector utilizing force sensors positioned on at least one of the jaws of the end effector. During the clamping process, a control system, such as controller 620, interrogates the sensors to determine the clamping load and uses the determined load to set a firing parameter of a firing system, such as firing motor drive assembly 604.

In some embodiments, the control system sets the firing parameter based on an amount of current delivered to the closure motor during the clamping stroke. In some embodiments, the control system sets the firing parameter based on a rate at which current is delivered to the closure motor during the clamped stroke. In some embodiments, the control system sets the firing parameter based on a comparison of a maximum current supplied to the motor against a current threshold or a plurality of current thresholds. In some embodiments, the current threshold(s) are stored in a memory, such as memory 624, and are retrievable by the control system. In some embodiments, the current threshold (s) are user-defined at an input interface. In various embodiments, the control system sets the firing parameter based on the amount of time the current has been delivered to the closure motor.

In various embodiments, the control system also determines a tissue type or a disease state of the tissue captured within the end effector. In some embodiments, once the end effector reaches a clamped state, the control system utilizes sensors, such as force sensors or current sensors, to determine a rate of change of force applied by the end effector to the tissue. In some embodiments, the clamped state is defined as a state where the end effector 1300 is in the closed configuration and the closure trigger 1032 is in the actuated position. In other embodiments, the clamped state is defined as a state where the elongate channel 1310 and the anvil 2000 of the end effector 1300 are within a threshold distance of one another. In other embodiments, the clamped state is defined as a state where the closure trigger 1032 has pivoted a threshold distance away from the unactuated position.

In some embodiments, as the end effector transitions to the clamped state, the control system utilizes sensors, such as force sensors or current sensors, to determine a rate of change of force applied by the end effector to the tissue. The control system compares the determined rate of change to rates of change associated with types/disease states of tissue stored in a memory, such as memory 624. In one embodiment, the control system detects that the rate of change of force captured in the end effector is a first rate of change. The control system compares the first rate of change to rates of change stored in the memory, where each stored rate of change corresponds to a tissue type and/or disease state of various types of tissue. Based on the comparison, the control system can identify the type and/or disease state of the tissue captured within the end effector.

Based on at least one of the determined clamping load applied to the tissue and the determined tissue type/disease state thereof, the control system sets a firing parameter of the firing system. In various embodiments, setting a firing parameter of a firing system comprises setting a duty cycle of the motor of the firing system. In various embodiments, setting a firing parameter of a firing system comprises setting a speed of the motor of the firing system. In various embodiments, setting a firing parameter of a firing system comprises controlling an amount of current to deliver to the motor of the firing system.

In one aspect, after the control system sets the firing parameter of the firing system, the control system can cause the firing system to drive a firing member, such as firing member 1900, through a firing stroke using a firing motor, such as firing motor 602. In some embodiments, the control system continues to monitor the current through the closure motor during the firing stroke and dynamically adjusts the firing parameter based on the monitored current. In various other embodiments, the control system monitors an elapsed time that the end effector has been in the clamped state and dynamically adjusts the firing parameter based on the elapsed time. In various other embodiments, the control system monitors an elapsed time since the end effector first made contact with tissue as the end effector transitioned to the clamped state and dynamically adjusts the firing parameter based on the elapsed time. In some embodiments, the control system can pause the advancement of the firing member based on a comparison of the current through the closure motor to a closure load threshold.

Figure 45:
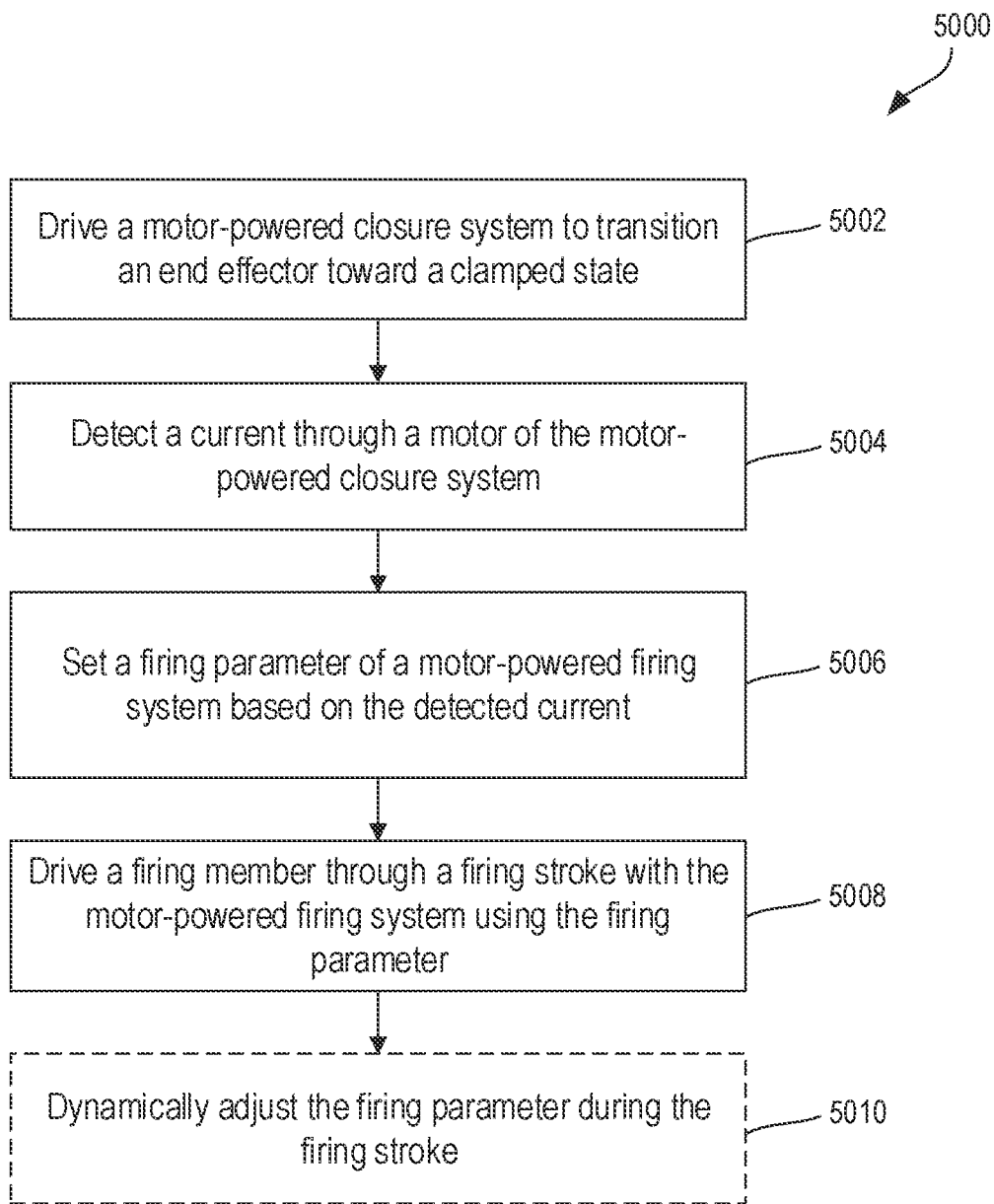
FIG. 45 illustrates a method for controlling a surgical instrument, according to at least one aspect of the present disclosure.

Referring now to FIG. 45, a method 5000 for controlling a surgical instrument is provided, according to at least one aspect of the present disclosure. The method 5000 comprises driving 5002 a motor-powered closure system to transition an end effector toward a clamped state. In various embodiments, a control system, such as controller 620, can transmit a control signal to a closure motor, such as closure motor 603, of a motor-powered closure system, such as closure motor drive assembly 605, to cause the motor-powered closure system to transition an end effector, such as end effector 1300, toward a clamped state.

The method 5000 further comprises detecting 5004 a current through a motor of the motor-powered closure system. In various embodiments, sensors, such as any number of sensors described elsewhere herein, can monitor a current provided to the closure motor 603 from a power source, such as power source 628.

The method 5000 further comprises setting 5006 a firing parameter of a motor-powered firing system based on the detected current. In various embodiments, the control system can utilize the detected current through the motor, as described elsewhere herein, in order to set a firing parameter of the a motor-powered firing system, such as firing motor drive assembly 604. In some embodiments, the firing parameter comprises a duty cycle of a firing motor, such as firing motor 602. In various embodiments, the firing parameter comprises a speed of the firing motor.

The method 5000 further comprises driving 5008 a firing member through a firing stroke with the motor-powered firing system using the firing parameter. In various embodiments, the control system can cause the motor-powered firing system to drive a firing member, such as firing member 1900, through a firing stroke using the firing motor 602 and the firing parameter. In some embodiments, the firing stroke of the firing member causes staples removably stored in a staple cartridge, such as staple cartridge 1301 removably positioned in the end effector, to be deployed into the tissue captured by the end effector.

The method 5000 optionally further comprises dynamically 5010 adjusting the firing parameter during the firing stroke. In various embodiments, the control system continues to monitor the current through the closure motor during the firing stroke and dynamically adjust the firing parameter based on the monitored current. In various embodiments, the control system measures an elapsed time from when the end effector first made contact with the tissue while transitioning to the clamped state and adjusts the firing parameter based on the elapsed time. In various embodiments, the control system measures an elapsed time from when the end effector reached the clamped state and adjusts the firing parameter based on the elapsed time.

Figure 46:
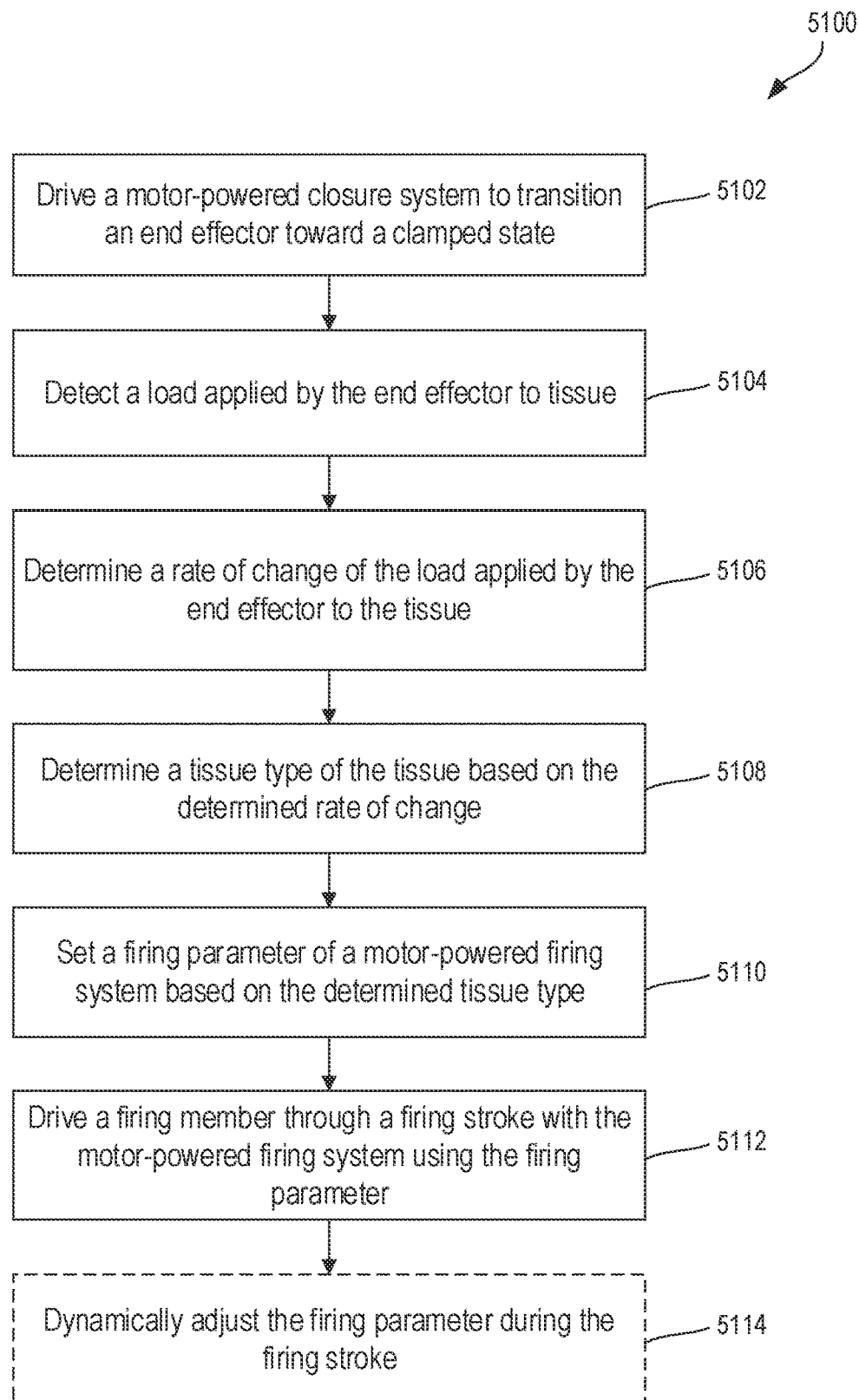
FIG. 46 illustrates a method for controlling a surgical instrument, according to at least one aspect of the present disclosure.

Referring now to FIG. 46, a method 5100 for controlling a surgical instrument is provided, according to at least one aspect of the present disclosure. The method 5100 comprises driving 5102 a motor-powered closure system to transition an end effector toward a clamped state. In various embodiments, a control system, such as controller 620, can transmit a control signal to a closure motor, such as closure motor 603, of a motor-powered closure system, such as closure motor drive assembly 605, to cause the motor-powered closure system to transition an end effector, such as end effector 1300, toward a clamped state.

The method 5100 further comprises detecting 5104 a load applied by the end effector to tissue. In various embodiments, sensors, such as any number of sensors described elsewhere herein, monitor a current provided to the closure motor 603 from a power source, such as power source 628, to measure the load applied by the end effector to the tissue. In various embodiments, force sensors positioned on the end effector measure the load applied by the end effector. In various embodiments, the control system interrogates, or receives signals from, the sensors to determine the load applied by the end effector to the tissue.

The method 5100 further comprises determining 5106 a rate of change of the load applied by the end effector to the tissue. In various embodiments, the control system monitors the readings from the sensors over time to determine a rate of change of the load over time. In various embodiments, the control system determines the rate of change as the end effector transitions toward the clamped state. In various embodiments, the control system determines the rate of change after the end effector has reached the clamped state. In various embodiments, the control system determines the rate of change as the end effector is transitioning to the clamped state and after the end effector has reached the clamped state.

The method 5100 further comprises determining 5108 a tissue type of the tissue based on the determined rate of change. In various embodiments, the control system, as described in more detail elsewhere herein, can determine the tissue type, and/or the disease state, of the tissue by comparing the determined rate of change to rates of change stored in a memory, where the stored rates of change correspond to different types of tissue and/or disease states of tissue.

The method 5100 further comprises setting 5110 a firing parameter of a motor-powered firing system based on the determined tissue type. In various embodiments, the control system can utilize the determined tissue type in order to set a firing parameter of a motor-powered firing system, such as firing motor drive assembly 604. In some embodiments, the firing parameter comprises a duty cycle of a firing motor, such as firing motor 602. In various embodiments, the firing parameter comprises a speed of the firing motor. In various embodiments, the firing parameter comprises a parameter suitable for cutting and stapling the determine type of tissue.

The method 5100 further comprises driving 5112 a firing member through a firing stroke with the motor-powered firing system using the firing parameter. In various embodiments, the control system can cause the motor-powered firing system to drive a firing member, such as firing member 1900, through a firing stroke using the firing motor 602 and the firing parameter. In some embodiments, the firing stroke of the firing member causes staples removably stored in a staple cartridge, such as staple cartridge 1301, removably positioned in the end effector to be deployed into the tissue captured by the end effector.

The method 5100 optionally further comprises dynamically 5114 adjusting the firing parameter during the firing stroke. In various embodiments, the control system monitors the current through a closure motor of the closure system during the firing stroke and adjusts the firing parameter based on the monitored current. In various embodiments, the control system measures an elapsed time from when the end effector first made contact with the tissue while transitioning to the clamped state and adjusts the firing parameter based on the elapsed time. In various embodiments, the control system measures an elapsed time from when the end effector reached the clamped state and adjusts the firing parameter based on the elapsed time.

Several surgical instruments have a portion of a stroke that requires a first compression level and would benefit from a second portion that has a different tissue compression level. In some embodiments, the force of a motorized clamp arm of an ultrasonic surgical instrument, similar to the ultrasonic instruments described in U.S. Pat. No. 10,842,523, which is hereby incorporated by reference in its entirety herein, would benefit from an increase in compression when the system is ready to cut, but a lower level when the system is tissue welding. In some other embodiments, RF energy activation of an electrosurgical instrument, similar to the electrosurgical instruments described in U.S. Pat. No. 10,842,523, which is hereby incorporated by reference in its entirety herein, benefits from a first compression at the beginning of welding, but a lower compression at the termination of welding to balance tissue heating and tissue sticking. In some other embodiments, a stapler, such as any of the surgical stapling instruments described elsewhere herein, would benefit from better tissue stability of higher compression at the start of the firing member staple deployment, but that same compression in combination with the anvil pressure could translate to higher frictions and force to fire (FTF) in the later portions of the stroke.

A surgical stapler utilizes different types of staple cartridges depending on the tissue thickness to be cut and staple. As one example, during a gastric surgery, the tissue thickness increases as portions of the stomach are resected. Accordingly, clinicians will use sequential cartridges for the increasing tissue thickness. In one aspect, the clamping system adapts as it is fired to account for the increased thickness and/or reduce the motor speed to prevent tissue flow and/or stall as it goes into the thicker tissue. In various embodiments, a control system, such as controller 620, determines the tissue thickness based on a tissue gap between the anvil and the elongate channel of the end effector once the end effector has reached the clamped state. In various embodiments, the control system includes a radio-frequency identification (RFID) scanner than scans an RFID tag on the inserted staple cartridge to determine the intended tissue thickness to be cut. Based on the determined tissue thickness, the control system sets a firing speed of the firing system.

In various embodiments, the control system dynamically adjusts the firing system of the surgical instrument based on, among other things, a stroke location of the firing member, a time since the activation of the firing system, a time since the activation of the electrosurgical system, such as a generator, a time since the activation of an ultrasonic system, such as an ultrasonic generator, loading measured on the firing activation system, or combinations thereof. Based on the foregoing parameters, the control system can dynamically adjust the surgical instrument as the tissue is cut and/or sealed to provide an appropriate tissue force.

In various embodiments, the control system causes a closure motor, such as closure motor 603, to apply a first force to tissue captured within the end effector. In some embodiments, in the context of an ultrasonic surgical instrument, the control system causes the closure motor to apply a first force prior to the ultrasonic blade beginning to cut and weld tissue. In some embodiments, in the context of an electrosurgical instrument, the control system causes the closure motor to apply a first force as the electrosurgical instrument begins to apply energy to the tissue. In some embodiments, in the context of a surgical stapling instrument, the control system causes the closure motor to apply a first force as a firing member, such as firing member 1900, begins to move through a staple firing stroke.

While applying the first force, the control system monitors for the occurrence of a predefined event. Based on detecting the predefined event, the control systems causes the closure motor to apply a second force different from the first force. In various embodiments, the control system utilizes sensors, such as any number of the sensors described elsewhere herein, to monitor for the predefined event. In various embodiments, in the context of an ultrasonic surgical instrument, the predefined event comprises the ultrasonic blade of the ultrasonic surgical instrument beginning to weld tissue. In some embodiments, the control system detects the ultrasonic blade beginning to weld tissue by detecting the actuation of a trigger on the ultrasonic instrument. In some embodiments, the control system detects the ultrasonic blade beginning to weld tissue by detecting an electric current being provided to the ultrasonic transducer. In some embodiments, the control system detects the ultrasonic blade beginning to weld tissue by detecting a change in the impedance of the tissue utilizing a sensor.

In various embodiments, in the context of an electrosurgical surgical instrument, the predefined event comprises the electrosurgical instrument ceasing to apply energy to the tissue. In some embodiments, the control system detects the cease in energy utilizing a sensor to detect the current flow to the electrodes in the end effector of the electrosurgical instrument. In some embodiments, the control system detects the cease in energy utilizing a sensor to detect energy being provided by an electrosurgical generator to the electrosurgical instrument. In one aspect, lowering the force at the termination of the welding process balances tissue heating and tissue sticking, resulting in a better surgical outcome.

In various embodiments, in the context of a surgical stapling instrument, the predefined event comprises the firing member reaching a predefined point along the firing stroke. In some embodiments, the control system detects the firing member reaching the predefined point using a position sensor, such as any number of position sensor described elsewhere herein. In some embodiments, the predefined position comprises a predefined position away from the starting position of the firing member. In some embodiments, the predefined position comprises a predefined position away from the ending position of the firing member. In one aspect, lowering the force at the end of the firing stroke results in lower frictions and lower forces to fire, resulting in a better surgical outcome.

In some embodiments, the second force is greater than the first force. In some embodiments, the second force is less than the first force. In some embodiments, the control system causes the end effector to gradually transition from the first force to the second force. In some embodiments, the control system causes the end effector to quickly transition from the first force to the second force.

Figure 47:
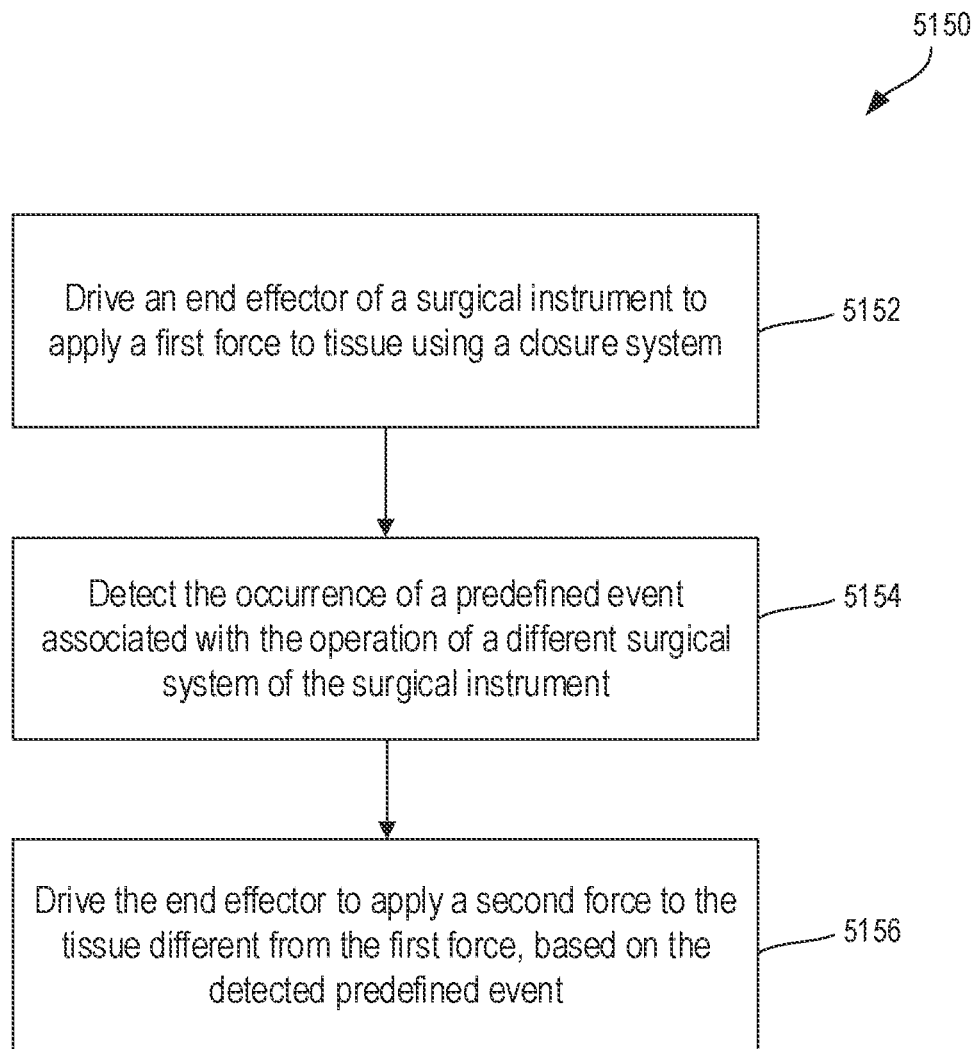
FIG. 47 illustrates a method for controlling a surgical instrument, according to at least one aspect of the present disclosure.

Referring now to FIG. 47, a method 5150 for controlling a surgical instrument is provided, according to at least one aspect of the present disclosure. In various embodiments, the method 5150 comprises driving 5152 an end effector of a surgical instrument to apply a first force to tissue using a closure system. In some embodiments, a control system, such as controller 620, drives a closure motor, such as closure motor 603, of a closure system, such as closure motor drive assembly 605, to cause an end effector, such as end effector 1300, to apply a first force to tissue.

The method 5150 further comprises detecting 5154 the occurrence of a predefined event associated with the operation of a different surgical system of the surgical instrument. In some embodiments, in the context an ultrasonic instrument, the different surgical system comprises an ultrasonic drive system that includes an ultrasonic blade and the predefined event comprises the ultrasonic blade beginning to cut and weld tissue. In some embodiments, in the context of an electrosurgical instrument, the different surgical system comprises an electrosurgical system that includes electrodes that apply energy to the tissue, and the predefined event comprises the electrodes ceasing to apply energy to the tissue. In some embodiments, in the context of a surgical stapling instrument, the different surgical system comprises a firing system, such as the firing motor drive assembly 604, and the predefined event comprises the firing member reaching a predefined location along the firing stroke. In various embodiments, the control system detects the predefined events described above using any number of sensors described elsewhere herein.

The method 5150 further comprises driving 5156 the end effector to apply a second force to the tissue different from the first force. In various embodiments, based on detecting the predefined event, the control system can control the closure system to adjust the closure force applied by the end effector. In various embodiments, the second force is less than the first force. In various embodiments, the second force is greater than the first force. In some embodiments, the control system causes the end effector to gradually transition from the first force to the second force. In some embodiments, the control system causes the end effector to quickly transition from the first force to the second force. In one aspect, changing the force applied by the end effector results in better surgical outcomes.

In one aspect, as a firing member, such as firing member 1900, is driven through the firing stroke, an upper flange, such as anvil engagement tab 1924, and a lower flange, such as lower channel engagement tabs 1926, thereof engage the jaws of the end effector. The engagement between the upper/lower flanges and the end effector causes the load applied by the end effector to the tissue to be distributed to both the upper/lower flanges and the closure system, such as closure motor drive assembly 605. Stated another way, prior to advancing the firing member through the firing stroke, the closure system is responsible for the closure load applied to the tissue. As the firing member traverses through the firing stroke, the firing member "lightens the load" on the closure system, causing the load to be distributed between the two systems of the surgical instrument. In various embodiments, the control system can detect how much load is being applied to the tissue by the closure system during the firing stroke. In some embodiments, the control system detects how much load is applied by the closure system using a current sensor that detects the current flow through the closure motor, such as closure motor 603, of the closure system. Based on the detected current flow, the control system can adjust the current supplied to the closure motor in order to maintain or adjust the closure load collectively applied by the closure system and firing member during the firing stroke. In one aspect, as described elsewhere herein, the control system can adjust the closure load applied by the closure system by controlling a position of a closure ring 4056 during the firing stroke.

During operation of a surgical instrument, a user can transition an end effector, such as end effector 1300, from an open state toward a clamped state using a clamping system, such as closure system 3000 or closure motor drive assembly 605, as examples. As the end effector transitions toward the clamped state, the end effector can reach a partially clamped state intermediate the open state and the clamped state. In some embodiments, the partially clamped state is defined as a state where the end effector first makes contact with and begins to apply force to the tissue. In some embodiments, the partially clamped state is defined as a state where the anvil of the end effector is within a threshold distance from the elongate channel of the end effector. After reaching the partially clamped state, the end effector can continue to transition toward the clamped state. In some instances, it would be desirable to provide a clinician with non-visual feedback indicative of how long the end effector has been in the partially clamped state and/or the clamped state. Providing non-visual feedback helps the clinician maintain their focus on the task at hand without needing to look to a visual indicator, such as an external display, to determine how long the end effector has been in the partially clamped or clamped states.

In various embodiments, the surgical instrument includes a control system, such as a circuit board 1100 or controller 620, as examples, that creates a haptic tactile response repeatably at a predetermined cadence cycle to provide the clinician with feedback regarding the time since the end effector reached the partially clamped state and/or the clamped state. In some embodiments, the magnitude of the vibration could be minimized every cycle or every several cycles to provide the user with "visibility" regarding the number of cycles that have passed and, thus, ascertain how long the end effector has been in the partially clamped state and/or the clamped state.

In some embodiments, the clinician transitions an end effector toward a clamped state using a motor drive closure system, such as closure motor drive assembly 605. The control system can detect the end effector reaching the clamped state using any number of sensors described elsewhere herein, such as with a Hall-Effect sensor, as an example. Based on the detection, the control system can cause a haptic device to operate at a predefined frequency, such as every other second, with each vibration decreasing in magnitude by a predefined amount, such as 50% per pulse. Accordingly, the clinician can ascertain how long the end effector has been in the clamped state based on the noticeable and decreasing feedback from the haptic device until the firing system is actuated.

In various embodiments, the control system can provide haptic feedback using motors of the surgical instrument. In some embodiments, after detecting the end effector has reached the clamped state and/or the partially clamped state, the control system, such as controller 620, can cause a 200 ms forward and 200 ms backward inrush current through the closure motor, such as closure motor 603, to induce slight movement in the motor pinion gear. This inward and outward rush of current causes noticeable handle movement that is detectable by the clinician but does not substantially move the closure drive train. In various other embodiments where the surgical instrument does not include a closure motor, the control system causes an inrush and backward rush of current through the firing motor to generate the haptic feedback. In various embodiments, the control system adjusts the inrush/backrush of current into the motor in order to provide decreasing feedback to the clinician, informing the clinician of the passing time since the end effector has been in the partially clamped or clamped state. In some embodiments, as time elapses, the control circuit decreases the amount of time in the forward and backward inrush current through the motor. In some embodiments, as time elapses, the control circuit decreases the intensity of the forward and backward inrush current through the motor.

In many instances, it would be desirable to adapt one drive system of a surgical instrument in accordance with measurements obtained while monitoring a second drive system of the surgical instrument. For instance, a control system of the surgical instrument can monitor a parameter, or parameters, associated with operating a first drive system of the surgical instrument. Such monitoring allows the control system to determine information about the type of tissue that is being worked on by the surgical instrument. Based on the monitored parameter(s), the surgical instrument can adjust, or adapt, a parameter, or parameters, of a second, different drive system of the surgical instrument. Such adaptation allows the control system to ensure that proper, optimal parameters of the second drive system are utilized according to information obtained when operating the first drive system.

In some instances, a surgical stapling instrument can be utilized by a clinician to cut and staple tissue captured within the jaws of an end effector. In some embodiments, the surgical stapling instrument can be similar to surgical instrument 1010 or any other suitable surgical instrument described elsewhere herein. In operation, the clinician can actuate the closure system, such as closure system 3000 or closure motor drive assembly 605, as examples, to cause an end effector, such as end effector 1300, to move toward a clamped state. A control system, such as circuit board 1100 or controller 620, as examples, can be in operable communication with sensors of the surgical instrument in order to monitor a parameter associated with the end effector moving toward the clamped state. In some embodiments, the parameter comprises a clamp load applied by the end effector to the tissue. In various other embodiments, the parameter comprises an amount of time taken to reach the clamped state. In various other embodiments, the parameter comprises an amount of time taken to reach a partially clamped state. In various other embodiments, the parameter comprises an amount of time that the end effector is in the clamped state prior to actuation of a second drive system. In various other embodiments, the parameter comprises a speed at which the end effector moves toward the clamped state. In various other embodiments, the parameter comprises a rate of change of force applied by the end effector to the tissue.

Based on the parameter monitored by the control system, via the sensors, the control system sets a parameter of a second drive system, such as a firing system, of the surgical instrument. In some embodiments, setting a parameter of a second drive system comprises setting a firing parameter of a firing system, such as firing drive system 1080 or firing motor drive assembly 604, as examples. In some embodiments, setting a parameter of the second drive system comprises setting a parameter for a motor, such as motor 1082 or firing motor 602, as examples, that drives a firing member, such as firing member 1900, through a firing stroke. In some embodiments, the parameter for the motor comprises a duty cycle of the motor. In some embodiments, the firing parameter comprises a speed of the motor. In some embodiments, the firing parameter comprises an amount of current or voltage supplied to the motor from a power source. In some embodiments, setting a firing parameter of the second drive system comprises setting multiple parameters of the second drive system.

In various other embodiments, the control system monitors a parameter associated with the second drive system, such as the firing system, in order to set a parameter for the first drive system, such as the closure system. In some embodiments, the control system monitors a parameter associated with driving the firing member through the firing stroke, such as the firing load on the firing member, an amount of current applied to the motor, or the speed of the motor, as examples. Based on the monitored parameter, the control system sets a parameter of the first drive system. In some embodiments, setting a parameter of the first drive system comprises setting a clamp load of the end effector. Accordingly, based on parameter(s) monitored during the firing of the surgical instrument, the control system can effect a change in the clamping system of the surgical instrument. In some embodiments, the change can comprise varying the clamping load applied to the tissue by the end effector during and/or after the firing stroke of the firing system.

In some instances, an electrosurgical instrument, similar to the electrosurgical instruments described in U.S. Pat. No. 10,842,523, which is hereby incorporated by reference in its entirety herein, can be utilized by a clinician to weld and cut tissue captured within the jaws of an end effector. In operation, the clinician can actuate a closure system of the electrosurgical instrument to move a clamp arm toward a clamped state. A control system, such as circuit board 1100 or controller 620, as examples, can be in operable communication with sensors of the electrosurgical instrument in order to monitor a parameter associated with the end effector moving toward the clamped state, similar to those described herein above concerning the surgical stapling instrument. In various embodiments, the control system can monitor a parameter associated with the end effector applying energy to the tissue. In some embodiments, the parameter associated with the end effector applying energy to the tissue comprises a magnitude of the energy applied to the tissue via an electrode. In some embodiments, the parameter associated with the end effector applying energy to the tissue comprises an amount of time that the end effector has been applying energy to the tissue via an electrode. In some embodiments, the parameter associated with the end effector applying energy to the tissue comprises an impedance of the tissue. In some embodiments, the parameter associated with the end effector applying energy to the tissue comprises a rate of change of the impedance of the tissue.

Based on the parameter monitored by the control system, via the sensors, the control system can set a parameter of a second drive system, such as a cutting system or a clamping system of the electrosurgical instrument. In some embodiments, setting a parameter of a second drive system comprises setting a firing parameter of the cutting system. In some embodiments, setting a firing parameter of the cutting system comprises setting a parameter for a motor that the drives a cutting member through a cutting stroke. In some embodiments, the parameter for the motor comprises a duty cycle of the motor. In some embodiments, the firing parameter comprises a speed of the motor. In some embodiments, the firing parameter comprises an amount of current or voltage supplied to the motor from a power source. In some embodiments, setting a firing parameter of the second drive system comprises setting multiple parameters of the second drive system.

In various embodiments, setting a parameter of the second drive system comprises setting a parameter of the closure system. In some embodiments, setting a parameter of the closure system comprises an amount of force applied to the tissue. In some embodiments, setting a parameter of the closure system comprises a rate of change of force applied to the tissue. In some embodiments, setting a parameter of the closure system comprises a speed at which the end effector moves toward the clamped state. Various other parameters associated with clamping systems are described elsewhere herein.

In some instances, an ultrasonic instrument, similar to the ultrasonic instruments described in U.S. Pat. No. 10,842,523, which is hereby incorporated by reference in its entirety herein, can be utilized by a clinician to cut tissue captured within the jaws of an end effector. In operation, the clinician can actuate a closure system of the ultrasonic instrument to move a clamp arm toward a clamped state. A control system, such as circuit board 1100 or controller 620, as examples, can be in operable communication with sensors of the ultrasonic instrument in order to monitor a parameter associated with the end effector moving toward the clamped state, similar to those described herein above concerning the surgical stapling instrument and the electrosurgical instrument.

In various embodiments, the control system can monitor a parameter associated with the end effector applying energy to the tissue. In some embodiments, the parameter associated with the end effector applying energy to the tissue comprises a magnitude of the energy applied to the tissue via an ultrasonic blade. In some embodiments, the parameter associated with the end effector applying energy to the tissue comprises an amount of time that the end effector has been applying energy to the tissue via an ultrasonic blade. In some embodiments, the parameter associated with the end effector applying energy to the tissue comprises an impedance of the tissue. In some embodiments, the parameter associated with the end effector applying energy to the tissue comprises a rate of change of the impedance of the tissue. In various embodiments, the parameter associated with the end effector applying energy to the tissue comprises a frequency of the ultrasonic blade.

Based on the parameter monitored by the control system, via the sensors, the control system can set a parameter of a second drive system, such as an ultrasonic drive system or a clamping system of the ultrasonic instrument. In some embodiments, setting a parameter of a second drive system comprises setting a parameter of the ultrasonic drive system. In some embodiments, setting a firing parameter of the ultrasonic drive system comprises setting a parameter for an ultrasonic transducer that oscillates an ultrasonic blade to cut tissue. In some embodiments, the parameter for the motor comprises a duty cycle of the motor. In some embodiments, the parameter comprises a frequency of the ultrasonic blade. In some embodiments, the parameter comprises an amount of current or voltage supplied to the transducer from a power source. In some embodiments, setting a parameter of the second drive system comprises setting multiple parameters of the second drive system.

In various embodiments, setting a parameter of the second drive system comprises setting a parameter of the closure system. In some embodiments, setting a parameter of the closure system comprises an amount of force applied to the tissue. In some embodiments, setting a parameter of the closure system comprises a rate of change of force applied to the tissue. In some embodiments, setting a parameter of the closure system comprises a speed at which the end effector moves toward the clamped state. Various other parameters associated with clamping systems are described elsewhere herein.

Figure 48:
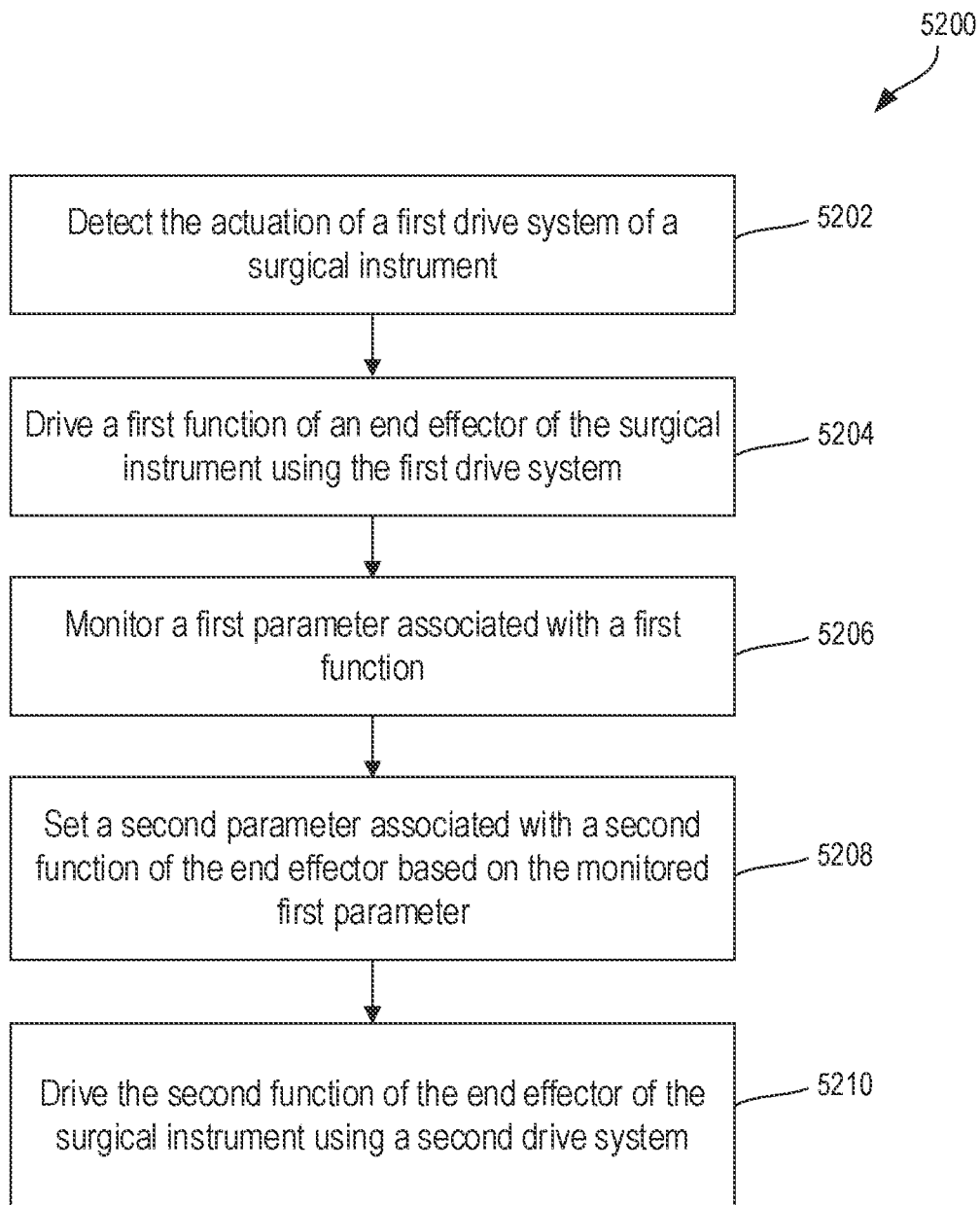
FIG. 48 illustrates a method for controlling a surgical instrument, according to at least one aspect of the present disclosure.

Referring now to FIG. 48, a method 5200 for controlling a surgical instrument is provided, according to at least one aspect of the present disclosure. The method 5200 comprises detecting 5202 the actuation of a first drive system of a surgical instrument. In various embodiments, a control system, such as controller 620, can detect the actuation of the first drive system utilizing any number of sensors described elsewhere, such as current sensors or position sensors, as examples. In some embodiments, the control system detects the actuation of the first drive system by monitoring a position of an actuator, such as the closure trigger 1032 or a firing trigger 1130, as examples. In various embodiments, the surgical instrument comprises a surgical stapling instrument, such as surgical instrument 1010. In various embodiments, the surgical instrument comprises an electrosurgical instrument. In various embodiments, the surgical instrument comprises an ultrasonic instrument.

The method 5200 further comprises driving 5204 a first function of an end effector of the surgical instrument using the first drive system. In various embodiments, the first function comprises transitioning a jaw of the end effector toward the clamped position. In various embodiments, the first function comprises applying energy to tissue positioned within the end effector with an energy delivery component. In various embodiments, the energy delivery component comprises an ultrasonic blade. In various embodiments, the energy delivery component comprises an electrode. In various embodiments, the first function comprises driving a firing member to deploy staples removably stored in a staple cartridge positioned within the end effector.

The method 5200 further comprises monitoring 5206 a first parameter associated with the first function. In various embodiments, the first parameter can be monitored by the control system using any number of sensors described elsewhere herein. In various embodiments, the first parameter comprises a load applied by the jaw to tissue positioned within the end effector. In various embodiments, the first parameter comprises an amount of time that energy has been applied to the tissue with the energy delivery component. In various embodiments, the first parameter comprises a rate of change in impedance of tissue. In various embodiments, the first parameter comprises a speed of a firing member or a cutting member through the end effector. In various embodiments, the first parameter comprises a current or voltage supplied to a motor or an ultrasonic transducer of the surgical instrument.

The method 5200 further comprises setting 5208 a second parameter associated with a second function of the end effector based on the monitored first parameter. In various embodiments, the control system utilizes the monitored first parameter to set a second parameter associated with a second function of the end effector. In various embodiments, the control system compares the monitored parameter to data stored in a memory, such as memory 624, in order to set the second parameter. In various embodiments, the second function comprises driving a firing member toward a fired position to deploy staples removably stored in a staple cartridge. In various embodiments, the second function comprises transitioning a jaw toward the clamped position. In various embodiments, the second function comprises applying energy to tissue positioned within the end effector with an energy delivery component. In various embodiments, the energy delivery component comprises an ultrasonic blade. In various embodiments, the energy delivery component comprises an electrode.

The method 5200 further comprises driving 5210 the second function of the end effector of the surgical instrument using a second drive system. In various embodiments, the control system transmits a control signal to a second drive system to cause the second drive system to drive the second function utilizing the second parameter. Accordingly, the foregoing method 5200 adapts one drive system in accordance with monitored parameters from a second, separate and distinct drive system of the surgical instrument. Such adaptation results in better surgical outcomes, such as cleaner cuts, as the control system utilizes dynamically obtained information to alter parameters associated with different drive systems of the same surgical instrument.

Referring now to FIG. 49, a table illustrating the transection performance of various staple cartridges is provided, according to at least one aspect of the present disclosure. As seen in FIG. 49, parameters associated with different staple cartridges of different colors are provided. The staple cartridges include a staple cartridge with a first color (Color A), a staple cartridge with a second color (Color B), a staple cartridge with a third color (Color C), a staple cartridge with a fourth color (Color D), a staple cartridge with a fifth color (Color E). Each of the staple cartridges can include at least one parameter different from the other staple cartridges. As one example, the Color A cartridge includes staples with a first unformed staple height and the Color B cartridge includes staples with a second unformed staple height greater than the first unformed staple height. As another example, the Color A cartridge includes staples comprised of a first material and the Color B cartridge includes staples comprised of a second material different than the first material. As another example, the Color A cartridge includes staples with a first wire diameter and the Color B cartridge includes staples with a second wire diameter. Various other parameters associated with staple cartridges are discussed elsewhere herein. It is understood that the different colors are merely visual representations of staple cartridges with different configurations. In certain aspects, instead of colors, the different staple cartridges can be equally represented with any suitable identifying, or distinguishing, characteristics.

Each of the staple cartridges is designed for a minimum (indicated) use, a maximum (design) use, and an overstress use. Each use corresponds to a recommended type of tissue and a recommended tissue thickness. As one example, the minimum (indicated) application for a Color A staple cartridge is for a Type A tissue and a corresponding tissue thickness of $t_1$.

As shown in FIG. 49, the Color A staple cartridge is designed to be used with a first tissue type (Type A) and a second tissue type (Type B) and with tissue in a tissue thickness range of $t_1$ to $t_3$. The Color B staple cartridge is designed to be used with a third tissue type (Type C) and with tissue in a tissue thickness range of $t_4$ to $t_6$. The Color C staple cartridge is designed to be used with the third tissue type (Type C) and with tissue in a tissue thickness range of $t_7$ to $t_9$. The Color D staple cartridge is designed to be used with the third tissue type (Type C) and with tissue in a tissue thickness range of $t_{10}$ to $t_{12}$. The Color E staple cartridge is designed to be used with the third tissue type (Type C) and with tissue in a tissue thickness range of $t_{13}$ to $t_{15}$.

In various embodiments, the tissue thickness values (minimum/maximum/overstressed) for the Color B staple cartridge are greater than the respectively tissue thickness values for the Color A staple cartridge. Similarly, the tissue thickness values for the Color C staple cartridge are greater than the respectively tissue thickness values for the Color B staple cartridge. Similarly, the tissue thickness values for the Color D staple cartridge are greater than the respectively tissue thickness values for the Color C staple cartridge. Similarly, the tissue thickness values for the Color E staple cartridge are greater than the respectively tissue thickness values for the Color D staple cartridge.

In various embodiments, the first tissue type (Type A) comprises jejunum tissue, the second tissue type (Type B) comprises colon tissue, and the third tissue type (Type C) comprises stomach tissue. In various embodiments, the tissue thickness for minimum design use ($t_4$, $t_7$, $t_{10}$, and $t_{13}$) and maximum design use ($t_5$, $t_8$, $t_{11}$, and $t_{14}$) can be less than the overstress design use for a lower cartridge ($t_3$, $t_6$, $t_9$, and $t_{12}$, respectively). In operation, a clinician can select an appropriate staple cartridge to use according to the data provided in the table of FIG. 49.

Figure 50:
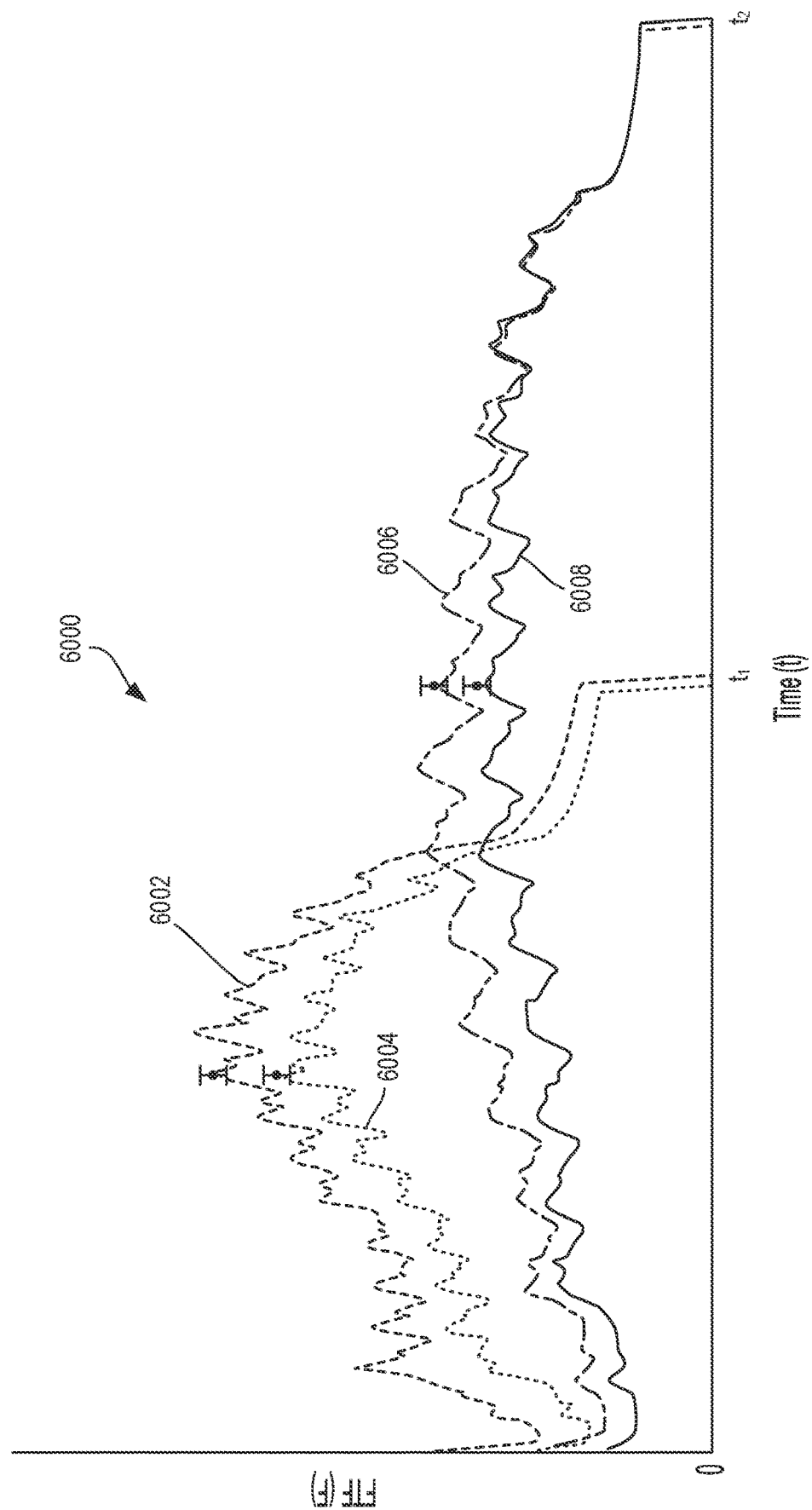
FIG. 50 is a graph illustrating the force to fire ("FTF") for a firing member at varying speeds, according to at least one aspect of the present disclosure.

Referring now to FIG. 50, a graph 6000 illustrates the force to fire ("FTF") for a firing member at varying speeds, according to at least one aspect of the present disclosure. The graph 6000 illustrates four instances of a motor, such as motor 1082 or motor 602, as examples, driving a firing member, such as firing member 1900, through similar types of tissue.

In two instances 6002, 6004, the motor drove the firing member at a first speed $V_1$ through a firing stroke. In two other instances 6006, 6008, the motor drove the firing member at a second speed $V_2$ less than the first firing speed $V_1$ through a firing stroke. As shown in FIG. 50, for instances 6002, 6004, driving the firing member at the first speed $V_1$ resulted in the firing stroke completing in approximately a first amount of time $t_1$ with a first general firing force profile. On the other hand, for instances 6006, 6008, driving the firing member at the second speed $V_2$ resulted in the firing stroke completing in approximately a second amount of time $t_2$ greater than the first amount of time $t_1$, owing to the slower speed, and a second general firing force profile. As seen in graph 600, owing to the slower speed, the maximum force to fire for the instances 6006, 6008 was less than the maximum force to fire for the instances 6002, 6004. Accordingly, firing speed plays a factor in force to fire through a firing stroke.

Force to fire is a significant issue causing limitations in articulation, shaft size, and even resultant formed staple height. With higher force to fire causing the need for more metal and support, the result is poor control in formed staple heights. It would be beneficial to leverage tissue creep and pausing of the firing stroke to drive down the FTF during the firing stroke.

Figure 51:
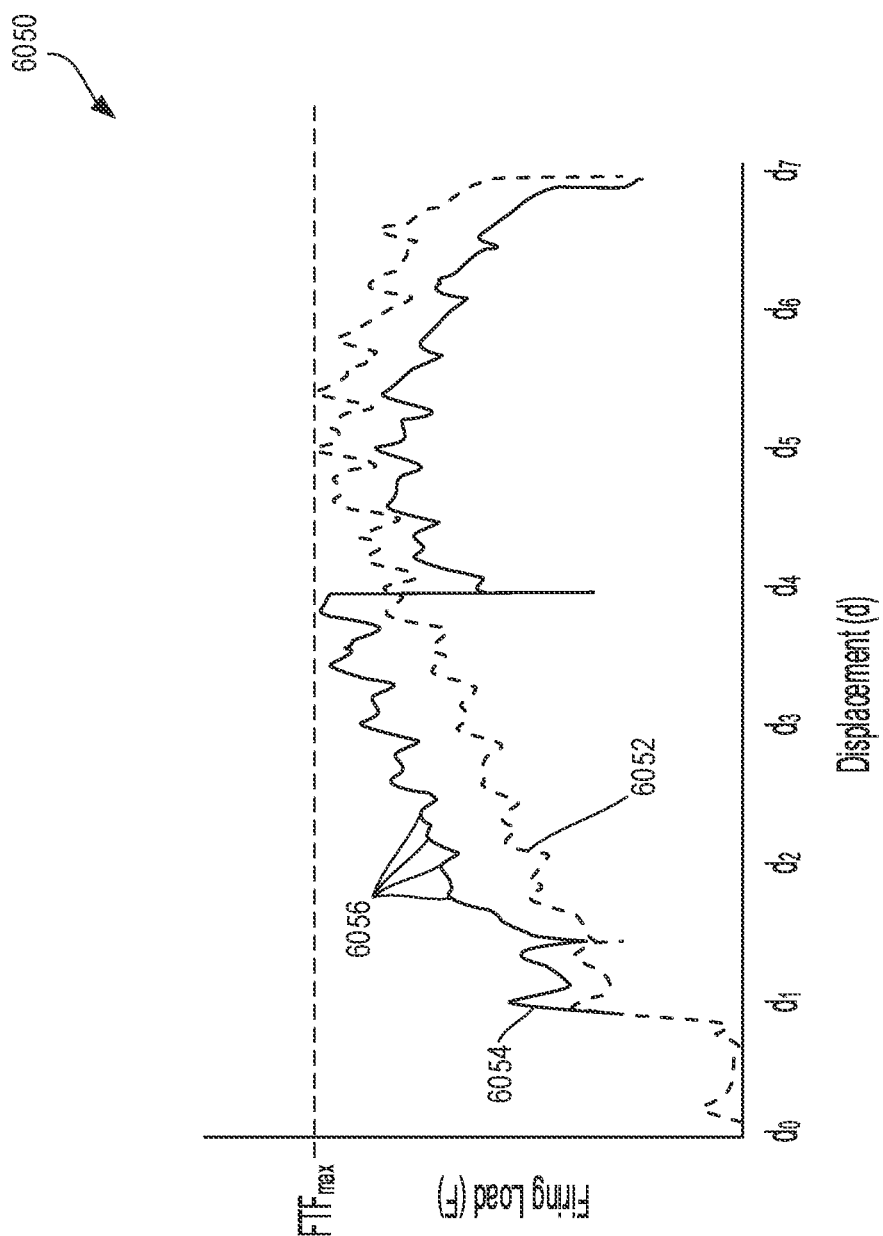
FIG. 51 is a graph illustrating the effects of pausing on FTF, according to at least one aspect of the present disclosure.

Referring now to FIG. 51, a graph 6050 illustrating the effects of pausing on FTF is provided, according to at least one aspect of the present disclosure. Graph 6050 illustrates firing loads on a firing member, such as firing member 1900, against the displacement of the firing member through firing strokes, as explained in more detail below.

In various instances, a firing system drives a firing member through a firing stroke to cut tissue captured between the jaws of an end effector, as well as to deploy staples removably stored in a staple cartridge. Referring to FIG. 51, the firing member begins at an unfired position, $d_0$, prior to initiation of the firing stroke. Based on the initiation of the firing stroke, such as actuation of a firing trigger, a firing system drives the firing member from the unfired position toward a fired position, $d_7$, to deploy staples from a staple cartridge and, optionally, to cut tissue captured within the end effector.

In certain instances, at $d_1$, the FTF 6052 the firing member ramps up based on the firing member encountering the tissue captured within the end effector and beginning to deploy the staples from the staple cartridge. From $d_1$ to $d_5$, the FTF 6052 gradually increases during the firing stroke, ultimately reaching a $FTF_{max}$ around $d_5$. From $d_5$ to the fired position, $d_7$, the FTF gradually decreases.

The present disclosure provides a way of controlling the FTF during a firing stroke of the firing member. In some embodiments, a control system, such as controller 620, can predict higher, upcoming forces to fire based on the size of the FTF peaks early in the firing stroke. Based on the prediction, the control system can trigger changes to a firing algorithm, an algorithm defining parameters of a firing stroke, to control the force to fire during the firing stroke.

In some embodiments, the change to the firing algorithm includes pausing the firing stroke. In some embodiments, the change to the firing algorithm includes adjusting the length of the pause of the firing stroke. In some embodiments, the change to the firing algorithm includes changing the speed of the firing member. In some embodiments, the change to the firing algorithm includes later trigger adjustments heights. In some embodiments, the change to the firing algorithm includes controlling a voltage or current applied to the motor of the firing system that drives the firing member. In some embodiments, the change to the firing algorithm includes changing a duty cycle of the motor that drives the firing member.

In some embodiments, the control system predicts, at a first time in the firing stroke, that the force to fire will exceed a force to fire threshold at a second time subsequent to the first time. Based on the prediction, the control system allows the firing member to continue through the firing stroke for a period of time before reaching or exceeding the force to fire threshold. In some embodiments, the control system predicts a time in which the force to fire will exceed the force to fire threshold. Based on the prediction, the control system allows the firing member to continue through the firing stroke for the predicted amount of time. In some embodiments, the control system can take other proactive actions, such as slowing the firing speed of the firing member or making adjustments to the motor, as examples. In some embodiments, the control system proactively determines how long the firing stroke will need to be paused, based on the prediction. In some embodiments, the control system proactively determines how long the firing stroke will need to be paused, based on a rate of change of the force to fire prior to the starting of the pause. In some embodiments, the control system proactively determines how long the firing stroke will need to be paused based on the number and/or magnitude of the force to fire peaks and valleys detected by the control system prior to the starting of the pause. In some embodiments, the control system proactively determines how many times the firing stroke will need to be paused in order to maintain the force to fire below a force to fire maximum threshold.

Accordingly, the control system proactively determines if a force to fire threshold will be reached or exceeded and takes proactive measures prior to reaching the force to fire threshold. This proactive action is an improvement over systems that take no action until the force to fire reaches or exceeds a force to fire threshold. By waiting until a force to fire threshold is reached or exceeded, the force to fire may inadvertently exceed the force to fire threshold and reach unacceptable levels while the control system is reacting exceeded threshold, which would result in the firing motor stalling. By taking proactive measures, the control system recognizes, ahead of time that, a force to fire threshold may, or will, be reached or exceeded, and plans accordingly.

Referring again to FIG. 51, a firing member, such as firing member 1900, begins at an unfired position, $d_0$, prior to initiation of the firing stroke. Based on the initiation of the firing stroke, such as actuation of a firing trigger, a firing system, such as firing motor drive assembly 604, drives the firing member from the unfired position toward a fired position, $d_7$, to cut tissue captured within the end effector, such as end effector 1300, and to deploy staples from a staple cartridge, such as staple cartridge 1301.

At $d_1$, the FTF 6054 the firing member ramps up based on the firing member encountering the tissue captured within the end effector and beginning to deploy the staples. In various embodiments, a control system, such as controller 620, can monitor the force to fire using any number of sensors described elsewhere herein. In some embodiments, the control system is in operable communication with a current sensor that senses a current supplied to a firing motor, such as firing motor 602, from a power source, such as power source 628, in order to determine FTF. In some embodiments, the control system is in operably communication with a force sensor in order to determine FTF.

Based on the detected FTF, the control system initiates an algorithm to predict the force to fire that the firing member will experience during the firing stroke. In various embodiments, the algorithm is stored in a memory, such as memory 624, and is executable by a processor, such as processor 622. In some embodiments, the control system predicts the force to fire based on the magnitude of the force to fire peaks, such as peaks 6056, as the firing member traverses through the firing stroke. In some embodiments, the control system predicts the force to fire based on a change in magnitude of the force to fire peaks, such as peaks 6056, as the firing member traverses through the firing stroke. In some embodiments, the control system predicts the force to fire based on the shape of the force to fire peaks. In some embodiments, the control system predicts the force to fire based on the number of occurrences of force to fire peaks, such as peaks 6056, as the firing member traverses through the firing stroke. In some embodiments, the control system predicts the force to fire based on the rate of change of the force to fire as the firing member traverses through the firing stroke. In some embodiments, the control system predicts the future force to fire based on a predefined amount of time of the firing stroke, such as a predetermined amount of time from when the firing member begins to encounter resistance. In some embodiments, the control system continuously predicts the future forces to fire based on data discretely, or continuously, received from the sensors.

Based on the predicted force to the fire, the control system can trigger changes to the firing algorithm to control the force to fire during the firing stroke, as described herein above. Referring to graph 6050, based on the prediction, the control system triggers the firing algorithm to pause displacement of the firing member at $d_4$. As seen on graph 6050, pausing the displacement causes the force to fire to drop. At a later time, such as a predefined or variable amount of time from the occurrence of the pause, as determined by the control system, the control system triggers the algorithm to resume advancement of the firing member toward the fired position $d_7$. In some embodiments, the length of the pause is based on the force to fire profile prior to the pause. In some embodiments, the length of the pause is based on the force to fire dropping below a force to file minimum threshold. In some embodiments, the control system further causes the firing member to resume advancement with a decreased speed. As seen on graph 6050, as the firing member resumes advancement, the force to fire has now dropped below the $FTF_{max}$ and gradually increases again toward $FTF_{max}$. However, owing to the triggered changes to the firing algorithm by the control system, the force to fire for the remainder of the firing stroke stays below $FTF_{max}$.

While the foregoing example illustrated on graph 6050 shows a single pause, it should be understood that the control system can continuously predict future force to fire loads during the firing stroke and trigger additional changes to the firing algorithm based on the predictions. For instance, referring now to FIG. 52, a graph 6070 illustrating the effects of multiple pauses on FTF is provided, according to at least one aspect of the present disclosure. Graph 6070 illustrates a firing load of a firing member, such as firing member 1900, against the displacement of the firing member through a firing stroke.

Similar to the above, graph 6070 illustrates a system in which, from $d_0$ to $d_5$, the FTF 6072 the firing member ramps up as the firing member encounters the tissue captured within the end effector and begins to deploy the staples, ultimately reaching a $FTF_{max}$ around $d_5$. From $d_5$ to the fired position, $d_7$, the FTF gradually decreases.

The present disclosure provides a way of controlling the FTF during a firing stroke of the firing member using multiple pauses and other changes to the firing algorithm, such as changing the speed of the firing member. In some embodiments, a control system, such as controller 620, predicts higher, upcoming forces to fire based on the FTF peaks early in the firing stroke. Based on the prediction, the control system can trigger changes to the firing algorithm to control the force to fire during the firing stroke.

In some embodiments, the change to the firing algorithm includes pausing the firing stroke multiple times. The control system can make predictions, early on in the firing stroke, in order to control the force to fire during the firing stroke. In some other embodiment, the control system can continuously make predictions during the firing stroke in order to control the force to fire. In some embodiments, a first control action taken in response to a first prediction is used to influence a subsequent prediction and a second control action taken to control the force to fire. In one embodiment, in response to a first prediction, the control system adjusts the firing algorithm to pause the firing stroke for a first amount of time. In response to a second prediction subsequent to the first prediction, the control system adjusts the firing algorithm to pause the firing stroke for a second amount of time different from the first amount of time, as well as slowing the speed of the firing member. In one aspect, the second prediction is made based on the FTFs response to the first pause.

Referring again to FIG. 52, a firing member, such as firing member 1900, begins at an unfired position, $d_0$, prior to initiation of the firing stroke. Based on the initiation of the firing stroke, such as actuation of a firing trigger, a firing system, such as firing motor drive assembly 604, drives the firing member from the unfired position toward a fired position, $d_7$, to cut tissue captured within the end effector, such as end effector 1300, and to deploy staples from a staple cartridge, such as staple cartridge 1301.

From $d_0$, the FTF 6074 the firing member ramps up as the firing member begins to encounter the tissue captured within the end effector and begins to deploy the staples. In various embodiments, a control system, such as controller 620, can monitor the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor positioned on the firing member in order to determine the force to fire the firing member.

Based on the detected force to fire, the control system initiates an algorithm to predict the force to fire that the firing member will experience during the firing stroke. In various embodiments, the algorithm is stored in a memory, such as memory 624, and is executable by a processor, such as processor 622. In some embodiments, the control system predicts the force to fire based on the rate of change of the force to fire. In some embodiments, the control system predicts the force to fire based on the magnitude of the force to fire peaks, such as peaks 6076, as the firing member traverses through the firing stroke. In some embodiments, the control system predicts the force to fire based on a change in magnitude of the force to fire peaks, such as peaks 6076, as the firing member traverses through the firing stroke. In some embodiments, the control system predicts the force to fire based on the number of occurrences of force to fire peaks, such as peaks 6076, as the firing member traverses through the firing stroke. In some embodiments, the control system predicts the force to fire based on both peaks and valleys in the force to fire profile. In some embodiments, the control system predicts the force to fire based on the shape of the force to fire peaks. In some embodiments, the control system predicts the force to fire based on the rate of change of the force to fire as the firing member traverses through the firing stroke. In some embodiments, the control system predicts the future force to fire based on a predefined amount of time of the firing stroke, such as a predetermined amount of time from when the firing member begins to encounter resistance. In some embodiments, the control system continuously predicts the future force to fire based on data discretely, or continuously, received from the sensors.

Further to the above, in some instances, the control system implements a first adjustment to one or more parameters influencing FTF such as, for example, a first pause, then monitors the effect, or result, of the first pause on the FTF profile. Additional adjustments can be implemented based on the effect, or result, of the first adjustment. For example, a second pause can be implemented at a set time period after the first pause, wherein the set time period is determined based on the effect, or result, of the first pause. In some instances, additional pauses can be implemented based on the effect, or result, of the second pause, or a combined effect, or result, of the first and second pauses. In such instances, the adjustments are dynamic adjustments that are influenced by the effects, or results, of one or more previous adjustments.

Based on the predicted force to fire, the control system can trigger changes to the firing algorithm to control the force to fire during the firing stroke, as described herein above. Referring to graph 6070, based on the prediction, the control system triggers the firing algorithm to pause displacement of the firing member at $d_1$. As seen on graph 6070, pausing the displacement causes the force to fire to drop. At a later time, such as a predefined or variable amount of time from the occurrence of the pause, as determined by the control system, the control system triggers the algorithm to resume advancement of the firing member toward the fired position $d_7$. In some embodiments, the length of the pause is based on the FTF profile prior to the pause. In some embodiments, the length of the pause is based on the force to fire dropping below a force to fire minimum threshold. In some embodiments, the length of the pause is based on the length of time from a previous pause. In some embodiments, the length of the pause is based on the number of occurrences of pauses during the firing stroke. For instance, the first pause is a first amount of time and the second pause subsequent to the first pause is a different amount of time, such as a greater or less amount of time. As seen on graph 6070, as the firing member resumes advancement, the force to fire has dropped below the force to fire value at the time of pausing. In some embodiments, when the firing member resumes advancement, the firing algorithm can be adjusted by the control system to change the speed of the firing member to further control the force to fire profile.

As the control system continues to drive the firing member toward the fired position, the control system continues to monitor the force to fire profile and continues to make predictions about future force to fire values. In some instances, the control system can monitor force to fire profile, such as peaks and valleys thereof, as the firing member is driven toward the fired position. Based on the prediction, referring again to graph 6070, the control system pauses displacement of the firing member again at $d_2$. At a later time, such as a predefined or variable amount of time from the occurrence of the pause, as determined by the control system, the control system triggers the algorithm to resume advancement of the firing member toward the fired position $d_7$. In some embodiments, the length and time of the second pause at $t_2$ can be based on the length and time of the first pause at $t_1$. In some instances, the length of the second and time of the second pause at $t_2$ is based on the FTF response of the first pause at $t_1$.

In some embodiments, the control system can proactively decide the time for a subsequent pause based on data receive prior to a previous pause. For instance, prior to the pause at $d_1$, the control system can determine that a pause will be necessary at $d_1$, and also at $d_2$. Accordingly, the control system can manage the force to fire profile for the entire, or at least a substantial amount, of the firing stroke based on data determined in an early portion of the firing stroke. In some embodiments, the control system can adaptively manage pauses and resumptions of the firing stroke to maintain the force to fire between a force to fire maximum value and a force to fire minimum value that can be retrieved from a memory, for example. In some embodiments, the control system can make other dynamic adjustments, such as changing the speed of the firing member or changing a current/voltage applied to the firing motor to control the force to fire during the firing stroke based on the FTF response to previous adjustments. In some embodiments, after each pause, the control system can change the speed of the firing member to change the rate at which the FTF the firing member rises based on the FTF response to previous adjustments.

Figure 52:
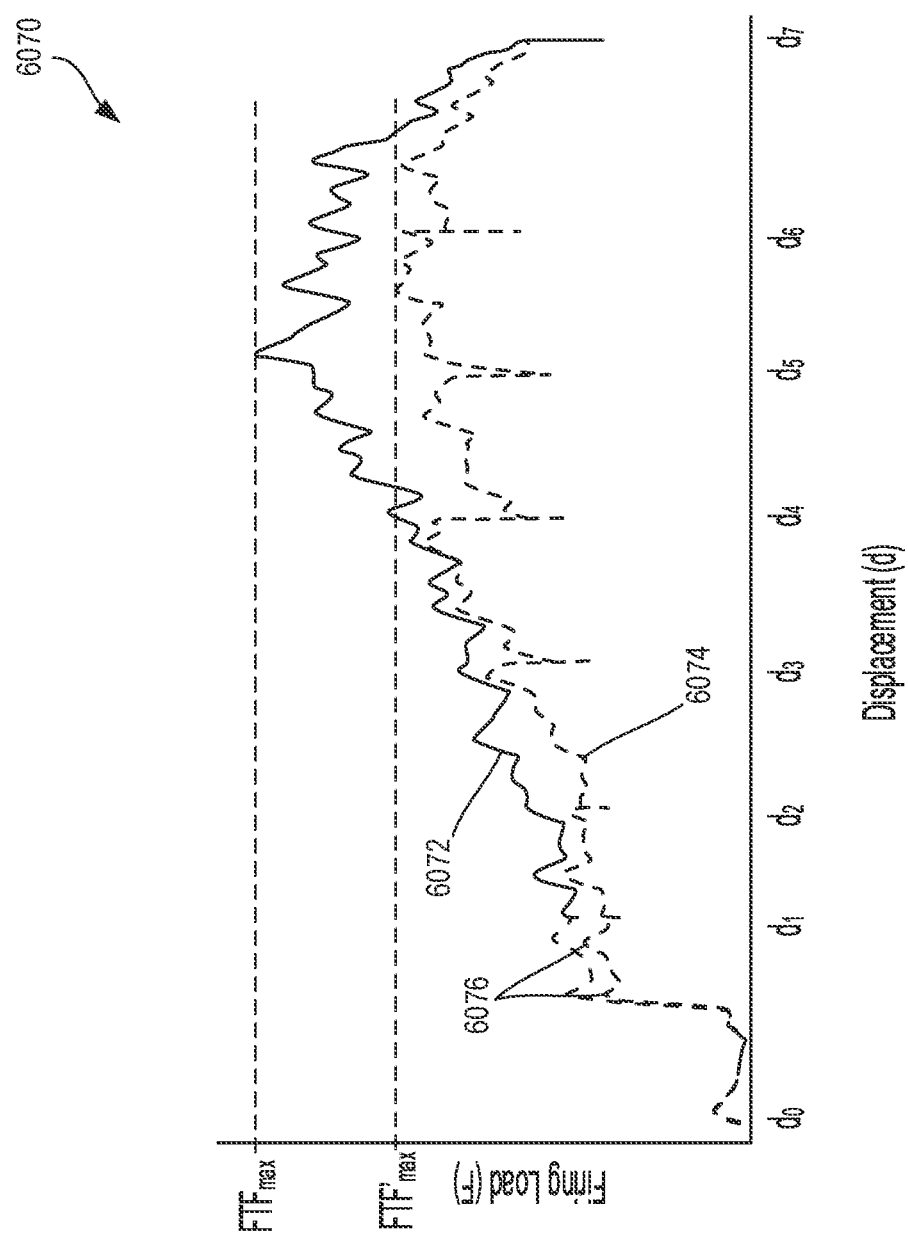
FIG. 52 is a graph illustrating the effects of pausing on FTF, according to at least one aspect of the present disclosure.

The control system can continue monitoring the firing force profile, dynamically making predictions, and taking corrective actions until the firing member reaches the fired position at $d_7$. As shown in FIG. 52, owing to the predictions and corrective actions taken by the control system, the force to fire reaches a $FTF'_{max}$ during the firing stroke, which is less than the $FTF_{max}$ for current systems. Accordingly, the predictive and corrective actions taken by the control circuit lowers the force to fire during a firing stroke.

In various embodiments, during a firing stroke and based on a first prediction, the control system can cause a default firing algorithm to be changed in a first way, such as pausing advancement of the firing member for a first amount of time. By analyzing the FTF response to the first pause, a second prediction can be made by the control system. Based on the second prediction, the control system can cause the default firing algorithm to be changed in a second way that can be different than the first way, such as pausing advancement for a second amount of time, different than the first amount of time, as well as decreasing a speed of the firing member. Accordingly, the control system dynamically adjusts the firing algorithm during the firing stroke based on an observed response of the FTF to one or more previous adjustment in order to maintain the force to firing the firing member within a predetermined threshold range that lowers the strain on the firing system.

Figure 53:
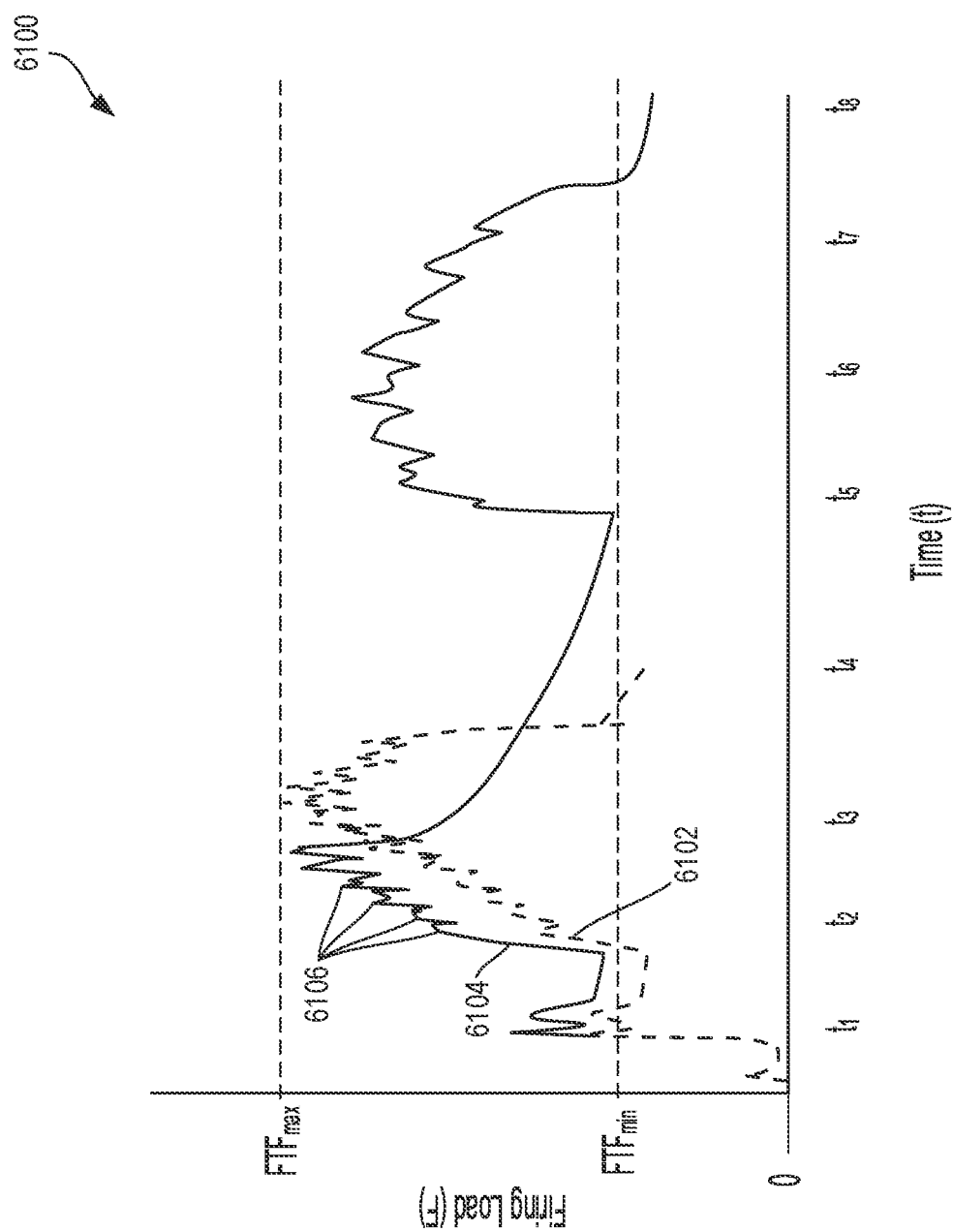
FIG. 53 is a graph illustrating the effects of pausing on FTF, according to at least one aspect of the present disclosure.

Referring now to FIG. 53, a graph 6100 illustrating the effects of pausing on FTF is provided, according to at least one aspect of the present disclosure. Graph 6100 illustrates firing loads of a firing member, such as firing member 1900, against time, as explained in more detail below.

In current systems, a firing system drives a firing member through a firing stroke to cut tissue captured between the jaws of an end effector, as well as to deploy staples removably stored in a staple cartridge. Referring to FIG. 53, at $t_0$, the firing member begins at an unfired position, prior to initiation of the firing stroke. At the initiation of the firing stroke, such as actuation of a firing trigger, a firing system drives the firing member from the unfired position toward a fired position to cut tissue captured within the end effector and to deploy staples from a staple cartridge.

For current systems, at $t_1$, the FTF 6102 peaks owing to the initial resistance of moving the firing member from the unfired position. At around $t_2$, the FTF 6102 begins to climb as the firing member encounters the tissue captured within the end effector and begins to deploy the staples. The FTF 6102 gradually increases over the firing stroke, ultimately reaching a $FTF_{max}$ around $t_3$. From $t_3$ to the fired position of the firing member, around $t_4$, the FTF sharply decreases.

As discussed above, the present disclosure provides a way of dynamically controlling the FTF during a firing stroke. Referring again to FIG. 53, a firing member, such as firing member 1900, at $t_0$, begins at an unfired position, prior to initiation of the firing stroke. At the initiation of the firing stroke, such as actuation of a firing trigger, a firing system, such as firing motor drive assembly 604, drives the firing member from the unfired position toward a fired position to cut tissue captured within the end effector, such as end effector 1300, and to deploy staples from a staple cartridge, such as staple cartridge 1301.

At $t_1$, the FTF 6104 the firing member peaks owing to the initial resistance of moving the firing member from the unfired position. At around $t_2$, the FTF 6104 begins to climb as the firing member encounters the tissue captured within the end effector and begins to deploy the staples. In various embodiments, a control system, such as controller 620, can monitor the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

Based on the detected force to fire, the control system initiates an algorithm to predict the force to fire that the firing member will experience during the firing stroke. In various embodiments, the algorithm is stored in a memory, such as memory 624, and is executable by a processor, such as processor 622. In some embodiments, the control system predicts the force to fire based on the magnitude of the force to fire peaks, such as peaks 6106, as the firing member traverses through the firing stroke. In some embodiments, the control system predicts the force to fire based on a change in magnitude of the force to fire peaks, such as peaks 6106, as the firing member traverses through the firing stroke. In some embodiments, the control system predicts the force to fire based on the number of occurrences of force to fire peaks, such as peaks 6106, as the firing member traverses through the firing stroke. In some embodiments, the control system predicts the force to fire based on the shape of the force to fire peaks. In some embodiments, the control system predicts the force to fire based on the rate of change of the force to fire as the firing member traverses through the firing stroke. In some embodiments, the control system predicts the future force to fire based on a predefined amount of time of the firing stroke, such as a predetermined amount of time from when the firing member begins to encounter resistance. In some embodiments, the control system continuously predicts the future forces to fire based on data discretely, or continuously, received from the sensors.

Based on the predicted force to the fire, the control system triggers changes to the firing algorithm to control the force to fire during the firing stroke, as described herein above. Referring to graph 6100, based on the prediction, the control system triggers the firing algorithm to pause advancement of the firing member at $t_3$ until $t_5$. In various embodiments, the control system pauses the force to fire 6104 until the force to fire reaches a force to fire threshold $FTF_{min}$. In various embodiments, the control system pauses the force to fire 6104 for a predetermined, or variable, amount of time. In some embodiments, the variable amount of time is determined based on the forces sensed as the control system was predicting the future force to fire. In some embodiments, the length of the pause is based on the force to fire profile prior to the pause. As seen on graph 6100, pausing the advancement between $t_3$ and $t_5$ causes the force to fire to gradually drop to a $FTF_{min}$. At $t_5$, the control system triggers the algorithm to resume advancement of the firing member toward the fired position. As seen on graph 6100, as the firing member resumes advancement, the force to fire gradually increases again to $FTF_{max}$. However, owing to the adjustments to the default firing algorithm by the control system, the force to fire for the remainder of the firing stroke stays well below $FTF_{max}$. In some embodiments, the control system can adjust the firing algorithm such that the firing member resumes advancement at a slower speed than prior to the pause of the firing stroke.

While the foregoing example illustrated on graph 6100 shows a single pause, it should be understood that the control system can continuously predict future force to fire loads during the firing stroke and trigger additional changes to the firing algorithm based on the predictions. For instance, referring now to FIG. 54, a graph 6120 illustrating the effects of multiple pauses on FTF is provided, according to at least one aspect of the present disclosure. Graph 6120 illustrates firing loads on a firing member, such as firing member 1900, against time, as explained in more detail below.

Similar to the above, graph 6120 illustrates a current system in which, from $t_0$ to $t_3$, the FTF 6122 the firing member ramps up as the firing member encounters the tissue captured within the end effector and begins to deploy the staples, ultimately reaching a $FTF_{max}$ around $t_3$. From $t_3$ to the end of the stroke, $t_4$, the FTF decreases.

The present disclosure provides a way of dynamically controlling the FTF during a firing stroke of the firing member. In some embodiments, a control system, such as controller 620, can predict higher, upcoming forces to fire based on the FTF peaks early in the firing stroke. Based on the prediction, the control system can trigger changes to the firing algorithm to control the force to fire during the firing stroke.

In some embodiments, the change to the firing algorithm includes pausing the firing stroke multiple times. The control system can make predictions, early on in the firing stroke, in order to control the force to fire during the firing stroke. In some other embodiment, the control system can continuously make predictions during the firing stroke in order to control the force to fire. In some embodiments, a first control action taken in response to a first prediction is used to influence a subsequent prediction and a second control action to take to control the force to fire. In one embodiment, in response to a first prediction, the control system adjusts the firing algorithm to pause the firing stroke for a first amount of time. In response to a second prediction subsequent to the first prediction, the control system adjusts the firing algorithm to pause the firing stroke for a second amount of time different from the first amount of time, as well as slowing the speed of the firing member.

Further to the above, in some instances, the control system implements a first adjustment to one or more parameters influencing FTF such as, for example, a first pause, then monitors the effect, or result, of the first pause on the FTF profile. Additional adjustments can be implemented based on the effect, or result, of the first adjustment. For example, a second pause can be implemented at a set time period after the first pause, wherein the set time period is determined based on the effect, or result, of the first pause. In some instances, additional pauses can be implemented based on the effect, or result, of the second pause, or a combined effect, or result, of the first and second pauses. In such instances, the adjustments are dynamic adjustments that are influenced by the effects, or results, of one or more previous adjustments.

Referring again to FIG. 54, a firing member, such as firing member 1900, begins at an unfired position, at $t_0$, prior to initiation of the firing stroke. Based on the initiation of the firing stroke, such as actuation of a firing trigger, a firing system, such as firing motor drive assembly 604, drives the firing member from the unfired position toward a fired position to cut tissue captured within the end effector, such as end effector 1300, and to deploy staples from a staple cartridge, such as staple cartridge 1301.

From $t_0$, the FTF 6124 the force to fire ramps up as the firing member encounters the tissue captured within the end effector and begins to deploy the staples. In various embodiments, a control system, such as controller 620, can monitor the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

Based on the detected force to fire, the control system initiates an algorithm to predict the force to fire that the firing member will experience during the firing stroke. In various embodiments, the algorithm is stored in a memory, such as memory 624, and is executable by a processor, such as processor 622. In some embodiments, the control system predicts the force to fire based on the rate of change of the force to fire. In some embodiments, the control system predicts the force to fire based on the magnitude of the force to fire peaks, such as peaks 6076, as the firing member traverses through the firing stroke. In some embodiments, the control system predicts the force to fire based on a change in magnitude of the force to fire peaks, such as peaks 6076, as the firing member traverses through the firing stroke. In some embodiments, the control system predicts the force to fire based on the number of occurrences of force to fire peaks, such as peaks 6076, as the firing member traverses through the firing stroke. In some embodiments, the control system predicts the force to fire based on the shape of the force to fire peaks and valleys as the firing member traverses through the firing stroke. In some embodiments, the control system predicts the force to fire based on both peaks and valleys in the force to fire profile. In some embodiments, the control system predicts the force to fire based on the rate of change of the force to fire as the firing member traverses through the firing stroke. In some embodiments, the control system predicts the future force to fire based on a predefined amount of time of the firing stroke, such as a predetermined amount of time from when the firing member begins to encounter resistance. In some embodiments, the control system continuously predicts the future force to fire based on data discretely, or continuously, received from the sensors.

Based on the predicted force to fire, the control system triggers changes to the firing algorithm to control the force to fire during the firing stroke, as described herein above. Referring to graph 6120, based on the prediction, the control system triggers the firing algorithm to pause displacement of the firing member at $t_1$. As seen on graph 6120, pausing the displacement causes the force to fire to drop. At a later time, such as a predefined or variable amount of time from the occurrence of the pause, as determined by the control system, the control system triggers the algorithm to resume advancement of the firing member toward the fired position. In some embodiments, the length of the pause is based on the force to fire profile prior to the pause. In some embodiments, the length of the pause is based on the force to fire dropping below a force to file minimum threshold. In some embodiments, the length of the pause is based on the number of occurrences of pauses during the firing stroke. For instance, the first pause can be a first amount of time and the second pause subsequent to the first pause can be a different amount of time from the first pause. As seen on graph 6120, as the firing member resumes advancement, the force to fire has dropped below the force to fire value at the time of pausing.

In some embodiments, the control system can monitor the effect, or result, of the first pause. For instance, the control system can detect the rate at which the force to fire dropped as a result of the pause. In other instances, the control system can detect a magnitude at which the force to fire dropped as a result of the pause. Based on the effect, or result, of the first pause, the control system can determine a second time period after the first pause to re-pause the firing stroke. Furthermore, in some instances, based on the effect, or result, of the first pause, the control system can determine a length of the pause at the second time period after the first pause. Accordingly, the control system dynamically adjusts the firing algorithm during the firing stroke.

As the control system continues to drive the firing member toward the fired position, the control system continues to monitor the force to fire profile and continues to make predictions about future force to fire values. In some instances, the control system can monitor force to fire peaks, such as peaks and valleys, as the firing member is driven toward the fired position. Based on the prediction, referring again to graph 6120, the control system can pause displacement of the firing member again at $t_2$. In other instances, the control system can pause advancement of the firing stroke at $t_2$ based on the prediction and an adjustment made to the firing algorithm during a previous pause, as discussed above.

At a later time, such as a predefined or variable amount of time from the occurrence of the pause, as determined by the control system, the control system triggers the algorithm to resume advancement of the firing member toward the fired position. In some embodiments, the length and time of the second pause at $t_2$ can be based on the length and time of the pause at $t_1$. In some embodiments, the length and time of the second pause at $t_2$ can be based on the effect, or result, of the first pause. In some embodiments, the control system can proactively decide the time for a subsequent pause based on data receive prior to a previous pause. For instance, prior to the pause at $t_1$, the control system can determine that a pause will be necessary at $t_1$, but also at $t_2$. Accordingly, the control system can manage the force to fire profile for the entire, or at least a substantial amount, of the firing stroke based on data determined in an early portion of the firing stroke. In some embodiments, the control system can manage pauses and resumptions of the firing stroke to maintain the force to fire between a force to fire maximum value and a force to fire minimum value. In some embodiments, the control system can make other adjustments, such as changing the speed of the firing member or changing a current/voltage applied to the firing motor to control the force to fire during the firing stroke. In some embodiments, after each pause, the control system can decrease the speed of the firing member to decrease the rate at which the FTF the firing member rises.

Figure 54:
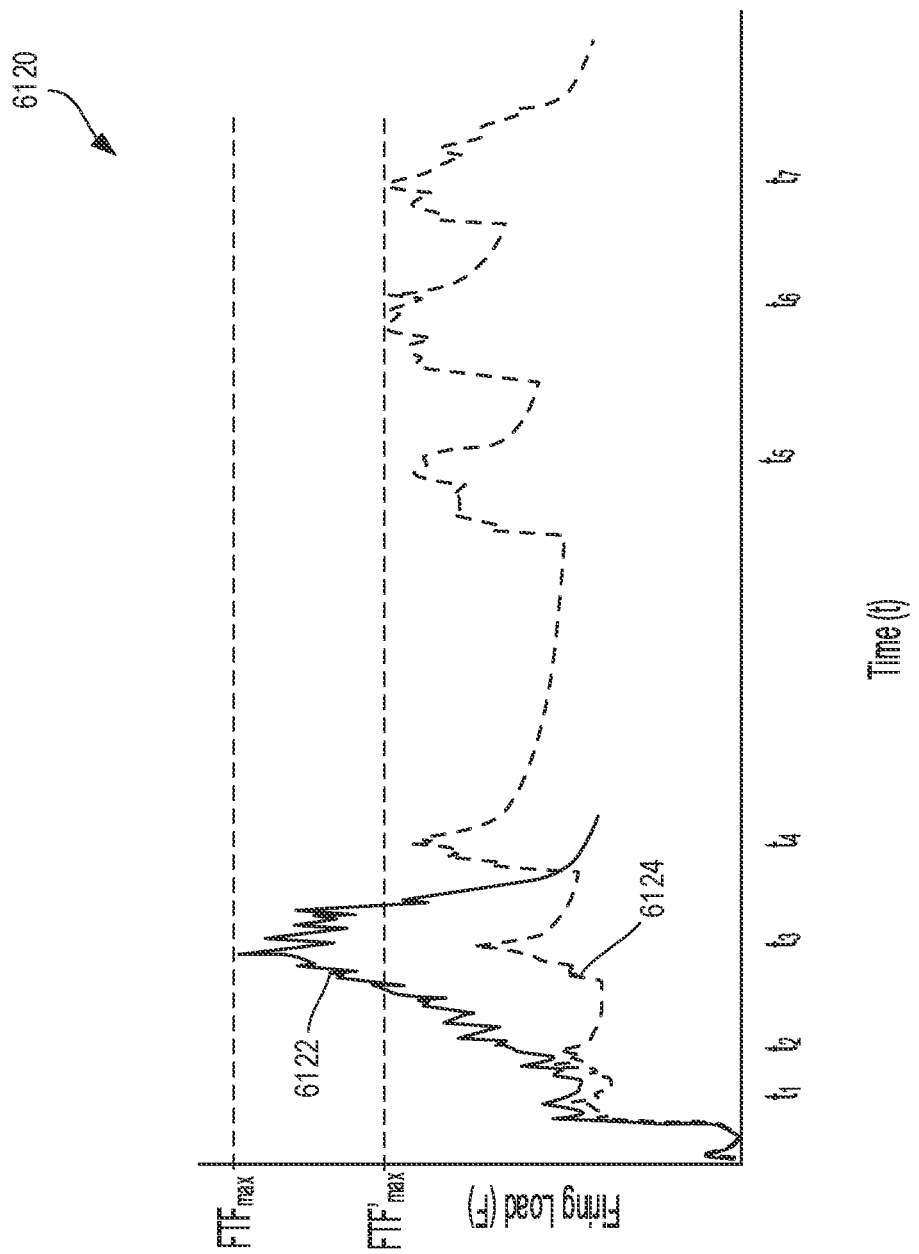
FIG. 54 is a graph illustrating the effects of pausing on FTF, according to at least one aspect of the present disclosure.

The control system can continue monitoring the firing force profile, making predictions, and taking corrective actions until the firing member reaches the fired position, such as at $t_3$, $t_4$, $t_5$, $t_6$, and $t_7$. As shown in FIG. 54, owing to the predictions and corrective actions taken by the control system, the force to fire reaches a $FTF'_{max}$ during the firing stroke, which is less than the $FTF_{max}$ for current systems. Accordingly, the predictive and corrective actions taken by the control circuit lower the force to fire during a firing stroke.

In various embodiments, during a firing stroke and based on a first prediction, the control system can cause the firing algorithm to be changed in a first way, such as pausing advancement for a first amount of time. Based on a second prediction during the firing stroke subsequent to the fire prediction, the control system can cause the firing algorithm to be changed in a second way different than the first way, such as pausing advancement for a second amount of time, different than the first amount of time, as well as decreasing a speed of the firing member. Accordingly, the control system dynamically adjusts the firing algorithm during the firing stroke in order to control the force to firing the firing member. Controlling the force to fire to remain low can lower the strain on the firing system and ultimately result in cleaner staple cuts on patient tissue.

Figure 55:
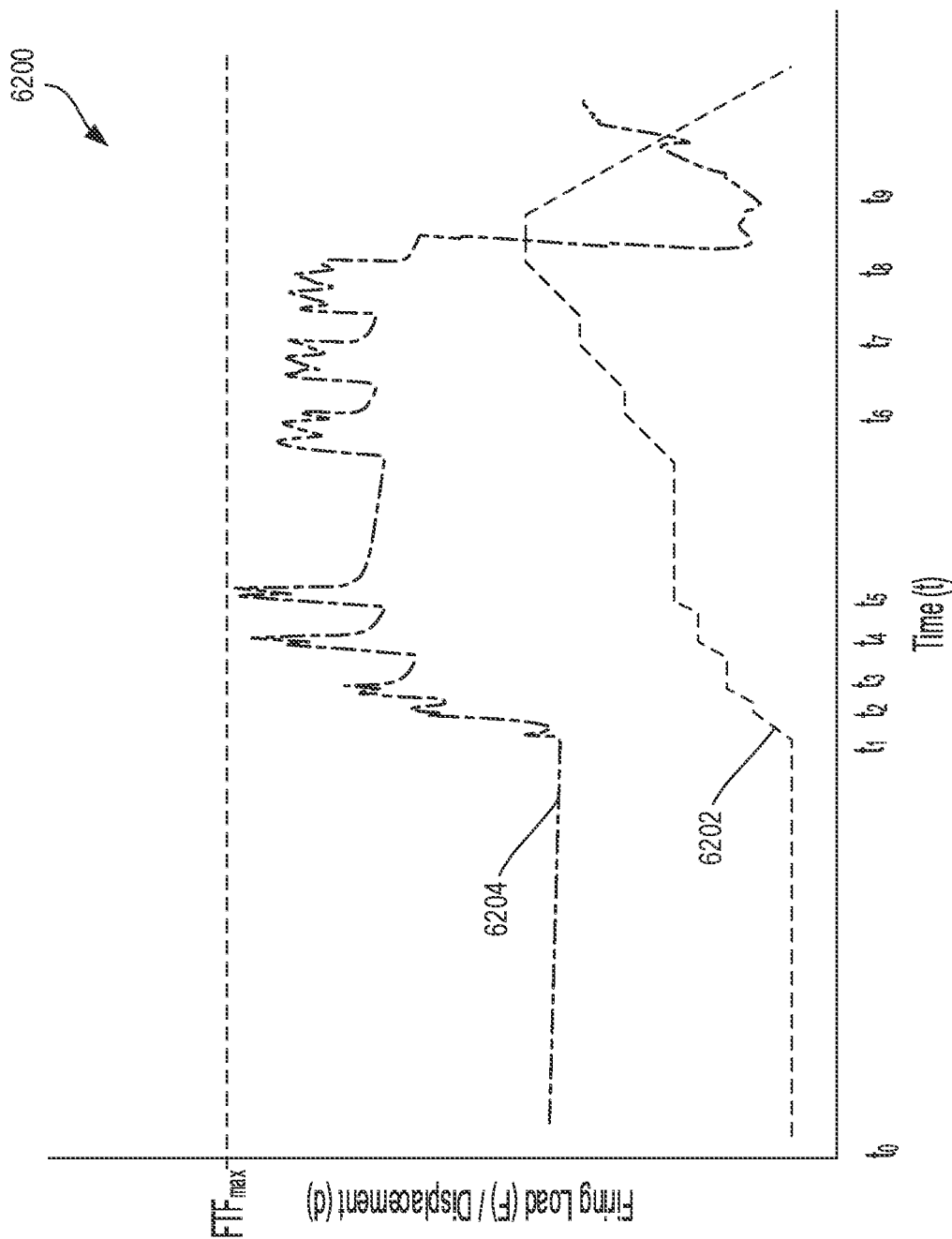
FIG. 55 is a graph illustrating the effects of pausing on FTF, according to at least one aspect of the present disclosure.

Referring now to FIG. 55, another graph 6200 illustrating the effects of pausing on FTF is provided, according to at least one aspect of the present disclosure. Graph 6200 illustrates both a firing load of a firing member, such as firing member 1900, against time (dash/dot line) and position of the firing member against time (dashed line).

As shown in graph 6200, the firing member begins in an unfired position at $t_0$. At $t_1$, a clinician initiates the firing stroke, such as by actuating a firing trigger, such as firing trigger 1130, causing forward displacement 6202 of the firing member toward a fired position. As the firing member traverses through the firing stroke, the force to fire 6204 the firing member increases.

During the firing stroke, as discussed above, a control system, such as controller 620, predicts future forces to fire and proactively adjusts the firing algorithm, as described elsewhere herein. For instance, at $t_2$, based on the predictions, the control system pauses displacement 6202 of the firing member for a period of time, resulting in the force to fire 6204 diminishing.

The above-described predicting and corrective actions by the control system continues for the remainder of the firing stroke. Specifically, as shown in FIG. 55, the control system causes displacement 6202 of the firing member to be paused at $t_2$, $t_3$, $t_4$, $t_5$, $t_6$, and $t_7$, controlling the force to fire 6204 to remain below a force to fire maximum threshold $FTF_{max}$. As shown in FIG. 55, the control system controls the force to fire using multiple pauses with varying lengths. In some embodiments, the lengths of the pauses are based on the force to fire detected by the control system early in the firing stroke, such as between $t_1$ and $t_2$. In some embodiments, the lengths of the pauses are based on the force to fire detected by the control system after the firing member resumes advancement from a pause. In some embodiments, the control system can pause the firing stroke until the force to fire has dropped a predefined amount. In some embodiments, the control system pauses the firing stroke for a predefined, or variable, amount of time, as described elsewhere herein. In some embodiments, the length of the pause is based on the rate of change of the firing stroke prior to the pause. In some embodiments, the length of the pause is based on the length of a previous pause.

As shown in FIG. 55, at $t_8$, the firing member reaches the fired position, resulting in the force to fire sharply dropping. At $t_9$, the firing system retracts the firing member toward the starting position of the firing member.

In many instances, a first pause within the firing stroke is used to influence a second, subsequent pause in the firing stroke. In some embodiments, the control system pauses the firing stroke at a first time for a first amount of time. In one aspect, the first amount of time is selected by the control system to allow the force to fire to drop a predefined amount. In one aspect, the first amount of time is selected by the control system to allow the force to fire to drop to a force to fire minimum threshold. Various other ways that the control system selects an appropriate pause length are described elsewhere herein.

After the first amount of time, the control system can resume advancement of the firing member through the firing stroke. At a second time subsequent to the first time, the control system pauses the firing stroke again. In some embodiments, the second pause is influenced by the first pause. In one aspect, the length of the second pause is the same as the length of the first pause. In one aspect, the length of the second pause is less than the length of the first pause. In one aspect, the length of the second pause is greater than the length of the first pause. In one aspect, the time at which the second pause occurs is the same amount of time as before the first pause occurred. Stated another way, at a first time point, the clinician actuates the firing system and at a second time, the control system pauses the firing stroke. After the first pause, at a third time point, the control system resumes advancement of the firing stroke and at a fourth time, the control system pauses the firing stroke again. In many instances, the elapsed time between the first and second time points is the same, or at least substantially the same, as the elapsed time between the third and fourth time points.

In various embodiments, a first pause in the firing stroke is used to influences multiple pauses later in the firing stroke. In one instance, during the firing stroke, the control system detects a rapid increase in the force to fire and predicts that a force to fire threshold will be reached. Based on the detection and prediction, the control system pauses the firing stroke at a first time for a first amount of time. Based on the detected increase in the firing stroke, the control system can determine that multiple pauses will be required to complete the firing stroke so as to stay below the force to fire threshold. Accordingly, the control system sets times and lengths of pauses based on the detected force to fire early in the firing stroke. In many instances, the length of the first pause is used to influence the length and time for subsequent pauses in the firing stroke. In one aspect, the control system pauses the firing stroke for a first amount of time to lower the force to fire the firing member. The control system then resumes advancement of the firing member and pauses the firing stroke at later times to maintain the force to fire below the force to fire threshold. In some embodiments, a first pause in the firing stroke causes a cascade of pauses later in the firing stroke to maintain the force to fire below the force to fire threshold.

Figure 56:
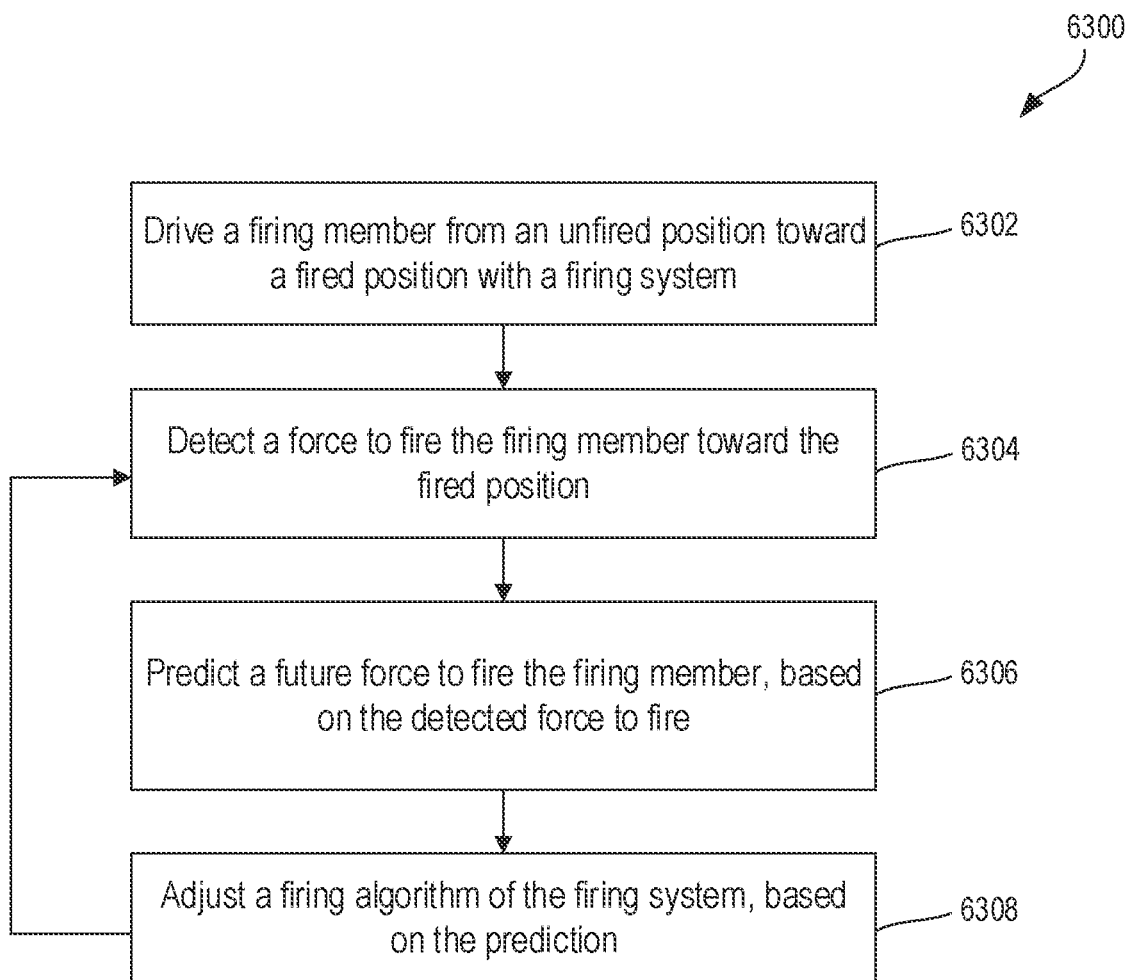
FIG. 56 illustrates a method of controlling a surgical instrument, according to at least one aspect of the present disclosure.

Referring now to FIG. 56, a method 6300 for controlling a surgical instrument is provided, according to at least one aspect of the present disclosure. The method 6300 comprises driving 6302 a firing member from an unfired position toward a fired position with a firing system. In various embodiments, a control system, such as controller 620, drives a firing member, such as firing member 1900, in response to the actuation of a firing system, such as firing motor drive assembly 604. In one aspect, driving the firing member toward a fired position causes the firing member to deploy staples removably stored in a staple cartridge, such as staple cartridge 1301, into tissue captured between an end effector, such as end effector 1300.

The method 6300 further includes detecting 6304 a force to fire the firing member toward the fired position. In various embodiments, the control system monitors the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

The method 6300 further includes predicting 6306 a future force to fire the firing member, based on the detected force to fire. In various embodiments, the algorithm is stored in a memory, such as memory 624, and is executable by a processor, such as processor 622. In some embodiments, the control system predicts the force to fire based on the rate of change of the force to fire. In some embodiments, the control system predicts the force to fire based on the magnitude of the force to fire peaks as the firing member traverses through the firing stroke. In some embodiments, the control system predicts the force to fire based on a change in magnitude of the force to fire peaks as the firing member traverses through the firing stroke. In some embodiments, the control system predicts the force to fire based on the number of occurrences of force to fire peaks as the firing member traverses through the firing stroke. In some embodiments, the control system predicts the force to fire based on both peaks and valleys in the force to fire profile. In some embodiments, the control system predicts the force to fire based on the shape of the peaks and valleys of the firing force profile. In some embodiments, the control system predicts the force to fire based on the rate of change of the force to fire as the firing member traverses through the firing stroke. In some embodiments, the control system predicts the future force to fire based on a predefined amount of time of the firing stroke, such as a predetermined amount of time from when the firing member begins to encounter resistance. In some embodiments, the control system continuously predicts the future force to fire based on data discretely, or continuously, received from the sensors.

The method 6300 further includes adjusting 6308 a firing algorithm of the firing system, based on the prediction. In various embodiments, the control system dynamically adjusts the algorithm that is currently being used to drive the firing member toward the fired position, based on the prediction. In some embodiments, the dynamic adjustment to the firing algorithm includes pausing the firing stroke. In some embodiments, the dynamic adjustment to the firing algorithm includes adjusting the length of the pause of the firing stroke. In some embodiments, the dynamic change to the firing algorithm includes changing the speed of the firing member. In some embodiments, the adjustment to the firing algorithm includes late trigger adjustments heights. In some embodiments, the dynamic adjustment to the firing algorithm includes controlling a voltage or current applied to the motor of the firing system that drives the firing member. In some embodiments, the dynamic adjustment to the firing algorithm includes changing a duty cycle of the motor that drives the firing member. In some embodiments, the dynamic adjustment comprises planning multiple pauses of the firing stroke in order to maintain the force to fire within a force to fire range, such as between an upper and lower threshold. In some embodiments, the dynamic adjustment is based on a previous adjustment made to the algorithm.

In various embodiments, the dynamic adjustment to the firing algorithm occurs at a time after the control system makes the prediction. For instance, at a first time, the control system makes a prediction that the force to fire will exceed a force to fire threshold. Based on the prediction, the control system causes the firing algorithm to be changed at a second time subsequent to the first time. In some embodiments, the control system allows the firing algorithm to resume for a predefined, or variable, amount of time from the prediction. In some embodiments, the amount of time is based on a prediction of how long it will take until the force to fire will reach the force to fire threshold.

In various embodiments, the method 6300 can further include monitoring the effect, or result, of the adjustment to the firing algorithm. In some embodiments, monitoring the effect, or result, of the adjustment to the firing algorithm comprises monitoring a rate of change of the force to fire profile as a result the adjustment. In some embodiments, monitoring the effect, or result, of the adjustment to the firing algorithm comprises monitoring a magnitude of change in the force to fire profile as a result of the adjustment. Based on the monitored effect, or result, of the adjustment, the method 6300 can further include implementing a second adjustment to the firing system, based on the effect, or result, of the first adjustment. For instance, where the first adjustment is a first pause in the firing stroke, the control system can implement a second pause at a subsequent time based on the effect, or result, of the first pause. In some instances, the subsequent time can be determined based on the effect, or result, of the first pause. In some instances, the length of the second pause can be based on the effect, or result, of the first pause. In some instances, additional adjustments can be implemented based on the effect, or result, of the first adjustment. In such instances, the adjustments are dynamic adjustments that are influenced by the effects, or results, of one or more previous adjustments. In some other embodiments, the first adjustment is a change in the speed of the firing member and a subsequent adjustment to the firing algorithm is based on the response to the force to fire profile in changing the speed of the firing member. Accordingly, the method 6300 adapts the firing algorithm in order to control the force to fire profile associated with driving the firing member through the firing stroke.

As described herein above, the control system can dynamically adjust the firing algorithm during the firing stroke to control the force to fire. In various embodiments, as seen in FIG. 56, after the firing algorithm is adjusted 6308, the method 6300 can again detect 6304 a force to fire the firing member toward the fired position and predict 6306 a future force to fire the firing member, based on the detected force to fire such that subsequent adjusts to the firing algorithm can be made. In some instances, the subsequent adjustments to the firing algorithm are based on both predictions, as well as adjustments to the firing algorithm made at a previous pause, as explained above.

Figure 57:
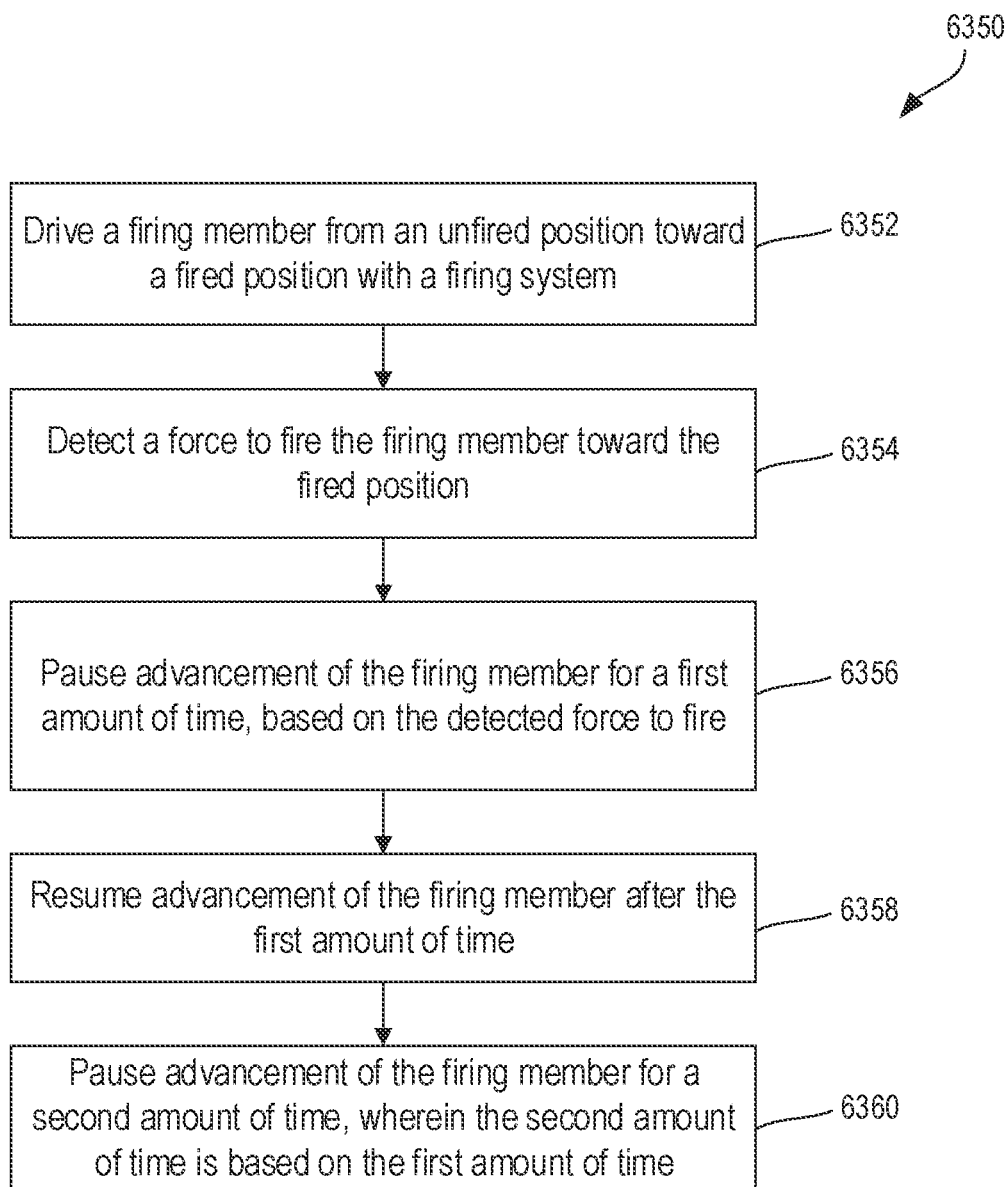
FIG. 57 illustrates a method of controlling a surgical instrument, according to at least one aspect of the present disclosure.

Referring now to FIG. 57, a method 6350 for controlling a surgical instrument is provided, according to at least one aspect of the present disclosure. The method 6350 comprises driving 6352 a firing member from an unfired position toward a fired position with a firing system. In various embodiments, a control system, such as controller 620, drives a firing member, such as firing member 1900, in response to the actuation of a firing system, such as firing motor drive assembly 604. In one aspect, driving the firing member toward a fired position causes the firing member to deploy staples removably stored in a staple cartridge, such as staple cartridge 1301, into tissue captured between an end effector, such as end effector 1300.

The method 6350 further includes detecting 6354 a force to fire the firing member toward the fired position. In various embodiments, the control system monitors the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

The method 6350 further includes pausing 6356 advancement of the firing member for a first amount of time, based on the detected force to fire. In various embodiments, the control system pauses the firing stroke of the firing member based on the detected force to fire. In some embodiments, the pause is based on a prediction made by the control system that the force to fire will reach or exceed a force to fire threshold. In some embodiments, the first amount of time is based on the rate of change of the force to fire prior to the pause. In some embodiments, the first amount of time is a time required to lower the force to fire a predefined amount. In some embodiments, the first amount of time is a time required to lower the force to fire to a force to fire minimum threshold. In some embodiments, the first amount of time is predefined. In some embodiments, the first amount of time is selected based on the shape of the force to fire profile, such as the shape of the peaks and valleys in the force to fire profile. In some embodiments, the first amount of time is selected based on the magnitude of the force to fire peaks and valleys in the force to file profile.

In various embodiments, after pausing 6356 advancement of the firing member, the method 6300 includes monitoring the effect, or result, of the pause. In some embodiments, monitoring the effect, or result, of the pause comprises monitoring a rate of change of the force to fire as a result of the pause. In some embodiments, monitoring the effect, or result, of the pause comprises monitoring a magnitude of change in the force to fire as a result of the pause. Based on the monitored effect, or result, of the pause, the method 6300 can further include implementing an adjustment to firing algorithm, based on the effect, or result, of the pause. For instance, the control system can implement a second pause at a subsequent time based on the effect, or result, of the first pause. In some instances, the subsequent time can be determined based on the effect, or result, of the first pause. In some instances, the length of the second pause can be based on the effect, or result, of the first pause. In some instances, additional adjustments can be implemented based on the effect, or result, of the first pause. In such instances, the adjustments are dynamic adjustments that are influenced by the effects, or results, of one or more previous adjustments.

The method 6350 further includes resuming 6358 advancement of the firing member after the first amount of time. In various embodiments, the control system can control the firing system to resume advancement of the firing member, based on the first amount of time elapsing.

The method 6350 further includes pausing 6360 advancement of the firing member for a second amount of time, wherein the second amount of time is based on the first amount of time. In various embodiments, after the control system resumes advancement of the firing member, the control system again pauses the firing stroke. In various embodiments, the control system pauses the firing stroke of the firing member based on the detected force to fire. In some embodiments, the pause is based on a prediction made by the control system that the force to fire will reach or exceed a force to fire threshold. In various embodiments, the control system pauses the firing stroke of the firing member based on an amount of time elapsing from when the control system paused the firing stroke the first time. For instance, the control system pauses the firing stroke for a first time in response to a detected force to firing early in the firing stroke.

In one aspect, the control system can adapt the firing algorithm such that multiple pauses will be performed in order to maintain the force to fire below a force to fire threshold. For instance, at the first pause, the control system can detect the effect, or result, of the first pause by detecting a change in the force to fire profile and dynamically plan when and how long future pauses in the firing stroke should be. In some embodiments, the control system determines that a pause should occur after a predefined amount of time after resuming advancement of the firing stroke. Accordingly, after resuming advancement of the firing stroke, the firing stroke is paused again according to the plan created by the control system. In various other embodiments, the control system dynamically adjusts the pausing plan at each pause to determine if the current pausing plan is still suitable for use. For instance, if the rate of change in the force to fire profile after a pause is less than the rate of change prior to a pause, the control system determines that thinner tissue is being encountered and, thus, dynamically adjusts the firing algorithm such that less pauses are performed for the remainder of the firing stroke. In some instances, additional pauses can be implemented based on the effect, or result, of the second pause, or a combined effect, or result, of the first and second pauses. In such instances, the adjustments are dynamic adjustments that are influenced by the effects, or results, of one or more previous adjustments.

In various embodiments, the second amount of time that the firing stroke is paused is based on the first amount of time that the firing stroke is paused. In some embodiments, the second amount of time is the same as the first amount of time. In some embodiments, the second amount of time is greater than the first amount of time. In some embodiments, the second amount of time is less than the first amount of time. In various embodiments, the second amount of time is based on the plan created by the control system at the first pause.

Figure 58:
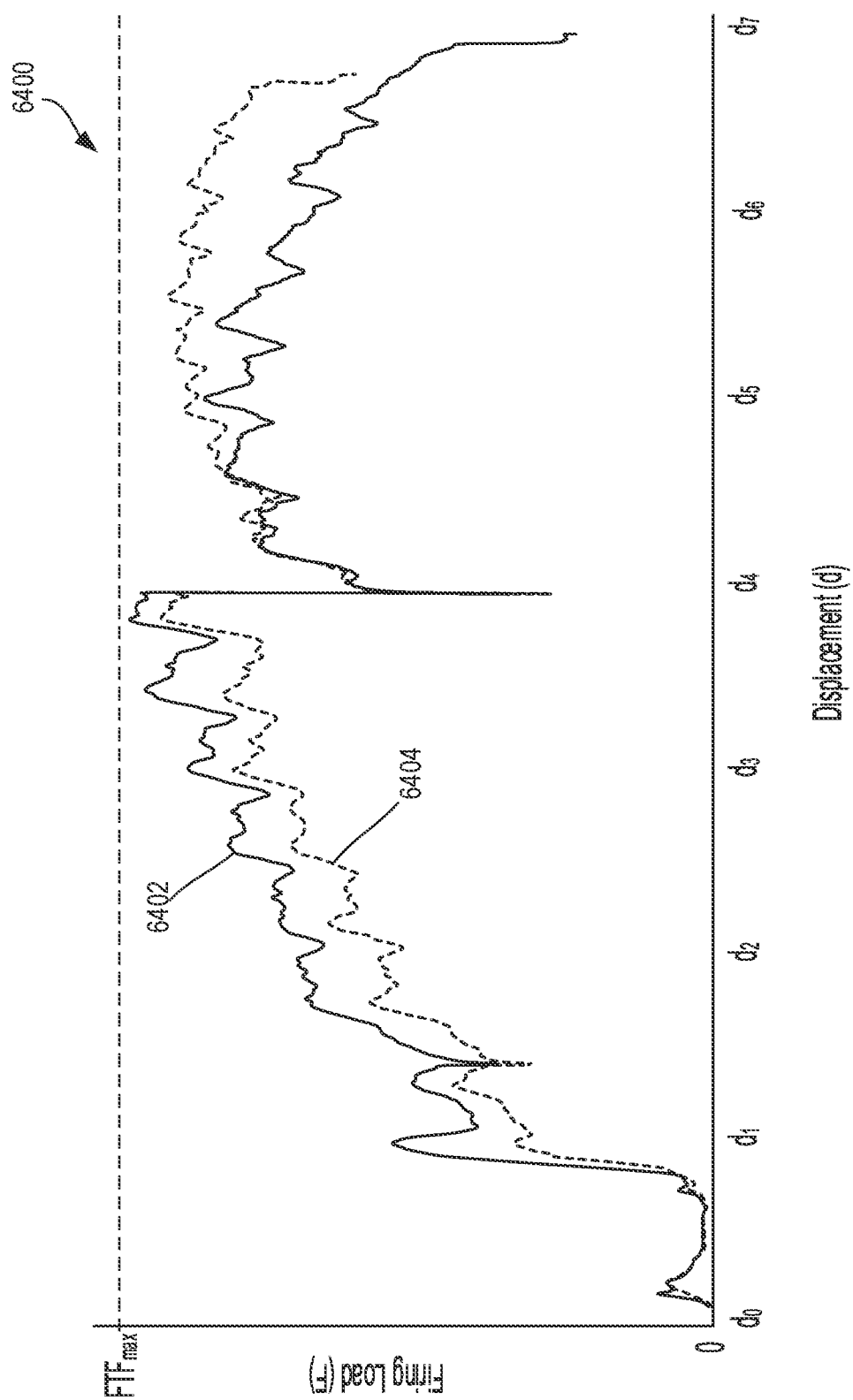
FIG. 58 is a graph illustrating the effects of pausing on FTF with varying closure loads, according to at least one aspect of the present disclosure.

Referring now to FIG. 58, a graph 6400 illustrating the impact of a closure system for separate and distinct firing and closing systems is provided, according to at least one aspect of the present disclosure. Graph 6400 illustrates the firing loads on a firing member, such as firing member 1900, against time. Graph 6400 illustrates two firing load profiles—a first firing load profile 6402 of a first surgical instrument that applies a first closure load and a second firing load profile 6404 of a second surgical instrument that applied a second closure load that is 1.75 times greater than the fire closure load.

As shown in graph 6400, the firing stroke for both systems initiates at $d_0$, resulting in a slight uptick in the firing load as the firing member overcomes the initial static resistance. At $d_1$, the firing members of the respective surgical instruments encounter tissue and begin to deploy staples from a staple cartridge. As seen in graph 6400, from $d_1$ to around $d_4$, the firing load of the second surgical instrument (which applies a closure load greater than the first surgical instrument) is less than that of the firing load of the first surgical instrument.

During the firing strokes of the two surgical instruments, a control system, such as controller 620, for each respective surgical instrument predicts future firing loads and adjusts the respective firing algorithms to control the force to fire. As shown in graph 6400, each control system causes the firing strokes to pause around $d_4$, resulting in a drop of the firing load in each instrument.

After a predefined, or variable, amount of time from the pauses, as determined by the control system (described elsewhere herein), the control systems reinitiate the firing strokes of the surgical instruments. As shown in graph 6400, after the respective pauses, the firing load 6404 on the surgical instrument with the increased closure load saw a larger firing load than the surgical instrument without the increased closure load until the end of the firing strokes at $d_7$. In some embodiments, the second surgical instrument is paused for a shorter time than the first surgical instrument, resulting in the increased firing load relative to the first surgical instrument. In some embodiments, the firing member of the second surgical instrument is maintained at the same speed as prior to the pause, resulting in the increased firing load relative to the first surgical instrument which had its firing member speed reduced. In various embodiments, the increased closure load prior to the pause allows the control system to make fewer changes to the firing algorithm, yet still remain below a force to fire threshold $FTF_{max}$. As one example, with an increased closure load, the control system only needs to pause the firing stroke for a first amount of time and make no adjustments to the speed of the firing member. With a "regular" closure load, the control system needs to adjust the firing algorithm to pause the firing stroke for a second amount of time greater than the first amount of time, as well as change the speed of the firing member, in order to maintain the force to fire below the force to fire threshold $FTF_{max}$. Accordingly, an increase in the closure load can result in fewer changes being needed to the firing control algorithm.

Figure 59:
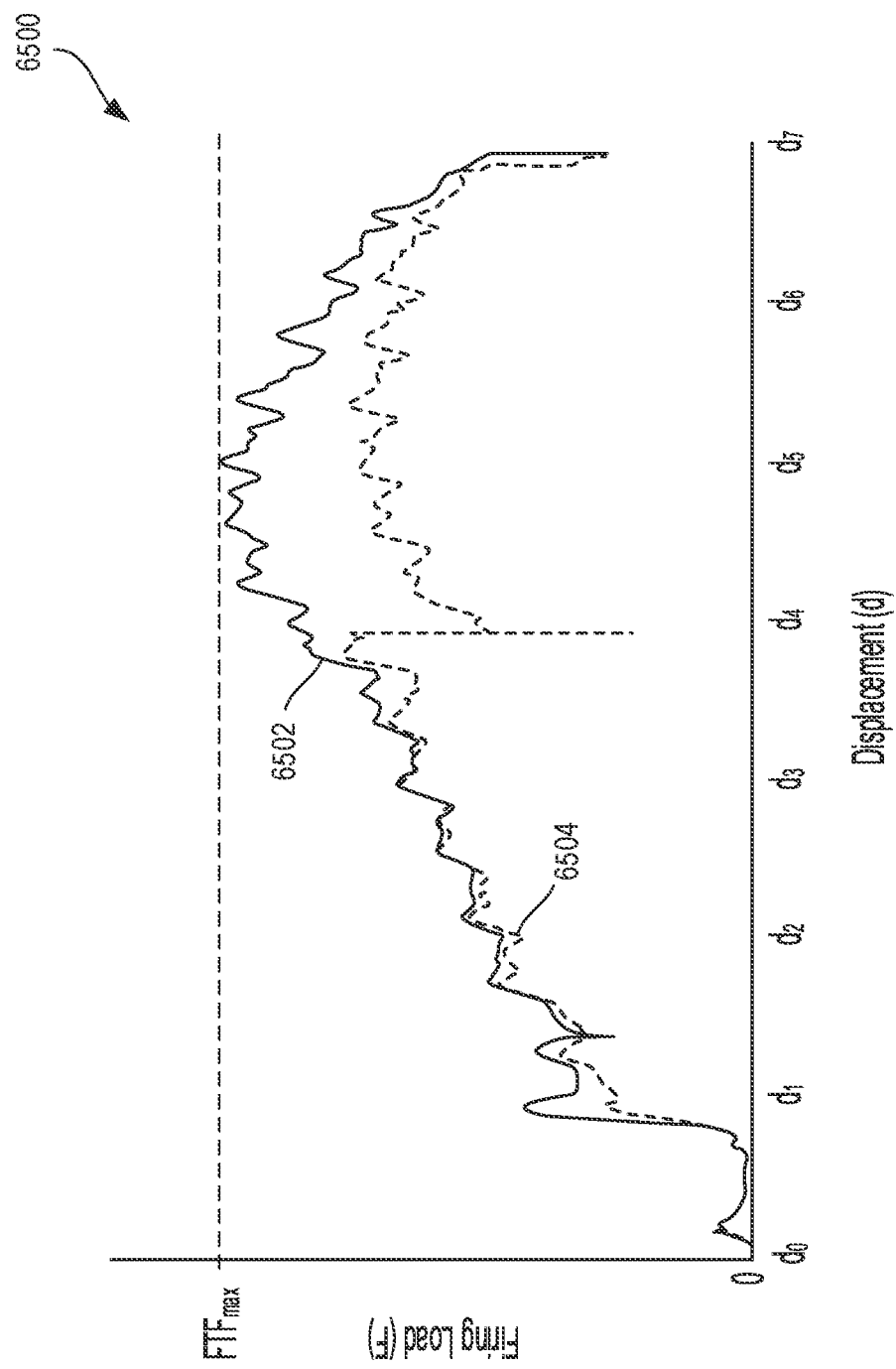
FIG. 59 is a graph illustrating the effects of pausing on FTF with varying tissue thicknesses during a firing stroke, according to at least one aspect of the present disclosure.

Referring now to FIG. 59, a graph 6500 illustrating firing force profiles is provided, according to at least one aspect of the present disclosure. The graph 6500 illustrates firing loads on a firing member, such as firing member 1900, over time. As seen in FIG. 59, the graph 6500 illustrates two firing force profiles—a first firing force profile 6502 during a first firing stroke and a second firing force profile 6504 during a second firing stroke. For both firing strokes, the thickness of the tissue encountered by the firing member doubled at $d_3$.

For the first firing force profile 6502, a firing member is driven through the firing stroke from $d_0$ to $d_7$. As seen in graph 6500, the firing load steadily increases at a first rate from $d_1$ to $d_3$ and then increases at a second rate (owing to the thicker tissue) from $d_3$ until ultimately reaching a maximum force to fire $FTF_{max}$ at around $d_5$. From $d_5$, the firing load drops below until the firing member completes its firing stroke.

For the second firing force profile 6504, the firing member is driven through its firing stroke from do. As the firing member is driven through its firing stroke, a control system, such as controller 620, predicts future force to fire loads and adjusts the firing algorithm based on the predictions. For instance, as described above, the control system detects an increase in the force to firing when the thickness doubles in size at $d_3$. In some embodiments, the control system detects the increase in thickness based on a change in the peaks and valleys of the firing load profile. In some embodiments, the change comprises a change in magnitude of the peaks and valleys. In some embodiments, the change comprises a change in shape of the peaks and valleys. In some embodiments, the change comprises a change in the number of occurrences of the peaks and valleys. In some embodiments, the control system detects the increase in thickness based on the change the magnitude of the peaks and/or valleys of the firing load profile. In some embodiments, the control system detect the increase in thickness based on the rate of change of the firing load. Based on the detected increase in thickness, the control system predicts a future force to fire that will exceed a force to fire threshold, and thus, adjusts the firing control algorithm, causing the firing stroke to be paused at around $d_4$.

In some embodiments, based on the detection and prediction from the control system, the control system determines that resuming the firing stroke at the same speed as prior to the pause would result in an increase in the firing load and quickly lead to another pause being required. Accordingly, after the pause, the control system can decrease the speed of the firing member to maintain the firing load within an acceptable range, such as below the maximum force to fire threshold $FTF_{max}$. For instance, as shown in graph 6500, after the firing stroke of the firing member is paused and the speed of the firing member is decreased, the second firing force profile 6504 does not reach or exceed the firing load that was experienced prior to the firing stroke being paused. Accordingly, the control system is able to take multiple control actions, such as pausing the firing stroke and changing the firing speed of the firing member, in response to predictions from the control system in order to control the force to fire. Furthermore, the control system is able to adapt its predictions based on changing characteristics of the tissue, such as an increase in the tissue thickness. In some embodiments, the control system determines other parameters associated with the tissue, such as a type of tissue or a disease state of the tissue, and adapt the predictions accordingly.

Figure 60:
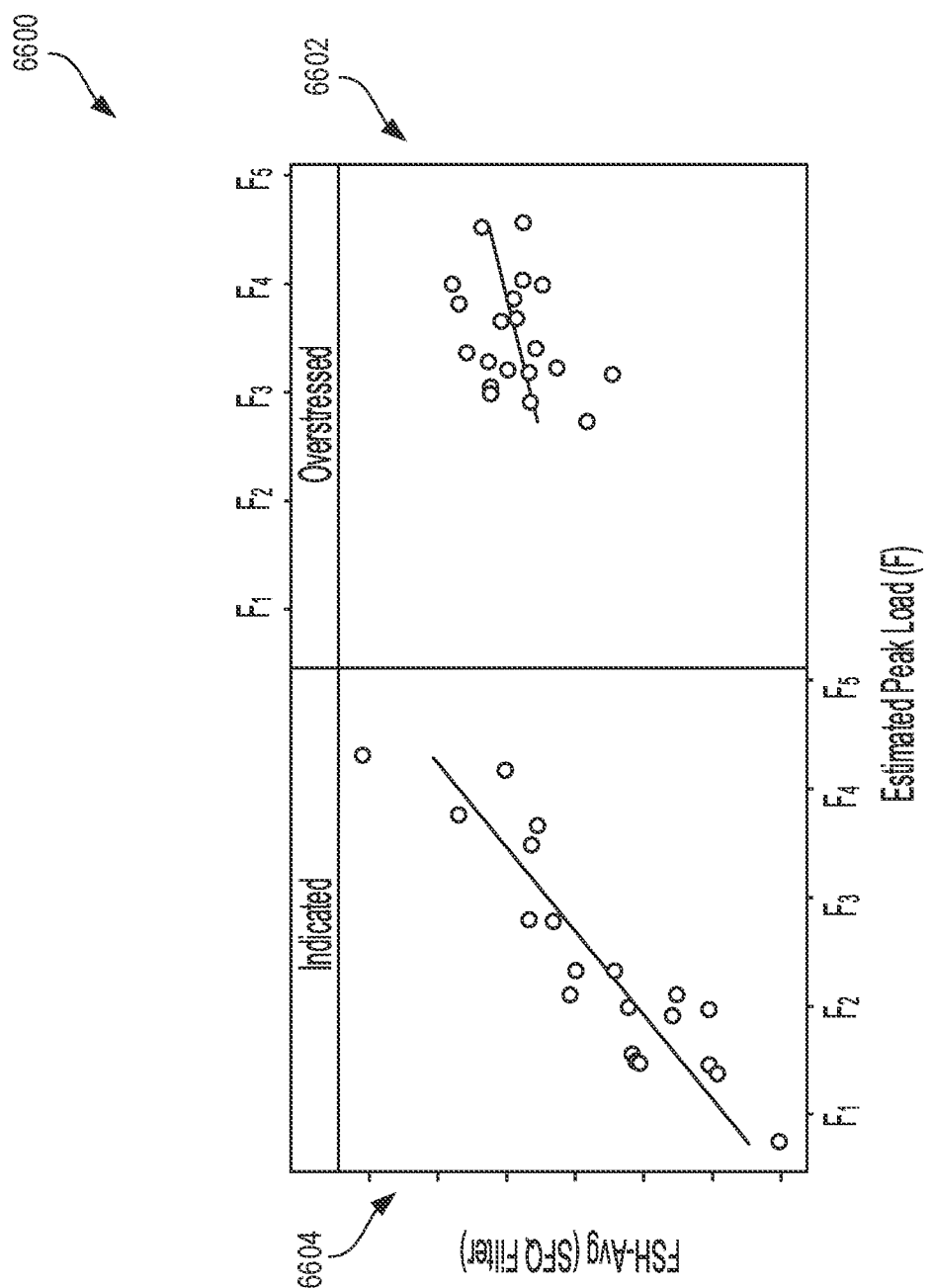
FIG. 60 is a scatterplot showing the effects of force to fire on staple heights, according to at least one aspect of the present disclosure.

Referring now to FIG. 60, a scatterplot 6600 showing the effects of force to fire on staple height for the Color D cartridge from FIG. 49 is provided, according to at least one aspect of the present disclosure. The scatterplot 6600 illustrates a correlation between the FSH average (SGQ filter) against estimated peak loads. The left hand portion 6602 of the scatterplot illustrates the minimum (indicated) use of the Color D cartridge and the right hand portion 6604 of the scatterplot 6600 illustrates the overstress use of the Color D cartridge at various estimated peak loads ($F_1$-$F_5$). As seen in scatterplot 6600, the $R^2$ value of the trendline for the minimum (indicated) use is greater than the $R^2$ value of the trendline for the overstressed use.

Figure 61:
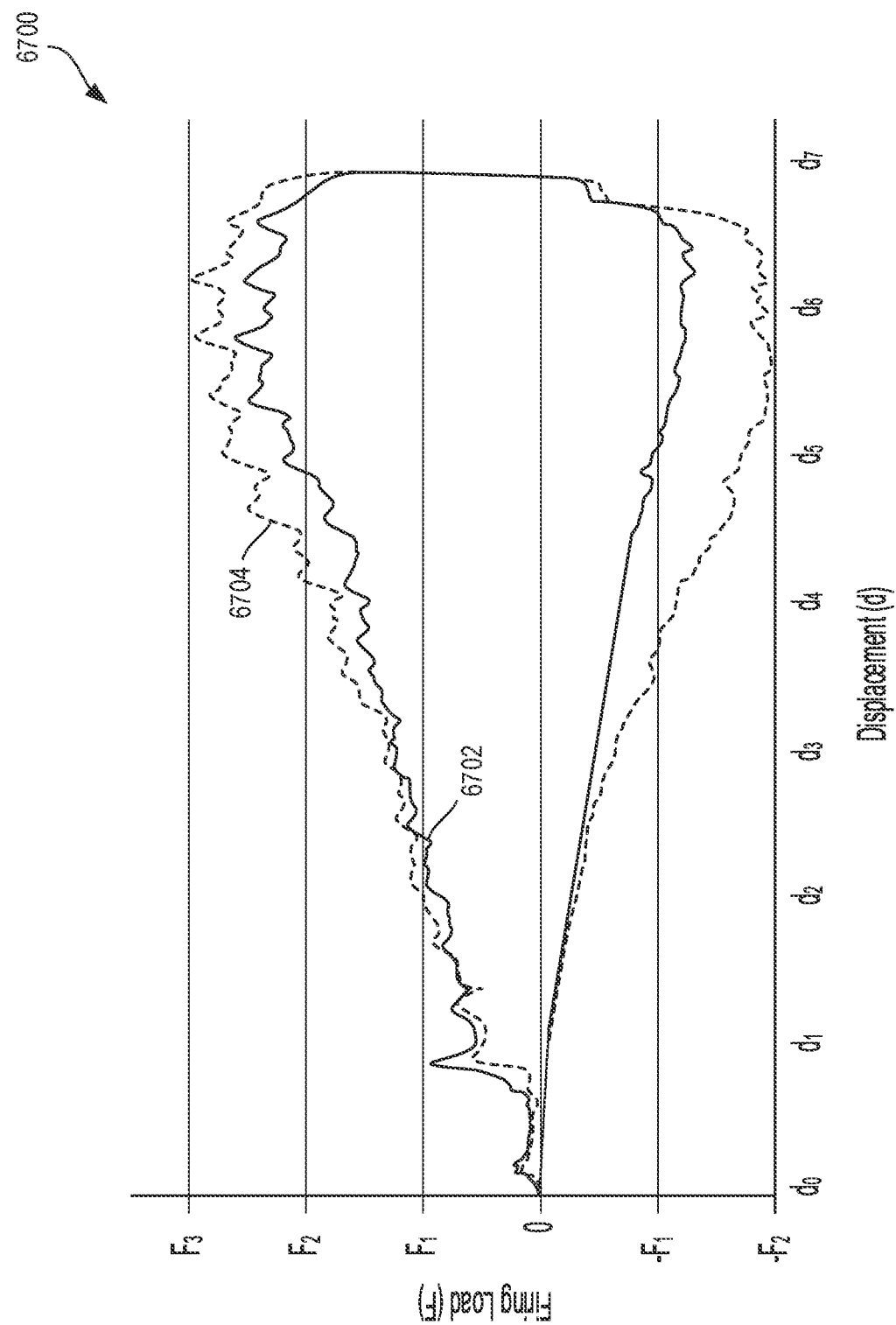
FIG. 61 is a graph showing firing force profiles for firing member that encounter a changing tissue thickness during a firing stroke, according to at least one aspect of the present disclosure.

Referring now to FIG. 61, a graph 6700 illustrating firing force profiles is provided, according to at least one aspect of the present disclosure. The graph 6700 illustrates the firing load on a firing member, such as firing member 1900, over time. As seen in FIG. 61, the graph 6700 illustrates two firing force profiles—a first firing force profile 6702 during a first firing stroke and a second firing force profile 6704 during a second firing stroke. For both firing strokes, the thickness of the tissue encountered by the firing member doubled at $d_3$.

As described above, the present disclosure provides a way of controlling the FTF during a firing stroke of the firing member. In some embodiments, a control system, such as controller 620, can predict higher, upcoming forces to fire based on the size of the FTF peaks early in the firing stroke.

Based on the prediction, the control system can trigger changes to the firing algorithm to control the force to fire during the firing stroke.

As seen in FIG. 61, for both firing force profiles 6702, 6704, a firing member, such as firing member 1900, begins at an unfired position, $d_0$, prior to initiation of the firing stroke. Based on the initiation of the firing stroke, such as actuation of a firing trigger, a firing system, such as firing motor drive assembly 604, drives the firing member from the unfired position toward a fired position, $d_7$, to cut tissue captured within the end effector, such as end effector 1300, and to deploy staples from a staple cartridge, such as staple cartridge 1301.

At $d_1$, the FTF 6054 the firing member ramps up based on the firing member encountering the tissue captured within the end effector and beginning to deploy the staples. In various embodiments, a control system, such as controller 620, can monitor the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

Based on the detected force to fire, the control system initiates an algorithm to predict the force to fire that the firing member will experience during the firing stroke. In various embodiments, the algorithm is stored in a memory, such as memory 624, and is executable by a processor, such as processor 622. In some embodiments, the control system predicts the force to fire based on the magnitude of the force to fire peaks as the firing member traverses through the firing stroke. In some embodiments, the control system predicts the force to fire based on a change in magnitude of the force to fire peaks as the firing member traverses through the firing stroke. In some embodiments, the control system predicts the force to fire based on the shape of the force to fire peaks. In some embodiments, the control system predicts the force to fire based on the number of occurrences of force to fire peaks as the firing member traverses through the firing stroke. For instance, as referenced above, at around $d_3$, the thickness of the tissue doubles. Accordingly, the control system can detect the changes in the peaks/valleys of the firing force profiles 6702, 6704 in order to make predictions about the future forces to fire and trigger changes to the firing algorithms.

Furthermore, in various embodiments, the control system can determine the thickness of the tissue based on the detected properties of the force to fire peaks and valleys. In some embodiments, the control system can compare the firing force profile (and peaks and/or valleys thereof) to firing force profiles stored in a memory, such as memory 624, in order to determine the type of tissue and/or the thickness of the tissue that is currently being encountered. Based on the determined tissue type and/or thickness, the control algorithm can trigger adjustments to the firing algorithm that are appropriate for the determined type and/or thickness of tissue.

Based on the predicted forces to the fire, the control system can trigger changes to the firing algorithms to control the force to fire profiles 6702, 6704, as described elsewhere herein. In some embodiments, based on the predictions, the control system triggers the firing algorithms to slow the speed of the firing member rather than pausing the displacement of the firing member. Based on the slower speed, the force to fire profiles 6702, 6704 are controlled and maintained below a force to fire maximum threshold ($F_3$).

As seen in FIG. 61, the firing members reach the fired position at $d_7$. In various embodiments, the control system determines the thickness of the tissue based on the peaks and valleys of the firing force profile at the fired position $d_7$. In some embodiments, the control system determines the thickness of the tissue based on a final portion of the firing stroke, such as the peaks and valleys detected from $d_6$ to $d_7$. Based on the determined thickness at the fired position, the control system can communicate the determined thickness to the clinician, such as via a display. Based on the determined thickness, the control system can also recommend an appropriate staple cartridge to use for a subsequent stapling operation. For example, a first cutting and stapling operation is performed using a Color A staple cartridge, seen in FIG. 49. At the end of the cutting and stapling operation, the control system can determine that the tissue has a tissue thickness of $t_6$, based on the peaks and valleys of the force to fire profile. Based on the determined tissue thickness $t_6$, the control system can recommend that a user utilize either a Color B staple cartridge (which would be utilized in an overstressed application) or a Color C staple cartridge (which would utilize in a minimum/maximum application). Accordingly, the peaks and valleys from a first cutting and stapling operation can be utilized to determine a tissue thickness and influence a staple cartridge that will be utilize for subsequent cutting and stapling operation.

Figure 62:
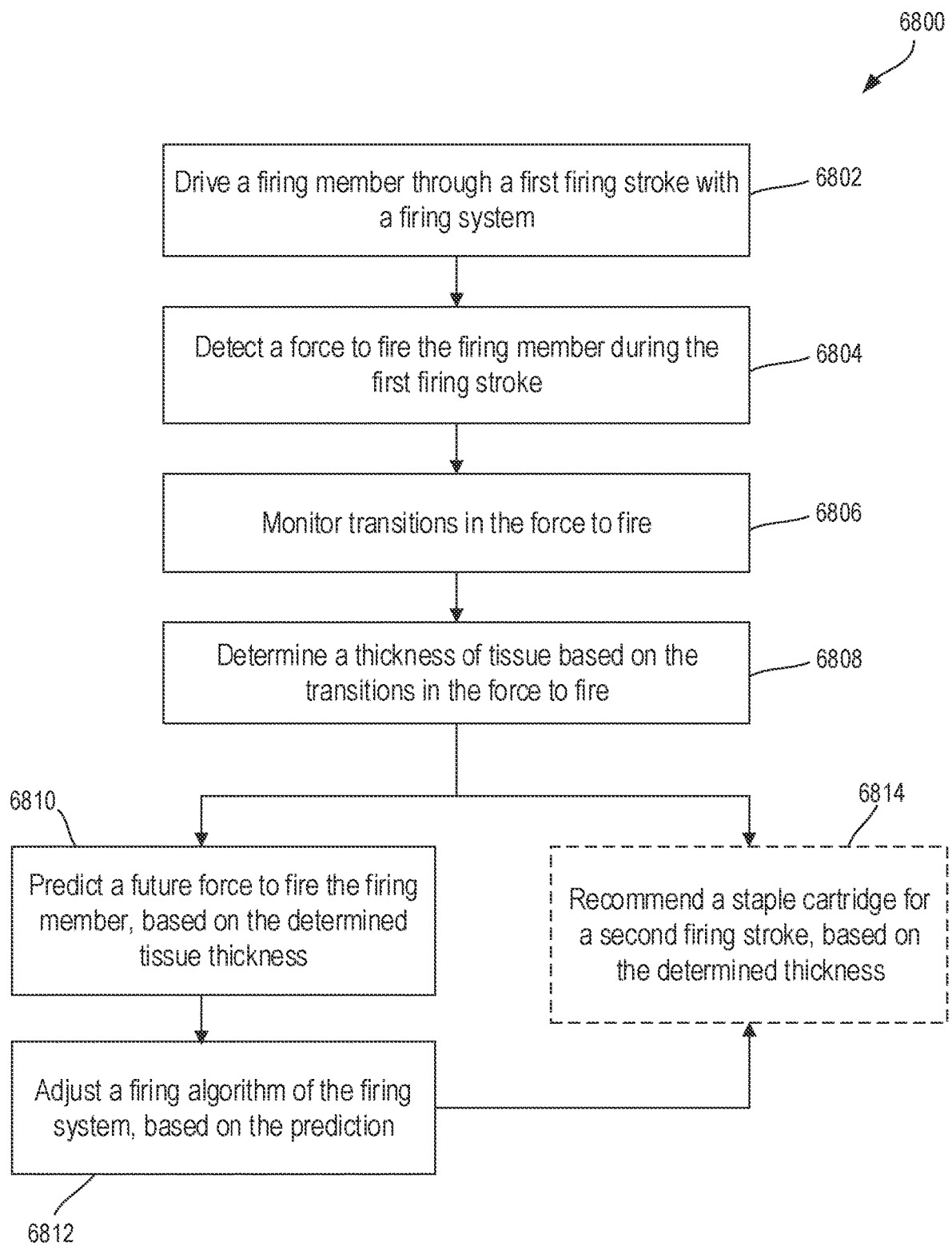
FIG. 62 illustrates a method of controlling a surgical instrument, according to at least one aspect of the present disclosure.

Referring now to FIG. 62, a method 6800 of controlling a surgical instrument is provided, according to at least one aspect of the present disclosure. The method 6800 comprises driving 6802 a firing member through a first firing stroke with a firing system. In various embodiments, a control system, such as controller 620, drives a firing member, such as firing member 1900, in response to the actuation of a firing system, such as firing motor drive assembly 604. In one aspect, driving the firing member through a firing stroke causes the firing member to deploy staples removably stored in a staple cartridge, such as staple cartridge 1301, into tissue captured between an end effector, such as end effector 1300.

The method 6800 further includes detecting 6804 a force to fire the firing member. In various embodiments, the control system monitors the force to fire using any number of sensors described elsewhere herein. In some embodiments, the control system is in operable communication with a current sensor that senses a current supplied to a firing motor, such as firing motor 602, from a power source, such as power source 628, in order to determine the force to fire the firing member. In some embodiments, the control system is in operably communication with a force sensor in order to determine the force to fire the firing member.

The method 6800 further includes monitoring 6806 transitions in the force to fire. In some embodiments, the transitions comprise peaks in the firing force profile. In some embodiments, the transitions comprise valleys in the firing force profile. In some embodiments, the transitions comprise peaks and valleys in the firing force profile. In some embodiments, monitoring the transitions in the force to fire comprises monitoring the magnitude or the peaks and/or valleys during the firing stroke. In some embodiments, monitoring the transitions in the force to fire comprises the shapes of the peaks and/or valleys. In some embodiments, monitoring the transitions in the force to fire comprises monitoring the number of occurrences of peaks and/or valleys. In some embodiments, monitoring the number of occurrences of peaks and/or valleys comprises monitoring the number of occurrences of peaks and/or valleys over a predefined amount of time. In some embodiments, monitoring the number of occurrences of peaks and/or valleys comprises monitoring the number of occurrences of the peaks and/or valleys over a portion of the firing stroke.

The method 6800 further comprises determining 6808 a thickness of the tissue based on the transitions in the force to fire. In various embodiments, the control system can compare parameters associated with the peaks and valleys to values stored in a memory, such as memory 624. In some embodiments, the memory includes a look-up table that can be utilized to determine a corresponding tissue thickness based on parameters associated with the peaks and valleys. In some embodiments, the parameters of the peaks and valleys comprise a number of occurrences in peaks and/or valleys, a magnitude of the peaks and/or valleys, or a shape of the peaks and/or valleys, as examples.

The method 6800 further comprises predicting 6810 a future force to fire the firing member, based on the determined tissue thickness. In various embodiments, the control system can predict a future force to fire the firing member, as described elsewhere herein. The method 6800 further comprises adjusting a firing algorithm of the firing system, based on the prediction. In various embodiments, the control system can adjust the firing algorithm based on the predictions, such as pausing the firing stroke and/or slowing the speed of the firing member, as examples, as described elsewhere herein.

The method 6800 optionally further includes recommending 6814 a staple cartridge for a second firing stroke, based on the determined thickness. In various embodiments, as described elsewhere herein, based on the determined thickness, the control system can recommend to a clinician, via a display, as an example, a staple cartridge to use for a subsequent staple firing stroke. In various embodiments, the recommendation can occur at the conclusion of the staple firing stroke. In various embodiments where the firing algorithm isn't adjusted based on predictions from the control system, the control system can still recommend a staple cartridge for a subsequent staple firing stroke.

Various aspects of the subject matter described herein are set out in the following examples.

Example 1—A surgical instrument comprising an end effector configurable between an open state and a clamped state, a firing member movable from an unfired position toward a fired position during a firing stroke, a manually-driveable closure system configured to transition the end effector between the open state and the clamped state, a motor-powered firing system comprising a motor, and a control system. The end effector comprises a first jaw, a second jaw moveable relative to the first jaw, and a staple cartridge comprising staples removably stored therein. The staples are deployable from the staple cartridge based on the firing member moving toward the fired position. The motor-powered firing system is configured to drive the firing member through the firing stroke. The control system is configured to detect, at a first time point, the end effector reaching the clamped state with the manually-driveable closure system, detect, at a second time point, the actuation of the motor-powered firing system, set a firing motion parameter of the motor-powered firing system based on an elapsed time from the first time point to the second time point, and drive the firing member through the firing stroke with the motor-powered firing system using the firing motion parameter.

Example 2—The surgical instrument of Example 1, wherein the firing motion parameter comprises a duty cycle of the motor.

Example 3—The surgical instrument of Examples 1 or 2, wherein the firing motion parameter comprises a velocity of the motor.

Example 4—The surgical instrument of any one of Examples 1-3, wherein the control system is further configured to detect, at a third time point before the first time point, the end effector moving toward the clamped state, and wherein setting the firing motion parameter of the motor-powered firing system is further based on an elapsed time from the third time point to the first time point.

Example 5—The surgical instrument of any one of Examples 1-4, wherein the control system is further configured to detect, at a third time point before the first time point, the second jaw of the end effector contacting tissue while the end effector transitions toward the clamped state, and wherein setting the firing motion parameter of the motor-powered firing system is further based on an elapsed time from the third time point to the second time point.

Example 6—The surgical instrument of any one of Examples 1-5, wherein the control system is further configured to dynamically adjusting the firing motion parameter during the firing stroke based an elapsed time from the first time point to a current time point.

Example 7—The surgical instrument of any one of Examples 1-6, further comprising an elongate shaft and an articulation joint, wherein the end effector is rotatable relative to the elongate shaft about the articulation joint, wherein the control system is further configured to detect an articulation angle of the end effector, and wherein setting the firing motion parameter of the motor-powered firing system is further based on the articulation angle.

Example 8—The surgical instrument of any one of Examples 1-7, wherein the control system is further configured to detect, at a third time point before the first time point, the end effector reaching a partially clamped state, and wherein setting the firing motion parameter of the motor-powered firing system is further based on an elapsed time from the third time point to the second time point.

Example 9—A surgical instrument comprising an end effector configurable between an open state and a clamped state, a firing member movable from an unfired position toward a fired position during a firing stroke, a closure system configured to transition the end effector between the open state and the clamped state, a motor-powered firing system comprising a motor, and a control system. The end effector comprises a first jaw, a second jaw moveable relative to the first jaw, and a staple cartridge comprising staples removably stored therein. The staples are deployable from the staple cartridge based on the firing member moving toward the fired position. The motor-powered firing system is configured to drive the firing member through the firing stroke. The control system is configured to detect, at a first time point, the end effector moving toward the clamped state, detect, at a second time point, the end effector reaching the clamped state, detect, at a third time point, the actuation of the motor-powered firing system, set a firing motion parameter of the motor-powered firing system based on a first elapsed time from the first time point to the second time point and a second elapsed time from the second time point to the third time point, and drive the firing member through the firing stroke with the motor-powered firing system using the firing motion parameter.

Example 10—The surgical instrument of Example 9, further comprising an elongate shaft and an articulation joint, wherein the end effector is rotatable relative to the elongate shaft about the articulation joint, wherein the control system is further configured to detect an articulation angle of the end effector, and wherein setting the firing motion parameter of the motor-powered firing system is further based on the articulation angle.

Example 11—The surgical instrument of Examples 9 or 10, wherein the control system is further configured to detect, at a fourth time point between the first time point and the second time point, the second jaw contacting tissue while the end effector transitions toward the clamped state, and wherein setting the firing motion parameter of the motor-powered firing system is further based on an elapsed time from the fourth time point to the third time point.

Example 12—The surgical instrument of any one of Examples 9-11, wherein the control system is further configured to dynamically adjusting the firing motion parameter during the firing stroke based an elapsed time from the second time point to a current time point.

Example 13—A surgical instrument comprising an end effector configurable between an open state and a clamped state, a firing member movable from an unfired position toward a fired position during a firing stroke, a manually-driveable closure system configured to transition the end effector between the open state and the clamped state, a motor-powered firing system comprising a motor, and a control system comprising a timer. The end effector comprises a first jaw, a second jaw moveable relative to the first jaw, and a staple cartridge comprising staples removably stored therein. The staples are deployable from the staple cartridge based on the firing member moving toward the fired position. The motor-powered firing system is configured to drive the firing member through the firing stroke. The control system is configured to detect the end effector reaching an initial clamped state with the manually-drivable closure system, initiate the timer based on the end effector reaching the initial clamped state, detect the end effector transitioning away from the initial clamped state after initiating the timer, maintain the timer, based on the end effector failing to transition a threshold amount away from the initial clamped state, detect the end effector reaching a second clamped state after failing to transition the threshold amount away from the clamped state, detect the actuation of the motor-powered firing system after detecting the end effector reaching the second clamped state, set a firing motion parameter of the motor-powered firing system based on an elapsed time from the initiation of the timer to the actuation of the motor-powered firing system, and drive the firing member through a firing stroke with the motor-powered firing system using the firing motion parameter.

Example 14—The surgical instrument of Example 13, wherein the control system is further configured to reset the timer, based on the end effector transitioning the threshold amount away from the initial clamped state, detect the end effector reaching the second clamped state after resetting the timer, reinitiate the timer, based on the end effector reaching the second clamped state after resetting the timer, detect the actuation of the motor-powered firing system after reaching the second clamped state, set a second firing motion parameter of the motor-powered firing system based on an elapsed time from the reinitiation of the timer to the actuation of the motor-powered firing system, and drive the firing member through the firing stroke with the motor-powered firing system using the second firing motion parameter.

Example 15—The surgical instrument of Examples 13 or 14, wherein the firing motion parameter comprises a duty cycle of the motor.

Example 16—The surgical instrument of any one of Examples 13-15, wherein the firing motion parameter comprises a velocity of the motor.

Example 17—The surgical instrument of any one of Examples 13-16, wherein the control system is further configured to detect a first elapsed clamp time taken to transition the end effector toward the initial clamped state, and wherein setting the firing motion parameter of the motor-powered firing system is further based on the first elapsed clamp time.

Example 18—The surgical instrument of Example 17, wherein the control system is further configured to detect a second elapsed clamp time taken to transition the end effector toward the second clamped state, and wherein setting the firing motion parameter of the motor-powered firing system is further based on the second elapsed clamp time.

Example 19—The surgical instrument of any one of Examples 13-18, wherein the control system is further configured to dynamically adjusting the firing motion parameter during the firing stroke based an elapsed time from the end effector reaching the initial clamped state to a current time point.

Example 20—The surgical instrument of any one of Examples 13-19, further comprising an elongate shaft and an articulation joint, wherein the end effector is rotatable relative to the elongate shaft about the articulation joint, wherein the control system is further configured to detect an articulation angle of the end effector, and wherein setting the firing motion parameter of the motor-powered firing system is further based on the articulation angle.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, and is incorporated herein by reference in its entirety.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRU- MENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in one or more aspects of the present disclosure, a microcontroller may generally comprise a memory and a microprocessor ("processor") operationally coupled to the memory. The processor may control a motor driver circuit generally utilized to control the position and velocity of a motor, for example. In certain instances, the processor can signal the motor driver to stop and/or disable the motor, for example. In certain instances, the microcontroller may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet.

It should be understood that the term processor as used herein includes any suitable microprocessor, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In at least one instance, the processor may be any single core or multicore processor such as those known under the trade name ARM Cortex by Texas Instruments. Nevertheless, other suitable substitutes for microcontrollers and safety processor may be employed, without limitation.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Various instruments, tools, hubs, devices and/or systems, in accordance with the present disclosure, may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

One or more motor assemblies, as described herein, employ one or more electric motors. In various forms, the electric motors may be a DC brushed driving motor, for example. In other arrangements, the motor may include a brushless motor, a cordless motor, a synchronous motor, a stepper motor, or any other suitable electric motor. The electric motors may be powered by a power source that in one form may comprise a removable power pack. Batteries may each comprise, for example, a Lithium Ion ("LI") or other suitable battery. The electric motors can include rotatable shafts that operably interface with gear reducer assemblies, for example. In certain instances, a voltage polarity provided by the power source can operate an electric motor in a clockwise direction wherein the voltage polarity applied to the electric motor by the battery can be reversed in order to operate the electric motor in a counter-clockwise direction. In various aspects, a microcontroller controls the electric motor through a motor driver via a pulse width modulated control signal. The motor driver can be configured to adjust the speed of the electric motor either in clockwise or counter-clockwise direction. The motor driver is also configured to switch between a plurality of operational modes which include an electronic motor braking mode, a constant speed mode, an electronic clutching mode, and a controlled current activation mode. In electronic braking mode, two terminal of the drive motor are shorted and the generated back EMF counteracts the rotation of the electric motor allowing for faster stopping and greater positional precision.

As used in any aspect herein, a wireless transmission such as, for example, a wireless communication or a wireless transfer of a data signal can be achieved, by a device including one or more transceivers. The transceivers may include, but are not limited to cellular modems, wireless mesh network transceivers, Wi-Fi® transceivers, low power wide area (LPWA) transceivers, and/or near field communications transceivers (NFC). The device may include or may be configured to communicate with a mobile telephone, a sensor system (e.g., environmental, position, motion, etc.) and/or a sensor network (wired and/or wireless), a computing system (e.g., a server, a workstation computer, a desktop computer, a laptop computer, a tablet computer (e.g., iPad®, GalaxyTab® and the like), an ultraportable computer, an ultramobile computer, a netbook computer and/or a subnotebook computer; etc. In at least one aspect of the present disclosure, one of the devices may be a coordinator node.

The transceivers may be configured to receive serial transmit data via respective universal asynchronous receiver-transmitters (UARTs) from a processor to modulate the serial transmit data onto an RF carrier to produce a transmit RF signal and to transmit the transmit RF signal via respective antennas. The transceiver(s) can be further configured to receive a receive RF signal via respective antennas that includes an RF carrier modulated with serial receive data, to demodulate the receive RF signal to extract the serial receive data and to provide the serial receive data to respective UARTs for provision to the processor. Each RF signal has an associated carrier frequency and an associated channel bandwidth. The channel bandwidth is associated with the carrier frequency, the transmit data and/or the receive data. Each RF carrier frequency and channel bandwidth is related to the operating frequency range(s) of the transceiver(s). Each channel bandwidth is further related to the wireless communication standard and/or protocol with which the transceiver(s) may comply. In other words, each transceiver may correspond to an implementation of a selected wireless communication standard and/or protocol, e.g., IEEE 802.11 a/b/g/n for Wi-Fi® and/or IEEE 802.15.4 for wireless mesh networks using Zigbee routing.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

In this specification, unless otherwise indicated, terms "about" or "approximately" as used in the present disclosure, unless otherwise specified, means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Also, all ranges recited herein are inclusive of the end points of the recited ranges. For example, a range of "1 to 10" includes the end points 1 and 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical instrument, comprising:
an end effector configurable between an open state and a clamped state, wherein the end effector comprises:
a first jaw;
a second jaw moveable relative to the first jaw; and
a staple cartridge comprising staples removably stored therein;
a firing member movable from an unfired position toward a fired position during a firing stroke, wherein the staples are deployable from the staple cartridge based on the firing member moving toward the fired position;
a manually-driveable closure system configured to transition the end effector between the open state and the clamped state;
a motor-powered firing system comprising a motor, wherein the motor-powered firing system is configured to drive the firing member through the firing stroke; and
a control system, configured to:
detect, at a first time point, the end effector reaching the clamped state with the manually-driveable closure system;

detect, at a second time point, the actuation of the motor-powered firing system;
set a firing motion parameter of the motor-powered firing system based on an elapsed time from the first time point to the second time point; and
drive the firing member through the firing stroke with the motor-powered firing system using the firing motion parameter.

2. The surgical instrument of claim 1, wherein the firing motion parameter comprises a duty cycle of the motor.

3. The surgical instrument of claim 1, wherein the firing motion parameter comprises a velocity of the motor.

4. The surgical instrument of claim 1, wherein the control system is further configured to detect, at a third time point before the first time point, the end effector moving toward the clamped state, and wherein setting the firing motion parameter of the motor-powered firing system is further based on an elapsed time from the third time point to the first time point.

5. The surgical instrument of claim 1, wherein the control system is further configured to detect, at a third time point before the first time point, the second jaw of the end effector contacting tissue while the end effector transitions toward the clamped state, and wherein setting the firing motion parameter of the motor-powered firing system is further based on an elapsed time from the third time point to the second time point.

6. The surgical instrument of claim 1, wherein the control system is further configured to dynamically adjust the firing motion parameter during the firing stroke based on an elapsed time from the first time point to a current time point.

7. The surgical instrument of claim 1, further comprising:
an elongate shaft; and
an articulation joint, wherein the end effector is rotatable relative to the elongate shaft about the articulation joint;
wherein the control system is further configured to detect an articulation angle of the end effector, and wherein setting the firing motion parameter of the motor-powered firing system is further based on the articulation angle.

8. The surgical instrument of claim 1, wherein the control system is further configured to detect, at a third time point before the first time point, the end effector reaching a partially clamped state, and wherein setting the firing motion parameter of the motor-powered firing system is further based on an elapsed time from the third time point to the second time point.

9. A surgical instrument, comprising:
an end effector configurable between an open state and a clamped state, wherein the end effector comprises:
a first jaw;
a second jaw moveable relative to the first jaw; and
a staple cartridge comprising staples removably stored therein;
a firing member movable from an unfired position toward a fired position during a firing stroke, wherein the staples are deployable from the staple cartridge based on the firing member moving toward the fired position;
a closure system configured to transition the end effector between the open state and the clamped state;
a motor-powered firing system comprising a motor, wherein the motor-powered firing system is configured to drive the firing member through the firing stroke; and
a control system, configured to:
detect, at a first time point, the end effector moving toward the clamped state;
detect, at a second time point, the end effector reaching the clamped state;
detect, at a third time point, the actuation of the motor-powered firing system;
set a firing motion parameter of the motor-powered firing system based on a first elapsed time from the first time point to the second time point and a second elapsed time from the second time point to the third time point; and
drive the firing member through the firing stroke with the motor-powered firing system using the firing motion parameter.

10. The surgical instrument of claim 9, further comprising:
an elongate shaft; and
an articulation joint, wherein the end effector is rotatable relative to the elongate shaft about the articulation joint;
wherein the control system is further configured to detect an articulation angle of the end effector, and wherein setting the firing motion parameter of the motor-powered firing system is further based on the articulation angle.

11. The surgical instrument of claim 9, wherein the control system is further configured to detect, at a fourth time point between the first time point and the second time point, the second jaw contacting tissue while the end effector transitions toward the clamped state, and wherein setting the firing motion parameter of the motor-powered firing system is further based on an elapsed time from the fourth time point to the third time point.

12. The surgical instrument of claim 9, wherein the control system is further configured to dynamically adjusting the firing motion parameter during the firing stroke based an elapsed time from the second time point to a current time point.

* * * * *